US008932860B2

(12) United States Patent
Rozwadowski et al.

(10) Patent No.: US 8,932,860 B2
(45) Date of Patent: Jan. 13, 2015

(54) RETRONS FOR GENE TARGETING

(75) Inventors: Kevin L. Rozwadowski, Saskatoon (CA); Derek J. Lydiate, Saskatoon (CA)

(73) Assignee: Her Majesty in Right of Canada as Represented by the Minister of Agriculture and Agri-Food Canada, Saskatoon (CA)

( * ) Notice: Subject to any disclaimer, the term of this patent is extended or adjusted under 35 U.S.C. 154(b) by 411 days.

(21) Appl. No.: 12/197,215

(22) Filed: Aug. 22, 2008

(65) Prior Publication Data

US 2009/0123991 A1 May 14, 2009

Related U.S. Application Data

(63) Continuation of application No. 10/516,779, filed as application No. PCT/CA03/00850 on Jun. 5, 2003, now abandoned.

(60) Provisional application No. 60/386,640, filed on Jun. 5, 2002.

(51) Int. Cl.
*C12N 15/82* (2006.01)
*C12N 1/14* (2006.01)
*C12N 15/00* (2006.01)
*C12N 15/02* (2006.01)
*C12N 15/63* (2006.01)
*C12N 15/74* (2006.01)
*C12N 15/87* (2006.01)
*C12N 15/10* (2006.01)
*C12N 9/12* (2006.01)
*C12N 15/90* (2006.01)
*A61K 48/00* (2006.01)

(52) U.S. Cl.
CPC ............ *C12N 15/102* (2013.01); *C12N 9/1276* (2013.01); *C12N 15/902* (2013.01); *A01K 2217/05* (2013.01); *A61K 48/00* (2013.01)
USPC ...................... 435/468; 435/254.2; 435/320.1; 435/410; 435/455; 435/463; 435/471

(58) Field of Classification Search
CPC .. C12N 15/102; C12N 15/902; C12N 9/1276; A01K 2217/05; A61K 48/00
USPC ........... 435/254.2, 320.1, 410, 455, 463, 468, 435/471
See application file for complete search history.

(56) References Cited

U.S. PATENT DOCUMENTS

| 5,320,958 A | 6/1994 | Inouye et al. |
| 5,405,775 A | 4/1995 | Inouye et al. |
| 5,436,141 A | 7/1995 | Miyata et al. |
| 5,780,269 A * | 7/1998 | Inouye et al. ................. 435/91.1 |
| 5,849,563 A | 12/1998 | Miyata et al. |
| 6,017,737 A | 1/2000 | Inouye et al. |
| 6,504,081 B1 | 1/2003 | Westphal et al. |
| 2003/0082800 A1 | 5/2003 | Conrad et al. |

FOREIGN PATENT DOCUMENTS

| CA | 2075515 | 8/1992 |
| EP | 0 532 380 A2 | 3/1993 |
| WO | WO 02/062986 | 8/2002 |

OTHER PUBLICATIONS

Freeman et al., Histone H3 transcription in *Saccharomyces cerevisiae* is controlled by multiple cell cycle activation sites and a constitutive negative regulatory element, Mol Cell Biol. 12(12):5455-63, 1992.*
Gorecki, D., 2001, Expert Opin. Emerging Drugs, 6(2): 187-198.*
Bennett, J., 2003, Gene Therapy, vol. 10, p. 977-982.*
Thomas et al., 2003, Nature Reviews/ Genetics, vol. 4, p. 346-358.*
Lebedeva et al., 2003, Seminars in Cancer Biology, vol. 12, p. 169-178.*
Kodama et al., 2006, Current Medicinal Chemistry, vol. 13, p. 2155-2161.*
Ach, R.A., Durfee,T., Miller, A.B., Taranto, P., Hanley-Bowdoin, L., Zambryski, P.C., Gruissem, W., "RRB1 and RRB2 encode maize retinoblastoma-related proteins that interact with a plant D-type cyclin and geminivirus replication protein", *Mol Cell Biol* 17: 5077-5086 (1997).
Ainley, W.M., Key, J.L., "Development of a heat shock inducible expression cassette for plants: characterization of parameters for its use in transient expression assays", *Plant Mol.Biol.* 14: 949-967 (1990).
Akbar Behjatnia, S.A. et al., "Identification of the replication-associated protein binding domain within the intergenic region of tomato leaf curl geminivirus", *Nucleic Acids Res* 26: 925-931 (1998).

(Continued)

*Primary Examiner* — Shin Lin Chen
(74) *Attorney, Agent, or Firm* — Klarquist Sparkman, LLP

(57) ABSTRACT

The invention provides methods and nucleic acid constructs that may be used to modify a nucleic acid of interest at a target locus within the genome of a host. In some aspects, the invention contemplates producing in vivo a gene targeting substrate (GTS), which may be comprised of both DNA and RNA components. The gene targeting substrate may comprise a gene targeting nucleotide sequence (GTNS), which is homologous to the target locus, but comprises a sequence modification compared to the target locus. The gene targeting substrate may be produced by reverse transcription of a gene targeting message RNA (gtmRNA). The gene targeting message RNA may be folded for self-priming for reverse transcription by a reverse transcriptase. The gene targeting message RNA may in turn be the product of transcription of a gene targeting construct (GTC) encoding the gene targeting message RNA. The gene targeting construct may for example be a DNA sequence integrated into the genome of the host, or integrated into an extrachromosomal element. Following expression of the gene targeting systems of the invention, hosts may for example be selected having genomic modifications at a target locus that correspond to the sequence modification present on the gene targeting nucleotide sequence. In some embodiments, the structure of retrons may be adapted for use in the gene targeting systems of the invention.

24 Claims, 18 Drawing Sheets

(56) References Cited

OTHER PUBLICATIONS

Alexeev, V., Igoucheva, O., Domashenko, A., Cotsarelis, G., Yoon, K., "Localized in vivo genotypic and phenotypic correction of the albino mutation in skin by RNA-DNA oligonucleotide", *Nat. Biotechnol.* 18: 43-47 (2000).
Alonso, J.C., Ayora, S., Canosa, I., Weise, F., Rojo, F., "Site-specific recombination in gram-positive theta-replicating plasmids", *FEMS Microbiol Lett* 142: 1-10 (1996).
Altschul et al., "Basic Local Alignment Search Tool", *J. Mol. Biol.* 215:403-10 (1990).
An, Y.Q., Huang, S., McDowell, J.M., McKinney, E.C., Meagher, R.B., "Conserved expression of the *Arabidopsis* ACT1 and ACT 3 actin subclass in organ primordia and mature pollen", *Plant Cell* 8: 15-30 (1996).
An, Y.Q., McDowell, J.M., Huang, S., McKinney, E.C., Chambliss, S., Meagher, R.B., "Strong, constitutive expression of the *Arabidopsis* ACT2/ACT8 actin subclass in vegetative tissues", *Plant J* 10: 107-121 (1996).
Aoyama, T., Chua, N.H., *Plant J.* 11(3): 605-612 (1997), Abstract.
Arai, N., Kornberg, A., "Rep protein as a helicase in an active, isolatable replication fork of duplex phi X174 DNA", *J Biol Chem* 256: 5294-5298 (1981).
Arezi, B., Kuchta, R.D., "Eukaryotic DNA primase", *Trends Biochem Sci* 25: 572-576 (2000).
Asano, S., Higashitani, A., Horiuchi, K., "Filamentous phage replication initiator protein gpII forms a covalent complex with the 5' end of the nick it introduced", *Nucleic Acids Res* 27: 1882-1889 (1999).
Atanassova, R., Chaubet, N., Gigot, C., "A 126 bp fragment of a plant histone gene promoter confers preferential expression in meristems of transgenic *Arabidopsis*", *Plant J* 2: 291-300 (1992).
Ausubel, et al. (eds), *Current Protocols in Molecular Biology*, vol. 1, Green Publishing Associates, Inc., and John Wiley & Sons, Inc., New York, at p. 2.10.1 (1993).
Backert, S., Dorfel, P., Lurz, R., Borner, T., "Rolling-circle replication of mitochondrial DNA in the higher plant *Chenopodium album* (L.)", *Mol Cell Biol* 16: 6285-6294 (1996).
Basile, G., Aker, M., Mortimer, R.K., "Nucleotide sequence and transcriptional regulation of the yeast recombinational repair gene RAD51", *Mol.Cell Biol.* 12: 3235-3246 (1992).
Bastia, D., "Determination of restriction sites and the nucleotide sequence surrounding the relaxation site of ColE1", *J Mol Biol* 124: 601-639 (1978).
Bechtold, N., Pelletier, G., "In planta *Agrobacterium*-mediated transformation of adult *Arabidopsis thaliana* plants by vacuum infiltration", *Methods Mol Biol* 82: 259-266 (1998).
Beck, E., Zink, B., "Nucleotide sequence and genome organisation of filamentous bacteriophages f1 and fd", *Gene* 16: 35-58 (1981).
Beetham, P.R., Kipp, P.B., Sawycky, X.L., Arntzen, C.J., May, G.D., "A tool for functional plant genomics: chimeric RNA/DNA oligonucleotides cause in vivo gene-specific mutations", *Proc. Natl. Acad. Sci. U.S.A* 96: 8774-8778 (1999).
Bell, J.B., Jones, M.E., "Purification and characterization of yeast orotidine 5'-monophosphate decarboxylase overexpressed from plasmid PGU2", *J Biol Chem* 266: 12662-12667 (1991).
Bennett, C.B., Lewis, A.L., Baldwin, K.K., Resnick, M.A., "Lethality induced by a single site-specific double-strand break in a dispensable yeast plasmid", *Proc Natl Acad Sci USA* 90: 5613-5617 (1993).
Benton, B.M., Eng, W.K., Dunn, J.J., Studier, F.W., Sternglanz, R., Fisher, P.A., "Signal-mediated import of bacteriophage T7 RNA polymerase into the *Saccharomyces cerevisiae* nucleus and specific transcription of target genes", *Mol.Cell Biol.* 10: 353-360 (1990).
Bernardi, A., Bernardi, F., "Complete sequence of pSC101", *Nucleic Acids Res* 12: 9415-9426 (1984).
Bertling, W., "Gene Targeting", In: Vega, MA (ed), *Gene Targeting*, pp. 1-44. CRC Press, Boca Raton (1995).
Bertling, W.M., Aigner, T., "Evidence for tissue specific activation of the retrotransposon L1 in mice", *J. Cell. Biochem.* suppl. 18B, p. 45 (1994).
Bevan, M.W., Flavell, R.B., Chilton, M.D., "A chimaeric antibiotic resistance gene as a selectable marker for plant cell transformation", *Nature* 304: 184-187 (1983).
Bialkowska-Hobrzanska, H., Denhardt, D.T., "The rep mutation. VII. Cloning and analysis of the functional rep gene of *Escherichia coli* K-12", *Gene* 28: 93-102 (1984).
Biswas, I., Gruss, A., Ehrlich, S.D., Maguin, E., "High-efficiency gene inactivation and replacement system for gram-positive bacteria", *J Bacteriol* 175: 3628-3635 (1993).
Boe, L., Gros, M.F., Te, R.H., Ehrlich, S.D., Gruss, A., "Replication origins of single-stranded-DNA plasmid pUB110", *J Bacteriol* 171: 3366-3372 (1989).
Bohner, S., Lenk, I., Rieping, M., Herold, M., Gatz, C., "Technical advance: transcriptional activator TGV mediates dexamethasone-inducible and tetracycline-inactivatable gene expression", *Plant J.* 19: 87-95 (1999).
Boulikas, T., "Common structural features of replication origins in all life forms", *J Cell Biochem* 60: 297-316 (1996).
Boyer, H., "Genetic control of restriction and modification in *Escherichia coli.*", *J Bacteriol* 88, pp. 1652-1660 (1964).
Brandstatter, I., Kieber, J.J., *Plant Cell* 10: 1009-1019 (1998).
Bratthauer, G.L., Fanning, T.G., "Active LINE-1 retrotransposons in human testicular cancer", *Oncogene* 7: 507-510 (1992).
Bravo-Angel, A.M., Gloeckler, V., Hohn, B., Tinland, B., "Bacterial conjugation protein MobA mediates integration of complex DNA structures into plant cells", *J Bacteriol* 181: 5758-5765 (1999).
Brinster, R.L., Braun, R.E., Lo, D., Avarbock, M.R., Oram, F., Palmiter, R.D., "Targeted correction of a major histocompatibility class II E alpha gene by DNA microinjected into mouse eggs", *Proc Natl Acad Sci U.S.A.* 86: 7087-7091 (1989).
Brister, J.R., Muzyczka, N., "Mechanism of Rep-mediated adeno-associated virus origin nicking", *J Virol* 74: 7762-7771 (2000).
Brosius, J., Holy, A., "Regulation of ribosomal RNA promoters with a synthetic lac operator", *Proc Natl Acad Sci U.S.A.* 81: 6929-6933 (1984).
Broverman, S., MacMorris, M., Blumenthal, T., "Alteration of *Caenorhabditis elegans* gene expression by targeted transformation", *Proc. Natl. Acad. Sci. U.S.A* 90: 4359-4363 (1993).
Byrd, D.R., Matson, S.W., "Nicking by transesterification: the reaction catalysed by a relaxase", *Mol Microbiol* 25: 1011-1022 (1997).
Caddick, M.X. et al, *Nature Biotech.* 16: 177-180 (1998).
Callis, J., Raasch, J.A., Vierstra, R.D. "Ubiquitin extension proteins of *Arabidopsis thaliana*. Structure, localization, and expression of their promoters in transgenic tobacco", *J Biol Chem* 265: 12486-12493 (1990).
Carles-Kinch, K., Kreuzer, K.N., "RNA-DNA hybrid formation at a bacteriophage T4 replication origin", *J Mol Biol* 266: 915-926 (1997).
Carrington et al., *Plant Cell* 3: 953-962 (1991).
Castellano, M.M., Sanz-Burgos, A.P., Gutierrez, C., "Initiation of DNA replication in a eukaryotic rolling-circle replicon: identification of multiple DNA-protein complexes at the geminivirus origin", *J Mol Biol* 290: 639-652 (1999).
Chang, A.C., Cohen, S.N. "Construction and characterization of amplifiable multicopy DNA cloning vehicles derived from the P15A cryptic miniplasmid", *J Bacteriol* 134: 1141-1156 (1978).
Chang, T.L., Kramer, M.G., Ansari, R.A., Khan, S.A., "Role of individual monomers of a dimeric initiator protein in the initiation and termination of plasmid rolling circle replication", *J Biol Chem* 275: 13529-13534 (2000).
Choi, I.R., Stenger, D.C., "Strain-specific determinants of beet curly top geminivirus DNA replication", *Virology* 206: 904-912 (1995).
Chu, P.W., Keese, P., Qiu, B.S., Waterhouse, P.M., Gerlach, W.L., "Putative full-length clones of the genomic DNA segments of subterranean clover stunt virus and identification of the segment coding for the viral coat protein", *Virus Res* 27: 161-171 (1993).
Chu, S., DeRisi, J., Eisen, M., Mulholland, J., Botstein, D., Brown, P.O., Herskowitz, I., "The transcriptional program of sporulation in budding yeast", *Science* 282: 699-705 (1998).
Clark, A.B., Cook, M.E., Tran, H.T., Gordenin, D.A., Resnick, M.A., Kunkel, T.A., "Functional analysis of human MutSalpha and MutSbeta complexes in yeast", *Nucleic Acids Res.* 27: 736-742 (1999).

(56) References Cited

OTHER PUBLICATIONS

Clough, S.J., Bent, A.F., "Floral dip: a simplified method for *Agrobacterium*-mediated transformation of *Arabidopsis thaliana*", *Plant J* 16: 735-743 (1998).

Colasanti, J., Denhardt, D.T., "Expression of the cloned bacteriophage phi X174 A* gene in *Escherichia coli* inhibits DNA replication and cell division", *J Virol* 53: 807-813 (1985).

Cole-Strauss, A., Gamper, H., Holloman, W.K., Munoz, M., Cheng, N., Kmiec, E.B., "Targeted gene repair directed by the chimeric RNA/DNA oligonucleotide in a mammalian cell-free extract", *Nucleic Acids Res* 27: 1323-1330 (1999).

Cole-Strauss, A., Yoon, K., Xiang, Y., Byrne, B.C., Rice, M.C., Gryn, J., Holloman, W.K., Kmiec, E.B., "Correction of the mutation responsible for sickle cell anemia by an RNA-DNA oligonucleotide", *Science* 273: 1386-1389 (1996).

Colleaux, L., D'Auriol, L., Galibert, F., Dujon, B., "Recognition and cleavage site of the intron-encoded omega transposase", *Proc Natl Acad Sci U.S.A.* 85: 6022-6026 (1988).

Cotmore, S.F., Tattersall, P., "High-mobility group 1/2 proteins are essential for initiating rolling-circle-type DNA replication at a parvovirus hairpin origin", *J Virol* 72: 8477-8484 (1998).

Coupland, G.M., Brown, A.M., Willetts, N.S., "The origin of transfer (oriT) of the conjugative plasmid R46: characterization by deletion analysis and DNA sequencing", *Mol Gen Genet* 208: 219-225 (1987).

Critchlow, S.E., Jackson, S.P., "DNA end-joining: from yeast to man", *Trends Biochem. Sci.* 23: 394-398 (1998).

Crossway, A., Oakes, J.V., Irvine, J.M., Ward, B., Knauf, V.C., Shewmaker, C.K., "Integration of foreign DNA following microinjection of tobacco mesophyll protoplasts", *Mol Gen Genet* 202: 179. (1986).

Cummings, W.J., Zolan, M.E., "Functions of DNA repair genes during meiosis", *Curr.Top.Dev.Biol.* 37: 117-140 (1998).

D'Halluin, K., Bonne, E., Bossut, M., De Beuckeleer, M., Leemans, J., "Transgenic maize plants by tissue electroporation", *Plant Cell* 4: 1495-1505 (1992).

Datsenko, K.A., Wanner, B.L., "One-step inactivation of chromosomal genes in *Escherichia coli* K-12 using PCR products", *Proc Natl Acad Sci U.S.A.* 97: 6640-6645 (2000).

Datta and Glazer, "Intracellular generation of single-stranded DNA for chromosomal triplex formation and induced recombination," *Nucleic Acids Research* 29(24):5140-5147 (2001).

Dawe, R.K., "Meiotic Chromosome Organization and Segregation in Plants", standard. dtl *Annu. Rev. Plant Physiol. Plant Mol. Biol.* 49: 371 (1998).

de Boer, H.A., Comstock, L.J., Vasser, M., "The tac promoter: a functional hybrid derived from the trp and lac promoters", *Proc. Natl. Acad. Sci. U.S.A* 80: 21-25 (1983).

de Groot, M.J., Offringa, R., Does, M.P., Hooykaas, P.J., van den Elzen, P.J., "Mechanisms of intermolecular homologous recombination in plants as studied with si", *Nucleic Acids Res.* 20: 2785-2794 (1992).

Dean, R.B., Dixon, W., "Simplified statistics for small numbers of observations", *Anal. Chem.* 23: 636-638 (1951).

del Solar, G., Giraldo, R., Ruiz-Echevarria, M.J., Espinosa, M., Diaz-Orejas, R., "Replication and control of circular bacterial plasmids", *Microbiol Mol Biol Rev* 62: 434-464 (1998).

Deng, C., Capecchi, M.R. "Reexamination of gene targeting frequency as a function of the extent of homology between the targeting vector and the target locus", *Mol Cell Biol* 12: 3365-3371 (1992).

Dente, L., Cesareni, G., Cortese, R., "pEMBL: a new family of single stranded plasmids", *Nucleic Acids Res* 11: 1645-1655 (1983).

Dente, L., Cortese, R., "pEMBL: a new family of single-stranded plasmids for sequencing DNA", *Methods Enzymol.* 155: 111-119 (1987).

Desbiez, C., David, C., Mettouchi, A., Laufs, J., Gronenborn, B., "Rep protein of tomato yellow leaf curl geminivirus has an ATPase activity required for viral DNA replication", *Proc Natl Acad Sci U.S.A.* 92: 5640-5644 (1995).

Deshayes, A., Herrera-Estrella, L., Caboche, M., "Liposome-mediated transformation of tobacco mesophyll protoplasts by an *Escherichia coli* plasmid", *EMBO J* 4: 2731-2737 (1985).

Dhundale et al., "A New Species of Multicopy Single-stranded DNA from *Myxococcus xanthus* with Conserved Structural Features," *J. Biol. Chem* 263: 9055-9058 (1988).

Dhundale et al., "Structure of msDNA from *Myxococcus xanthus*: Evidence for a Long, Self-Annealing RNA Precursor for the Covalently Linked, Branched RNA," *Cell* 51: 1105-1112 (1987).

Dotto, G.P., Enea, V., Zinder, N.D., "Functional analysis of bacteriophage f1 intergenic region", *Virology* 114: 463-473 (1981).

Dotto, G.P., Horiuchi, K., "Replication of a plasmid containing two origins of bacteriophage", *J Mol Biol* 153: 169-176 (1981).

Dotto, G.P., Horiuchi, K., Zinder, N.D., "Initiation and termination of phage f1 plus-strand synthesis", *Proc Natl Acad Sci U.S.A.* 79: 7122-7126 (1982).

Dotto, G.P., Horiuchi, K., Zinder, N.D., "The functional origin of bacteriophage f1 DNA replication. Its signals and domains", *J Mol Biol* 172: 507-521 (1984).

Dotto, G.P., Zinder, N.D., "Increased intracellular concentration of an initiator protein markedly reduces the minimal sequence required for initiation of DNA synthesis", *Proc Natl Acad Sci U.S.A.* 81: 1336-1340 (1984).

Doutriaux, M.P., Couteau, F., Bergounioux, C., White, Cl, "Isolation and characterisation of the RAD51 and DMC1 homologs from *Arabidopsis thaliana*", *Mol.Gen.Genet.* 257: 283-291 (1998).

Dry, I.B., Rigden, J.E., Krake, L.R., Mullineaux, P.M., Rezaian, M.A., "Nucleotide sequence and genome organization of tomato leaf curl geminivirus", *J Gen Virol* 74: 147-151 (1993).

Dujon, B., "Group I introns as mobile genetic elements: facts and mechanistic speculations—a review", *Gene* 82: 91-114 (1989).

Espinosa, M., del Solar, G., Rojo, F., Alonso, J.C., "Plasmid rolling circle replication and its control", *FEMS Microbiol Lett* 130: 111-120 (1995).

Fekete, R.A., Frost, L.S., "Mobilization of chimeric oriT plasmids by F and R100-1: role of relaxosome formation in defining plasmid specificity", *J Bacteriol* 182: 4022-4027 (2000).

Finlay, B.B., Frost, L.S., Paranchych, W., "Origin of transfer of IncF plasmids and nucleotide sequences of the type II oriT, traM, and traY alleles from ColB4-K98 and the type IV traY allele from R100-1", *J Bacteriol* 168: 132-139 (1986).

Firth, N., Ippen-Ihler, K., Skurray, R.A., "Structure and function of the F factor and mechanism of conjugation", In: Neidhardt, F (ed), *Escherichia coli* and *Salmonella*, pp. 2377-2401. American Society for Microbiology, (1995).

Fluit, A.C., Baas, P.D., Jansz, H.S., "The complete 30-base-pair origin region of bacteriophage phi X174 in a plasmid is both required and sufficient for in vivo rolling-circle DNA replication and packaging", *Eur J Biochem* 149: 579-584 (1985).

Fluit, A.C., Baas, P.D., Van Boom, J.H., Veeneman, G.H., Jansz, H.S., "Gene A protein cleavage of recombinant plasmids containing the phi X174 replication origin", *Nucleic Acids Res* 12: 6443-6454 (1984).

Fontes, E.P., Eagle, P.A., Sipe, P.S., Luckow, V.A., Hanley-Bowdoin, L., "Interaction between a geminivirus replication protein and origin DNA is essential for viral replication", *J Biol Chem* 269: 8459-8465 (1994).

Fujioka et al., "Targeted recombination with single-stranded DNA vectors in mammalian cells," *Nucleic Acids Research* 21(3):407-412 (1993).

Furste, J.P., Pansegrau, W., Ziegelin, G., Kroger, M., Lanka, E., "Conjugative transfer of promiscuous IncP plasmids: interaction of plasmid-encoded products with the transfer origin", *Proc Natl Acad Sci U.S.A.* 86: 1771-1775 (1989).

Furuichi et al., "Biosynthesis and Structure of Stable Branched RNA Covalently Linked to the 5' End of Multicopy Single-Stranded DNA of *Stimatella aurantiaca*," *Cell* 48: 55-62 (1987).

Furuichi et al., "Branched RNA Covalently Linked to the 5' End of a Single-Stranded DNA in *Stigmatella aurantiaca*: Structure of msDNA," *Cell* 48: 47-52 (1987).

Furukawa, K., Hayashida, S., Taira, K., "Gene-specific transposon mutagenesis of the biphenyl/polychlorinated biphenyl-degradation-controlling bph operon in soil bacteria", *Gene* 98: 21-28 (1991).

(56) References Cited

OTHER PUBLICATIONS

Furuya, N., Nisioka, T., Komano, T., "Nucleotide sequence and functions of the oriT operon in IncI1 plasmid R64", *J Bacteriol* 173: 2231-2237 (1991).
Gallego, M.E., Sirand-Pugnet, P., White, C.I., "Positive-negative selection and T-DNA stability in *Arabidopsis* transformation", *Plant Mol Biol* 39: 83-93 (1999).
Galli, A., Schiestl, R.H., "Effects of DNA double-strand and single-strand breaks on intrachromosomal recombination events in cell-cycle-arrested yeast cells", *Genetics* 149: 1235-1250 (1998).
Gamper, H.B., Jr., Cole-Strauss, A., Metz, R., Parekh, H., Kumar, R., Kmiec, E.B., "A plausible mechanism for gene correction by chimeric oligonucleotides", *Biochemistry* 39: 5808-5816 (2000).
Gari, E., Piedrafita, L., Aldea, M., Herrero, E., "A set of vectors with a tetracycline-regulatable promoter system for modulated gene expression in *Saccharomyces cerevisiae*", *Yeast* 13: 837-848 (1997).
Gasser, C.S., Fraley, R.T., "Genetically engineering plants for crop improvement", *Science* 244: 1293 (1989).
Gatz, C., "Chemical Control of Gene Expression," *Ann. Rev. Plant Physiol. Plant Mol. Biol.* 48: 89-108 (1997).
Gatz, C., Kaiser, A., Wendenburg, R., "Regulation of a modified CaMV 35S promoter by the Tn10-encoded Tet repressor in transgenic tobacco", *Mol. Gen. Genet.* 227: 229-237 (1991).
Gatz, C., Lenk, I.R.P., "Promoters that respond to chemical inducers," *Trends Plant Sci.* 3: 352-358 (1998).
Gheysen, G., Villarroel, R., Van Montagu, M., "Illegitimate recombination in plants: a model for T-DNA integration", *Genes Dev.* 5: 287-297 (1991).
Gielow, A., Diederich, L., Messer, W., "Characterization of a phage-plasmid hybrid (phasyl) with two independent origins of replication isolated from *Escherichia coli*", *J Bacteriol* 173: 73-79 (1991).
Gietz, R.D., Schiestl, R.H., Willems, A.R., Woods, R.A., "Studies on the transformation of intact yeast cells by the LiAc/SS-DNA/PEG procedure", *Yeast* 11: 355-360 (1995).
Gietz, R.D., Sugino, A., "New yeast-*Escherichia coli* shuttle vectors constructed with in vitro mutagenized yeast genes lacking six-base pair restriction sites", *Gene* 74: 527-534 (1988).
Godson, G.N., Barren, B.G., Staden, R., Fiddes, J.C., "Nucleotide sequence of bacteriophage G4 DNA", *Nature* 276: 236-247 (1978).
Goetz, G.S., Hurwitz, J., Studies on the role of the phi X174 gene A protein in phi X viral strand synthesis. I. Replication of DNA containing an alteration in position 1 of the 30-nucleotide icosahedral bacteriophage origin, *J Biol Chem* 263: 16421-16432 (1988).
Goetz, G.S., Hurwitz, J., "Studies on the role of the phi X174 gene A protein in phi X174 viral strand synthesis. III. Replication of DNA containing two viral replication origins", *J Biol Chem* 263: 16443-16451 (1988).
Goetz, G.S., Schmidt-Glenewinkel, T., Hu, M.H., Belgado, N., Hurwitz, J., "Studies on the role of the phi X174 gene A protein in phi X viral strand synthesis. II. Effects of DNA replication of mutations in the 30-nucleotide icosahedral bacteriophage origin", *J Biol Chem* 263: 16433-16442 (1988).
Goldfarb, D.S., Gariepy, J., Schoolnik, G., Kornberg, R.D., "Synthetic peptides as nuclear localization signals", *Nature* 322: 641-644 (1986).
Grandoso, G., Avila, P., Cayon, A., Hernando, M.A., Llosa, M., de la, C.F., "Two active-site tyrosyl residues of protein TrwC act sequentially at the origin of transfer during plasmid R388 conjugation", *J Mol Biol* 295: 1163-1172 (2000).
Grandoso, G., Llosa, M., Zabala, J.C., de la, C.F., "Purification and biochemical characterization of TrwC, the helicase involved in plasmid R388 conjugal DNA transfer", *Eur J Biochem* 226: 403-412 (1994).
Greenstein, D., Horiuchi, K., "Double-strand cleavage and strand joining by the replication initiator protein of filamentous phage f1", *J Biol Chem* 264: 12627-12632 (1989).
Gros, M.F., Te, R.H., Ehrlich, S.D., "Replication origin of a single-stranded DNA plasmid pC194", *EMBO J* 8: 2711-2716 (1989).
Gros, M.F., Te, R.H., Ehrlich, S.D., "Rolling circle replication of single-stranded DNA plasmid pC194", *EMBO J* 6: 3863-3869 (1987).
Gruss, A., Ehrlich, S.D., "The family of highly interrelated single-stranded deoxyribonucleic acid plasmids", *Microbiol Rev* 53: 231-241 (1989).
Guyer, D., Tuttle, A., Rouse, S., Volrath, S., Johnson, M., Potter, S., Gorlach, J., Goff, S., Crossland, L., Ward, E., "Activation of latent transgenes in *Arabidopsis* using a hybrid transcription factor", *Genetics* 149: 633-639 (1998).
Haber, J.E., "DNA recombination: the replication connection", *Trends Biochem.Sci.* 24: 271-275 (1999).
Habu, T., Taki, T., West, A., Nishimune, Y., Morita, T., "The mouse and human homologs of DMC1, the yeast meiosis-specific homologous recombination gene, have a common unique form of exon-skipped transcript in meiosis", *Nucleic Acids Res.* 24: 470-477 (1996).
Hafner, G.J., Stafford, M.R., Wolter, L.C., Harding, R.M., Dale, J.L., "Nicking and joining activity of banana bunchy top virus replication protein in vitro", *J Gen Virol* 78: 1795-1799 (1997).
Hanai, R., Wang, J.C., "The mechanism of sequence-specific DNA cleavage and strand transfer by phi X174 gene A* protein", *J Biol Chem* 268: 23830-23836 (1993).
Harding, R.M., Burns, T.M., Hafner, G., Dietzgen, R.G., Dale, J.L., "Nucleotide sequence of one component of the banana bunchy top virus genome contains a putative replicase gene", *J Gen Virol* 74: 323-328 (1993).
Haren, L., Ton-Hoang, B., Chandler, M., "Integrating DNA: transposases and retroviral integrases". *Annu.Rev Microbiol* 53: 245-281 (1999).
Harris, P., Navarro Poulsen, J.C., Jensen, K.F., Larsen, S., "Structural basis for the catalytic mechanism of a proficient enzyme: orotidine 5'-monophosphate decarboxylase", *Biochemistry* 39: 4217-4224 (2000).
Harth, G., Baumel, I., Meyer, T.F., Geider, K., "Bacteriophage fd gene-2 protein. Processing of phage fd viral strands replicated by phage T7 enzymes", *Eur J Biochem* 119: 663-668 (1981).
Hartung, F., Puchta, H., "Molecular characterisation of two paralogous SPO11 homologues in *Arabidopsis thaliana*", *Nucleic Acids Res.* 28: 1548-1554 (2000).
Hayashi, M., Aoyama, A., Richardson Jr., D., Hayashi, M.N., "Biology of the bacteriophage phiX174", In: Calendar, R (ed), *The Bacteriophages*, pp. 1-71, Plenum Press, New York (1988).
Heidekamp, F., Baas, P.D., Jansz, H.S., "Nucleotide sequences at the phi X gene A protein cleavage site in replicative form I DNAs of bacteriophages U3, G14, and alpha 3", *J Virol* 42: 91-99 (1982).
Hendrickson, E.A., "Cell-cycle regulation of mammalian DNA double-strand-break repair", *Am.J.Hum.Genet.* 61: 795-800 (1997).
Henikoff and Henikoff, "Amino acid substitution matrices from protein blocks," *Proc. Natl. Acad. Sci. USA* 89: 10915-10919 (1992).
Herzer, P.J., Inouye, S., Inouye, M., "Retron-Ec107 is inserted into the *Escherichia coli* genome by replacing a palindromic 34bp intergenic sequence", *Mol.Microbiol.* 6: 345-354 (1992).
Heslip, T.R., Hodgetts, R.B., "Targeted transposition at the vestigial locus of *Drosophila melanogaster*", *Genetics* 138: 1127-1135 (1994).
Heyraud-Nitschke, F., Schumacher, S., Laufs, J., Schaefer, S., Schell, J., Gronenborn, B., "Determination of the origin cleavage and joining domain of geminivirus Rep proteins", *Nucleic Acids Res* 23: 910-916 (1995).
Higashitani, A., Greenstein, D., Hirokawa, H., Asano, S., Horiuchi, K., "Multiple DNA conformational changes induced by an initiator protein precede the nicking reaction in a rolling circle replication origin", *J Mol Biol* 237: 388-400 (1994).
Higashitani, A., Greenstein, D., Horiuchi, K., "A single amino acid substitution reduces the superhelicity requirement of a replication initiator protein", *Nucleic Acids Res* 20: 2685-2691 (1992).
Hoffmann, G.R., "Induction of genetic recombination: consequences and model systems", *Environ.Mol Mutagen.* 23 Suppl 24: 59-66 (1994).
Hopfner, K.P., Putnam, C.D., Tainer, J.A., "DNA double-strand break repair from head to tail", *Curr. Opin. Struct. Biol.* 12: 115-122 (2002).

(56) References Cited

OTHER PUBLICATIONS

Hopp, T., Prickett, S., Price, V., Libby, R., Mar., C., Cerretti, D., Urdal, D., Conlon, P., "A short polypeptide marker sequence useful for recombinant protein identification and purification", *Bio/technology* 6: 1204-1210 (1988).

Horvath, G.V., Pettko-Szandtner, A., Nikovics, K., Bilgin, M., Boulton, M., Davies, J.W., Gutierrez, C., Dudits, D., "Prediction of functional regions of the maize streak virus replication-associated proteins by protein-protein interaction analysis", *Plant Mol Biol* 38: 699-712 (1998).

Huang, S., An, Y.Q., McDowell, J.M., McKinney, E.C., Meagher, R.B., "The *Arabidopsis thaliana* ACT4/ACT12 actin gene subclass is strongly expressed throughout pollen development", *Plant J* 10: 189-202 (1996).

Huang, S., An, Y.Q., McDowell, J.M., McKinney, E.C., Meagher, R.B., "The *Arabidopsis* ACT11 actin gene is strongly expressed in tissues of the emerging inflorescence, pollen, and developing ovules", *Plant Mol.Biol.* 33: 125-139 (1997).

Huntley, R., Healy, S., Freeman, D., Lavender, P., de Jager, S., Greenwood, J., Makker, J., Walker, E., Jackman, M., Xie, Q., Bannister, A.J., Kouzarides, T., Gutierrez, C., Doonan, J.H., Murray, J.A., "The maize retinoblastoma protein homologue ZmRb-1 is regulated during leaf development and displays conserved interactions with G1/S regulators and plant cyclin D (CycD) proteins", *Plant Mol Biol* 37: 155-169 (1998).

Huntley, R.P., Murray, J.A., "The plant cell cycle", *Curr.Opin.Plant Biol* 2: 440-446 (1999).

Ilyina, T.V., Koonin, E.V., "Conserved sequence motifs in the initiator proteins for rolling circle DNA replication encoded by diverse replicons from eubacteria, eucaryotes and archaebacteria", *Nucleic Acids Res* 20: 3279-3285 (1992).

Im, D.S., Muzyczka, N., "The AAV origin binding protein Rep68 is an ATP-dependent site-specific endonuclease with DNA helicase activity", *Cell* 61: 447-457 (1990).

Inouye et al., "In vivo production of oligodeoxyribonucleotides of specific sequences: application to antisense DNA," *CIBA Foundation Symposium*. Netherlands 209:224-233 (1997).

Inouye, M., Inouye, S., "Retrons and multicopy single-stranded DNA", *J.Bacteriol.* 174: 2419-2424 (1992).

Inouye, M., Mao, J.R., Shimamoto, T., Inouye, S., "In vivo production of oligodeoxyribonucleotides of specific sequences: application to antisense DNA", Ciba Found.Symp. 209: 224-33; discussion 233-4.: 224-233 (1997).

Jacobs, M., Dolferus, R., Van den, B.D., "Isolation and biochemical analysis of ethyl methanesulfonate-induced alcohol dehydrogenase null mutants of *Arabidopsis thaliana* (L.) Heynh", *Biochem Genet* 26: 105-122 (1988).

Jasin, M., Berg, P., "Homologous integration in mammalian cells without target gene selection", *Genes Dev.* 2: 1353-1363 (1988).

Jin, Y., Binkowski, G., Simon, L.D., Norris, D., "Ho endonuclease cleaves MAT DNA in vitro by an inefficient stoichiometric reaction mechanism", *J Biol Chem* 272: 7352-7359 (1997).

Jupin, I., Hericourt, F., Benz, B., Gronenborn, B., "DNA replication specificity of TYLCV geminivirus is mediated by the amino-terminal 116 amino acids of the Rep protein", *FEBS Lett* 362: 116-120 (1995).

Kaeppler, S.M., Kaeppler, H.F., Rhee, Y., "Epigenetic aspects of somaclonal variation in plants", *Plant Mol Biol* 43: 179-188 (2000).

Kakimoto, T., "CKI1, a Histidine Kinase Homolog Implicated in Cytokinin Signal Transduction," *Science* 274, 982-985 (1996).

Kalderon, D., Roberts, B.L., Richardson, W.D., Smith, A.E. "A short amino acid sequence able to specify nuclear location", *Cell* 39: 499-509 (1984).

Kanaar, R., Troelstra, C., Swagemakers, S.M., Essers, J., Smit, B., Franssen, J.H., Pastink, A., Bezzubova, O.Y., Buerstedde, J.M., Clever, B., Heyer, W.D., Hoeijmakers, J.H., "Human and mouse homologs of the *Saccharomyces cerevisiae* RAD54 DNA repair gene: evidence for functional conservation", *Curr.Biol.* 6: 828-838 (1996).

Keeney, S., Baudat, F., Angeles, M., Zhou, Z.H., Copeland, N.G., Jenkins, N.A., Manova, K., Jasin, M., "A mouse homolog of the *Saccharomyces cerevisiae* meiotic recombination DNA transesterase Spo11p", *Genomics* 61: 170-182 (1999).

Keeney, S., Giroux, C.N., Kleckner, N., "Meiosis-specific DNA double-strand breaks are catalyzed by Spo11, a member of a widely conserved protein family", *Cell* 88: 375-384 (1997).

Kleckner, N., "Meiosis: how could it work?", *Proc. Natl. Acad. Sci.U.S.A* 93: 8167-8174 (1996).

Klein, T.M., Harper, E.C., Svab, Z., Sanford, J.C., Fromm, M.E., Maliga, P., "Stable genetic transformation of intact *Nicotiana* cells by the particle bombardment process", *Proc Natl Acad Sci U.S.A*. 85: 8502 (1988).

Kleiner, D., Paul, W., Merrick, M.J., "Construction of multicopy expression vectors for regulated over-production of proteins in *Klebsiella pneumoniae* and other enteric bacteria", *J Gen Microbiol* 134: 1779-1784 (1988).

Klimyuk,V.I., Jones, J.D., "AtDMC1, the *Arabidopsis* homologue of the yeast DMC1 gene: characterization, transposon-induced allelic variation and meiosis-associated expression", *Plant J*. 11: 1-14 (1997).

Kobayashi, T., Hotta, Y., Tabata, S., "Isolation and characterization of a yeast gene that is homologous with a meiosis-specific cDNA from a plant", *Mol. Gen. Genet*. 237: 225-232 (1993).

Kobayashi, T., Kobayashi, E., Sato, S., Hotta, Y., Miyajima, N., Tanaka, A., Tabata, S., "Characterization of cDNAs induced in meiotic prophase in lily microsporocytes", *DNA Res*. 1: 15-26 (1994).

Koepsel, R.R., Murray, R.W., Rosenblum, W.D., Khan, S.A., "The replication initiator protein of plasmid pT181 has sequence-specific endonuclease and topoisomerase-like activities", *Proc Natl Acad Sci U.S.A*. 82: 6845-6849 (1985).

Koncz, C., Schell, J., "The promoter of TL-DNA gene 5 controls the tissue-specific expression of chimaeric genes carried by a novel type of *Agrobacterium* binary vector", *Mol. Gen. Genet*. 204: 383-396 (1986).

Kowalczykowski, S.C., Dixon, D.A., Eggleston, A.K., Lauder, S.D., Rehrauer, W.M., "Biochemistry of homologous recombination in *Escherichia coli*", *Microbiol.Rev*. 58: 401-465 (1994).

Kowalski, D., Eddy, M.J., "The DNA unwinding element: a novel, cis-acting component that facilitates opening of the *Escherichia coli* replication origin", *EMBO J* 8: 4335-4344 (1989).

Kren and Steer, "The application of DNA repair vectors to gene therapy," *Current Opin. Biotech*. 13:473-481 (2002).

Krens, F.A., Molendijk, L., Wullems, G.J., Schilperoort, R.A., "In vitro transformation of plant protoplasts with Ti-plasmid DNA", *Nature* 296: 72 (1982).

Labow, M.A., Baim, S.B., Shenk, T., Levine, A.J., "Conversion of the lac repressor into an allosterically regulated transcriptional activator for mammalian cells", *Mol.Cell Biol*. 10: 3343-3356 (1990).

Lai, L.W., Lien, Y.H., "Homologous recombination based gene therapy", *Exp Nephrol*. 7: 11-14 (1999).

Lampson et al., "Reverse Transcriptase in a Clinical Strain of *Escherichia coli*: Production of Branched RNA-Linked msDNA," *Science* 243: 1033-1038 (1989).

Lanzov, V.A., "Gene targeting for gene therapy: prospects", *Mol. Genet. Metab* 68: 276-282 (1999).

Laufs, J., Jupin, I., David, C., Schumacher, S., Heyraud-Nitschke, F., Gronenborn, B., "Geminivirus replication: genetic and biochemical characterization of Rep protein function, a review", *Biochimie* 77: 765-773 (1995).

Laufs, J., Schumacher, S., Geisler, N., Jupin, I., Gronenborn, B., "Identification of the nicking tyrosine of geminivirus Rep protein", *FEBS Lett* 377: 258-262 (1995).

Laufs, J., Traut, W., Heyraud, F., Matzeit, V., Rogers, S.G., Schell, J., Gronenborn, B., "In vitro cleavage and joining at the viral origin of replication by the replication initiator protein of tomato yellow leaf curl virus", *Proc Natl Acad Sci U.S.A*. 92: 3879-3883 (1995).

Lazarowitz, S.G., Wu, L.C., Rogers, S.G., Elmer, J.S., "Sequence-specific interaction with the viral AL1 protein identifies a geminivirus DNA replication origin", *Plant Cell* 4: 799-809 (1992).

Lea, D., Coulson, C., "The distribution of the numbers of mutants in bacterial populations", *J. Genet*. 49: 264-285 (1948).

(56) References Cited

OTHER PUBLICATIONS

Leanna, C.A., Hannink, M., "The reverse two-hybrid system: a genetic scheme for selection against specific protein/protein interactions", *Nucleic Acids Res* 24: 3341-3347 (1996).

Lebkowski, J.S., DuBridge, R.B., Antell, E.A., Greisen, K.S., Calos, M.P., "Transfected DNA is mutated in monkey, mouse, and human cells", *Mol Cell Biol* 4: 1951-1960 (1984).

Lee, E.C., Yu, D., Martinez, D.V., Tessarollo, L., Swing, D.A., Court, D.L., Jenkins, N.A., Copeland, N.G., "A highly efficient *Escherichia coli*-based chromosome engineering system adapted for recombinogenic targeting and subcloning of BAC DNA", *Genomics* 73: 56-65 (2001).

Lessl, M., Lanka, E., "Common mechanisms in bacterial conjugation and Ti-mediated T-DNA transfer to plant cells", *Cell* 77: 321-324 (1994).

Levin, "A novel mechanism of self-primed reverse transcription defines a new family of retroelements", *Mol Cell Biol*. 15(6):3310-3317 (1995).

Lewis, L.K., Resnick, M.A., "Tying up loose ends: nonhomologous end-joining in *Saccharomyces cerevisiae*", *Mutat. Res*. 451: 71-89 (2000).

Lim, D., Maas, W.K., "Reverse transcriptase-dependent synthesis of a covalently linked, branched DNA-RNA compound in *E. coli* B", *Cell* 56: 891-904 (1989).

Lin, F.L., Sperle, K., Sternberg, N., "Recombination in mouse L cells between DNA introduced into cells and homologous chromosomal sequences", *Proc Natl Acad Sci U.S.A*. 82: 1391-1395 (1985).

Lin, N.S., Pratt, D., "Role of bacteriophage M13 gene 2 in viral DNA replication", *J Mol Biol* 72: 37-49 (1972).

Lin, S., Kowalski, D., "DNA helical instability facilitates initiation at the SV40 replication origin", *J Mol Biol* 235: 496-507 (1994).

Link, A.J., Olson, M.V., "Physical map of the *Saccharomyces cerevisiae* genome at 110-kilobase resolution", *Genetics* 127: 681-698 (1991).

Liu, L., Saunders, K., Thomas, C.L., Davies, J.W., Stanley, J., "Bean yellow dwarf virus RepA, but not rep, binds to maize retinoblastoma protein, and the virus tolerates mutations in the consensus binding motif", *Virology* 256: 270-279 (1999).

Llosa, M., Bolland, S., de la, C.F., "Structural and functional analysis of the origin of conjugal transfer of the broad-host-range IncW plasmid R388 and comparison with the related IncN plasmid R46", *Mol Gen Genet* 226: 473-483 (1991).

Llosa, M., Grandoso, G., de la, C.F., "Nicking activity of TrwC directed against the origin of transfer of the IncW plasmid R388", *J Mol Biol* 246: 54-62 (1995).

Llosa, M., Grandoso, G., Hernando, M.A., de la, C.F., "Functional domains in protein TrwC of plasmid R388: dissected DNA strand transferase and DNA helicase activities reconstitute protein function", *J Mol Biol* 264: 56-67 (1996).

Ludlow, J.W., "Interactions between SV40 large-tumor antigen and the growth suppressor proteins pRB and p53", *FASEB J* 7: 866-871 (1993).

Maes, T., De Keukeleire, P., Gerats, T., "Plant tagnology", *Trends Plant Sci* 4: 90-96 (1999).

Mahillon, J., Chandler, M., "Insertion sequences", *Microbiol Mol Biol Rev* 62: 725-774 (1998).

Malik, K., Wu, K., Li, X.Q., Martin-Heller, T., Hu, M., Foster, E., Tian, L., Wang, C., Ward, K., Jordan, M., Brown, D., Gleddie, S., Simmonds, D., Zheng, S., Simmonds, J., Miki, B., "A constitutive gene expression system derived from the tCUP cryptic promoter elements", *Theor.Appl.Genet*. 105: 505-514 (2002).

Mandel, T., Fleming, A.J., Krahenbuhl, R., Kuhlemeier, C., "Definition of constitutive gene expression in plants: the translation initiation factor 4A gene as a model", *Plant Mol Biol* 29: 995-1004 (1995).

Mankertz, A., Mankertz, J., Wolf, K., Buhk, H.J., "Identification of a protein essential for replication of porcine circovirus", *J Gen Virol* 79: 381-384 (1998).

Mankertz, A., Persson, F., Mankertz, J., Blaess, G., Buhk, H.J., "Mapping and characterization of the origin of DNA replication of porcine circovirus", *J Virol* 71: 2562-2566 (1997).

Mao et al., "Gene Regulation by Antisense DNA Produced in vivo," *J. Biol. Chem*. 270(34):19684-19687 (Aug. 25, 1995).

Mao, J.R., Shimada, M., Inouye, S., Inouye, M., "Gene regulation by antisense DNA produced in vivo", *J.Biol.Chem*. 270: 19684-19687 (1995).

Marsischky, G.T., Filosi, N., Kane, M.F., Kolodner, R., "Redundancy of *Saccharomyces cerevisiae* MSH3 and MSH6 in MSH2-dependent mismatch repair", *Genes Dev*. 10: 407-420 (1996).

Martinez, A., Sparks, C., Hart, C.A., Thompson, J., Jepson, I., "Ecdysone agonist inducible transcription in transgenic tobacco plants", *Plant J*. 19: 97-106 (1999).

Masai, H., Arai, K., "Mechanisms of primer RNA synthesis and D-loop/R-loop-dependent DNA replication in *Escherichia coli*", *Biochimie* 78: 1109-1117 (1996).

Mathews, D.H., Sabina, J., Zuker, M., Turner, D.H., "Expanded sequence dependence of thermodynamic parameters improves prediction of RNA secondary structure", *J Mol.Biol*. 288: 911-940 (1999).

Matson, S.W., Morton, B.S., "*Escherichia coli* DNA helicase I catalyzes a", *J Biol Chem* 266: 16232-16237 (1991).

Matson, S.W., Nelson, W.C., Morton, B.S., "Characterization of the reaction product of the oriT nicking reaction catalyzed by *Escherichia coli* DNA helicase I", *J Bacteriol* 175: 2599-2606 (1993).

McDowell, J.M., An, Y.Q., Huang, S., McKinney, E.C., Meagher, R.B., "The *Arabidopsis* ACTT actin gene is expressed in rapidly developing tissues and responds to several external stimuli", *Plant Physiol* 111: 699-711 (1996).

Mead, D.A., Szczesna-Skorupa, E., Kemper, B., "Single-stranded DNA 'blue' T7 promoter plasmids: a versatile tandem promoter system for cloning and protein engineering", *Protein Eng* 1: 67-74 (1986).

Meehan, B.M., Creelan, J.L., McNulty, M.S., Todd, D., "Sequence of porcine circovirus DNA: affinities with plant circoviruses", *J Gen Virol* 78: 221-227 (1997).

Merrill, G.F., "Cell synchronization", *Methods Cell Biol* 57: 229-249 (1998).

Messing, J., Crea, R., Seeburg, P.H., "A system for shotgun DNA sequencing", *Nucleic Acids Res* 9: 309-321 (1981).

Mett, V.L., Lochhead, L.P., Reynolds, P.H., "Copper-controllable gene expression system for whole plants", *Proc. Natl. Acad. Sci. U.S.A* 90: 4567-4571 (1993).

Mett, V.L., Podivinsky, E., Tennant, A.M., Lochhead, L.P., Jones, W.T., Reynolds, P.H., "A system for tissue-specific copper-controllable gene expression in transgenic plants: nodule-specific antisense of aspartate aminotransferase-P2", *Transgenic Res*. 5: 105-113 (1996).

Meyer, P., Saedler, H., "Homology-dependent gene silencing in plants", *Annu. Rev. Plant Physiol. Plant Mol. Biol*. 47: 23-48. 1996.

Meyer, T.F., Geider, K., "Enzymatic synthesis of bacteriophage fd viral DNA", *Nature* 296: 828-832 (1982).

Meyer, T.F., Geider, K., "Cloning of bacteriophage fd gene 2 and construction of a plasmid dependent on fd gene 2 protein", *Proc Natl Acad Sci U.S.A*. 78: 5416-5420 (1981).

Miao, Z.H., Lam, E., "Targeted disruption of the TGA3 locus in *Arabidopsis thaliana*", *Plant J*. 7: 359-365 (1995).

Michel, B., "Replication fork arrest and DNA recombination", *Trends Biochem Sci* 25: 173-178 (2000).

Miki and Iyer, "Fundamentals of Gene Transfer in Plants", In: *Plant Metabolism*, 2d Ed. D.T. Dennis, D.H. Turpin, D.D. Lefebrve, D.B. Layzell (eds), Addison Wesly, Langmans Ltd. London, pp. 561-579 (1997).

Milne, G.T., Weaver, D.T., "Dominant negative alleles of RAD52 reveal a DNA repair/recombination complex including Rad51 and Rad52", *Genes Dev*. 7: 1755-1765 (1993).

Mirochnitchenko et al., "Production of Single-stranded DNA in Mammalian Cells by Means of a Bacterial Retron," *J. Biol. Chem*. 269(4):2380-2383 (Jan. 28, 1994).

Mirochnitchenko, O., Inouye, S., Inouye, M., "Production of single-stranded DNA in mammalian cells by means of a bacterial retron", *J.Biol.Chem*. 269: 2380-2383 (1994).

(56) References Cited

OTHER PUBLICATIONS

Miyata et al., "In vivo production of a stable single-stranded cDNA in *Saccharomyces cerevisiae* by means of bacterial retron," *Proc. Natl. Acad. Sci. USA* 89:5735-5739 (Jul. 1992).

Miyata, S., Ohshima, A., Inouye, S., Inouye, M., "In vivo production of a stable single-stranded cDNA in *Saccharomyces cerevisiae* by means of a bacterial retron", *Proc. Natl. Acad. Sci.U.S.A* 89: 5735-5739 (1992).

Mlynarova, L., Keizer, L.C.P., Stiekema, W.J., Nap, J.P., "Approaching the lower limits of transgene variability", *Plant Cell* 8: 1589-1599 (1996).

Model, P., Russel, M., "Filamentous Bacteriophage", In: Calendar, R. (ed), *The Bacteriophages*, pp. 375-456, Plenum Press, New York (1988).

Mol, J.N., van der Krol, A.R., van Tunen, A.J., van Blokland, R., de Lange, P., Stuitje, A.R., "Regulation of plant gene expression by antisense RNA", *FEBS Lett* 268: 427-430 (1990).

Moncalian, G., Cabezon, E., Alkorta, I., Valle, M., Moro, F., Valpuesta, J.M., Goni, F.M., de la, C.F., "Characterization of ATP and DNA binding activities of TrwB, the coupling protein essential in plasmid R388 conjugation", *J Biol Chem* 274: 36117-36124 (1999).

Moncalian, G., Grandoso, G., Llosa, M., de la, C.F., "oriT-processing and regulatory roles of TrwA protein in plasmid R388 conjugation", *J Mol Biol* 270: 188-200 (1997).

Moore, I., Galweiler, L., Grosskopf, D., Schell, J., Palme, K., "A transcription activation system for regulated gene expression in transgenic plants", *Proc. Natl. Acad. Sci. U.S.A*. 95: 376-381 (1998).

Moran, E., "Mammalian cell growth controls reflected through protein interactions with the adenovirus E1A gene products", *Semin. Virol*. 5: 327-340 (1994).

Morel-Deville, F., Ehrlich, S.D., "Theta-type DNA replication stimulates homologous recombination in the *Bacillus subtilis* chromosome", *Mol Microbiol* 19: 587-598 (1996).

Muris, D.F., Bezzubova, O., Buerstedde, J.M., Vreeken, K., Balajee, A.S., Osgood, C.J., Troelstra, C., Hoeijmakers, J.H., Ostermann, K., Schmidt, H., "Cloning of human and mouse genes homologous to RAD52, a yeast gene involved in DNA repair and recombination", *Mutat.Res*. 315: 295-305 (1994).

Murphy, C.G., Malamy, M.H., "Characterization of a "mobilization cassette" in transposon Tn4399 from *Bacteroides fragilis*", *J Bacteriol* 175: 5814-5823 (1993).

Murphy, C.G., Malamy, M.H., "Requirements for strand- and sitespecific cleavage within oriT region of Tn4399, a mobilizing transposon from *Bacteroides fragilis*", *J Bacteriol* 177: 3158-3165 (1995).

Murray, R.W., Koepsel, R.R., Khan, S.A., "Synthesis of single-stranded plasmid pT181 DNA in vitro. Initiation and termination of DNA replication", *J Biol Chem* 264: 1051-1057 (1989).

Muyrers, J.P., Zhang, Y., Buchholz, F., Stewart, A.F., "RecE/RecT and Redalpha/Redbeta initiate double-stranded break repair by specifically interacting with their respective partners", *Genes Dev*. 14: 1971-1982 (2000).

Natale, D.A., Schubert, A.E., Kowalski, D., "DNA helical stability accounts for mutational defects in a yeast replication origin", *Proc Natl Acad Sci U.S.A*. 89: 2654-2658 (1992).

Natale, D.A., Umek, R.M., Kowalski, D., "Ease of DNA unwinding is a conserved property of yeast replication origins", *Nucleic Acids Res* 21: 555-560 (1993).

Navot, N., Pichersky, E., Zeidan, M., Zamir, D., Czosnek, H., "Tomato yellow leaf curl virus: a whitefly-transmitted geminivirus with a single genomic component", *Virology* 185: 151-161 (1991).

Needleman and Wunsch, "A general method applicable to the search for similarities in the amino acid sequence of two proteins," *J. Mol. Biol*. 48:443 (1970).

Negritto, M.T., Wu, X., Kuo, T., Chu, S., Bailis, A.M., "Influence of DNA sequence identity on efficiency of targeted gene replacement", *Mol Cell Biol* 17: 278-286 (1997).

Nelson, M., Silver, P., "Context affects nuclear protein localization in *Saccharomyces cerevisiae*", *Mol. Cell Biol*. 9: 384-389 (1989).

New England Biolabs: Cleavage of single-stranded DNA, New England Biolabs 1988/99 Catalogue, p. 262.

Nicolas, A.L., Munz, P.L., Falck-Pedersen, E., Young, C.S., "Creation and repair of specific DNA double-strand breaks in vivo following infection with adenovirus vectors expressing *Saccharomyces cerevisiae* HO endonuclease", *Virology* 266: 211-224 (2000).

Nishikawa, M., Suzuki, K., Yoshida, K., "Structural and functional stability of IncP plasmids during stepwise transmission by trans-kingdom mating: promiscuous conjugation of *Escherichia coli* and *Saccharomyces cerevisiae*", *Jpn. J Genet* 65: 323-334 (1990).

Noirot-Gros, M.F., Bidnenko, V., Ehrlich, S.D., "Active site of the replication protein of the rolling circle plasmid pC194", *EMBO J* 13: 4412-4420 (1994).

Norgren, M., Caparon, M.G., Scott, J.R., "A method for allelic replacement that uses the conjugative transposon Tn916: deletion of the emm6.1 allele in *Streptococcus pyogenes* JRS4", *Infect. Immun*. 57: 3846-3850 (1989).

Novick, R.P., "Contrasting lifestyles of rolling-circle phages and plasmids", *Trends Biochem Sci* 23: 434-438 (1998).

Nuesch, J.P., Cotmore, S.F., Tattersall, P., "Sequence motifs in the replicator protein of parvovirus MVM essential for nicking and covalent attachment to the viral origin: identification of the linking tyrosine", *Virology* 209: 122-135.

Ochman, H., Selander, R.K., "Standard reference strains of *Escherichia coli* from natural populations", *J. Bacteriol*. 157: 690-693 (1984).

Odell, J.T., Nagy, F., Chua, N.H., "Identification of DNA sequences required for activity of the cauliflower mosaic virus 35S promoter", *Nature* 313: 810-812 (1985).

Offringa, R., De Groot, M.J., Haagsman, H.J., Does, M.P., van den Elzen, P.J., Hooykaas, P.J., "Extrachromosomal homologous recombination and gene targeting in plant cells after *Agrobacterium* mediated transformation", *EMBO J*. 9: 3077-3084 (1990).

Offringa, R., Franke-van Dijk, M.E., De Groot, M.J., van den Elzen, P.J., Hooykaas, P.J., "Nonreciprocal homologous recombination between *Agrobacterium* transferred DNA and a plant chromosomal locus", *Proc. Natl. Acad. Sci. U.S.A*. 90: 7346-7350 (1993).

Orozco, B.M., Hanley-Bowdoin, L., "Conserved sequence and structural motifs contribute to the DNA binding and cleavage activities of a geminivirus replication protein", *J Biol Chem* 273: 24448-24456 (1998).

Orozco, B.M., Kong, L.J., Batts, L.A., Elledge, S., Hanley-Bowdoin, L., "The multifunctional character of a geminivirus replication protein is reflected by its complex oligomerization properties", *J Biol Chem* 275: 6114-6122 (2000).

Orozco, B.M., Miller, A.B., Settlage, S.B., Hanley-Bowdoin, L., "Functional domains of a geminivirus replication protein", *J Biol Chem* 272: 9840-9846 (1997).

Orr-Weaver, T.L., Szostak, J.W., Rothstein, R.J., "Yeast transformation: a model system for the study of recombination", *Proc Natl Acad Sci U.S.A*. 78: 6354-6358 (1981).

Osley, M.A., "The regulation of histone synthesis in the cell cycle", *Annu.Rev Biochem* 60: 827-861 (1991).

Pansegrau, W., Lanka, E., "Enzymology of DNA transfer by conjugative mechanisms", *Progress in Nucleic Acid Research and Molecular Biology* 54: 197-251. (1996).

Pansegrau, W., Lanka, E., "Mechanisms of initiation and termination reactions in conjugative DNA processing. Independence of tight substrate binding and catalytic activity of relaxase (TraI) of IncPalpha plasmid RP4", *J Biol Chem* 271: 13068-13076 (1996).

Pansegrau, W., Ziegelin, G., Lanka, E., "Covalent association of the traI gene product of plasmid RP4 with the 5'-terminal nucleotide at the relaxation nick site", *J Biol Chem* 265: 10637-10644 (1990).

Paques, F., Haber, J.E., "Multiple pathways of recombination induced by double-strand breaks in *Saccharomyces cerevisiae*", *Microbiol. Mol. Biol. Rev*. 63: 349-404 (1999).

Peach, C., Velten, J., "Transgene expression variability (position effect) of CAT and GUS reporter genes driven by linked divergent T-DNA promoters", *Plant Mol Biol* 17: 49-60 (1991).

Pearson and Lipman, "Improved tools for biological sequence comparison," *Proc. Natl. Acad. Sci. USA* 85: 2444 (1988).

(56) References Cited

OTHER PUBLICATIONS

Perucho, M., Hanahan, D., Wigler, M., "Genetic and physical linkage of exogenous sequences in transformed cells", *Cell* 22: 309-317 (1980).
Pittman, D.L., Schimenti, J.C., "Recombination in the mammalian germ line", *Curr. Top. Dev. Biol* 37: 1-35 (1998).
Puchta, H., Dujon, B., Hohn, B., "Homologous recombination in plant cells is enhanced by in vivo induction of double strand breaks into DNA by a site-specific endonuclease", *Nucleic Acids Res* 21: 5034-5040 (1993).
Puchta, H., Hohn, B., "From centiMorgans to base pairs: homologous recombination in plants", *Trends in Plant Science* 1: 340-348 (1996).
Rajan, J.V., Wang, M., Marquis, S.T., Chodosh, L.A., "Brca2 is coordinately regulated with Brca1 during proliferation and differentiation in mammary epithelial cells", *Proc.Natl.Acad.Sci.U.S.A* 93: 13078-13083 (1996).
Rauth, S., Song, K.Y., Ayares, D., Wallace, L., Moore, P.D., Kucherlapati, R., "Transfection and homologous recombination involving single-stranded DNA substrates in mammalian cells and nuclear extracts", *Proc Natl Acad Sci U.S.A.* 83: 5587-5591 (1986).
Reichheld, J.P., Gigot, C., Chaubet-Gigot, N., "Multilevel regulation of histone gene expression during the cell cycle in tobacco cells", *Nucleic Acids Res* 26: 3255-3262 (1998).
Reinberg, D., Zipursky, S.L., Weisbeek, P., Brown, D., Hurwitz, J., "Studies on the phi X174 gene A protein-mediated termination of leading strand DNA synthesis", *J Biol Chem* 258: 529-537 (1983).
Relic, B., Andjelkovic, M., Rossi, L., Nagamine, Y., Hohn, B., "Interaction of the DNA modifying proteins VirD1 and VirD2 of *Agrobacterium tumefaciens*: analysis by subcellular localization in mammalian cells", *Proc Natl Acad Sci U.S.A.* 95: 9105-9110 (1998).
Rigden, J.E., Dry, I.B., Krake, L.R., Rezaian, M.A., "Plant virus DNA replication processes in *Agrobacterium*: insight into the origins of geminiviruses?", *Proc Natl Acad Sci U.S.A.* 93: 10280-10284 (1996).
Riou-Khamlichi, C., Menges, M., Healy, J.M., Murray, J.A., "Sugar control of the plant cell cycle: differential regulation of *Arabidopsis* D-type cyclin gene expression", *Mol Cell Biol* 20: 4513-4521 (2000).
Ritchie, B.W., Niagro, F.D., Lukert, P.D., Steffens, W.L., III, Latimer, K.S., "Characterization of a new virus from cockatoos with psittacine beak and feather disease", *Virology* 171: 83-88 (1989).
Robbins et al., "Two interdependent basic domains in nucleoplasmin nuclear targeting sequence: identification of class of biapartite nuclear targeting sequence," *Cell* 64: 615-623 (1991).
Roeder, GS, "Meiotic chromosomes: it takes two to tango," *Genes Dev.* 11: 2600-2621 (1997).
Roessler, E., Fenwick, R.G., Jr., Chinault, A.C., "Analysis of mobilization elements in plasmids from *Shigella flexneri*", *J Bacteriol* 161: 1233-1235 (1985).
Rogers, SG, Horsch, RB, Fraley, RT, "Gene Transfer in Plants: Production of Transformed Plants Using Ti Plasmid Vectors," *Methods for Plant of Molecular Biology*, Weissbach and Weissbach, Academy Press, New York VIII, pp. 421-463 (1988).
Rohde, W., Randles, J.W., Langridge, P., Hanold, D., "Nucleotide sequence of a circular single-stranded DNA associated with coconut foliar decay virus", *Virology* 176: 648-651 (1990).
Rong, Y.S., Golic, K.G., "Gene targeting by homologous recombination in *Drosophila*", *Science* 288: 2013-2018 (2000).
Rose, M., Winston, F., "Identification of a Ty insertion within the coding sequence of the *S. cerevisiae* URA3 gene," *Mol Gen Genet* 193: 557-560 (1984).
Ross-Macdonald, P., Roeder, G.S., "Mutation of a meiosis-specific MutS homolog decreases crossing over but not mismatch correction", *Cell* 79: 1069-1080 (1994).
Roth, D.B., Wilson, J.H., "Illegitimate recombination in mammalian cells", In: Kucherlapati, R. and Smith, G. (eds), *Genetic Rcombination*, p. 621, American Society for Microbiology, Washington, D.C. (1988).
Rothstein, R., "Targeting, disruption, replacement, and allele rescue: integrative DNA transformation in yeast", *Methods Enzymol.* 194: 281-301 (1991).

Rozwadowski, K., Kreiser, T., Hasnadka, R., Lydiate, D., "AtMRE11: a component of meiotic recombination and DNA repair in plants", 10th International Conference on *Arabidopsis* Research, Melbourne, Australia, Jul. 4-8, 1999.
Russell and Hirata, "Human gene targeting by viral vectors," *Nature Genetics* 28:325-330 (Apr. 1998).
Russell, D., Bennet, G., "Construction and analysis of in vivo activity of *E. coli* promoter hybrids and promoter mutants that alter the -35 to -10 spacing", *Gene* 20:. 231-243. (1982).
Salas, M., "Protein-priming of DNA replication", *Annu. Rev. Biochem.* 60:39-71 (1991).
Salter, M.G. et al, "Characterization of the ethanol-inducible *alc* gene expression system for transgenic plants," *Plant Journal* 16: 127-132 (1998).
Sandler, S.J., Marians, K.J., "Role of PriA in replication fork reactivation in *Escherichia coli*", *J Bacteriol* 182: 9-13 (2000).
Sanger, F., Air, G.M., Barren, B.G., Brown, N.L., Coulson, A.R., Fiddes, C.A., Hutchison, C.A., Slocombe, P.M., Smith, M., "Nucliotide sequence of bacteriophage phi X174 DNA", *Nature* 265: 687-695 (1977).
Sanz-Burgos, A.P., Gutierrez, C., "Organization of the cis-acting element required for wheat dwarf geminivirus DNA replication and visualization of a rep protein-DNA complex", *Virology* 243: 119-129 (1998).
Sathasivan, K., Haughn, G.W., Murai, N., "Nucleotide sequence of a mutant acetolactate synthase gene from an imidazolinone-resistant *Arabidopsis thaliana* var. Columbia", *Nucleic Acids Res* 18: 2188 (1990).
Schaefer, D.G., Zryd, J.P., "Efficient gene targeting in the moss *Physcomitrella patens*", *Plant J.* 11: 1195-1206 (1997).
Schalk, H.J., Matzeit, V., Schiller, B., Schell, J., Gronenborn, B., "Wheat dwarf virus, a geminivirus of graminaceous plants needs splicing for replication", *EMBO J* 8: 359-364 (1989).
Scherzinger, E., Kruft, V., Otto, S., "Purification of the large mobilization protein of plasmid RSF1010 and characterization of its site-specific DNA-cleaving/DNA-joining activity", *Eur J Biochem* 217: 929-938 (1993).
Scherzinger, E., Lurz, R., Otto, S., Dobrinski, B., "In vitro cleavage of do", *Nucleic Acids Res* 20: 41-48 (1992).
Scherzinger, E., Ziegelin, G., Barcena, M., Carazo, J.M., Lurz, R., Lanka, E., "The RepA protein of plasmid RSF1010 is a replicative DNA helicase", *J Biol Chem* 272: 30228-30236 (1997).
Schiestl, R.H., "Nonmutagenic carcinogens induce intrachromosomal recombination in yeast", *Nature* 337: 285-288 (1989).
Schneider, J.C., Guarente, L., "Vectors for expression of cloned genes in yeast: regulation, overproduction, and underproduction", *Methods Enzymol.* 194: 373-388 (1991).
Scholthof, H. et al., "Plant virus gene vectors for transient expression of foreign proteins in plants", *Annu. Rev. of Phytopathol.* 34: 299-323 (1996).
Scott, J.R., Churchward, G.G., "Conjugative transposition", *Annu. Rev Microbiol* 49: 367-397 (1995).
Scully, R., Puget, N., Vlasakova, K., "DNA polymerase stalling, sister chromatid recombination and the BRCA genes", *Oncogene* 19: 6176-6183 (2000).
Shavitt, O., Livneh, Z., "Rolling-circle replication of UV-irradiated duplex DNA in the phi X174 replicative-form—single-strand replication system in vitro", *J Bacteriol* 171: 3530-3538 (1989).
Shcherbakova, O.G., Lanzov, V.A., Ogawa, H., Filatov, M.V., "Overexpression of bacterial RecA protein stimulates homologous recombination in somatic mammalian cells", *Mutat.Res*. 459: 65-71 (2000).
Sherman, J.A., Matson, S.W., "*Escherichia coli* DNA helicase I catalyzes a sequence-specific cleavage/ligation reaction at the F plasmid origin of transfer", *J Biol Chem* 269: 26220-26226 (1994).
Shillito, R.D., Saul, M.W., Paszkowski, J., Muller, M., Potrykus, I., "High efficiency direct gene transfer to plants", *Bio/technology* 3: 1099 (1985).
Shinohara, A., Ogawa, H., Matsuda, Y., Ushio, N., Ikeo, K., Ogawa, T., "Cloning of human, mouse and fission yeast recombination genes homologous to RAD51 and recA [published erratum appears in Nat Genet Nov. 1993;5(3):312]", *Nat.Genet.* 4: 239-243 (1993).

(56) References Cited

OTHER PUBLICATIONS

Short, J.M., Fernandez, J.M., Sorge, J.A., Huse, W.D., "Lambda ZAP: a bacteriophage lambda expression vector with in vivo excision properties", *Nucleic Acids Res* 16: 7583-7600 (1988).

Simon, J.R., Moore, P.D., "Homologous recombination between single-stranded DNA and chromosomal genes in *Saccharomyces cerevisiae*", *Mol Cell Biochem* 7: 2329-2334 (1987).

Sims, J., Capon, D., Dressler, D., "dnaG (primase)-dependent origins of DNA replication. Nucleotide sequences of the negative strand initiation sites of bacteriophages St-1, phi K, and alpha 3", *J Biol Chem* 254: 12615-12628 (1979).

Smith and Waterman, "Comparison of Biosequences," *Adv. Appl. Math* 2: 482 (1981).

Smith, A.E., "Viral vectors in gene therapy", *Annu.Rev Microbiol* 49: 807-838 (1995).

Snijders, A., van Putten, A.J., Veltkamp, E., Nijkamp, H.J., "Localization and nucleotide sequence of the bom region of Clo DF13", *Mol Gen Genet* 192: 444-451 (1983).

Snyder, R.O., Im, D.S., Ni, T., Xiao, X., Samulski, R.J., Muzyczka, N., "Features of the adeno-associated virus origin involved in substrate recognition by the viral Rep protein", *J Virol* 67: 6096-6104 (1993).

Song, B., Sung, P., "Functional interactions among yeast Rad51 recombinase, Rad52 mediator, and replication protein A in DNA strand exchange", *J Biol. Chem*. 275: 15895-15904 (2000).

Soni, R., Carmichael, J.P., Shah, Z.H., Murray, J.A., "A family of cyclin D homologs from plants differentially controlled by growth regulators and containing the conserved retinoblastoma protein interaction motif", *Plant Cell* 7: 85-103 (1995).

Sozhamannan, S., Dabert, P., Moretto, V., Ehrlich, S.D., Gruss, A., "Plus-origin mapping of single-stranded DNA plasmid pE194 and nick site homologies with other plasmids", *J Bacteriol* 172: 4543-4548 (1990).

Stellwagen, A.E., Craig, N.L., "Mobile DNA elements: controlling transposition with ATP-dependent molecular switches", *Trends Biochem Sci* 23: 486-490 (1998).

Strathern, J.N., Weinstock, K.G., Higgins, D.R., McGill, C.B., "A novel recombinator in yeast based on gene II protein from bacteriophage f1", *Genetics* 127: 61-73 (1991).

Sun et al., "Association of a Retroelement with a P4-Like Cyptic Prophage (Retronphage (φR73) Integrated into the Selenocystyl tRNA Gene of *Escherichia coli*," *J. Bacteriol*. 173: 4171-4181 (1991).

Sung, P., "Yeast Rad55 and Rad57 proteins form a heterodimer that functions with replication protein A to promote DNA strand exchange by Rad51 recombinase", *Genes Dev*. 11: 1111-1121 (1997).

Symington, L.S., Fortin, G.S., "A novel class of rad51 alleles that partially bypass the requirement for the yeast Rad51 paralogs in DNA repair", Marians, K.J., Rothestein, R.J. eds. p. 110, Keystone Symposium on Molecular Mechanisms of DNA Replication and Recombination (Jan. 7, 2002).

Tamura, K., Adachi, Y., Chiba, K., Oguchi, K., Takahashi, H., "Identification of Ku70 and Ku80 homologues in *Arabidopsis thaliana*: evidence for a role in the repair of DNA double-strand breaks", *Plant J*. 29: 771-781 (2002).

Taubes, "The Strange Case of Chimeraplasty," *Science* 298:2116-2120 (Dec. 13, 2002).

Tavakoli, N., Comanducci, A., Dodd, H.M., Lett, M.C., Albiger, B., Bennett, P., "IS1294, a DNA element that transposes by RC transposition", *Plasmid* 44: 66-84 (2000).

Thomas, K.R., Capecchi, M.R., "Site-directed mutagenesis by gene targeting in mouse embryo-derived stem cells", *Cell* 51: 503-512 (1987).

Thomas, K.R., Folger, K.R., Capecchi, M.R., "High frequency targeting of genes to specific sites in the mammalian genome", *Cell* 44: 419-428 (1986).

Thompson, S., Clarke, A.R., Pow, A.M., Hooper, M.L., Melton, D.W., "Germ line transmission and expression of a corrected HPRT gene produced by gene targeting in embryonic stem cells", *Cell* 56: 313-321 (1989).

Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993).

Tinland, B., Koukolikova-Nicola, Z., Hall, M.N., Hohn, B., "The T-DNA-linked VirD2 protein contains two distinct functional nuclear localization signals", *Proc Natl Acad Sci U.S.A*. 89: 7442-7446 (1992).

Tishkoff, D.X., Johnson, A.W., Kolodner, R.D., "Molecular and genetic analysis of the gene encoding the *Saccharomyces cerevisiae* strand exchange protein Sep1", *Mol. Cell Biol*. 11: 2593-2608 (1991).

Todd, D., Creelan, J.L., Mackie, D.P., Rixon, F., McNulty, M.S., "Purification and biochemical characterization of chicken anaemia agent", *J Gen Virol* 71: 819-823 (1990).

Tsuzuki, T., Fujii, Y., Sakumi, K., Tominaga, Y., Nakao, K., Sekiguchi, M., Matsushiro, A., Yoshimura, Y., Morita, T., "Targeted disruption of the Rad51 gene leads to lethality in embryonic mice", *Proc. Natl. Acad. Sci. U.S.A* 93: 6236-6240 (1996).

Turlan, C., Chandler, M., "Playing second fiddle: second-strand processing and liberation of transposable elements from donor DNA", *Trends Microbiol* 8: 268-274 (2000).

Ulmasov, T. et al., "Aux/IAA Proteins Repress Expression of Reporter Genes Containing Natural and Highly Active Synthetic Auxin Response Elements," *Plant Cell* 9: 1963-1971 (1997).

van der Ende, E.A., Teertstra, R., Weisbeek, P.J., "Initiation and termination of the bacteriophage phi X174 rolling circle DNA replication in vivo: packaging of plasmid single-stranded DNA into bacteriophage phi X174 coats", *Nucleic Acids Res* 10: 6849-6863 (1982).

van der Krol, A.R., Chua, N.H., "The basic domain of plant B-ZIP proteins facilitates import of a reporter protein into plant nuclei", *Plant Cell* 3: 667-675 (1991).

van Mansfeld, A.D., Baas, P.D., Jansz, H.S., "Gene A protein of bacteriophage phi X174 is a highly specific single-strand nuclease and binds via a tyrosyl residue to DNA after cleavage", *Adv Exp Med Biol* 179: 221-230 (1984).

van Mansfeld, A.D., van Teeffelen, H.A., Baas, P.D., Jansz, H.S., "Two juxtaposed tyrosyl-OH groups participate in phi X174 gene A protein catalysed cleavage and ligation of DNA", *Nucleic Acids Res* 14: 4229-4238 (1986).

van Mansfeld, A.D., van Teeffelen, H.A., Baas, P.D., Veeneman, G.H., Van Boom, J.H., Jansz, H.S., "The bond in the bacteriophage phi X174 gene A protein—DNA complex is a tyrosyl-5'-phosphate ester", *FEBS Lett* 173: 351-356 (1984).

Varagona et al., "Nuclear Localization Signal(s) Required for Nuclear Targeting of the Maize Regulatory Protein Opaque-2," *Plant Cell* 4: 1213-1227 (1992).

von Arnim, A.G., Deng, X.W., Stacey, M.G., "Cloning vectors for the expression of green fluorescent protein fusion proteins in transgenic plants", *Gene* 221: 35-43 (1998).

Voth, W.P., Richards, J.D., Shaw, J.M., Stillman, D.J., "Yeast vectors for integration at the HO locus", *Nucleic Acids Res* 29: E59-E59 (2001).

Vousden, K., "Interactions of human papillomavirus transforming proteins with the products of tumor suppressor genes", *FASEB J* 7: 872-879 (1993).

Wake, C.T., Gudewicz, T., Porter, T., White, A., Wilson, J.H., "How damaged is the biologically active subpopulation of transfected DNA?", *Mol Cell Biol* 4: 387-398 (1984).

Weinmann, P., Gossen, M., Hillen, W., Bujard, H., Gatz, C., "A chimeric transactivator allows tetracycline-responsive gene expression in whole plants", *Plant J*. 5: 559-569 (1994).

Whiteley, M., Kassis, J.A., "Rescue of *Drosophila* engrailed mutants with a highly divergent mosquito engrailed cDNA using a homing, enhancer-trapping transposon", *Development* 124: 1531-1541 (1997).

(56) References Cited

OTHER PUBLICATIONS

Wilmut, I., Schnieke, A.E., McWhir, J., Kind, A.J., Campbell, K.H., "Viable offspring derived from fetal and adult mammalian cells", *Nature* 385: 810-813 (1997).

Winzeler, E.A., Shoemaker, D.D., Astromoff, A., Liang, H., Anderson, K., Andre, B., Bangham, R., Benito, R., Boeke, J.D., Bussey, H., Chu, A.M., Connelly, C., Davis, K., Dietrich, F., Dow, S.W., El Bakkoury, M., Foury, F., Friend, S.H., Gentalen, E., Giaever, G., Hegemann, J.H., Jones, T., Laub, M., Liao, H., Davis, R.W., "Functional characterization of the S. cerevisiae genome by gene deletion and parallel analysis", *Science* 285: 901-906 (1999).

Wohlleben, W., Arnold, W., Broer, I., Hillemann, D., Strauch, E., Puhler, A., "Nucleotide sequence of the phosphinothricin N-acetyltransferase gene from *Streptomyces viridochromogenes* Tu494 and its expression in *Nicotiana tabacum*", *Gene* 70: 25-37 (1988).

Wold, M.S., "Replication protein A: a heterotrimeric, single-stranded DNA-binding protein required for eukaryotic DNA metabolism", *Annu. Rev. Biochem.* 66: 61-92 (1997).

Wong, E.A., Capecchi, M.R., "Homologous recombination between coinjected DNA sequences peaks in early to mid-S phase", *Mol Cell Biol* 7: 2294-2295 (1987).

Woolston, C.J., Barker, R., Gunn, H., Boulton, M.I., Mullineaux, P.M., "Agroinfection and nucleotide sequence of cloned wheat dwarf virus DNA", *Plant Mol. Biol.* 11: 35-43 (1988).

Wu, K., Malik, K., Tian, L., Hu, M., Martin, T., Foster, E., Brown, D/, Miki, B., "Enhancers and core promoter elements are essential for the activity of a cryptic gene activation sequence from tobacco, tCUP", *Mol Genet Genomics* 265: 763-770 (2001).

Xiang, C., Han, P., Lutziger, I., Wang, K., Oliver, D.J., "A mini binary vector series for plant transformation", *Plant Mol Biol* 40: 711-717 (1999).

Yamamoto, A., Taki, T., Yagi, H., Habu, T., Yoshida, K., Yoshimura, Y., Yamamoto, K., Matsushiro, A., Nishimune, Y., Morita, T., "Cell cycle-dependent expression of the mouse Rad51 gene in proliferating cells", , *Mol. Gen. Genet.* 251: 1-12 (1996).

Yanez, R.J., Porter, A.C., "Gene targeting is enhanced in human cells overexpressing hRAD51". *Gene Ther.* 6: 1282-1290 (1999).

Yang, X., McFadden, B.A., "A small plasmid, pCA2.4, from the cyanobacterium *Synechocystis* sp. strain *PCC 6803* encodes a rep protein and replicates by a rolling circle mechanism", *J Bacteriol* 175: 3981-3991 (1993).

Yang, X.W., Model, P., Heintz, N., "Homologous recombination based modification in *Escherichia coli* and germline transmission in transgenic mice of a bacterial artificial chromosome", *Nat. Biotechnol.* 15: 859-865 (1997).

Yanisch-Perron, C., Vieira, J., Messing, J., "Improved M13 phage cloning vectors and host strains: nucleotide sequences of the M13mp18 and pUC19 vectors", *Gene* 33: 103-119 (1985).

Yanovsky et al., The protein encoded by the *Arabidopsis* homeotic gene Agamous resembles transcription factors, *Nature* 346: 35-39 (1990).

Yasukawa, H., Hase, T., Sakai, A., Masamune, Y., "Rolling-circle replication of the plasmid pKYM isolated from a gram-negative bacterium", *Proc Natl Acad Sci U.S.A.* 88: 10282-10286 (1991).

Yasukawa, H., Masamune, Y., "Rolling-circle plasmid pKYM re-initiates DNA replication", *DNA Res* 4: 193-197 (1997).

Yeom, Y.I., Abe, K., Bennett, D., Artzt, K., "Testis-/embryo-expressed genes are clustered in the mouse H-2K region", *Proc Natl Acad Sci U.S.A.* 89: 773-777 (1992).

Yoon, K., Cole-Strauss, A., Kmiec, E.B., "Targeted gene correction of episomal DNA in mammalian cells mediated by a chimeric RNA. DNA oligonucleotide", *Proc.Natl.Acad.Sci. U.S.A.* 93: 2071-2076 (1996).

Yoshida, K., Takegami, T., Katoh, A., Nishikawa, M., Nishida, T., "Construction of a novel conjugative plasmid harboring a GFP reporter gene and its introduction into animal cells by transfection and trans-kingdom conjugation", *Nucleic Acids Symp Ser.* 157-158 (1997).

Yoshimatsu, T., Nagawa, F., "Control of gene expression by artificial introns in *Saccharomyces cerevisiae*", *Science* 244: 1346-1348 (1989).

Zhang, W., McElroy, D., Wu, R., "Analysis of rice Act1 5' region activity in transgenic rice plants", *Plant Cell* 3: 1155-1165 (1991).

Zhu, T., Mettenburg, K., Peterson, D.J., Tagliani, L., Baszczynski, C.L., "Engineering herbicide-resistant maize using chimeric RNA/DNA oligonucleotides", *Nat.Biotechnol.* 18: 555-558 (2000).

Zhu, T., Peterson, D.J., Tagliani, L., St. Clair, G., Baszczynski, C.L., Bowen, B., "Targeted manipulation of maize genes in vivo using chimeric RNA/DNA oligonucleotides", *Proc. Natl. Acad. Sci. U.S.A.* 96: 8768-8773 (1999).

Ziegelin, G., Lanka, E., "Bacteriophage P4 DNA replication", *FEMS Microbiol. Rev.* 17: 99-107 (1995).

Ziegelin, G., Pansegrau, W., Lurz, R., Lanka, E., "TraK protein of conjugative plasmid RP4 forms a specialized nucleoprotein complex with the transfer origin", *J Biol Chem* 267: 17279-17286 (1992).

European Communication dated Dec. 17, 2010, issued in European Patent Application No. 03727104.6, 4 pages.

\* cited by examiner

Part 1

WT

Part 2

Stem 3

Part 1

Stem 3

Part 2

Stem 3+50

Part 3

Stem 3+500

SEQUENCE LISTING

```
<160> NUMBER OF SEQ ID NOS: 9

<210> SEQ ID NO 1
<211> LENGTH: 1023
<212> TYPE: DNA
<213> ORGANISM: Artificial Sequence
<220> FEATURE:
```

<223> OTHER INFORMATION: NLS-RT Sequence

<400> SEQUENCE: 1

| | |
|---|---|
| ggatccaaaa aaatggctcc taagaagaag agaaaggttg gaggaggacc cgggaagtcc | 60 |
| gctgaatatt tgaacacttt tagattgaga aatctcggcc tacctgtcat gaacaatttg | 120 |
| catgacatgt ctaaggcgac tcgcatatct gttgaaacac ttcggttgtt aatctataca | 180 |
| gctgattttc gctataggat ctacactgta gaaaagaaag gcccagagaa gagaatgaga | 240 |
| accatttacc aaccttctcg agaacttaaa gccttacaag gatgggttct acgtaacatt | 300 |
| ttagataaac tgtcgtcatc tccttttttct attggatttg aaaagcacca atctattttg | 360 |
| aataatgcta ccccgcatat tggggcaaac tttatactga atattgattt ggaggatttt | 420 |
| ttcccaagtt taactgctaa caaagttttt ggagtgttcc attctcttgg ttataatcga | 480 |
| ctaatatctt cagttttgac aaaaatatgt tgttataaaa atctgctacc acaaggtgct | 540 |
| ccatcatcac ctaaattagc taatctaata tgttctaaac ttgattatcg tattcagggt | 600 |
| tatgcaggta gtcgggcctt gatatatacg agatatgccg atgatctcac cttatctgca | 660 |
| cagtctatga aaaaggttgt taaagcacgt gattttttat tttctataat cccaagtgaa | 720 |
| ggattggtta ttaactcaaa aaaaacttgt attagtgggc ctcgtagtca gaggaaagtt | 780 |
| acaggtttag ttatttcaca agagaaagtt gggataggta gagaaaaata taagaaatt | 840 |
| agagcaaaga tacatcatat attttgcggt aagtcttctg agatagaaca cgttagggga | 900 |
| tggttgtcat ttattttaag tgtggattca aaaagccata ggagattaat aacttatatt | 960 |
| agcaaattag aaaaaaaata tggaaagaac cctttaaata aagcgaagac ctaataactg | 1020 |
| cag | 1023 |

<210> SEQ ID NO 2
<211> LENGTH: 1106
<212> TYPE: DNA
<213> ORGANISM: Artificial Sequence
<220> FEATURE:
<223> OTHER INFORMATION: Resynthesized Version of NLS-RT

<400> SEQUENCE: 2

| | |
|---|---|
| ggatccaaaa caatggctcc taagaagaag aggaaggttg gagccggcgg agattacaag | 60 |
| gatgatgatg ataagggagt taacggagga ggtggaggag gtggaggtgg aggcgccaag | 120 |
| tctgctgagt acctcaacac cttcaggctc aggaacctcg actccctgt tatgaacaac | 180 |
| ctccacgata tgtctaaggc taccaggatc tctgttgaga ccctcaggct cctcatctac | 240 |
| accgctgatt tcaggtacag gatctacacc gttgagaaga agggacctga aagaggatg | 300 |
| aggaccatct accaaccttc tagggaactt aaggctctcc aaggatgggt tctcaggaac | 360 |
| atcctcgata agctctcttc ttctcctttc tctatcggat tcgagaagca ccaatctatc | 420 |
| ctcaacaacg ctaccccctca catcggagct aacttcatcc tcaacatcga tcttgaagat | 480 |
| ttcttccctt ctctcaccgc taacaaggtt ttcggagttt tccactctct cggatacaac | 540 |
| aggctcatct cttctgttct caccaagatc tgctgctaca gaacctcct ccctcaaggt | 600 |
| gctccttctt ctcctaagct cgctaacctc atctgctcta agctcgatta cagaattcaa | 660 |
| ggatacgctg gatctagggg actcatctac accaggtacg ctgatgatct caccctctct | 720 |
| gctcaatcta tgaagaaggt tgttaaggct gggatttcc tcttctctat catcccttct | 780 |
| gagggactcg ttatcaactc taagaagacc tgcatctctg acctaggtc tcaaaggaag | 840 |
| gttaccggac tcgttatctc tcaagagaag gttggaatcg aagggagaa gtacaaggag | 900 |

```
atcagggcta agatccacca catcttctgc ggaaagtctt ctgagatcga gcacgttagg    960
ggatggctct ctttcatcct ctctgttgat tctaagtctc acaggaggct catcacctac   1020
atctctaagc ttgaaaagaa gtacggaaag aaccctctca acaaggctaa gacctaatga   1080
gcggccgcac tagtgatatc tctaga                                        1106

<210> SEQ ID NO 3
<211> LENGTH: 237
<212> TYPE: DNA
<213> ORGANISM: Artificial Sequence
<220> FEATURE:
<223> OTHER INFORMATION: STEM3 Sequence

<400> SEQUENCE: 3 ggatccccccg ggcgccagca gtggctgcgc acccttagcg agaggtttat cattaaggtc    60
aacctctgga tgttgtttcg gcatcctgca ttgaatctga gttactgtct gttttccttg   120
ttggaacgga gagcatcgtc tagacaacga tatctgatgc tctccgagcc aaccaggaaa   180 cccgttttttt ctgacgtaag ggtgcgcagc cgctgttggc gtggccaatg cggccgc     237

<210> SEQ ID NO 4
<211> LENGTH: 268
<212> TYPE: DNA
<213> ORGANISM: Artificial Sequence
<220> FEATURE:
<223> OTHER INFORMATION: STOP-stem Sequence

<400> SEQUENCE: 4 ggatccccccg ggcgccagca gtggctgcgc acccttagcg agaggtttat cattaaggtc    60
aacctctgga tgttgtttcg gcatcctgca ttgaatctga gttactgtct gttttccttg   120
ttggaacgga gagcatcgtc tagaggatcc gggtcgctcg ctgcgtcgct gcggaattcg   180
atatctgatg ctctccgagc caaccaggaa accgttttt tctgacgtaa gggtgcgcag   240
ccgctgttgg cgtggccaat gcggccgc                                      268

<210> SEQ ID NO 5
<211> LENGTH: 221
<212> TYPE: DNA
<213> ORGANISM: Artificial Sequence
<220> FEATURE:
<223> OTHER INFORMATION: 3'-recruitment Sequence

<400> SEQUENCE: 5
tctagacccg gggatgctct ccgagccaac caggaaaccc gttttttctg acgtaagggt    60
gcgcagccac tgctggcgaa ttcgccagca gtggctgcgc acccttagcg agaggtttat   120
cattaaggtc aacctctgga tgttgtttcg gcatcctgca ttgaatctga gttactgtct   180
gttttccttg ttggaacgga gagcatcgcg gccgcctgca g                       221

<210> SEQ ID NO 6
<211> LENGTH: 54
<212> TYPE: DNA
<213> ORGANISM: Artificial Sequence
<220> FEATURE:
<223> OTHER INFORMATION: Cloned NLS Sequence

<400> SEQUENCE: 6
ggatccaaaa aaatggctcc taagaagaag agaaaggttg gaggaggacc cggg           54

<210> SEQ ID NO 7
```

```
<211> LENGTH: 169
<212> TYPE: DNA
<213> ORGANISM: Artificial Sequence
<220> FEATURE:
<223> OTHER INFORMATION: WT STEM3 Sequence

<400> SEQUENCE: 7
tgcgcaccct tagcgagagg tttatcatta aggtcaacct ctggatgttg tttcggcatc      60
ctgcattgaa tctgagttac tgtctgtttt ccttgttgga acggagagca tcgcctgatg     120
ctctccgagc caaccaggaa acccgttttt tctgacgtaa gggtgcgca                 169

<210> SEQ ID NO 8
<211> LENGTH: 207
<212> TYPE: DNA
<213> ORGANISM: Artificial Sequence
<220> FEATURE:
<223> OTHER INFORMATION: STEM3 Sequence

<400> SEQUENCE: 8
cgccagcagt ggctgcgcac ccttagcgag aggtttatca ttaaggtcaa cctctggatg      60
ttgtttcggc atcctgcatt gaatctgagt tactgtctgt tttccttgtt ggaacggaga     120
gcatcgtcta daccgatatc tgatgctctc cgagccaacc aggaaacccg ttttttctga     180
cgtaagggtg cgcagccgct gttggcg                                         207

<210> SEQ ID NO 9
<211> LENGTH: 256
<212> TYPE: DNA
<213> ORGANISM: Artificial Sequence
<220> FEATURE:
<223> OTHER INFORMATION: STEM3 Sequence + 50

<400> SEQUENCE: 9
cgccagcagt ggctgcgcac ccttagcgag aggtttatca ttaaggtcaa cctctggatg      60
ttgtttcggc atcctgcatt gaatctgagt tactgtctgt tttccttgtt ggaacggaga     120
gcatcgtcta gaacctgcag gaaacgatga taaatcatgt cgaaagctac atataaggaa     180
cgtgatatct gatgctctcc gagccaacca ggaaacccgt ttttctgac gtaagggtgc      240 gcagccgctg ttggcg                                                     256
```

RETRONS FOR GENE TARGETING

CROSS REFERENCE TO RELATED APPLICATIONS

This is a continuation of application Ser. No. 10/516,779, filed Jun. 29, 2005 now abandoned, which is the U.S. National Stage of International Application No. PCT/CA2003/000850, filed Jun. 5, 2003, which in turn claims the benefit of U.S. Provisional Application No. 60/386,640, filed Jun. 5, 2002. Each of these applications is incorporated herein in its entirety.

FIELD OF THE INVENTION

The present invention relates to nucleic acid constructs and manipulations that may be used for in vivo gene modification. More specifically the present invention relates to systems for producing gene targeting substrates using reverse transcriptase, as well as methods for promoting in vivo gene modification using such gene targeting substrates.

BACKGROUND OF THE INVENTION

Gene targeting generally refers to the directed alteration of a specific DNA sequence in its genomic locus in vivo. This may involve the transfer of genetic information from a nucleic acid molecule, which may be referred to as a gene targeting substrate, to a specific target locus in the host cell genome. In current methods, the gene targeting substrate usually exists as an extrachromosomal nucleic acid molecule. The target locus may be present in the host cell's nuclear chromosomes or organellar chromosomes (e.g. mitochondria or plastids) or a cellular episome. The gene targeting substrate typically encodes sequences homologous to the target locus. However, the sequence of the gene targeting substrate is modified to encode changed genetic information, vis-a-vis the target genetic locus, through the insertion or deletion of one or more base pairs or by the substitution of one or more bases for other types of bases. As a result, the gene targeting substrate may encode, for example, a different gene product than the target locus or a nucleic acid sequence which is non-functional or that functions differently than the nucleic acid sequence encoded by the target locus.

The process of gene targeting may involve the action of host nucleic acid recombination and repair functions. The homology between the target locus and the gene targeting substrate, in combination with host cell functions, is thought to facilitate the process of the gene targeting substrate "scanning" the host genome to find and associate with the target locus. Host nucleic acid recombination and repair functions may then act to transfer genetic information from the gene targeting substrate to the target locus by the processes of homologous recombination or gene conversion. In this manner, the novel sequence of the gene targeting substrate is transferred into the host genome at the targeted locus, which may result in loss of the wild-type genetic information at this locus. The modified target locus may now be stably inherited through cell divisions and, if present in germ cells and gametes, to subsequent progeny resulting from sexual reproduction.

This ability to perform precise genetic modifications of a host cell's genome at defined loci is an extremely powerful technology for basic and applied biological research. A principal advantage of gene targeting over conventional transformation technologies, which results in integration of the exogenously supplied DNA cassettes at random sites in the host genome is the maintenance of appropriate chromosomal context for the modified gene. In contrast, transformational integration of DNA cassettes into random sites of the host genome can have large negative effects on the host cell by causing insertional inactivation of the resident gene where the DNA cassette integrates, for example. In addition, integration at random sites can affect expression of the introduced gene encoded by a cassette. Such 'position effects' may result from epigenetic control of gene expression relating to the regulation of chromatin conformation (Mlynarova, L, et al., 1996, Plant Cell 8, pp. 1589-1599). Thus transgenes which integrate at random sites in the genome may not be expressed in the correct fashion to accurately reflect the biological effect of the gene under basic study, or provide the desired phenotype in a biotechnology application. Targeting of a transgene to its correct native site in the host genome may help to ensure correct epigenetic regulation of its expression.

Gene targeting may enable the accurate analysis of the phenotypic effects of modified genes by simultaneously replacing the endogenous gene copy. In contrast, placement of a transgene encoding a modified version of an endogenous gene at random sites in the genome may not enable accurate analysis of the effect of this transgene because the endogenous gene copy is still functioning. Expression of the endogenous gene copy may compensate for or impair the action of the gene product encoded by the transgene. Through gene targeting, the endogenous gene copy may be replaced by the introduced modified gene. As a result, the endogenous gene copy will not be able to interfere with the action of the introduced modified gene and an accurate interpretation of the biological effects of the modified gene may be possible. This ability is important for accurate assessment of gene function in basic studies, and is important for biotechnology applications aimed at modifying the physiological, biochemical or developmental paths and responses of cells and organisms.

Through gene targeting a non-exclusive list of possible modifications or combinations of modifications to the host genome includes:

1. Gene replacement and gene addition: by replacing the targeted chromosomal gene or genes, or promoter or promoters, or portions of the aforementioned, with another gene or genes, or promoter or promoters, or portions of the aforementioned; or adding a gene or genes and regulatory components, or portions thereof, at a targeted chromosomal locus adjacent to resident endogenous loci.

2. Gene inactivation and gene deletion: Inactivating a targeted chromosomal gene through disruption of transcription or translation by changing the sequence composition or by inserting or deleting one or more base pairs of the gene sequence. Furthermore, the coding region or regulatory components, or portions thereof, of a targeted chromosomal gene or genes may be deleted as required.

Using gene targeting, an absolute inactivation of specified target genes may be possible by, for example, creating insertion, deletion or substitution mutations in the target genes. Thus the phenotypic effects of the gene may be assessed by studying the engineered null-mutant. This null-mutant may also be genetically stable in subsequent generations ensuring the continued propagation of this line maintaining the same engineered phenotype. The modified line may also be isogenic to the original cell line or organism from which it is derived thus enabling reliable and accurate comparisons between the modified and original lines so that the effects of the modification may be accurately determined. Targeted gene inactivation may therefore have advantages over conventional means of gene silencing, such as antisense RNA and cosuppression, which may not provide absolute inactivation of the target gene and/or may not cause a stable and consistent level of inactivation through generations.

3. Allele modification: Changing the sequence of a targeted chromosomal gene to create a new allele which encodes a protein with a changed amino acid composition (i.e. protein engineering), or which has modified translatability or stability of the transcript.

Gene targeting has been demonstrated in several species including lower eukaryotes, invertebrate animals, mammals, lower plants and higher plants. Gene targeting substrates include single-stranded DNA (ssDNA; Simon J. R., Moore, P. D., 1987, Mol Cell Biochem 7, pp. 2329-2334), double-stranded DNA (dsDNA; Rothstein, R, 1991, Methods Enzymol. 194: 281-301), or hybrid molecules with RNA and DNA constituents. For some prior DNA-based gene targeting substrates, the amount of homology to the target locus present in the gene targeting substrate has varied from 10's of basepairs (bp) to 10's of kilobasepairs (kb; Yang, X W, et. al., 1997, Nat. Biotechnol. 15, pp. 859-865), depending upon the nature of the target locus and the type of host cell or species and the efficiency of homologous recombination functions in that host cell or species. For RNA/DNA hybrid gene targeting substrates, the homology in some cases has been 10's of basepairs (for example see Zhu, T, 2000, Nat. Biotechnol. 18: 555-558; Beetham, P. R., 1999, Proc. Natl. Acad. Sci. U.S.A 96: 8774-8778).

Successful gene targeting has been achieved by treatment of cultured cells, tissues or organisms with gene targeting substrate. This has resulted in modified target loci which are stable through cell divisions. However, the frequency of these events is low. To obtain modified target loci stably transmissible through sexual reproduction in mammals, specialized procedures employing specific embryonic stem cell lines may be employed. In other animal systems, gene targeting substrates may be injected into gonads, or gene targeting substrate may be engineered to be present in the cells at early developmental stages to ensure modification of germ line cells. Conversely, in some plants the totipotency of all cells may enable nearly any modified cell line to be regenerated into intact plants capable of transmitting the modified locus to progeny.

Application of gene targeting methods, especially in plants and mammals, may be inhibited by several limitations in conventional technology, which may be technically demanding, rely on tedious and expensive in vitro procedures, or be successful only in specialized cell lines. These limitations may be compounded by a low frequency of gene targeting events which may not be easily identifiable. In some applications, only target loci which when modified result in selectable or easily screenable phenotypes may be employed, so that the rare gene targeting events may be identified.

Conventional gene targeting strategies may rely on incorporation of a selectable marker at the target locus resulting in insertional-inactivation mutants by interruption of the target gene with the selectable marker, an approach that may not enable more subtle modifications such as single base-pair changes. Current selection and enrichment procedures may also be ineffective if they select false-positives with high frequency.

A principal factor affecting the frequency of gene targeting with some conventional approaches may be the mechanism of delivering gene targeting substrate to the host cells. Current procedures typically produce a gene targeting substrate exogenously and rely on various means, including chemical treatments, physical treatments, or biological vehicles, to get the gene targeting substrate into the host cell and nucleus. Such methods require extensive screening since the frequency of modifying the target locus is low, and background levels of insertion at non-target loci is high. Methods have accordingly been proposed to address this perceived problem, such as methods disclosed in U.S. Pat. No. 6,504,081 for transposon-mediated gene targeting which purportedly enhance the insertion and detection of desired genes in genomic exons.

International Patent Publication WO02/062986, published 15 Aug. 2002, describes a replicative gene targeting system that renews or regenerates a gene targeting cassette using various mechanisms of DNA replication, to enable repeated cycles of gene targeting substrate production in vivo. As disclosed therein, successive rounds of gene targeting cassette replication may allow the accumulation of multiple molecules of gene targeting substrate per cell or nucleus, so that the presence of more gene targeting substrate may result in a higher frequency of gene targeting events to produce heritable changes in a target host sequence.

Retrons have been known for some time as a class of retroelement, first discovered in gram-negative bacteria such as *Myxococcus xanthus, Stigmatella aurantiaca* and *Escherichia coli*. Retrons mediate the synthesis in host cells of multicopy single-stranded DNAs (msDNA), which typically include a DNA component and an RNA component. The native msDNA molecules reportedly exist as single-stranded DNA-RNA hybrids, characterized by a structure which comprises a single-stranded DNA branching out of an internal guanosine residue of a single-stranded RNA molecule at a 2',5'-phosphodiester linkage. Native retrons have been found to consist of the gene for reverse transcriptase (RT) and an msr-msd region under the control of a single promoter. The msd region typically codes for the DNA component of msDNA, and the msr region typically codes for the RNA component of msDNA. In some retrons, the msr and msd genes have overlapping 3' ends, and are oriented opposite one another with a promoter located upstream of msr which transcribes through the msd-msr region. The msd-msr region generally contains two inverted repeat sequences, designated "a" and "b", which together make up a stable stem structure in msDNAs. The single RNA transcript from the msr-msd region serves not only as a template for reverse transcription but, by virtue of its secondary structure, also serves as a primer for msDNA synthesis by a reverse transcriptase.

Retrons have been suggested for use in a variety of applications, including production of polypeptides and anti-sense inhibition of target genes, see for example U.S. Pat. No. 5,849,563; U.S. Pat. No. 6,017,737; U.S. Pat. No. 5,849,563; U.S. Pat. No. 5,780,269; U.S. Pat. No. 5,436,141; U.S. Pat. No. 5,405,775; U.S. Pat. No. 5,320,958; and CA 2,075,515.

SUMMARY OF THE INVENTION

In various aspects, the present invention relates to in vivo gene modification methods and constructs. More specifically the present invention relates to systems that may be used for producing gene targeting substrates in vivo, as well as methods for promoting in vivo gene modification using the gene targeting substrates of the invention. As such, in various aspects, the invention provides methods that may be used to mediate heritable genetic change in a host using heterologous gene targeting nucleic acid constructs. Such heritable genetic changes may be chosen to confer altered activity on a target sequence or locus of interest. The heritable genetic change, and altered activity of the target, may be manifest in subsequent generations of the host, including in subsequent generations that do not include the heterologous nucleic acid constructs that were originally used to mediate the genetic change in the progenitor host. Heritable genetic changes mediated by the methods of the invention may for example be targeted to coding or non-coding sequences.

In one aspect, the present invention provides a method to modify a nucleic acid of interest at a target locus within the genome of a host comprising steps that include the following. Expressing a gene targeting construct (GTC) nucleotide sequence encoding an RNA, to produce a gene targeting message RNA (gtmRNA). The GTC may for example be a DNA sequence integrated into the genome of the host, or integrated into an extrachromosomal element. The gtmRNA may be folded for self-priming for reverse transcription by a reverse transcriptase (RT). Reverse transcription of the gtmRNA produces a gene targeting substrate (GTS), which may be comprised of both DNA and RNA components. The GTS may comprise a gene targeting nucleotide sequence (GTNS), which is homologous to the target locus, but comprises a sequence modification compared to the target locus. Following expression of the gene targeting systems of the invention, hosts may for example be selected having genomic modifications at the target locus that correspond to the sequence modification present on the gene targeting nucleotide sequence.

In various embodiments, the present invention relates to gene targeting methods as described above, wherein the host is modified to express the RT prior to introducing the nucleotide sequence into the host that encodes the RNA that comprises the GTNS. The nucleotide sequence encoding an RNA that comprises the GTNS may for example be introduced into the host by transformation or cross breeding.

In alternative embodiments, the present invention includes gene targeting methods as described above, wherein the host is modified to express a nucleotide sequence encoding an RNA that comprises the GTNS, prior to introducing an RT expression system into the host. The nucleotide sequence encoding RT may for example be introduced into the host by transformation or cross breeding.

In some embodiments, there is provided a nucleotide sequence comprising msr and msd coding regions, a gene-targeting nucleotide sequence (GTNS) homologous to a target locus of interest, wherein the GTNS comprises at least one nucleotide difference compared to the target locus of interest. Such constructs may be used with a nucleotide sequence encoding a reverse transcriptase. If the reverse transcriptase is not included in the nucleotide sequence, then it may for example be provided on a second nucleotide sequence.

In some embodiments, to adapt retrons for use in gene targeting, the nucleotide sequence encoding a reverse transcriptase may further comprise a nuclear localization signal sequence. In alternative embodiments, the msr, and msd coding regions and the nucleotide sequence homologous to a target locus of interest may be operatively linked with a first regulatory region, and the nucleotide sequence encoding a reverse transcriptase may be operatively linked with a second regulatory region. In such embodiments, the first regulatory region and second regulatory region may be the same or different. In further alternative embodiments, these regulatory regions may be selected to be active in a selected cell cycle or growth phase, such as during the S phase or G1/S boundary phase or G2 phase of the cell cycle. For example, the first regulatory region and second regulatory region may be selected from the group consisting of histone promoters, cyclin promoters, promoters of cell division control genes, and promoters of genes encoding structural or catalytic proteins participating in DNA synthesis.

In some embodiments, the nucleotide sequence of the gene targeting constructs of the invention may further comprise a marker gene. Also, the marker gene may be operatively linked with a third regulatory region, which may for example be a constitutive promoter.

Further, according to the present invention as defined above, the gene targeting nucleotide sequence homologous to the target locus of interest may comprise less than about 5 kb. In an aspect of an embodiment the gene targeting nucleotide sequence may comprise less than about 2 kb. In alternative aspects, the gene targeting nucleotide sequence may be longer than a minimum length which is an integer between 15 and 500, such as at least 15, 25, 50, 100, 150, 200, 250, 300, 350, 400, 450 or 500 bp.

In some embodiments, the gene targeting constructs of the present invention may comprise all or a portion of a vector. The vector may for example comprise a vector adapted to integrate into a host genome, such as an *Agrobacterium* vector capable of integrating a nucleic acid sequence into a plant genome.

In some aspects, the invention provides a cell, tissue or organism transformed with the gene targeting constructs of the present invention, such as a eukaryotic cell, a plant cell, an animal cell, an insect cell, or a yeast cell. Transformed tissues may for example include a plant tissue or animal tissue. Transformed organisms may for example be plants or animals.

In some embodiments, the invention provides a branched msDNA hybrid molecule capable of being produced from a gene targeting retron of the invention, wherein the msDNA comprises:
  i) an RNA portion covalently linked to a single stranded DNA portion by a 2',5' phosphodiester bond between a 2'OH group of an internal rG residue and a 5' phosphate of the DNA molecule; and wherein,
  ii) the RNA portion may be non-covalently linked to the DNA portion by base pairing between complementary 3' ends of the RNA and DNA; and wherein,
  iii) the msDNA comprises,
    a) a stable stem-loop structure in the RNA, DNA or both portions of the molecule; and,
    b) a gene targeting nucleic acid sequence which comprises one or more regions that are homologous to a target locus of interest, wherein the gene targeting nucleic acid sequence encoding at least one nucleotide difference compared to the target locus of interest.

In some embodiments, the gene targeting nucleic acid sequence of the msDNA of the invention may be located within the stable stem-loop structure in the RNA, DNA or both portions of the msDNA molecule.

In one aspect, the invention provides methods of modifying a gene of interest within an organism comprising:
  i) transforming the organism with a nucleotide sequence encoding msr-GTNS-msd; and,
  ii) producing msDNA in sufficient quantities to promote modification of the target locus of interest with the gene targeting nucleotide sequence, wherein the GTNS is homologous to the target locus of interest and encodes at least one nucleotide difference from the target locus of interest.

In some embodiments, the invention provides a library of transformed hosts, wherein the hosts comprise a target genomic sequence that has been altered using the methods of the invention. In one aspect, such libraries will be the result of the relatively error-prone generation of gene targeting substrates by reverse transcriptase, using the methods of the invention. For example, a pool of hosts may be modified by the methods of the invention, to generate a library of transformed hosts having altered target sequences, and the library may be subject to selection for a desired alteration in the target sequence.

In alternative embodiments, a gene targeting construct may be excised from the genome of a host. For example, the gene targeting construct may be flanked on each side by a recognition sequence for a site-specific recombinase such as, for example, FLP protein of the 2 micron element. Such embodiments may be adapted so that by the action of the recombinase on its respective recognition sequence the gene targeting construct is excised, typically as a circular dsDNA molecule (having been excised from a chromosomal locus or an extra-chromosomal locus on a vector where it is integrated). This may for example be useful for producing subsequent generations of hosts in which the heritable genetic change mediated by the gene targeting construct is present, while the construct itself is absent from such hosts. Accordingly, in one aspect the invention provides hosts having a heritable genetic change mediated by the methods and constructs of the invention, in which the heterologous constructs used to mediate the genetic change are not present.

In alternative embodiments, the invention provides isolated gene targeting substrates produced by the methods and constructs of the invention. A first host may for example be used to produce a gene targeting substrate for isolation, and the isolated gene targeting substrate may then be used to modify a target locus in a second host. Similarly, an isolated gene targeting RNA produced in a first host may be used to transform and modify a target locus in a second host.

In alternative embodiments, first and second complimentary gene targeting substrates may be produced in a host, so that the gene targeting substrates hybridize to form a double stranded gene targeting substrate, the double stranded gene targeting substrate having a gene targeting nucleotide sequence that is homologous to a target locus in a host genome.

In alternative embodiments, recombinant hosts are provided having a cloning site in a gene targeting construct in the genome of the host, the cloning site being positioned so that heterologous sequences introduced into the cloning site will be expressed as part of the gene targeting substrate.

This schematic illustration is adapted from published reports to show a putative mechanism by which an RNA transcript encoding the msr-msd elements may fold to create stem-and-loop structures as a result of base-pairing between complimentary inverted repeat sequences, such as the a1 and a2 or b1 and b2 sequences. As illustrated, a stem-and-loop structure within the msr element is thought to recruit reverse transcriptase, which may be expressed in trans, to place the enzyme in an appropriate context so that it can use the 2'-hydroxyl group of a specific guanosine residue in the msr element to prime reverse transcription. Reverse transcription is shown proceeding through the msd element and terminating at a juncture between msr and msd elements. In the absence of an RNaseH-like activity, an extended RNA-DNA hybrid molecule may result. As shown in the alternative, in the presence of an RNaseH-like activity, an extended ssDNA molecule may result.

Figure 2:
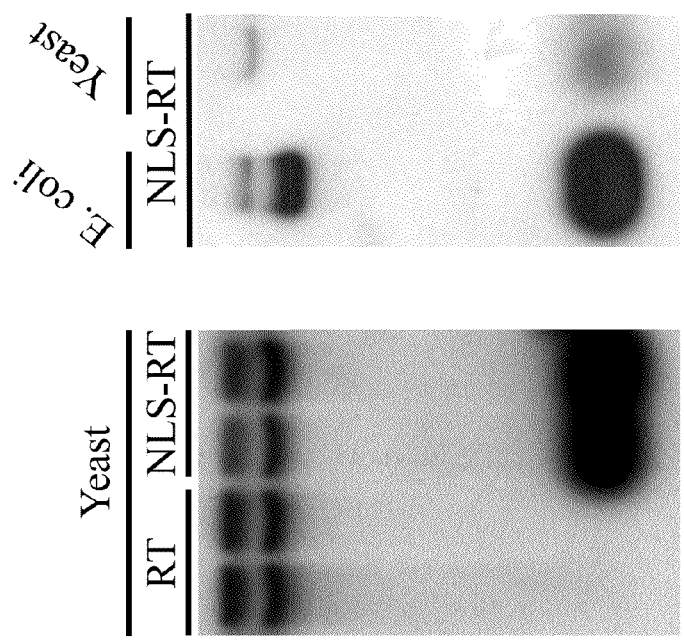

FIG. 2: The Effect of Nuclear Localisation on Functionality of Prokaryotic Reverse Transcriptase in Eukaryotic Cells.

This Figure shows a Southern blot of DNA samples collected from E. coli and yeast cells expressing components of a reverse transcription system. The blot was probed with a DNA fragment that can detect the product of reverse transcription (lower molecular weight signal). The higher molecular weight signal is the parental construct which hybridises to the probe. Left panel: Yeast cells expressing wild type Ec86 msr-msd (pMW29) in combination with wild type Ec86 reverse transcriptase (RT; pMW25) or Ec86 reverse transcriptase engineered to encode a nuclear localisation sequence (NLS-RT; pMW27). Products resulting from reverse transcription are only detectable when NLS-RT is expressed in the eukaryotic cells. Right panel: A comparison of the products of reverse transcription resulting from the action of NLS-RT in E. coli (pMW16, pMW7) and yeast (pMW27, pMW29).

Figure 3A:
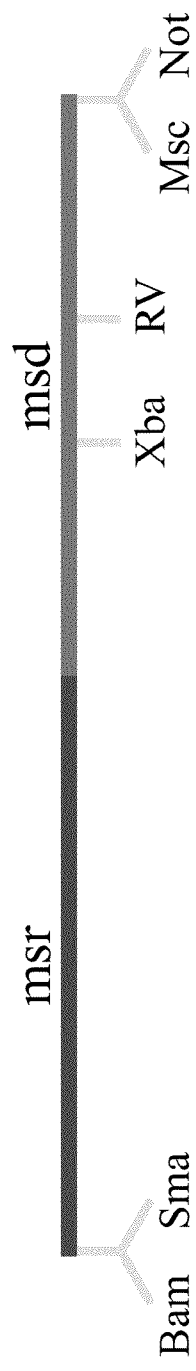
Figure 3B:
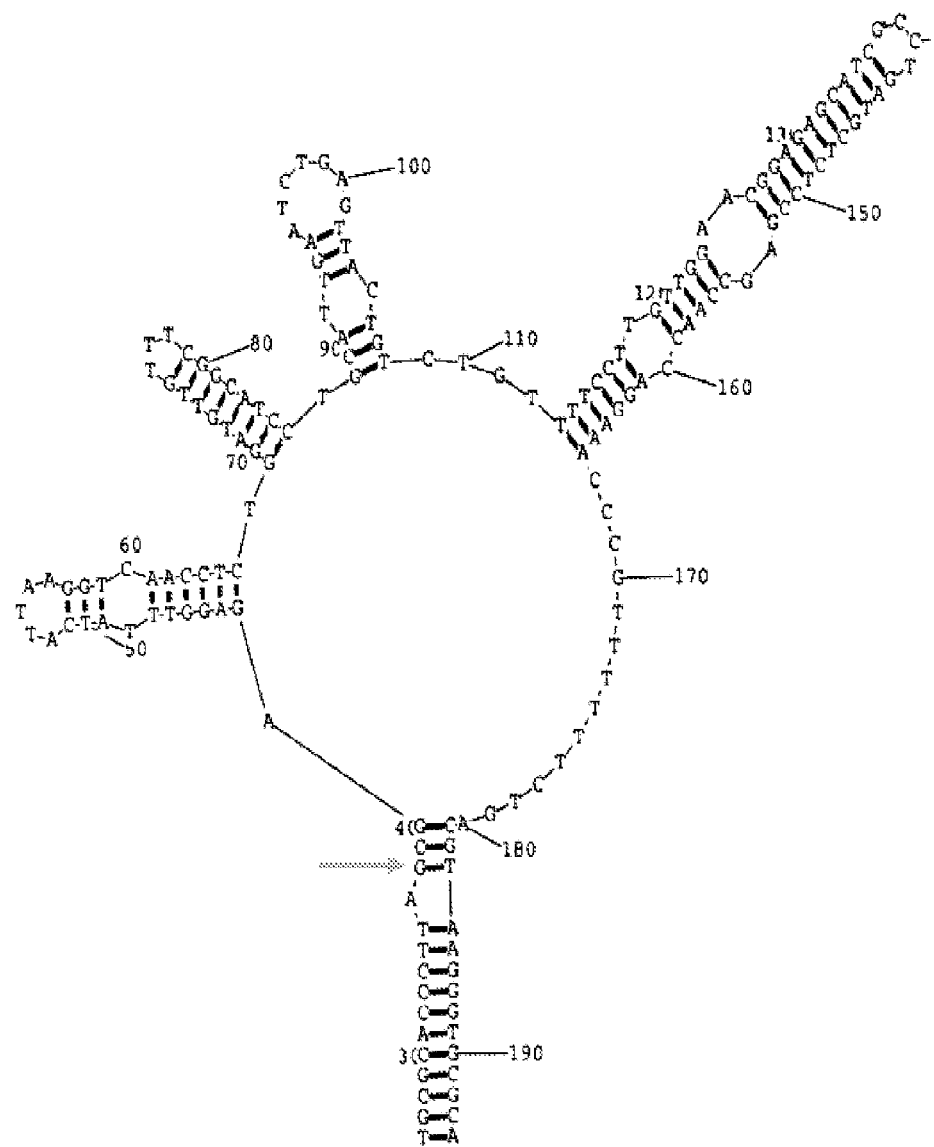
Figure 3B:
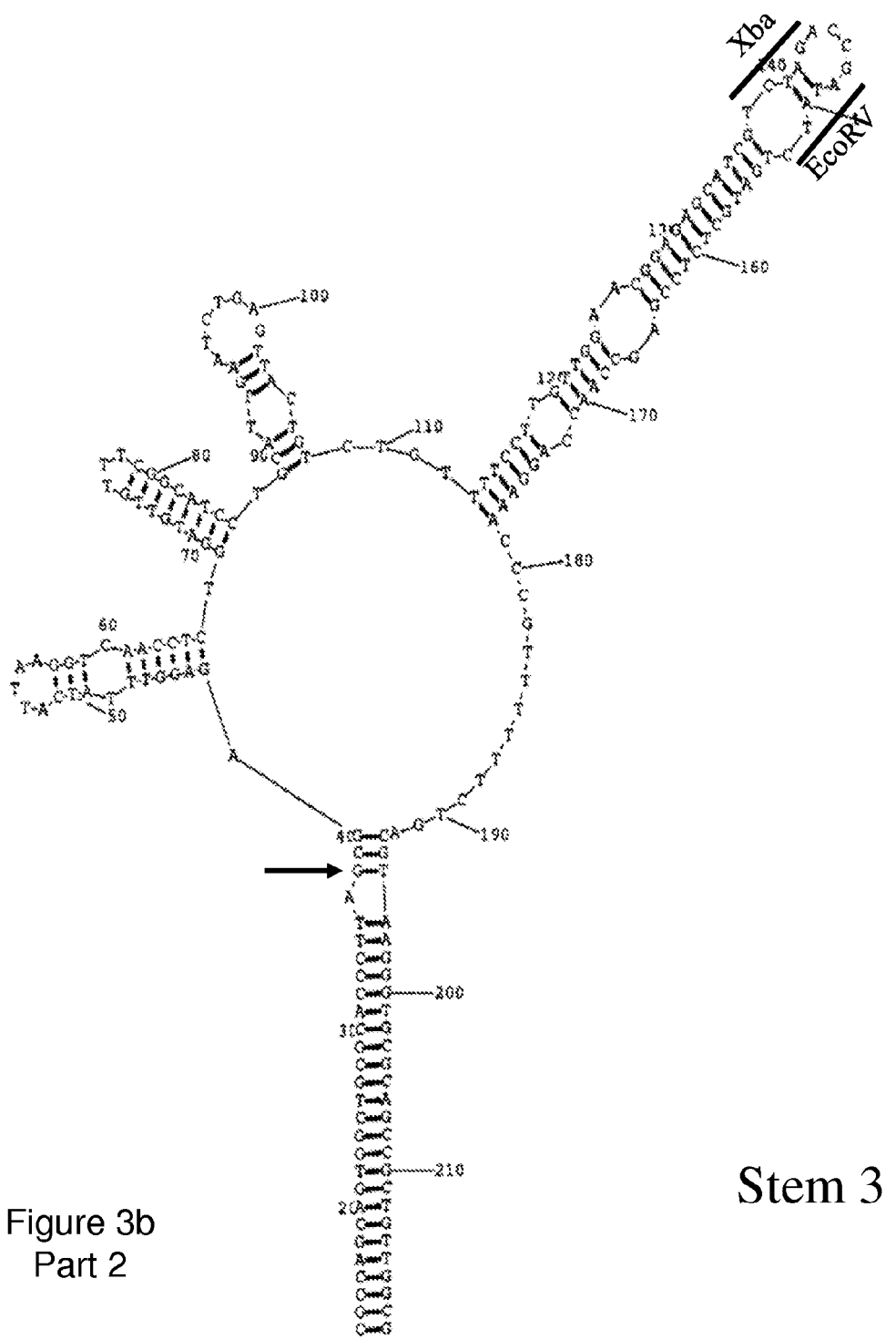

FIG. 3: The STEM3 Derivative of msr-msd.

This Figure shows: A) Diagrammatic representation of STEM3 highlighting the positions of restriction enzyme recognition sites. B) structural comparison of STEM3 (FIG. 3B, Part 2; SEQ ID NO: 8) to wild type (FIG. 3B, Part 1; SEQ ID NO: 7) Ec86 msr-msd. Sequences were folded using a molecular modeling computer program. The arrow indicates the position of the guanosine residue used to prime reverse transcription. The position of restriction enzyme sites for cloning novel sequences into STEM3 are shown (XbaI, EcoRV). Note that the double-stranded region created in STEM3 resulting from pairing of the a1' and a2' sequences is 13 bp longer than that in the wild type msr-msd resulting from pairing of a1 and a2 sequences.

Figure 4:
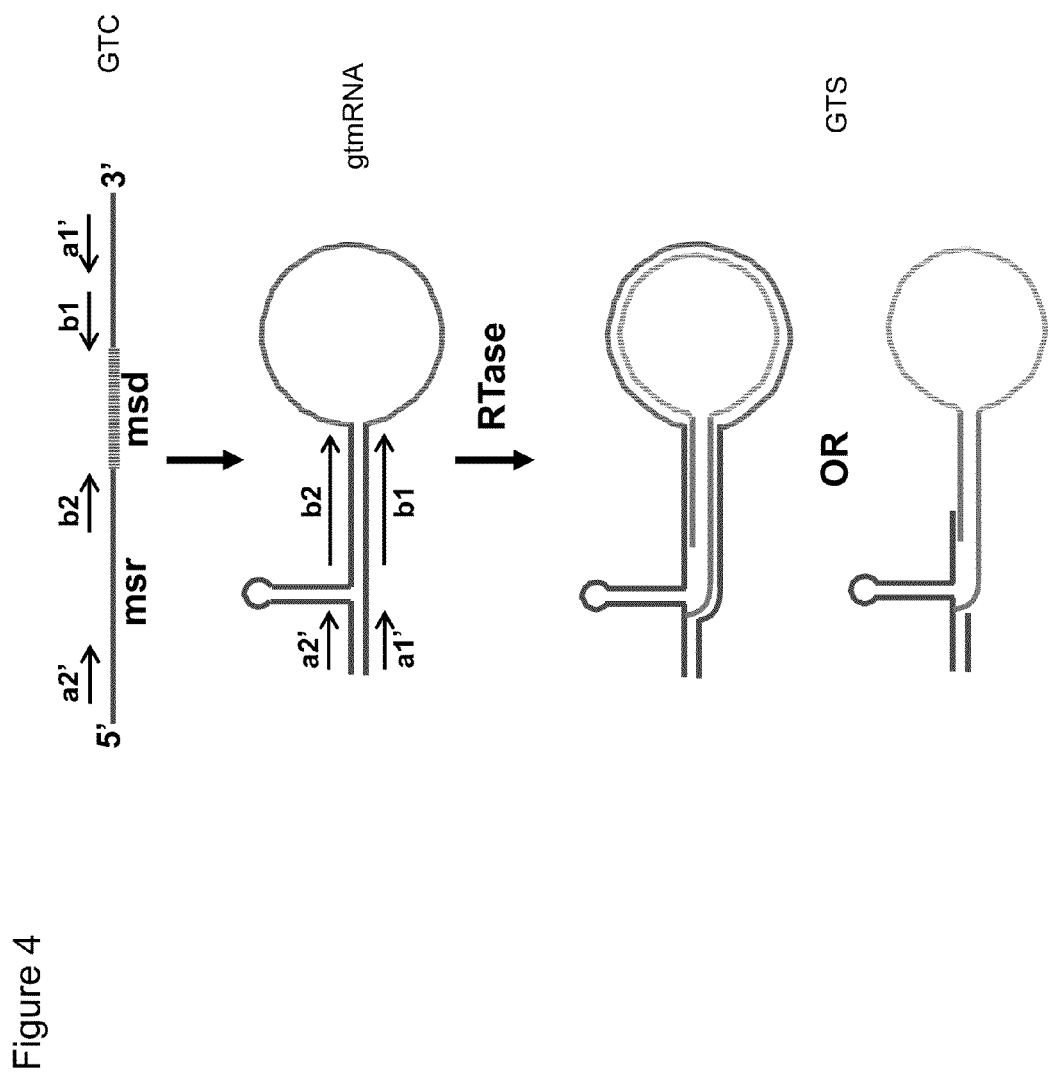

FIG. 4: Products of Reverse Transcription of STEM3.

This is a schematic representation of reverse transcription of STEM3 encoding an insert in the msd element (hatched region). The overall process is similar to that described for wild type msr-smd in FIG. 1. Note that an extended loop structure encoding the sequence inserted into msd is formed at the end of the stem created by annealing of the b1 and b2 sequences. The reverse transcriptase facilitates conversion of this insertion sequence into cDNA. In the absence of an RNaseH-like activity, an extended RNA-DNA hybrid molecule may result. In the presence of an RNaseH-like activity an extended ssDNA molecule may result.

Figure 5:
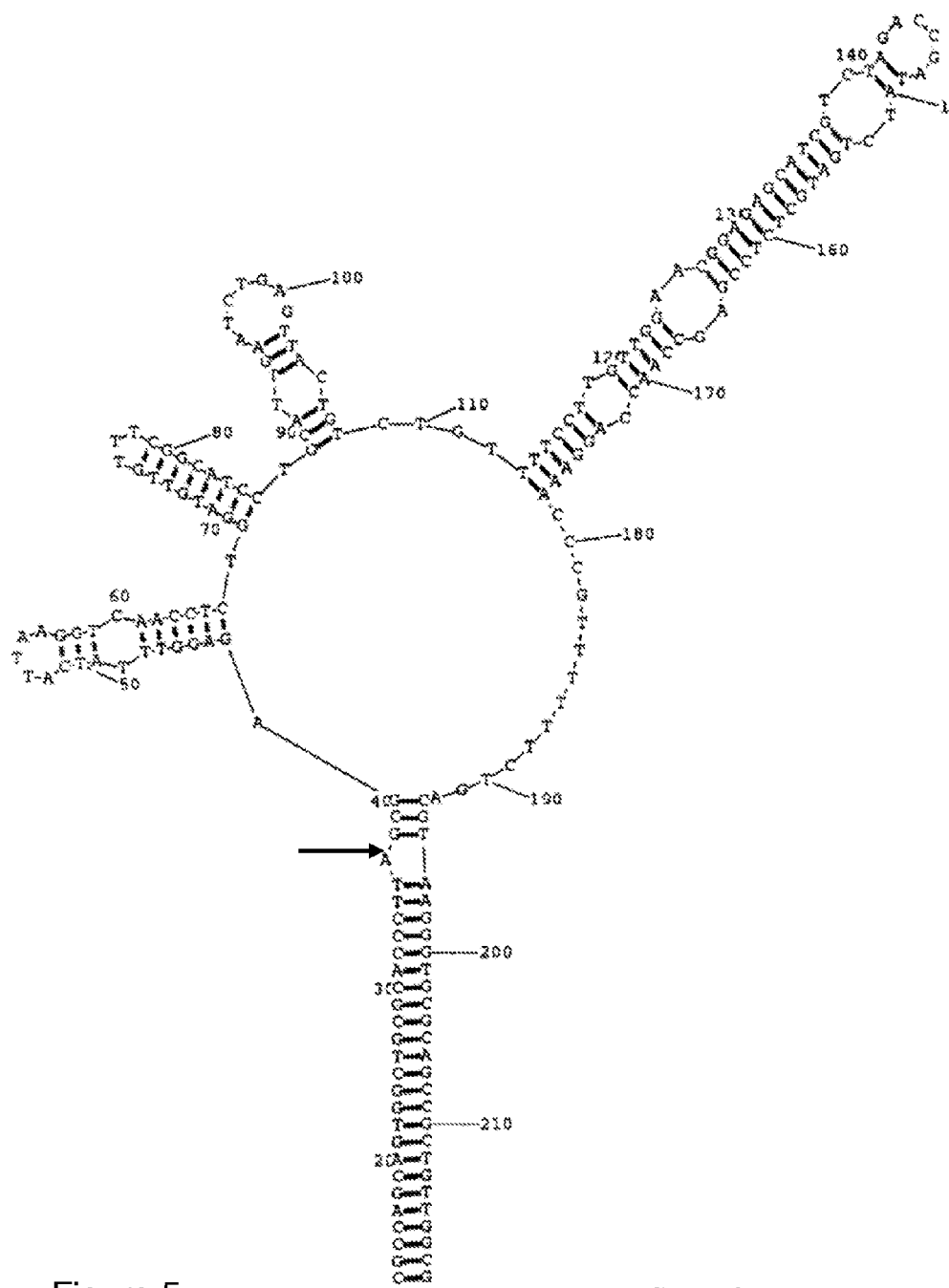
Figure 5:
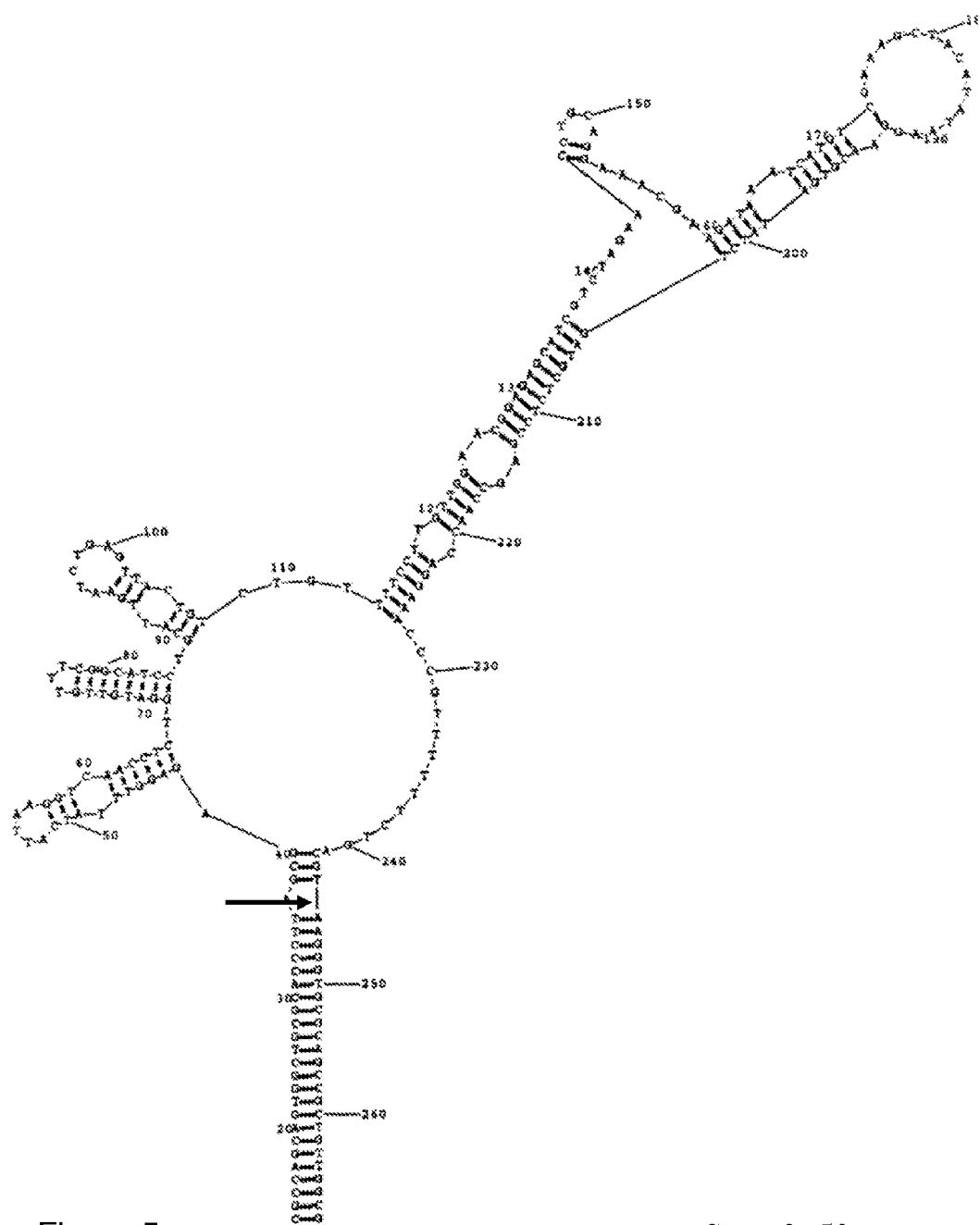
Figure 5:
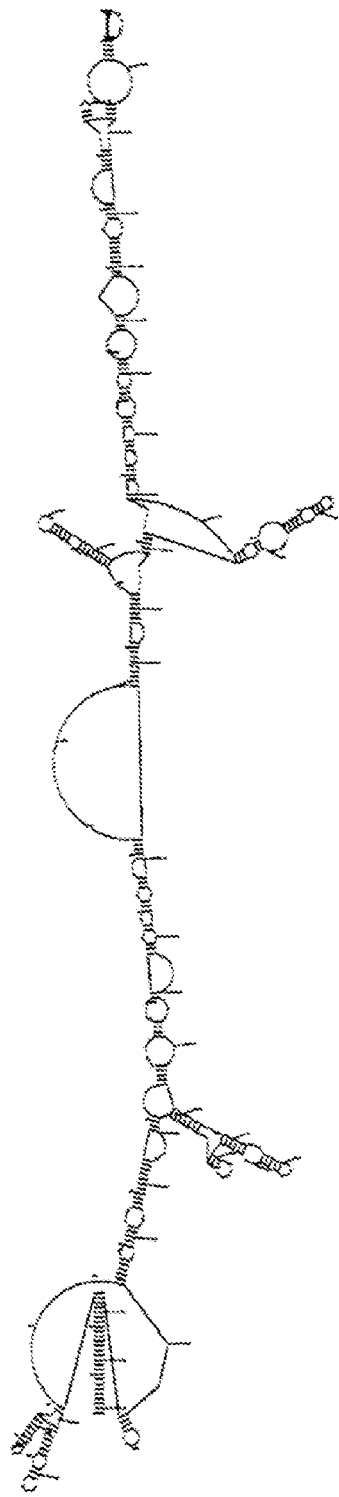

FIG. 5: Structural Modeling-Based Prediction of Insert Size Tolerance by Retrons.

The illustrated models represent putative structures of stems containing no insert (FIG. 5, Part 1; Stem 3; SEQ ID NO: 8) or insertions of 50 bp (FIG. 5, Part 2; Stem3+50; SEQ ID NO: 9) or 500 bp (FIG. 5, Part 3; Stem3+500) cloned into the unique XbaI and EcoRV restriction sites. Structures were predicted using a molecular modeling computer program. The arrow indicates the position of the guanosine residue used to prime reverse transcription.

Figure 6:
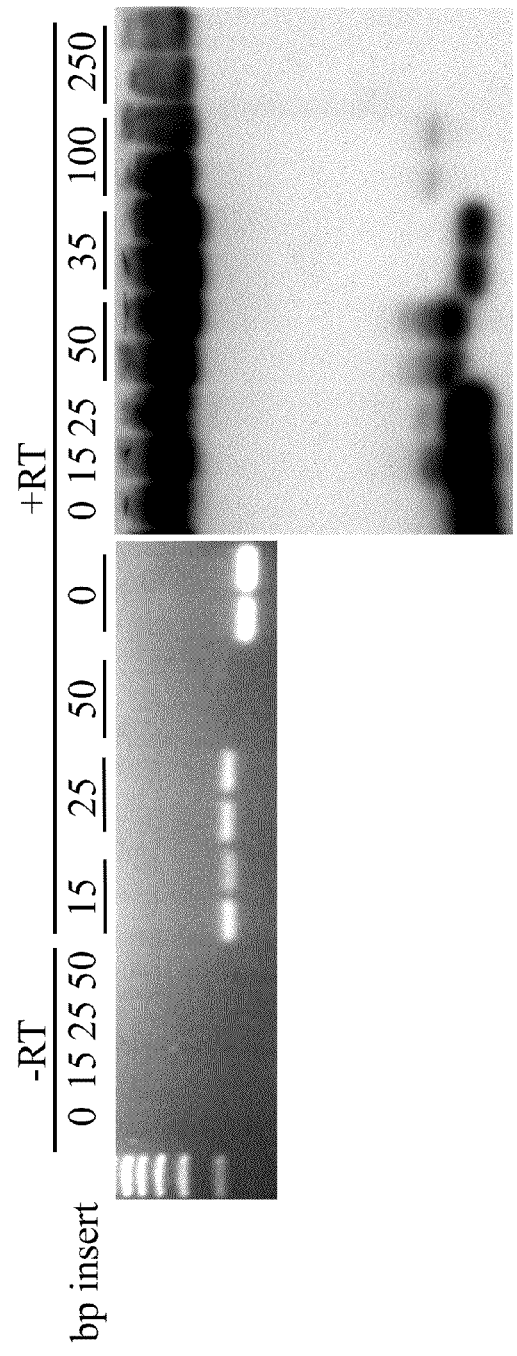

FIG. 6: Insert Size Tolerance of Retrons Expressed in Prokaryotic Cells.

This Figure illustrates results obtained in assessments of the ability of an msr-msd STEM3 derivative to facilitate in vivo synthesis of cDNAs of different lengths in the absence (−RT) or presence (+RT) of reverse transcriptase. DNA samples from E. coli expressing msr-msd STEM3 derivative containing insert sequences of 0 bp (pMW7), 15 bp (pMW161), 25 bp (pMW162), 35 bp (pMW198), 50 bp (pMW163), 100 bp, (pMW199), or 250 bp (pMW200) were resolved by agarobe gel electrophoresis and detected by staining with ethidium bromide (left panel) or by probing a Southern blot with msr-msd (right panel). The reverse transcriptase was expressed from pMW7. The high molecular weight signals represent the parental plasmids encoding STEM3 components which cross-react with the probe.

Figure 7:
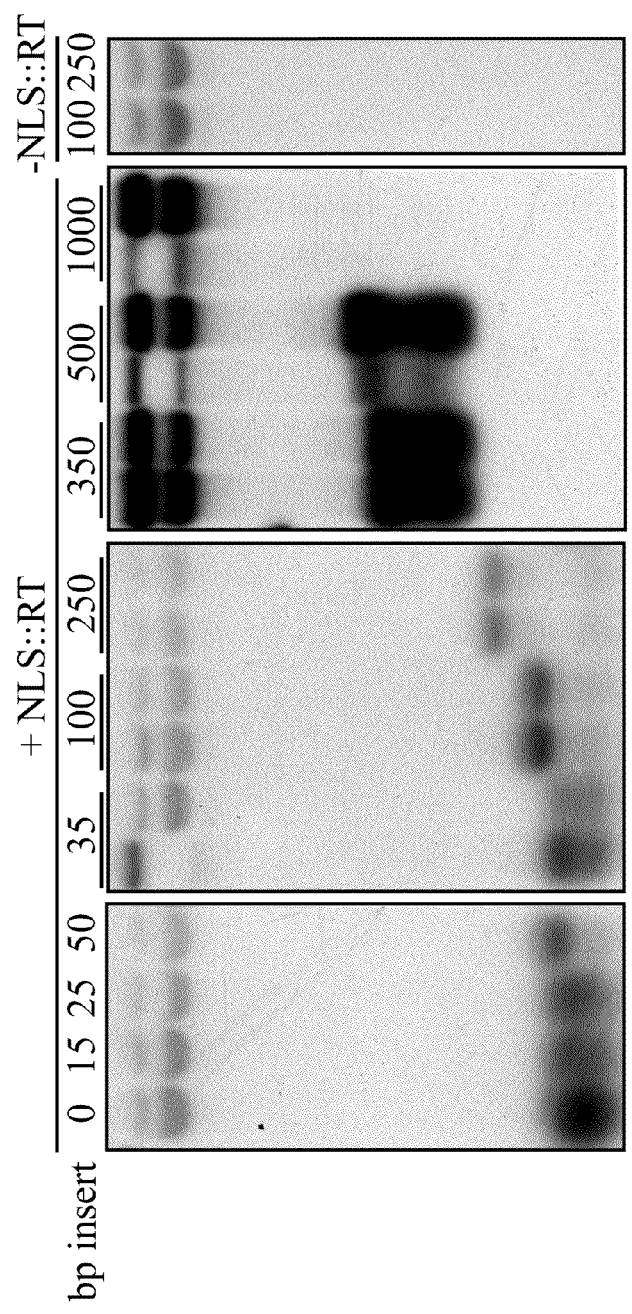

FIG. 7: Insert Size Tolerance of Retrons Expressed in Eukaryotic Cells.

This Figure illustrates results obtained in assessments of the ability of an msr-msd STEM3 derivative to facilitate in vivo synthesis of cDNAs of different lengths in the absence (−NLS::RT) or presence (+NLS::RT) of reverse transcriptase encoding a nuclear localization sequence. DNA samples from S. cerevisiae expressing msr-msd STEM3 derivative containing insert sequences of 0 bp (pMW166), 15 bp (pMW167), 25 bp pMW168), 35 bp (pMW202), 50 bp (pMW169), 100 bp (pMW203), 250 bp (pMW204), 320 bp (pMW211), 500 bp (pMW212), or 1000 bp (pMW213) were resolved by agarose gel electrophoresis and detected by probing a Southern blot with msr-msd. The reverse transcriptase encoding a nuclear localization sequence was expressed from pMW27. The high molecular weight signals represent the parental plasmids encoding STEM3 components which cross-react with the probe.

Figure 8:
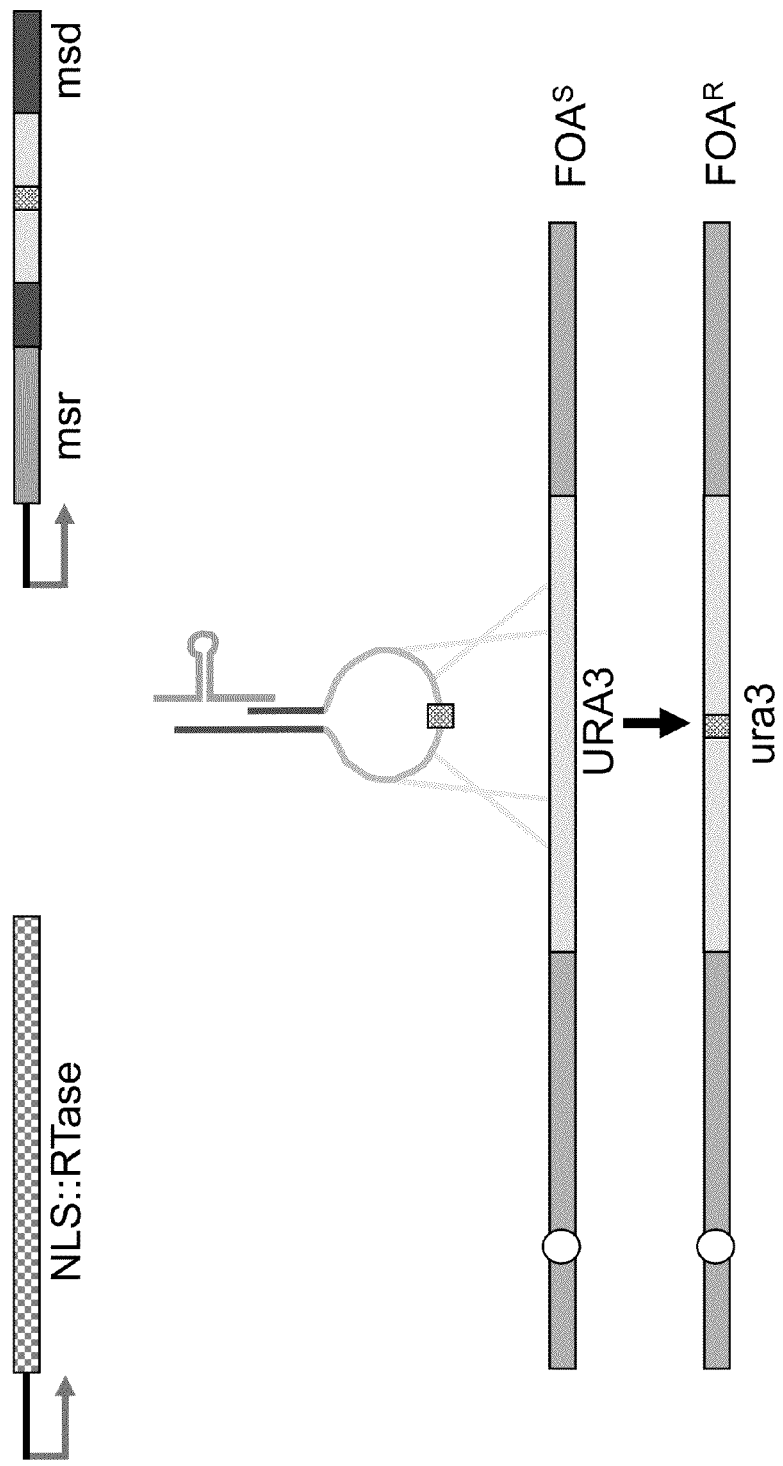

FIG. 8: Diagrammatic Representation of Gene Targeting Assay.

This schematic illustration shows one aspect of the invention, in which separate cassettes may be used for expressing reverse transcriptase and the msr-msd element encoding the gene targeting sequence. The gene targeting sequence encodes homology to the chromosomal target locus as well as the genetic change (hatched area) to be transferred to the target locus. The RNA transcript of the element is acted upon by the reverse transcriptase to convert the gene targeting sequence into a cDNA-based gene targeting substrate. Host recombination and repair processes facilitate transfer of genetic information from the gene targeting substrate to the chromosomal target locus. In this example, the gene targeting event converts the chromosomal URA3 allele to a mutant ura3 allele. The altered gene product encoded by ura3 confers resistance to 5-fluoroorotic acid ($FOA^R$) whereas the URA3 allele confers sensitivity ($FOA^S$). Note the cross-over events depicted in this figure between the gene targeting substrate and the target locus are solely for illustration and do not necessarily represent the mechanism for transferring the genetic information from the gene targeting substrate to the target locus. For example, alteration of the target locus may occur by a gene conversion event and not involve double and reciprocal cross-over events suggested in the illustration.

Figure 9:
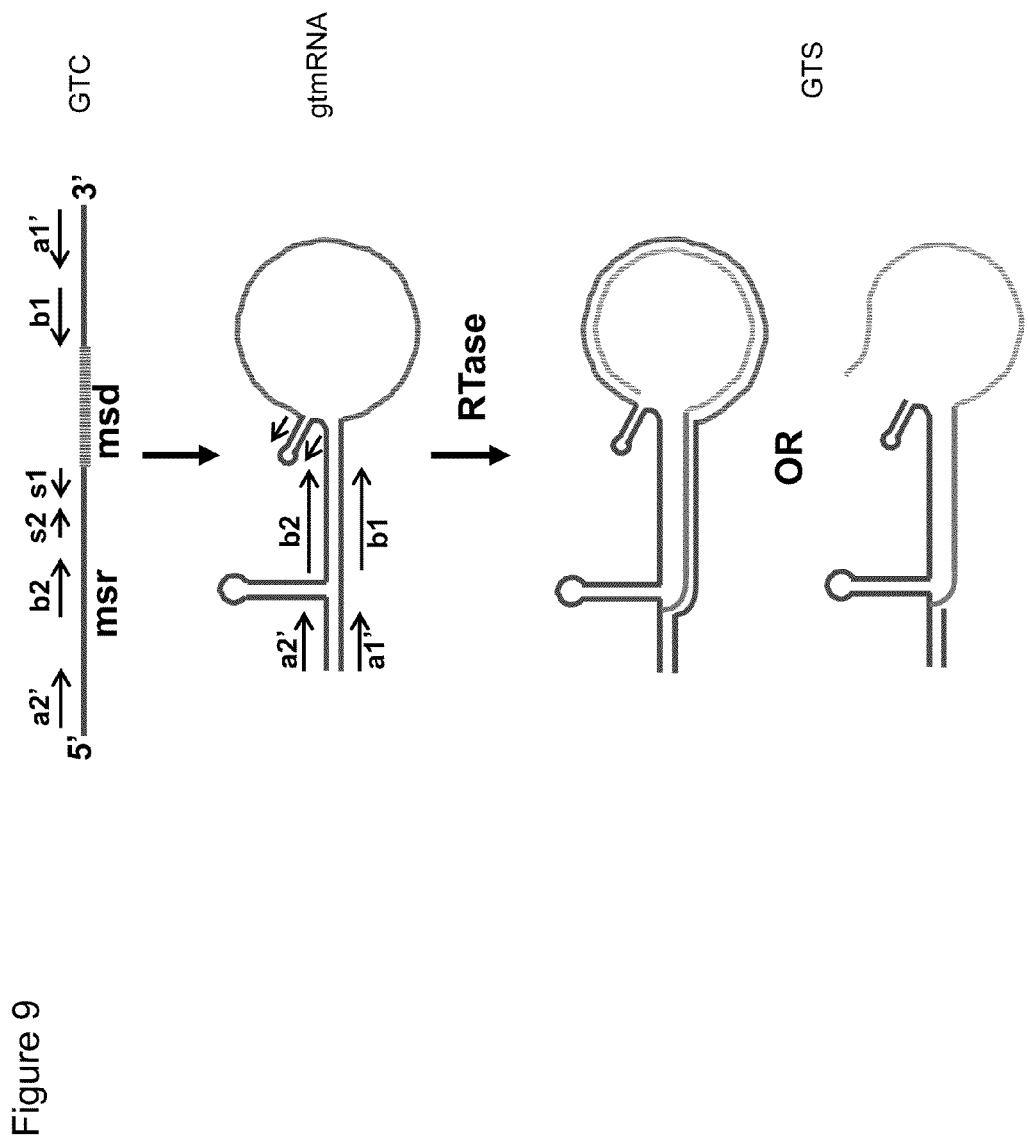

FIG. 9: Products of Reverse Transcription of STOPstem.

This is a schematic representation of reverse transcription of STOPstem encoding an insert in the msd element (hatched region). The overall process is similar to that described for STEM3 in FIG. 4. This illustration highlights the position of the novel inverted repeat sequences S1 and S2 and the resultant stem-and-loop structure adjacent to the insert sequence. This novel stem-and-loop promotes termination of reverse transcription at the end of the insert sequence. As a result, the 3' end of the cDNA may encode insert sequence rather than retron sequence as would normally occur if reverse transcription terminated at the normal site between the msr and msd elements. In the absence of an RNaseH-like activity an extended RNA-DNA hybrid molecule may result. In the presence of a RNaseH-like activity an extended ssDNA molecule may result.

Figure 10:
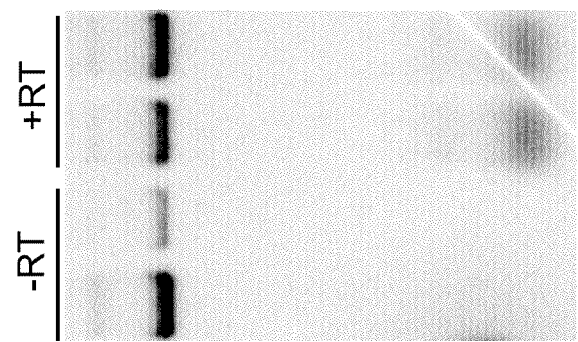

FIG. 10: Production of cDNA in Eukaryotic Cells by the STOPstem System.

The msr-msd STOPstem derivative was assessed for its ability to facilitate in vivo synthesis of cDNA in eukaryotic cells in the absence (−RT) or presence (+RT) of reverse transcriptase encoding a nuclear localisation sequence. DNA samples from S. cerevisiae expressing the STOPstem containing an insert of 500 bp (pMW306) with or without the reverse transcriptase (pMW27) were resolved by agarose gel electrophoresis and detected by probing a Southern blot with msr-msd. The high molecular weight signals represent the parental plasmids encoding STOPstem components which cross-react with the probe.

Figure 11:
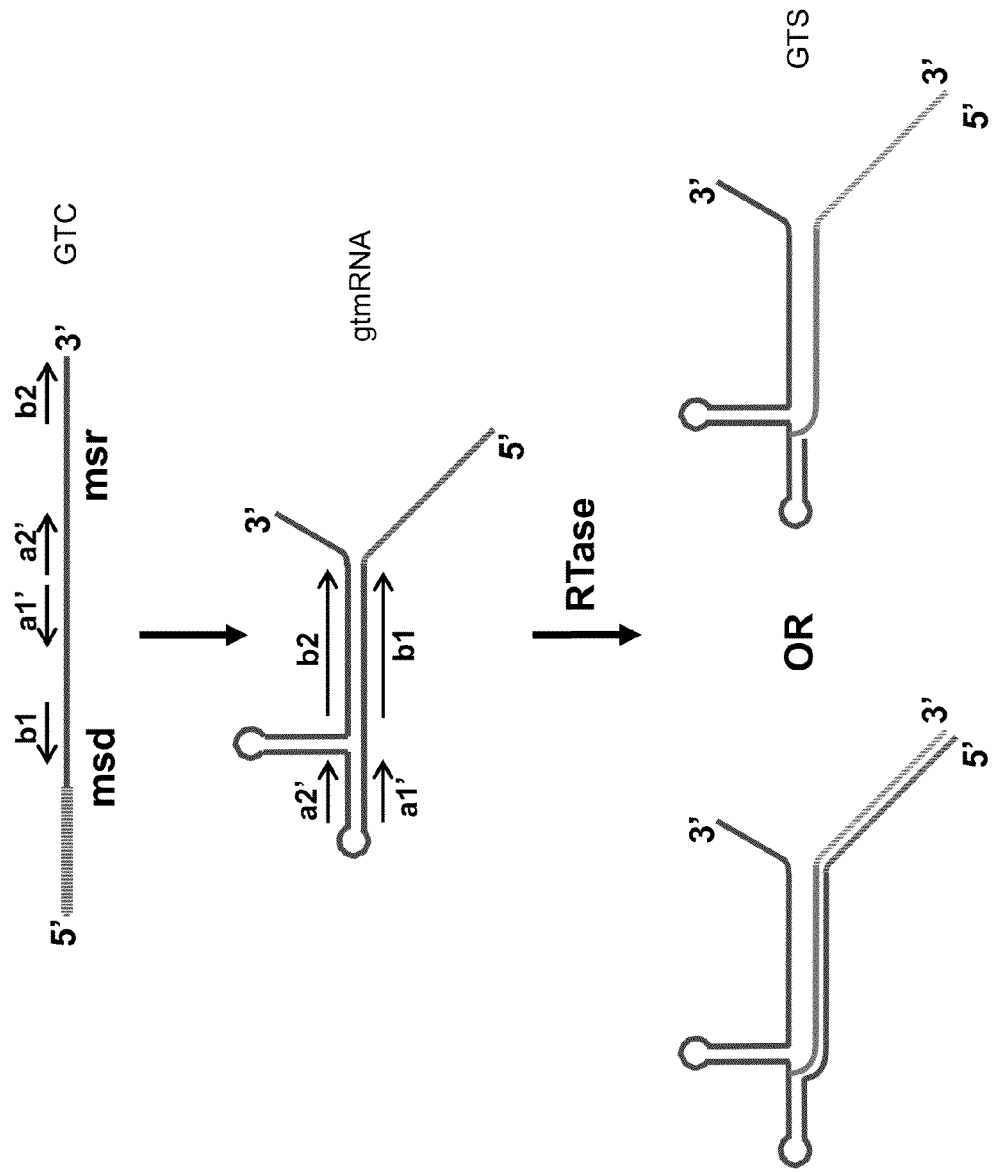

FIG. 11: Products of Reverse Transcription of the 3'-Recruitment System.

Figure 1:
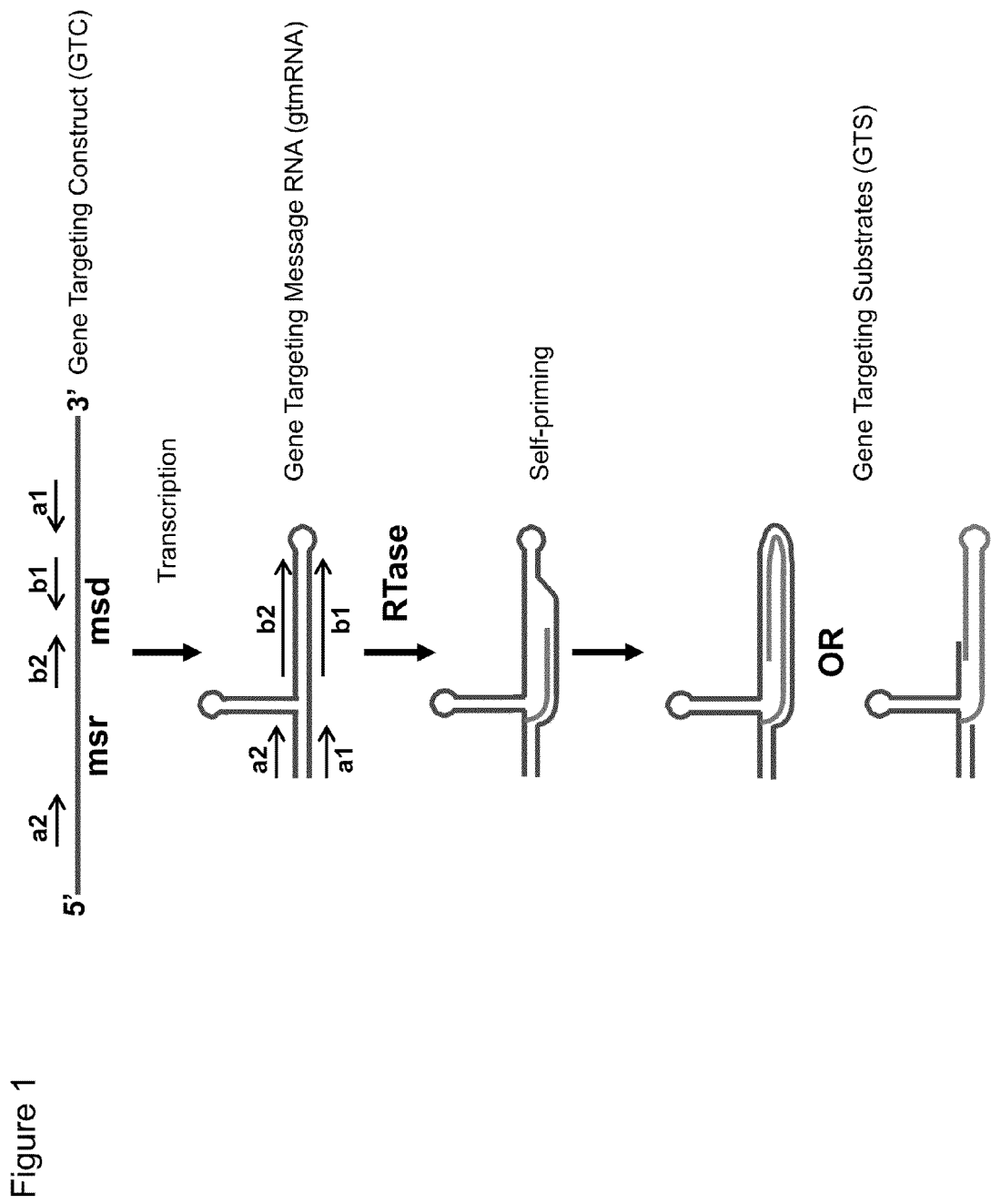
FIG. 1: Reverse Transcription of Wild Type msr-msd Elements.

This is a schematic representation of reverse transcription of the 3'-recruitment system encoding an insert in the msd element (hatched region). Note that the positions of the inverted repeat sequences a1', a2', b1 and b2 have been rearranged versus that of STEM3 (FIG. 4) or the wild type retron (FIG. 1). However, this novel rearrangement may still form a structure that recruits reverse transcriptase and primes conversion of an insert sequence into cDNA. Note that the insert sequence size or composition may not confer any structural constraints on the msr-msd elements required to facilitate reverse transcription in the 3'-recruitment configuration. By the action of the reverse transcriptase, the insert sequence may be converted to cDNA. In the absence of an RNaseH-like activity an extended RNA-DNA hybrid molecule may result. In the presence of an RNaseH-like activity an extended ssDNA molecule may result.

Figure 12:
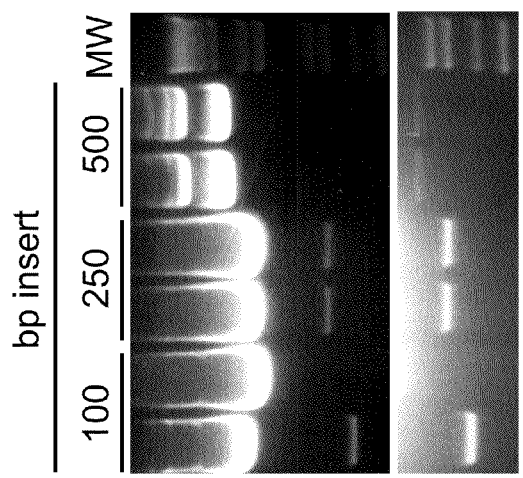

FIG. 12: Insert Size Tolerance of 3'-Recruitment System Expressed in Prokaryotic Cells.

The msr-msd 3'-recruitment derivative was assessed for its ability to facilitate in vivo synthesis of cDNAs of different lengths. in prokaryotic cells. DNA samples from E. coli strains expressing the 3'-recruitment system encoding inserts of 100 bp (pMW159), 250 bp (pMW164) or 500 bp (pMW65) were resolved by agarose gel electrophoresis and detected by staining with ethidium bromide. The reverse transcriptase was expressed from pMW120 in all samples. The upper bands represent parental plasmids and position of cDNA products is indicated. The lower panel is a longer exposure image of the same gel as the upper panel.

Figure 13:
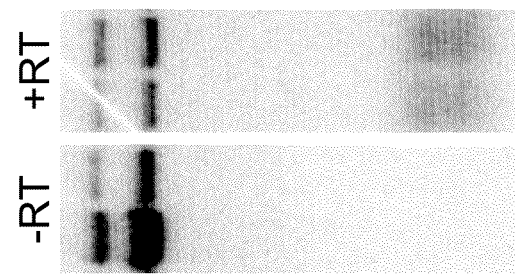

FIG. 13: Production of cDNA in Eukaryotic Cells by the 3-Recruitment System.

The msr-msd 3'-recruitment derivative was assessed for its ability to facilitate in vivo synthesis of cDNA in eukaryotic cells in the absence (−RT) or presence (+RT) of reverse transcriptase encoding a nuclear localisation sequence. DNA samples from S. cerevisiae expressing the 3'-recruitment system containing an insert of 500 bp (pMW220) with or without the reverse transcriptase (pMW27) were resolved by agarose gel electrophoresis and detected by probing a Southern blot with msr-msd. The high molecular weight signals represent the parental plasmids encodings 3'-recruitment components which cross-react with the probe.

Figure 14:
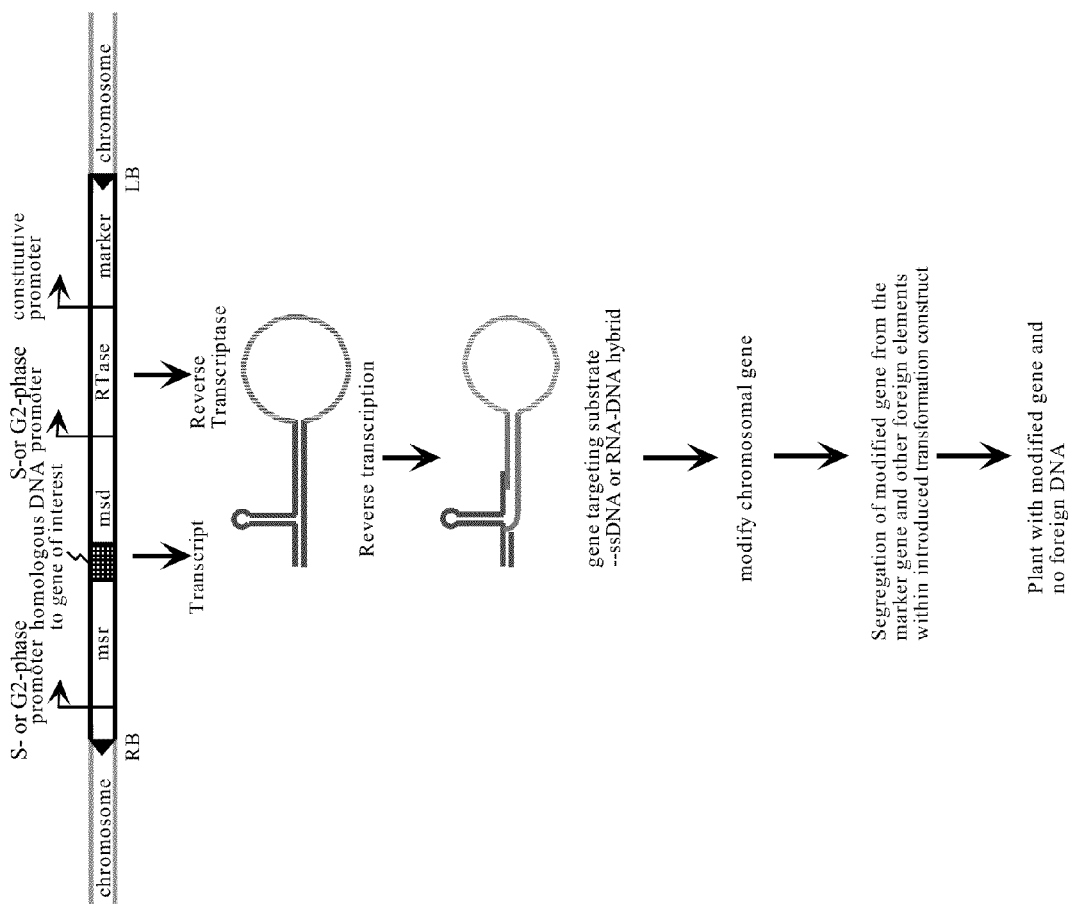

FIG. 14: Application of Reverse Transcription-Based Gene Targeting Systems to Plants.

The figure illustrates one embodiment of the invention where a transgene construct encoding a gene targeting system is integrated into the host plant chromosome. The transcript encoding the gene targeting sequence is reverse transcribed by the reverse transcriptase to form a cDNA which can act as a gene targeting substrate. Because multiple transcripts of the gene targeting sequence may be produced and reverse transcribed, multiple copies of the gene targeting substrate may be produced in cells throughout plant developmental stages. Thus multiple opportunities may occur for the gene targeting substrate to modify the target chromosomal locus. The transformation construct may be eliminated from the genome of a plant encoding the modified chromosomal locus by breeding.

SEQUENCE LISTING

The Sequence Listing is submitted as an ASCII text file, created on Jul. 7, 2010, ~38 KB, which is incorporated by reference herein.

DETAILED DESCRIPTION OF THE INVENTION

The present invention relates to in vivo gene modification. More specifically the present invention relates to systems for producing gene targeting substrates using RNA intermediaries, as well as methods for promoting in vivo gene modification using such gene targeting substrates.

In various aspects, the invention provides methods and nucleic acid constructs that may be used to modify a nucleic acid of interest at a target locus within the genome of a host. In some aspects, the invention contemplates producing in vivo a gene targeting substrate (GTS), which may be comprised of both DNA and RNA components. The GTS may comprise a gene targeting nucleotide sequence (GTNS), which is homologous to the target locus, but which comprises a sequence modification compared to the target locus. The GTS may be produced by reverse transcription of a gene targeting message RNA (gtmRNA). The gtmRNA may be folded or hybridized for self-priming for reverse transcription by a reverse transcriptase (RT). The gtmRNA may in turn be the product of transcription of a gene targeting construct (GTC) encoding the gene targeting message RNA. The gene targeting construct may for example be a DNA sequence integrated into the genome of the host, or integrated into an extrachromosomal element. Following expression of the gene targeting systems of the invention, hosts may for example be selected having genomic modifications at a target locus that correspond to the sequence modification present on the gene targeting nucleotide sequence. In some embodiments, the structure of retrons may be adapted for use in the gene targeting systems of the invention. The gene targeting substrate may for example be similar in structure to a multicopy single stranded DNA (msDNA), as produced by a retron.

According to an aspect of the present invention, there is provided a method to modify or insert a nucleic acid of interest at a target locus within the genome of a host. The nucleic acid of interest is synthesized in vivo from a suitable RNA template using reverse transcriptase. An example of this method comprises:

i) introducing into a host, a nucleotide sequence encoding an RNA that comprises a gene targeting nucleotide sequence, and a second nucleotide sequence encoding a reverse transcriptase;

ii) synthesizing an RNA template from the nucleotide sequence;

iii) generating a reverse transcribed product from the RNA template within the host using the reverse transcriptase, to produce a gene targeting substrate (GTS); and iv) selecting for modification the target locus within the genome of the host.

Alternatively, the host may already be modified to express either a gene targeting nucleotide sequence (GTNS), or a reverse transcriptase. In the case where the RT is expressed within the host, the method would involve:

i) introducing into a host capable of expressing a reverse transcriptase, a nucleotide sequence encoding an RNA that comprises a gene targeting nucleotide sequence;

ii) synthesizing an RNA template from the nucleotide sequence;

iii) generating a reverse transcribed product from the RNA template within the host, to produce a gene targeting substrate (GTS); and iv) selecting for modification the target locus within the genome of the host.

The nucleotide sequence encoding an RNA that comprises a gene targeting nucleotide sequence may be introduced using any suitable method for example but not limited to, transformation (either stable or transient), or by cross breeding.

Similarly, if the host were modified to produce a nucleotide sequence encoding an RNA that comprises a gene targeting nucleotide sequence, the i) introducing into a host capable of expressing a nucleotide sequence encoding an RNA that comprises a gene targeting nucleotide sequence, a second nucleotide sequence encoding a reverse transcriptase;

ii) synthesizing an RNA template from the nucleotide sequence;

iii) generating a reverse transcribed product from the RNA template within the host, to produce a gene targeting substrate (GTS); and iv) selecting for modification the target locus within the genome of the host.

The second nucleotide sequence encoding the RT may be introduced using any suitable method for example but not limited to, transformation (either stable or transient), or by cross breeding.

A wide variety of reverse transcriptases (RT) may be used in alternative embodiments of the present invention, including prokaryotic and eukaryotic RT, provided that the RT functions within the host to generate a GTS from the gene targeting RNA template. If desired, the nucleotide sequence of a native RT may be modified, for example using known codon optimization techniques, so that expression within the desired host is optimized. By codon optimization it is meant the selection of appropriate DNA nucleotides for the synthesis of oligonucleotide building blocks, and their subsequent enzymatic assembly, of a structural gene or fragment thereof in order to approach codon usage within the host.

It is preferred that the RT be targeted to the nucleus so that efficient utilization of the RNA template may take place. An example of such a RT includes any known RT, either prokaryotic or eukaryotic, fused to a nuclear localization signal (NLS). Any suitable NLS may also be used, providing that the NLS assists in localizing the RT within the nucleus. Even though it is preferred that the RT be fused to a NLS, the use of an RT in the absence of an NLS may also be used if the RT is present within the nuclear compartment at a level that synthesizes a product from the RNA template.

A wide variety of RNA templates may be used as described herein. Examples of alternative RNA templates include retron-like RNA, retroviral-like RNA, or RNA derived from a retrotransposon. In some embodiments, for example, the gene targeting message RNA may further comprise a sequence encoding a reverse transcriptase.

In one embodiment, a method to modify or insert a nucleic acid of interest at a target locus within the genome of a host using a reverse transcribed (retron-based) RNA template comprises:

i) introducing into the host, a nucleotide sequence encoding an msr coding region, a gene targeting nucleotide sequence, an msd coding region (msr-GTNS-msd), and a nucleotide sequence encoding a reverse transcriptase;

ii) replicating the msr-GTNS-msd within the host to produce a gene targeting substrate (GTS); and iii) selecting for modification the target locus within the genome of the host.

In one aspect, the present invention provides a nucleotide sequence comprising:

i) an msr and an msd nucleotide coding region in operative association with;

ii) a gene-targeting nucleotide sequence (GTNS), and optionally;

iii) a nucleotide sequence encoding a reverse transcriptase (RT).

The nucleotide sequence may comprise, in the following order, an msr element ORF, a gene-targeting nucleotide sequence, and an msd element ORF (as shown in FIG. 1), and is referred to herein as "msr-GTNS-msd". Alternatively, the GTNS may be inserted within the msd region, preferably within a hairpin region of msd (see for example FIGS. 4, 3B, 5). In alternative embodiments, the msr and msd regions may be modified (inverted) as shown in FIG. 11 so that the 3' msr, and 5' msd, termini are spatially separated from the internal rG residue used to prime the synthesis of msDNA. In this manner foreign inserts may added to the 5' ends of msd. Synthesis of msDNA (gene targeting substrate; GTS) has been observed using the constructs outlined in FIG. 3B, 5 (modified msd hairpin), as shown in FIGS. 6 and 7. Similarly, synthesis of a GTS has been observed using constructs shown in FIG. 11 (inverted msr-msd regions) as shown in FIGS. 12 and 13.

A nucleotide sequence comprising msr and a GTNS inserted within the msd region is also referred to as "msr-GTNS-msd". The msr-GTNS-msd may be transcribed to produce an msDNA comprising the gene targeting nucleotide sequence.

As used herein, the product msDNA may also be termed "gene targeting substrate" (GTS). The msDNA may be produced from a msr-GTNS-msd sequence encoded by a construct that has been introduced into the genome of a host and that is stably integrated, for example, but not limited to *Agrobacterium* mediated transformation, or the msDNA may be produced from a transiently expressed construct, for example introduced into the via biolistics or via a viral vector.

The nucleotide sequence encoding a reverse transcriptase may be part of the same construct comprising the nucleic acid sequence encoding msr-GTNS-msd, or the nucleotide sequence comprising the reverse transcriptase (RT) may be separate from the nucleotide sequence encoding msr-GTNS-msd, and introduced into the host separately. If the RT is introduced separately, it may be introduced to the host as a second vector (re-transformation), it may be introduced by cross breeding, or it maybe introduced into the host using any other method known in the art. Furthermore, the vector comprising the RT may be introduced into a host already comprising a nucleotide sequence encoding msr-GTNS-msd in a transient manner, for example via biolostics, or viral transformation as is known in the art. It is preferred that the nucleotide sequence encoding the RT also encode a nuclear localization signal (NLS) to promote targeting of the RT to the nuclear compartment for efficient production of msDNA (FIG. 2).

By the term "retron" it is meant a genetic element which encodes components enabling the synthesis of branched RNA-linked single stranded DNA (msDNA) and a reverse transcriptase. Retrons which encode msDNA are known in the art, for example, but not limited to U.S. Pat. No. 6,017,737; U.S. Pat. No. 5,849,563; U.S. Pat. No. 5,780,269; U.S. Pat. No. 5,436,141; U.S. Pat. No. 5,405,775; U.S. Pat. No. 5,320,958; CA 2,075,515; all of which are herein incorporated by reference).

The msr element ORF of a retron provides for the RNA portion of the msDNA molecule, while the msd element ORF provides for the DNA portion of the msDNA molecule. The primary transcript from the msr-msd region is thought to serve as both a template and a primer to produce the msDNA (60). Synthesis of msDNA is primed from an internal rG residue of the RNA transcript using its 2'-OH group. The msDNA of the present invention comprises:

i) a branched RNA portion that is:
a) covalently linked, near the 5' end of the RNA, to the 2' end of a single stranded DNA portion by a 2',5' phosphodiester bond between the 2'-OH group of an internal rG residue and the 5' phosphate of the DNA molecule; and
b) non-covalently linked, at the 3' the RNA, to the other end of the DNA, by base pairing between complementary 3' ends of the RNA and DNA molecules ii) a stable stem loop structure (secondary structure) in the RNA portion, the DNA portion, or both; and iii) a gene targeting nucleotide sequence (GTNS), comprising a gene of interest, wherein at least a portion of the GTNS is homologous to a target gene within the host.

In some embodiments, the GTNS, GTS or both, may be an integer length of from about 15 bps to about 5000 bp, for example of from about 15 bp to about 2000 bp, or from about 15 bp to about 1000 bp. The regions of homology between the GTNS or GTS and the target gene within the host may for example comprise one or several regions of homology such as regions or high homology or strict identity of at least about 5, 10, 15, 20, or 25 bp in length.

Several msDNAs have been described in the literature, including but not limited to:
i) Mx162 (Dhundale et al., cell, 51, 1105-1112, 1987);
ii) Mx65 (Dhundale et al., J. Biol. Chem., 263, 9055-9058, 1988);
iii) Sal 63 (Furuichi et al., Cell 48, 47-52, 1987) and Furuichi et al., Cell, 48, 55-62, 1987);
iv) Ec67 (Lamson et al, Science, 243, 1033-1038, 1989);
v) Ec86 (Lim and Maas, *Cell*, 56, 891-904, 1989);
vi) Ec73 (Sun et al., J. Bacteriol. 173, 4171-4181, 1991);
vii) Ec107 (Herzer et al., Mol. Microbiol. August 1991), and;
viii) msDNA from *E. coli* (Lim and Maas, Cell, 56, 891-904, 1989).

Further, several retrons which produce msDNA are known in the art, for example, but not limited to U.S. Pat. No. 6,017,737; U.S. Pat. No. 5,849,563; U.S. Pat. No. 5,780,269; U.S. Pat. No. 5,436,141; U.S. Pat. No. 5,405,775; U.S. Pat. No. 5,320,958; CA 2,075,515 (all of which are herein incorporated by reference). In some embodiments, a GTNS or GTS may be added to adapt these native msDNAs for use in the invention.

At least a portion of the gene-targeting nucleotide sequence (GTNS), gene targeting substrate (GTS), or both, of the present invention is homologous to a target locus within a cell. In various embodiments, the GTNS or GTS further comprises at least one nucleotide difference when compared to the target locus sequence. In comparison with a target locus, the gene-targeting nucleotide sequence may comprise one or more single base pair modifications, deletions, additions or any combination thereof, provided that sufficient homology between the GTNS or GTS and the target locus remains to permit modification of the target locus. Alternately, the GTNS or GTS may comprise two or more segments that boarder a nucleotide sequence of interest, where the nucleotide sequence of interest is not homologous with the target locus. In this alternative, the boarder segments comprise sufficient homology with a target locus to permit modification of the target locus arising from the nucleotide sequence of interest. Furthermore, a decrease in the overall homology between a GTNS or GTS and a target locus may arise due to a deletion or an insertion within either the target locus, the GTNS or GTS, or the use of a cDNA to encode the GTNS or GTS and sequence differences arising due to introns present within the target locus. Other reasons for dissimilarity may also occur, however, such dissimilar sequences may still be used to modify a target locus provided that a sufficient portion of the GTNS or GTS is homologous with the target locus to result in modification of the target locus.

By the term "homologous" or "homology" it is meant that a first nucleotide sequence comprises between about 70% and about 100% sequence similarity with a second nucleic acid sequence. Preferably, the nucleotide sequences exhibit between about 85% to about 99% similarity, more preferably between about 95% and 100% similarity. An example of a first nucleotide sequence may be a GTNS or a GTS, or a segment of a GTNS or GTS, for example a boarder segment. An example of a second nucleic acid sequence may be a target locus of interest. It is to be understood that the degree of homology between a GTNS or GTS and a target locus will vary depending on whether a full length GTNS or GTS exhibits homology to the target locus, or whether segments that boarder, or that are within the GTNS or GTS, comprises one or more than one nucleotide sequences that are homologous with a target locus of interest.

Therefore, the present invention pertains to a GTNS comprising one, or more than one, region of 15 to about 300, or to about 500 nucleotides in length, and exhibiting about 70% to about 100% sequence similarity with a target locus sequence (determined using the following conditions: Program: blastp; Database: nr; Expect 10; filter: default; Alignment: pairwise; Query genetic Codes: Standard (1)).

The GNTS may further comprise a nucleic acid sequence of interest that may or may not exhibit homology with the target locus of interest. Using this method, a target locus of interest may be modified with a partially homologous nucleic acid sequence, or a non-homologous nucleic acid sequence that also comprises regions of homology as described above to permit recombination with the target locus.

The homology between the GTNS or GTS, or boarder segments of the GTNS or GTS, and the target locus may be readily determined by one of skill in the art using any suitable sequence alignment algorithm, for example but not limited to BLAST (GenBank URL: www.ncbi.nlm.nih.gov/cgi-bin/BLAST/, using default parameters: Program: blastp; Database: nr; Expect 10; filter: default; Alignment: pairwise; Query genetic Codes: Standard (1)).

The degree of homology between sequences may be expressed as a percentage of identity when the sequences are optimally aligned, meaning the occurrence of exact matches between the sequences. Optimal alignment of sequences for comparisons of identity may be conducted using a variety of algorithms, such as, but not limited to the local homology algorithm of Smith and Waterman, 1981, *Adv. Appl. Math* 2: 482, the homology alignment algorithm of Needleman and Wunsch, 1970, J. Mol. Biol. 48:443, the search for similarity method of Pearson and Lipman, 1988, *Proc. Natl. Acad. Sci. USA* 85: 2444, and the computerised implementations of algorithms such as, but not limited to GAP, BESTFIT, FASTA and TFASTA in the Wisconsin Genetics Software Package, Genetics Computer Group, Madison, Wis., U.S.A. Sequence alignment may also be carried out using the BLAST algorithm, described in Altschul et al., 1990, *J. Mol. Biol.* 215: 403-10 (using the published default settings or others). Software for performing BLAST analysis is also available through the National Center for Biotechnology Information (through the internet at http://www.ncbi.nlm.nih.gov/). The BLAST programs may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (which may be changed in alternative embodiments to 1 or 0.1 or 0.01 or 0.001 or 0.0001; although E values much higher than 0.1 may not identify functionally similar sequences, it is useful to examine hits with lower significance, E values between 0.1 and 10, for short regions of similarity), M=5, N=4, for nucleic acids a comparison of both strands. For protein comparisons, BLASTP may be used with defaults as follows: G=11 (cost to open a gap); E=1 (cost to extend a gap); E=10 (expectation value, at this setting, 10 hits with scores equal to or better than the defined alignment score, S, are expected to occur by chance in a database of the same size as the one being searched; the E value can be increased or decreased to alter the stringency of the search.); and W=3 (word size, default is 11 for BLASTN, 3 for other blast programs). The BLOSUM matrix assigns a probability score for each position in an alignment that is based on the frequency with which that substitution is known to occur among consensus blocks within related proteins. The BLOSUM62 (gap existence cost=11; per residue gap cost=1; lambda ratio=0.85) substitution matrix is used by default in BLAST 2.0. A variety of other matrices may be used as alternatives to BLOSUM62, including: PAM30 (9,1,0.87); PAM70 (10,1,0.87) BLOSUM80 (10,1,0.87); BLOSUM62 (11,1,0.82) and BLOSUM45 (14,2,0.87). One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, but not wishing to be limiting, stringent conditions are selected to be about 5° C. lower than the thermal melting point for the specific sequence at a defined ionic strength and pH.

By the term "target locus" it is meant one or more regions of the genome of a host. The target locus may comprise any nucleotide sequence of interest within a cell that is to be modified or replaced. It is to be understood that several loci may have similar sequences, that exhibit sufficient homology with a GTNS, or a segment thereof, and that a host may comprise multiple target loci. Preferably, the gene of interest at the target locus is normally found in nature within the cell. However, a target locus may also comprise an exogenous nucleotide sequence that has been integrated in the genome of a cell. The target locus may comprise a nucleotide sequence that encodes a protein, or a portion of a protein. Alternatively, the target locus may comprise a nucleotide sequence, such as, but not limited to a regulatory region. Examples of regulatory regions may include, but are not limited to promoters, enhancers terminators, matrix attachment regions, splicing sites, or portions thereof. Any nucleotide sequence within the genome of a cell may be considered a target locus according to the present invention.

The cell may for example be a eukaryotic cell, such as a plant cell, animal cell, insect cell, or yeast cell. The invention also provides hosts comprising the nucleotide constructs of the invention. The host may for example be a eukaryotic host such as a plant, animal, insect, or yeast host. The invention provides lineal relatives of a host. By lineal relative, it is meant either a parent or progeny of the host.

The GTNS may for example be homologous to a wide variety of nucleic acids of interest within a host. A nucleic acid of interest may include for example, coding and non-coding regions of a gene encoding a protein or a fragment thereof, or snRNA genes. A nucleic acid of interest may for example include, a portion of a gene that encodes a pharmaceutically active protein or fragment thereof, for example growth factors, growth regulators, antibodies, antigens, their derivatives useful for immunization or vaccination and the like. Such proteins include, but are not limited to, interleukins, insulin, G-CSF, GM-CSF, hPG-CSF, M-CSF or combinations thereof, interferons, for example, interferon-alpha, interferon-β, interferon-gamma, blood clotting factors, for example, Factor VIII, Factor IX, or tPA or combinations thereof. A nucleic acid of interest may also encode an industrial enzyme, protein supplement, nutraceutical, or a value-added product for feed, food, or both feed and food use. Examples of such proteins include, but are not limited to proteases, oxidases, phytases, chitinases, invertases, lipases, cellulases, xylanases, enzymes involved in oil biosynthesis, hydrogenases, dehydrogenases, hydroxylases, dehydroxylases, etc.

The msr-msd region and a sequence of interest are "operably linked" when the sequences are functionally connected so as to permit transcription of the sequence of interest resulting in the production of msDNA. Similarly, a transcriptional regulatory region and a sequence of interest are "operably linked" when the sequences are functionally connected so as to permit transcription of the sequence of interest to be mediated or modulated by the transcriptional regulatory region.

The gene-targeting nucleotide sequence (GTNS) of the present invention, which exhibits some homologys to a gene of interest at a target locus, may be located in the msr, msd, between the msr and msd coding regions, or at and end of a mofied msd region in such a manner that the GTNS does not affect folding or function of the msr-GRNS-msd transcript. Further, the position of the gene targeting sequence is such that it does not prevent recognition of the ribonucleotide G residue used by the reverse transcriptase to prime transcription. In some embodiments, the GTNS is positioned between the msr and msd coding regions of the retron, within the msd region (see FIG. 5), or in some cases at an end of the msd region (e.g. FIG. 11). For example, which is not to be considered limiting in any manner, the msd region may be modified to accept a GTNS within the hairpin loop as shown in FIGS. 4, 3B, 5. In some embodiments, a GTS of up to 500 nucleotides in length have been produced (FIGS. 5 and 6).

The retron may also be modified so that the free 5' and 3' termini of msd and msr regions are spatially separated from the internal rG residue of the RNA transcript required for priming reverse transcription in the synthesis of msDNA (as described earlier; see FIG. 11). This structure provides a 5' end for addition of a GTNS. Termination of replication of the msr-GTNS-msd results by the reverse transcriptase falling off the end of the GTNS. Using this cassette, synthesis of a GTS of up to 500 base pairs has been observed (FIGS. 12 and 13).

Other modifications of msd, or msr may also be made to permit insertion of a GTNS within msd without altering the functioning of msr-GTNS-msd or the production of msDNA. For example, which is not to be considered limiting, the msd region may be altered to introduce a second stem-loop structure, in addition to the insertion of the GTNS within the hairpin of the first stem-loop structure, as shown in FIGS. 4 and 9. This second stem-loop structure (stop stem) ensures specific termination of replication by the reverse transcriptase so as to produce a GTS with a well defined 3' terminus.

Canadian Patent Application No. 2,075,515 (which is incorporated herein by reference) describes heterologous nucleotide sequences incorporated into retrons which may be used to produce polypeptides or inhibit production of genes via antisense technology. The gene-targeting nucleotide sequence of the present invention may also be located in a similar location when employed with the same retron or different retrons as described therein.

The gene-targeting nucleotide sequence may be any length but is preferably less than about 5 kb nucleotides, or also less than about 2 kb, provided that an msDNA product is produced. Non-limiting examples of production of msDNA are provided using a GTNS of about less than about 500 nucleotides (FIGS. 5, 6, 12 and 13), however, it is to be understood that longer nucleotide sequences may also be used. As demonstrated in FIGS. 3B and 11, the msr-msd sequence may be altered to permit the insertion of longer GTNS.

In some embodiments, a nucleotide sequence if interest resides between segments of the GTNS that are homologous, or preferably, identical to the target locus. In this regard, the GTNS may comprise more than about 15 nucleotides, preferably more than about 25 nucleotides in length, over the region of homology or identity with the target locus sequence. In some embodiments, the region of the gene targeting sequence which is dissimilar to the target locus sequence is located between regions of higher homology or identity to the gene targeting nucleotide sequence.

In some embodiments, increasing the degree of homology between the GTS and the target locus may promote modification of the genome of a cell by gene conversion, homologous recombination or other process. Accordingly, in one aspect of the invention, the nucleotide sequence of the target locus of interest may be changed to be the same as or complimentary to the nucleotide sequence encoded by the gene-targeting nucleotide sequence of the present invention.

In some embodiments, at least one of the copies of the gene targeting sequence, or a portion thereof, interacts with a target sequence in the genome of the host to modify the target sequence to produce a heritable change, for example by the processes of homologous recombination, or gene conversion or nucleic acid repair. As discussed above, a portion of the GTS may have a high degree of identity to a portion of the target sequence, such that the sequence is sufficiently identical to facilitate homologous pairing with the target sequence.

The relevant portion of the reproducible sequence may in some embodiments be 5, 10, 15, 20, 25 or more nucleotides in length, and the identity between the portions of the reproducible and target sequences may for example be 50%-100%, more than 60%, 70%, 80%, 90% or 95%. In some embodiments, the degree of homology and the length of the relevant portion of the reproducible sequence may be selected so that the reproducible sequence is homologous only to the target sequence in the genome, and not to other sequences in the genome. The relevant portion of the reproducible sequence may differ from the corresponding portion of the target sequence by having at least one nucleic acid deletion, substitution or addition.

In alternative embodiments, the methods of the present invention may utilize a variety of reverse transcriptases, for example being of either eukaryotic or prokaryotic origin, or an analog or derivative thereof, provided that the RT is capable of recognizing and reverse transcribing the RNA transcription product produced by a gene targeting construct of the invention (such as the msr-GTNS-msd region of such a transcription product). The sequence encoding RT may be separate from the RNA template, for example, msr-GTNS-msd, or may be fused to the RNA template encoding for example, msr-GTNS-msd as required.

In an aspect of the invention, the nucleotide sequence encoding a reverse transcriptase further comprises a nuclear localization signal sequence (NLS). The NLS may be selected to promote accumulation of the RT in the nucleus of a host cell, and to increases the yield of msDNA produced (see FIG. 2). The use of an NLS may be particularly advantageous with an RT of prokaryotic origin. The NLS may for example be added to the 3' or 5' ends, or within the interior of the RT. Also, the RT sequence may be modified to encode an NLS, rather than fusing an NLS to the RT. A variety of nuclear localization signal sequences may be employed in the present invention, selected for example so that the NLS is active within the cell type in which the reverse transcriptase is produced. Examples of nuclear localization signal sequences are listed in Table 1.

TABLE 1

Nuclear Localization Signals

| Nuclear Protein | Organism | NLS | Ref |
|---|---|---|---|
| AGAMOUS | A | RienttnrqvtfcKRR | (i) |
| TGA-1A | T | RRlaqnreaaRKsRlRKK | (ii) |
| TGA-1B | T | KKRaRlvrnresaqlsRqRKK | (ii) |
| O2 NLS B | M | RKRKesnresaRRsRyRK | (iii) |
| NIa | V | KKnqkhklkm-32aa-KRK | (iv) |
| Nucleoplasmin | X | KRpaatkkagqaKKKKl | (v) |
| NO38 | X | KRiapdsaskvpRKKtR | (v) |
| N1/N2 | X | KRKteeesplKdKdaKK | (v) |
| Glucocorticoid receptor | M, R | RKclqagmnleaRKtKK | (v) |
| α receptor | H | RKclqagmnleaRKtKK | (v) |
| β receptor | H | RKclqagmnleaRKtKK | (v) |
| Progesterone receptor | C, H, Ra | RKccqagmvlggRKfKK | (v) |
| Androgen receptor | H | RKcyeagmtlgaRKlKK | (v) |
| p53 | C | RRcfevrvcacpgRdRK | (v) |

†A, *Arabidopsis*; X, *Xenopus*; M, mouse; R, rat; Ra, rabbit; H, human; C, chicken; T, tobacco; M, maize; V, potyvirus.
References:
(i), Yanovsky et al., 1990, Nature, 346: 35-39.
(ii), van der Krol and Chua, 1991, Plant Cell, 3: 667-675.
(iii), Varagona et al., 1992, Plant Cell, 4: 1213-1227.
(iv), Carrington et al., 1991, Plant Cell, 3: 953-962.
(v), Robbins et al., 1991, Cell, 64: 615-623.

In various embodiments, the msr-GTNS-msd, and the nucleotide sequence encoding the RT, are in operative association with one or more appropriate regulatory regions, for example but not limited to a promoter, that mediates transcription of the respective sequences. The msr-GTNS-msd and nucleotide sequence encoding the RT may for example be in operative association with a single regulatory region. Alternatively, the msr-GTNS-msd may be in operative association with a first regulatory region, and the nucleotide sequence encoding the RT in operative association with a second regulatory region. In such embodiments, the first regulatory region and the second regulatory region may be the same or different.

By "regulatory region" or "regulatory element" it is meant a portion of nucleic acid typically, but not always, upstream of the protein coding region of a gene, which may be comprised of either DNA or RNA, or both DNA and RNA. When a regulatory region is active, and in operative association with a gene of interest, this may result in expression of the gene of interest. A regulatory element may be capable of directly or indirectly mediating organ specificity, or controlling developmental or temporal gene activation. A "regulatory region" includes promoter elements, core promoter elements exhibiting a basal promoter activity, elements that are inducible in response to an external or developmental stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element typically comprises a basal promoter element, responsible for the initiation of transcription, as well as other regulatory elements that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well.

An inducible regulatory region is one that is capable of directly or indirectly activating transcription of one or more DNA sequences or genes in response to an inducer. In the absence of an inducer the DNA sequences or genes will not be transcribed. Typically the protein factor, that binds specifically to an inducible regulatory region to activate transcription, may be present in an inactive form which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, radiation, or toxic elements or indirectly through the action of a pathogen or disease agent such as a virus. A plant cell containing an inducible regulatory region may be exposed to an inducer by externally applying the inducer to the cell or plant such as by spraying, watering, heating, exposing to radiation, culturing in an inducing agent, or similar methods. Inducible regulatory elements may be derived from either plant or non-plant genes (e.g. Gatz, C. and Lenk, I. R. P., 1998, Trends Plant Sci. 3, 352-358; which is incorporated by reference). Examples, of potential inducible promoters include, but not limited to, teracycline-inducible promoter (Gatz, C., 1997, Ann. Rev. Plant Physiol. Plant Mol. Biol. 48, 89-108; which is incorporated by reference), steroid inducible promoter (Aoyama, T. and Chua, N. H., 1997, Plant J. 2, 397-404; which is incorporated by reference) and ethanol-inducible promoter (Salter, M. G., et al, 1998, Plant Journal 16, 127-132; Caddick, M. X., et al, 1998, Nature Biotech. 16, 177-180, which are incorporated by reference) cytokinin inducible IB6 and CKI1 genes (Brandstatter, I. and Kieber, J. J., 1998, Plant Cell 10, 1009-1019; Kakimoto, T., 1996, Science 274, 982-985; which are incorporated by reference) and the auxin inducible element, DR5 (Ulmasov, T., et al., 1997, Plant Cell 9, 1963-1971; which is incorporated by reference).

In some embodiments, the regulatory region or regions employed in the constructs of the invention are cell-cycle-specific, such as regulatory regions active in the S phase, G1/S boundary phase, G2 phase, or combinations thereof of the cell cycle. Examples of such regulatory regions include, but are not limited to histone promoters, for example H4 promoter from *Arabidopsis* (AtH4; Atanassova et al. 1994), cyclins (such as CycD3), DNA replication proteins and DNA recombination and DNA repair proteins.

The nucleotide sequence of the present invention may also comprise a marker gene in addition to the msr-GTNS-msd and reverse transcriptase coding regions. The marker gene may be separate from, or fused with the msr-GTNS-msd and reverse trasncriptase sequence and comprise a portion of the retron and be expressed within the msDNA (GTS). Any marker gene in the art may be used in the present invention. Examples of marker genes include, but are not limited to antibiotic resistance genes, genes encoding enzymes that may be detected by enzyme assays, genes encoding products that may be detected immunologically, or genes that give rise to an observable phenotype. Useful selectable markers include enzymes which provide for resistance to an antibiotic such as gentamycin, phosphinothricin, hygromycin, kanamycin, and the like. Similarly, enzymes providing for production of a compound identifiable by colour change such as GUS (glucuronidase), or luminescence, such as luciferase or GFP may also be used. Further, as would be understood by a person of skill in the art, the marker gene may comprise an appropriate regulatory sequence that permits the marker gene to be expressed in a cell or tissue, for example, but not limited to a plant or animal cell or tissue.

In some embodiments, the msr-GTNS-msd of the present invention comprises at least two sets of inverted repeat nucleotide sequences. The inverted repeat sequences permit base pairing between specific regions of the retron transcription product, and may be adapted to enhances recognition and reverse transcription of the retron transcription product by the selected reverse transcriptase. The inverted repeats of known retrons vary considerably in sequence and size. For example, the inverted repeats in the Mx162 retron, termed a1 and a2, are 34 nucleotides long, while the inverted repeats in the Ec86 retron of *E. coli* B are 12 nucleotides long. Although the inverted repeat sequences are different in size, they are typically located within the same approximate position within a retron. The inverted repeat regions of the constructs of the present invention may be similarly varied.

The msr-GTNS-msd of the present invention may be assembled in an appropriate vector to facilitate transfer of the gene targeting system components into a cell. Methods which may be employed to enhance entry of the vector into a cell include, but are not limited to biolistic delivery (Klein, T M, et al. 1988, Proc Natl Acad Sci USA 85, p. 8502), chemical treatment (Kresn, F A, et al., 1982, Nature 296, p. 72; Deshayes, A, et al., 1985, EMBO J. 4: 2731-2737), physical treatment (Shillito, R D, 1985, Bio/technology 3, p. 1099; D'Halluin, K, et al., 1992, Plant Cell 4: 1495-1505; Crossway, A, 1986, Mol Gen Genet. 202, p. 179), or combination thereof. In an aspect of an embodiment wherein the cell is a plant cell, the vector may be an *Agrobacterium* Ti plasmid delivered by an *Agrobacterium* (Gasser, C. S., and Fraley, R. T., 1989, Science 244, p. 1293). The constructs of the present invention can be introduced into plant cells using Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, *Fundamentals of Gene Transfer in Plants*. In *Plant Metabolism,* 2d Ed. DT. Dennis, D H Turpin, D D Lefebrve, D B Layzell (eds), Addison Wesly, Langmans Ltd. London, pp. 561-579 (1997). The present invention further includes a suitable vector comprising the chimeric gene construct.

Following transformation of a host cell with a nucleotide sequence of the present invention, the msr-GTNS-msd may be integrated into the host genome. If the nucleotide sequence of the msr-GTNS-msd comprises a marker gene, the transformed cells may be selected from non-transformed cells using an appropriate selection method.

In an aspect of the invention, there is provided temporal and/or spatial regulation of the production of a msDNA comprising the gene targeting nucleotide sequence of the present invention. For example, by using appropriate regulatory sequences, the production of msDNA may be coordinated with selected points in the cell cycle or made to occur in particular tissues or during particular developmental stages so as to regulate the timing of gene targeting when endogenous homologous recombination functions may be activated. In alternative embodiments, the invention may for example provide for expression of a msDNA comprising a gene targeting sequence in the following manner:

i) Constitutive: msDNA comprising the gene targeting nucleotide sequence of the present invention may be produced in all cells, tissues and at all developmental and physiological stages. In some instances, constitutive production of msDNA comprising a gene targeting nucleotide sequence may be undesirable because of unwanted physiological or genetic load in the cell. Therefore, more specific expression may be advantageous in some situations.

ii) Cell cycle coordination: Endogenous homologous recombination and DNA repair activities may be elevated during S-phase of the cell cycle (Wong, E A, Capecchi, M R, 1987 Mol Cell Biol 7: 2294-2295) as well as during G-2-phase [REFs]. Therefore, production of msDNA comprising a gene targeting nucleotide sequence may be coordinated with S-phase and/or G-2-phase so that endogenous DNA recombination and repair enzymes may promote modification of the target locus by transfer of the genetic information from the gene targeting nucleotide sequence to the gene of interest.

Synchronization of the production and presence of msDNA comprising a gene targeting nucleotide sequence in vivo with selected points in the cell cycle may for example be achieved through the use of cell-cycle specific promoters. Examples of cell-cycle specific promoters include, but are not limited to histone promoters and promoters of gene encoding cyclins, cell division control genes, and genes encoding proteins involved in homologous recombination (e.g. RAD51, RAD54, RAD52, RAD55, RAD57, MRE11, RAD50, BRCA1, BRCA2). In the case of histone promoters, histone genes are expressed coordinately with DNA replication to produce the abundant proteins required to package the newly synthesized DNA (Reichheld, J. P., et. al. 1998, Nucleic Acids Res 26: 3255-3262; Osley, M. A., 1991, Annu. Rev Biochem 60: 827-861). A non limiting example is AtH4. In the case of cyclins and cell division control genes are expressed at various points in the cell cycle to initiate and terminate passage through the different stages of the cell cycle (Huntley, R. P., and Murray, J. A. 1999, Curr. Opin. Plant Biol 2: 440-446), for example but not limited to AtCycD3.

In an aspect of an embodiment of the present invention, the coordination of the production of msDNA comprising a gene targeting nucleotide sequence with cell division may allow the msDNA comprising a gene targeting nucleotide sequence to be produced in dividing cells, for example, but not limited to, in the apical meristem of a plant. This may provide opportunities for a gene targeting event to occur in a cell which will, directly or indirectly, later give rise to the germ line, so that progeny plants may stably inherit the modified target locus.

Further alternatives are as follows:

iii) Developmental stage coordination: Endogenous recombination and repair activities may be elevated during certain developmental stages, for example meiosis (Roeder, G. S., 1997, Genes Dev. 11: 2600-2621). Therefore, production of msDNA comprising a gene targeting nucleotide sequence (GTS) may be coordinated with these developmental stages so as to exploit the elevated levels of endogenous recombination and repair activities to promote or enhance the transfer the genetic information from the gene targeting nucleotide sequence to the target locus. For example, but not wishing to be limiting, this may be achieved using meiosis-specific promoters. Numerous examples exist of genes which are expressed during meiosis and whose promoters may be adapted for use in this invention (for example but not limited to Klimyuk, V. I., et. al. 1997, Plant J. 11: 1-14; Ross-Macdonald, P., and Roeder, G. S., 1994, Cell 79: 1069-1080; Kobayashi, T., 1994, DNA Res. 1: 15-26; Chu, S, et. al. 1998, Science 282: 699-705).

iv) Tissue specific promoters: Specific tissues may have elevated endogenous recombination and repair activity and/or be more amenable for increased gene targeting frequency due to other biochemical, cellular, physiological or developmental states. For example, developing embryos undergo rapid cell division and have active recombination and repair systems. Production and accumulation of GTS in embryos or embryonic tissues could lead to increased gene targeting frequency. In another example, developing and mature male and female gametophytes (i.e. pollen and egg cells) are haploid. Haploid cells may be more recombinogenic and amenable to gene targeting than diploid cells (Schaefer, D. G., and Zryd, J. P.: 1997, Plant J. 11: 1195-1206). Therefore, production of GTS in these cells and tissues using appropriate promoters may increase gene targeting frequency.

Tissue specific promoters could also be employed if gene targeting is to occur only within a particular tissue, or so that other tissues are not altered by the gene targeting nucleotide sequence. Thus, without wishing to be limiting, a tissue or organ-specific promoter may be employed to create a chimeric plant or animal containing both unmodified and modified target genes, each being present in different tissues or organs.

Achieving gene targeting during meiosis and/or in gametes may also have additional advantages in alternative embodiments, including, but not limited to, embodiments adapted to generate homozygous lines with targeted changes. If the gene targeting event is adapted to occur at Meiosis I, then each of the resultant four gametes may contain the specified genetic change. When the GTS is produced in or delivered to meiotic cells, such as in early stages of Meiosis I, large numbers of male and female gametes with the desired targeted genetic changes may result.

In plants and other monoecious organisms where both male and female gametes are produced by the same individual, simply self-crossing the individual may result in a relatively high frequency of diploid progeny which are homozygous for the targeted genetic change. In alternative embodiments, in the case of plants, one may obtain individuals homozygous for the targeted genetic change by performing microspore culture after delivering gene targeting substrate to the meiotic cells. Microspores are haploid cells resulting from meiosis in the plant anther. These cells can in some cases be cultured to regenerate entire plants (Coventry, J, Kott, L, Beversdorf, W: 1998, Manual for microspore culture technique for *Brassica napus*. University of Guelph, Guelph). The plants can be chemically treated to create a diploid chromosome content and are thus homozygous for all genetic information. Therefore, microspores carrying the targeted genetic change as a result of treating meiotic cells or the microspores themselves with GTS may be cultured and converted into plants that are homozygous for the targeted genetic change.

Alternatively, where male and female gametes are produced by different individuals, the gene targeting process could be performed in both male and female plants, and the two crossed. In addition, achieving gene targeting during meiosis and/or in gametes may be advantageous in embodiments adapted for direct germ-line transmission of a targeted genetic change. Targeted genetic change generated in a gamete in accordance with the invention may be heritable in the offspring. In contrast, gene targeting conducted in somatic cells will only be heritable if the somatic cell can directly or indirectly give rise to the germ-line from which gametes are derived.

In alternative embodiments, orchestrating gene targeting during meiosis and/or in gametes may be advantageous in embodiments adapted to target changes to either maternal or paternal derived chromosomes. Targeted changes in either maternal or paternal chromosomes may for example be obtained with this invention by producing or delivering GTS to either female or male reproductive organs.

Further alternatives are as follows:

v) Environmentally stimulated: In some embodiments, the invention may provide for activation of gene targeting by environmental stimuli, for example by linking expression of components of the gene targeting system of the invention to promoters that are responsive to environmental stimuli. Exposure of cells to different environmental conditions can elevate activity of endogenous DNA recombination and repair processes (Friedberg, E C, et al., 1995, Amer. Soc. Microbiol., Washington, D.C.; Hoffmann, G R 1994, Environ. Mol. Mutagen. 23 Suppl 24: 59-66; Schiestl, R H., 1989, Nature 337: 285-288). Therefore, it may be beneficial to coordinate production of gene targeting substrate in response to these stimuli to take advantage of the elevated recombination and repair activity so as to transfer the genetic information from the gene targeting substrate to the target locus.

For example, the RAD51 gene encodes an enzyme involved in DNA recombination and repair that is induced in response to DNA damaging agents (Basile, G., 1992, Mol. Cell Biol. 12: 3235-3246; Rozwadowski, K, et al., 1999, 10th International Conference on *Arabidopsis* Research, Melbourne, Australia, Jul. 4-8, 1999). Components of the gene targeting system of the invention could be fused to the RAD51 promoter to coordinate induction and production of gene targeting substrate with endogenous recombination and repair functions in response to environmental stimuli.

vi) Inducible: In alternative aspects of the invention, inducible promoters may be provided to drive expression of components of the gene targeting system. For example, a sequence encoding components of the gene targeting system may be cloned behind an inducible or repressible promoter. The promoter may then be induced (or de-repressed) by appropriate external treatment of the organism when organismal development proceeds to a point when gene targeting is desired. Regulation of such promoters may be mediated by environmental conditions such as heat shock (Ainley, W M, 1990, Plant Mol. Biol. 14: 949-967), or chemical stimulus. Examples of chemically regulatable promoters active in plants and animals include the ecdysone, dexamethasone, tetracycline and copper systems (Martinez, A, et al., 1999, Plant J. 19: 97-106; Bohner, S, et al., 1999, Plant J. 19: 87-95; Gatz, C, et al., 1991, Mol. Gen. Genet. 227: 229-237; Weinmann, P, et al., 1994, Plant J. 5: 559-569; Mett, V L, 1996, Transgenic Res. 5: 105-113; Mett, V L, et al. Proc. Natl. Acad. Sci. U.S.A 90: 4567-4571).

vii) Bipartitie Systems: nuclear localization signal sequence In alternative embodiments, bipartite promoters may be used to express components of the gene targeting system. Bipartite systems may for example consist of 1) a minimal promoter containing a recognition sequence for 2) a specific transcription factor. The bipartite promoter is inactive unless it is bound by the transcription factor. The gene of interest may be placed behind the minimal promoter so that it is not expressed, and the transcription factor may be linked to a 'control promoter' which is, for example, a tissue-specific, developmental stage specific, or environmental stimuli responsive promoter. The transcription factor may be a naturally occurring protein or a hybrid protein composed of a DNA-binding domain and a transcription-activating domain. Because the activity of the minimal promoter is dependent upon binding of the transcription factor, the operably-linked coding sequence will not be expressed unless conditions are appropriate for expression by the 'control promoter'. When such conditions are met, the 'control promoter' will be turned on facilitating expression of the transcription factor. The transcription factor will act in trans and bind to the DNA recognition sequence in the minimal promoter via the cognate DNA-binding domain. The activation domain of the transcription factor will then be in the appropriate context to aid recruitment of RNA polymerase and other components of the transcription machinery. This will cause transcription of the target gene. With this bipartite system, the gene of interest will only be expressed in cells where the 'control promoter' is expressed (i.e. the target gene will be expressed in a spatial and temporal pattern mirroring the 'control promoter' expressing the transcription factor). In addition, a bipartite system could be used to coordinate expression of more than one gene. Different genes could be placed behind individual minimal promoters all of which have the same recognition sequence for a specific transcription factor and whose expression, therefore, is reliant upon the presence of the transcription factor. The transcription factor is linked to a 'control promoter'. Therefore, when cells enter an appropriate stage where gene targeting is to be initiated, the control promoter expresses the transcription factor which then can coordinately activate expression of the suite of target genes. Use of a bipartite system may have the advantage that if expression of the target genes is no longer required in a particular plant or animal line, then the transcription factor may be bred out, so that without the transcription factor present, the target gene(s) will no longer be expressed in this line. If the target genes are desired to be expressed at a later stage, the promoter::transcription factor locus may be bred back into the line.

Minimal promoter elements in bipartite promoters may include, for example:

1) truncated CaMV 35S (nucleotides −59 to +48 relative to the transcription start site; Guyer, D, et al. 1988, Genetics 149: 633-639);
2) DNA recognition sequences: *E. coli* lac operator (Moore, I, et al. 1998, Proc. Natl. Acad. Sci. U.S.A 95: 376-381; Labow, M A, et al., 1990, Mol. Cell Biol. 10: 3343-3356) yeast GAL4 upstream activator sequence (Guyer, D, et al. 1988, Genetics 149: 633-639); TATA BOX, transcription start site, and may also include a ribosome recruitment sequence.

Bipartite promoters may for example include transcription factors such as: the yeast GAL4 DNA-binding domain fused to maize C1 transcription activator domain (Guyer, D, et al. 1988, Genetics 149: 633-639); *E. coli* lac repressor fused to yeast GAL4 transcription activator domain (Moore, I, et al. 1998, Proc. Natl. Acad. Sci. U.S.A 95: 376-381); or the *E. coli* lac repressor fused to herpes virus VP16 transcription activator domain (Labow, M A, et al., 1990, Mol. Cell Biol. 10: 3343-3356).

In some embodiments, the 'control promoter', which may be for example, a tissue-specific, developmental stage specific, or environmental stimuli responsive promoter may promote transcription at too low of a level (i.e. weakly expressed) or at too high of a level (i.e. strongly expressed) to achieve the desired effect for gene targeting. Therefore, for example, a weak control promoter may be used in a bipartite system to express a transcription factor which can promote a high level of expression when it binds to the minimal promoter adjacent to an appropriate nucleotide sequence. Thus, while the nucleotide sequences of the present invention may be expressed at low levels if they were fused directly to the 'control promoter', this promoter can indirectly facilitate high level transcription of the target gene of interest by expressing a very active transcription factor. Without wishing to be bound by theory, the transcription factor may be present at low levels when expressed by a weak "control promoter" but because it is so effective at activating transcription at the minimal promoter fused to a specific nucleotide sequence to be expressed, a higher level of expression of the specific nucleotide sequence may be achieved than if the gene was directly fused to the weak 'control promoter'. In addition, the transcription factor may also be engineered so that its mRNA transcript is more stable or is more readily translated, or that the reverse transcriptase protein itself is more stable. Conversely, if the "control promoter' is too strong for a desired application, it may be used to express a transcription factor with low ability to promote transcription at the minimal promoter.

In alternative embodiments, a 'control promoter' may be used in the nucleotide sequence of the present invention to express a heterologous RNA-polymerase which recognizes specific sequences not naturally present in the cell. For example, T7 RNA Polymerase may be used in eukaryotes to specifically promote transcription of a target gene linked to the T7 RNA Pol recruitment DNA sequence (Benton, B. M., 1990, Mol. Cell Biol. 10: 353-360). Components of the gene targeting system may then be regulated by the expression of T7 RNA Polymerase.

The embodiments of the invention relating to the control of production of msDNA comprising a gene targeting sequence as exemplified for plants may be applicable to animals as well as other eukaryotes, and prokaryotes, where there is conservation of processes and abilities to achieve gene expression, such as, but not limited to the constitutive, cell-cycle coordinated, developmentally coordinated, tissue specific, environmentally responsive, inducible, bipartite or any combination thereof.

In an aspect of the present invention, gene modification of a target locus mediated by the gene targeting nucleotide sequence of the present invention may for example occur at any stage from the initial transformation event, through all subsequent cell divisions, right up to a fully regenerated host, for example a plant or animal, and the production of gametes. Thus there are numerous opportunities for the gene targeting event to occur. When a cell that gives rise to the germ line has undergone the gene targeting event, the genetic change may be present in the gametes and stably passed on to subsequent generation. If one allele of the target locus is altered by the gene targeting substrate in a diploid organism then up to 50% of the gametes from that particular germ line may be expected to carry the modified allele. However, if both alleles of the target locus are altered then all gametes from that germ line would be expected to carry the modified allele.

During meiosis normal chromosome recombination and reassortment may produce gametes which have the targeted change but no longer carry the nucleotide sequence of the invention comprising the retron. Thus self-crossing or outcrossing of a modified host, for example a plant, can lead to progeny that possess the modified target locus but not the initial nucleic acid sequence comprising the retron of the present invention. This may be especially likely if the target locus has little or no genetic linkage to the genomic locus where the nucleotide sequence of the present invention has inserted. Therefore, in an aspect of a embodiment of the invention, it may be possible to produce genetically changed hosts, including either plants or animals which no longer have any foreign DNA sequences.

According to an aspect of the invention, the creation of plants with specific genetic alterations at a gene of interest may involve a single tissue culture procedure, for example, but not limited to following the initial transformation process wherein the retron of the present invention which comprises the gene targeting nucleotide sequence is introduced to a plant cell. It may be possible for the cell or a progeny thereof to undergo gene targeting during cell proliferation and regeneration into a plant. When this plant sexually reproduces, it may be possible for numerous progeny plants containing the genetic change resulting from gene targeting to be produced, which may be derived from the initial single transformation event. Thus the present invention may be employed to minimize the number of tissue culture propagules required to be maintained in order to identify a plant which comprises replacement of a gene of interest with the homologous nucleotide sequence of the present invention. Further, reducing tissue culture procedures may be advantageous if genetic changes resulting from somaclonal variation during tissue culture may occur. In an alternate embodiment of the present invention, it may be possible to employ plant transformation procedures that require no tissue culture steps (for example, Bechtold, N., and Pelletier, G: 1998, Methods Mol Biol 82: 259-266; Clough, S. J., and Bent, A. F., 1998 Plant J 16: 735-74).

In alternative embodiments, specific changes to a gene of interest, for example a target locus of interest, may also be achieved when the msDNA comprising the gene targeting sequence of the present invention is expressed from vectors that are not integrated into the host genome. Accordingly, the invention provides for methods of transiently transforming cells with msDNA comprising a gene targeting sequence.

Also according to the present invention, if the host is a plant or an animal, plant or animal viruses may be used as vectors to carry the retron of the present invention. For example, the retron of the present invention may be cloned into a viral vector. In an aspect of an embodiment, cells or tissues are transformed with the viral vector which comprises the retron of the present invention. In such an embodiment, the reverse transcriptase is transcribed and translated and in turn, produces msDNA (GTS) by reverse transcribing the primary transcript of the retron so that a gene targeting substrate is produced in vivo.

If the viral vector is adapted to be localized and replicate in the host cell nucleus, then the gene targeting substrate may accumulate in nucleo. If the viral vector is localized and replicates in the cytoplasm, movement of the gene targeting substrate into the nucleus may be enhanced, for example, by covalently or non-covalently linking the gene targeting substrate to protein(s) encoding a nuclear localization sequence. The gene targeting substrate may then facilitate the desired genetic change at the target genomic locus. Cells with the targeted genetic change can then be directly regenerated into a plant independently or as part of a chimera with cells not containing the targeted change. When the germ line of the regenerated plant is derived from a cell with the targeted genetic alteration, then the genetic change will be heritable.

In alternative embodiments, the targeted genomic change results in a selectable phenotype so that selection may be applied, resulting in enrichment for the survival and growth of only the cells with the targeted genetic alteration. Thus, the gene targeting events can be enriched and non-modified cells eliminated. If the cells are plant cells, the cells in which the gene of interest has been modified with the gene targeting nucleotide sequence can then be regenerated into plants. Selecting for non-chimeric, genetically altered plants may increase the frequency of obtaining plants homozygous for the specified genetic change in a subsequent generation.

In other embodiments, the viral vector comprising the retron of the present invention may have a conditional ability for propagation. Cells may be treated with such a vector and cultured under "permissive" conditions allowing viral vector replication to occur. Gene targeting events may then be induced to occur and screened or selected. For example, but not wishing to be limiting, the cultured cells/tissues may then be placed under "stringent" conditions which disable the viral vector, so that plants with the specified genetic alteration can be regenerated which are free of the virus vector.

In other embodiments, intact plants are treated with a viral vector comprising the retron of the present invention. Transcription of the retron and genetic alteration of the gene of interest may occur in random cells of the plant tissues. Cells or tissues collected from the treated plant can be cultured appropriately to select or identify cells which have undergone the gene targeting event. These cells may then be regenerated into plants which may pass the genetically modified locus to progeny.

In some aspects, retron constructs of the present invention may be present in the desired host on an extrachromosomal nucleic acid vector, such as, but not limited to an episome, plasmid, virus, or artificial chromosome. In some embodiments these extrachromosomal vectors may be capable of replicating in the host cells by means of a DNA origin of replication inherent to the vector, for example, as in a viral vector or engineered into the vector, for example, as in a plasmid vector. In some embodiments where the retron of the present invention may be cloned into such vectors, the sequence encoding the retron may be replicated as a component of the vector so that the number of copies of retron encoding sequence per cell may equal the number of vector molecules per cell.

In some embodiments, transcription of the msr-GTNS-msd which comprises the gene targeting nucleotide sequence of the present invention and nucleotide sequence encoding the reverse transcriptase may occur independently of the replication of the remainder of the vector. In this manner, the ratio of the number of copies per cell of the msDNA comprising the gene targeting nucleotide sequence compared to the number of copies per cell of the vector backbone encoding the retron may be different than one. The capability to alter this frequency may result in a desired frequency of gene targeting. The preferential amplification of a GTS from the vector backbone may also facilitate modification of a target locus in a fashion that reduces the chance that sequences other than those of the gene targeting nucleotide sequence, such as, but not limited to vector sequences, are incorporated into the target locus. The presence of vector sequences, or other sequences in the target locus may be undesirable because, for example, but not wishing to be limiting or bound by theory, these sequences may confer reduced genetic stability of the modified locus (due to recombination involving vector sequences), or they may incorporate undesirable genetic components into the host genome (such as selectable markers or viral sequences), or they may have undesirable effects on the expression, function or both of the targeted gene nucleotide sequence, or other genes in the host chromosome, for example, but not limited to by the incorporation of additional promoter or enhancer sequences encoded by the vector.

In some embodiments, the nucleotide sequence comprising a retron construct of the invention may be introduced into a cell, for example, but not limited to a plant cell or animal cell by treating the cells with chemicals (Kresn, F A., et. al. 1982, Nature 296, p. 72; Deshayes, A, et. al., 1985, EMBO J. 4: 2731-2737, electrical current (Shillito, R. D., et. al, 1985, Bio/technology 3, p. 1099; D'Halluin, K, et. al., 1992, Plant Cell 4: 1495-1505), by biolistic introduction of particles coated with DNA (Klein, T. M., et. al., 1988, Proc Natl Acad Sci USA 85, p. 8502), by microinjection (Crossway, A, et. al., 1986, Mol Gen Genet. 202, p. 179), or a combination thereof. Any method known in the art may be employed to introduce the nucleotide sequence comprising the retron of the present invention into a cell, tissue or subject.

In alternative embodiments, the present invention may be applied to animals and animal cells, in a variety of ways analogous to those described for plants. Cells and tissues from many animal species can be cultured in such embodiments, in accordance with methods known in the art, including procedures for the transfer of exogenous vector DNA into animal cells to achieve transient or stable expression of vector-encoded genetic elements (with the vector remaining extrachromosomal or being integrated directly into the chromosome, respectively). In accordance with this aspect of the invention, vectors may be engineered to encode the retron of the present invention. The nucleotide sequence of the present invention which comprises the retron may be transferred into target cells by various chemical or physical means known in the art. As with plants, production of msDNA comprising a gene targeting nucleotide sequence results in accumulation of gene targeting sequence in vivo and in nucleo, and gene targeting nucleic acid sequences may be acted upon by host recombination and repair functions to transfer the information encoded by the GTS to the target genomic locus.

In various embodiments, alteration of one or both alleles in a diploid genome or multiple alleles in a polyploid genome may for example be achieved by the invention. Modified alleles may also be identified using various types of molecular markers, as is known in the art.

In animals, if it is desired for the modified target locus to be passed on and heritable then specialized cell types may be employed (Thomas, K. R., and Capecchi, M. R., 1987, Cell 51: 503-512; Thompson, S, et. al. 1989, Cell 56: 313-321). For example, but not wishing to be limiting, stem cells may be transformed with the retron of the present invention, and the target locus modified as described above. Such stem cells comprising the modified target locus may then be used to create chimeric animals by adaptation of procedures known in the art (Thomas, K. R., and Capecchi, M. R., 1987, Cell 51: 503-512; Thompson, S, et. al. 1989, Cell 56: 313-321). Some of these animals produced by these procedures may then be able to transfer the modified target locus to their progeny. Alternatively, procedures are known in the art for cloning animals using somatic cells (Wilmut, I, et. al. 1997, Nature 385: 810-813). These somatic cells may have a target locus modified using the retron of the present invention. The cells comprising the modified target locus may then be used for development of the cloned animal. Progeny from this animal may then comprise the modified target locus and stably transfer it to progeny or other progeny derived from repeating such a cloning process.

In some embodiments, a mechanism for generating a heritable modified targeted genomic locus is to perform the gene targeting in gametes or gonadal cells capable of differentiating into gametes. Gametes could be collected and treated in vitro with the retron comprising the gene targeting nucleotide sequence. The resultant production of msDNA comprising a gene targeting nucleotide sequence may result in genetic modification of the target locus. Such gametes could then be used in fertilization. The resulting zygote and organism may carry the modified locus in all of its cells and be capable of passing it to progeny. Gametes may also be modified in situ by using a retron capable of systemic spread through the host and entry into host cells, particularly the germ-line and derivatives, or by direct application or injection of the retron comprising the gene targeting nucleotide sequence to gametes or gonadal cells differentiating into gametes. In such an embodiment, gametes or germ-line cells may take up the construct. The msDNA from the retron may then be produced in vivo to facilitate the desired change to the target locus in these cells. The gametes upon fertilization would thus result in an organism carrying the modified target locus in all of its cells and would be capable of passing it to progeny. Methods of treatment of gonadal cells with exogenous gene targeting substrate may be adapted for use in alternative aspects of the present invention.

In addition to development of whole organisms carrying a targeted genetic change, the invention may also be applied to gene therapy in specific tissues or organs of an individual animal. In accordance with this aspect of the invention, the animal may be treated with a retron comprising a gene targeting nucleotide sequence as provided by the present invention, that is capable of systemic spread and entry into cells. Production of msDNA (GTS) from the retron may be regulated by tissue-specific or organ-specific promoters. The gene targeting nucleotide sequence may be produced in vivo and only in the desired tissues or organs where the promoters are active, so that gene targeting would occur in those specified tissues and organs, or be enriched to occur there. Furthermore, cells may be treated exogenously and reintroduced into the host.

The present invention further contemplates cells, tissue or entire organisms comprising the retron of the present invention, msDNA comprising the gene targeting nucleotide sequence (GTS) produced from the msr-GTNS-msd of the present invention, or both. The cells, tissue or entire organisms may comprise any eukaryotic cell for example but not limited to plant, animal or yeast cell, tissue or organism.

Also according to the present invention, there is provided a method of modifying a gene of interest in a cell, tissue or organism comprising the steps of, a) expressing in said cell, tissue or organism a retron comprising,
  i) msr and msd nucleotide coding regions;
  ii) a gene-targeting nucleotide sequence homologous to a target locus of interest but comprising at least one nucleotide difference compared to the gene of interest, and;
  iii) a nucleotide sequence encoding a reverse transcriptase in sufficient quantities to enhance and promote modification of the locus of interest with the gene-targeting nucleotide sequence.

Modification of the target locus of interest with a homologous GTNS may for example be used to modify a target locus associated with a disease, or aberrant phenotype to a nucleotide sequence gene of interest which is not associated with disease or an aberrant phenotype. Alternatively, the method may be employed to modify a normal nucleotide sequence of a gene of interest to a modified nucleotide sequence which may result in a disease or aberrant phenotype. For example, but not wishing to be limiting, the method of the present invention may be employed to study the function of specific DNA sequences, expressed proteins, or both in a cell, tissue or organism. In an alternate embodiment of the present invention which is not meant to be limiting in any manner, the gene-targeting nucleotide sequence homologous to a gene of interest may encode elements such as stop codons that result in "knockout", inactivation or deletion of the protein encoded by the gene of interest.

In alternative embodiments, the methods of the invention may be employed to modify a locus or gene of interest in a wide variety of eukaryotic cells, tissues or organisms, such as yeast, plant cells, insect cells, or animal cells. In an aspect of a preferred embodiment the eukaryotic cell is a plant cell or a human cell or a non-human cell or host.

In some embodiments, the retron constructs of the present invention may be adapted to permit multiple copies of msDNA comprising a gene targeting nucleotide sequence to accumulate within a nucleus of a cell. In nucleo accumulation of multiple copies of the gene targeting nucleotide sequence may facilitate gene targeting and modification of the target locus.

In alternative aspects, the invention includes a variety of self-RT-priming gene targeting RNA constructs that act as an in vivo template for RT. Such constructs include retron-like constructs, which do not necessarily include all of the structural features of native retrons. A wide variety of retron-like self-RT-priming gene targeting RNA constructs may be used, provided that they are capable of mediating reverse transcription of a GTNS. For example, a 3' region of an mRNA may be adapted to fold back on itself, with complimentary sequences annealing to create a self-priming 3' untranslated region, such as a hairpin, that is capable of recruiting a RT to reverse transcribe a portion of the RNA. Similarly, intron splicing constructs may be modified to provide self-RT-priming gene targeting RNA constructs in which a portion of the mRNA folds back on itself to create a self-priming RNA that is capable of recruiting RT to reverse transcribe a portion of the RNA. In alternative embodiments, the self-RT-priming gene targeting RNA construct may comprise two or more separate RNA molecules, wherein the sequence of the RNAs facilitates base-pairing to produce a 3'-hydroxyl that may recruit and prime RT to reverse transcribe portions of one of the RNA molecules into a cDNA-based gene targeting substrate.

In various aspects, the present invention provides methods to modify a nucleic acid of interest at a target locus within the genome of a host comprising, expressing a gene targeting construct nucleotide sequence encoding a self-RT-priming gene targeting message RNA (gtmRNA), wherein the gtmRNA comprises a gene targeting message that is reverse transcribed within the host in the presence of a reverse transcriptase (RT), thereby producing an in vivo gene targeting substrate having a gene targeting nucleotide sequence (GTNS), and selecting for modification of the target locus within the genome of the host.

In some embodiments, the present invention also relates to methods wherein the host is modified to express the RT prior to introducing the nucleotide sequence encoding an RNA that comprises the GTNS into the host. The nucleotide sequence encoding an RNA that comprises the GTNS may for example be introduced into the host by transformation or cross breeding.

The terms "nucleic acid" or "nucleic acid molecule" encompass both RNA (plus and minus strands) and DNA, including cDNA, genomic DNA, and synthetic (e.g., chemically synthesized) DNA. The nucleic acid may be double-stranded or single-stranded. Where single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. By "RNA" is meant a sequence of two or more covalently bonded, naturally occurring or modified ribonucleotides. One example of a modified RNA included within this term is phosphorothioate RNA. By "DNA" is meant a sequence of two or more covalently bonded, naturally occurring or modified deoxyribonucleotides. By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

An "isolated nucleic acid" is a nucleic acid molecule that is substantially free of the nucleic acid molecules that normally flank it in the genome. Therefore, an "isolated" gene or nucleic acid molecule is intended to mean a gene or nucleic acid molecule which is not flanked by nucleic acid molecules which normally (in nature) flank the gene or nucleic acid molecule (such as in genomic sequences) and/or has been completely or partially purified from other transcribed sequences (as in a cDNA or RNA library). For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. The term therefore includes, e.g., a recombinant nucleic acid incorporated into a vector, such as an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant nucleic acid which is part of a hybrid gene encoding additional polypeptide sequences. Preferably, an isolated nucleic acid comprises at least about 50, 80 or 90 percent (on a molar basis) of all macromolecular species present. Thus, an isolated gene or nucleic acid molecule can include a gene or nucleic acid molecule which is synthesized chemically or by recombinant means. Recombinant DNA contained in a vector are included in the definition of "isolated" as used herein. Also, isolated nucleic acid molecules include recombinant DNA molecules in heterologous host cells, as well as partially or substantially purified DNA molecules in solution. In vivo and in vitro RNA transcripts of the DNA molecules of the present invention are also encompassed by "isolated" nucleic acid molecules. Such isolated nucleic acid molecules are useful in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue, such as peripheral blood), such as by Northern blot analysis.

Various genes and nucleic acid sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as 'recombinant' therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

As used herein, "heterologous" in reference to a nucleic acid or protein is a molecule that has been manipulated by human intervention so that it is located in a place other than the place in which it is naturally found. For example, a nucleic acid sequence from one species may be introduced into the genome of another species, or a nucleic acid sequence from one genomic locus may be moved to another genomic or extrachromasomal locus in the same species. A heterologous protein includes, for example, a protein expressed from a heterologous coding sequence or a protein expressed from a recombinant gene in a cell that would not naturally express the protein.

By "antisense," as used herein in reference to nucleic acids, is meant a nucleic acid sequence that is complementary one strand of a nucleic acid molecule. In some embodiments, an antisense sequence is complementary to the coding strand of a gene, preferably, a SARS virus gene. The preferred antisense nucleic acid molecule is one which is capable of lowering the level of polypeptide encoded by the complementary gene when both are expressed in a cell. In some embodiments, the polypeptide level is lowered by at least 10%, or at least 25%, or at least 50%, as compared to the polypeptide level in a cell expressing only the gene, and not the complementary antisense nucleic acid molecule.

A "probe" or "primer" is a single-stranded DNA or RNA molecule of defined sequence that can base pair to a second DNA or RNA molecule that contains a complementary sequence (the target). The stability of the resulting hybrid molecule depends upon the extent of the base pairing that occurs, and is affected by parameters such as the degree of complementarity between the probe and target molecule, and the degree of stringency of the hybridization conditions. The degree of hybridization stringency is affected by parameters such as the temperature, salt concentration, and concentration of organic molecules, such as formamide, and is determined by methods that are known to those skilled in the art. Probes can be detectably-labeled, either radioactively or non-radioactively, by methods that are known to those skilled in the art. Probes can be used for methods involving nucleic acid hybridization, such as nucleic acid sequencing, nucleic acid amplification by the polymerase chain reaction, single stranded conformational polymorphism (SSCP) analysis, restriction fragment polymorphism (RFLP) analysis, Southern hybridization, northern hybridization, in situ hybridization, electrophoretic mobility shift assay (EMSA), and other methods that are known to those skilled in the art.

By "complementary" is meant that two nucleic acids, e.g., DNA or RNA, contain a sufficient number of nucleotides which are capable of forming Watson-Crick base pairs to produce a region of double-strandedness between the two nucleic acids. Thus, adenine in one strand of DNA or RNA pairs with thymine in an opposing complementary DNA strand or with uracil in an opposing complementary RNA strand. It will be understood that each nucleotide in a nucleic acid molecule need not form a matched Watson-Crick base pair with a nucleotide in an opposing complementary strand to form a duplex.

By "vector" is meant a DNA molecule derived, e.g., from a plasmid, bacteriophage, or mammalian or insect virus, or artificial chromosome, that is used to introduce a polypeptide, for example a SARS virus polypeptide, into a host cell. A vector may contain one or more unique restriction sites and may be capable of autonomous replication in a defined host or vehicle organism such that the cloned sequence is reproducible. By "DNA expression vector" is meant any autonomous element capable of directing the synthesis of a recombinant peptide. Such DNA expression vectors include bacterial plasmids and phages and mammalian and insect plasmids and viruses. A "shuttle vector" is understood as meaning a vector which can be propagated in at least two different cell types, or organisms, for example vectors which are first propagated or replicated in prokaryotes in order for, for example, eukaryotic cells then to be able to be transfected with these.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. The following examples are for illustrative purposes only, and alternative aspects of the invention are exemplified without implication that the invention necessarily includes each of the facets disclosed in each exemplary embodiment. Similarly, the advantages and features of some embodiments are not to be taken to be achieved with all embodiments. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. All publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

EXAMPLES

Example 1

Genetic Assay and Test Alleles

Several variations of gene targeting cassettes were developed and tested to demonstrate the potential of using reverse transcription to generate gene targeting substrates in vivo to facilitate genetic alteration of a chromosomal locus in eukaryotic cells. In some examples components of retroelements (i.e. genetic elements which can convert the entire or partial region of an RNA molecule encoded by the genetic elements into a cDNA through the action of a reverse transcriptase) were used. One example of such an element is referred to as the retron, different versions of which are encoded by various bacterial species and strains. One example of a retron is denoted Ec86 from the *E. coli* strain HB8 [1685]. Another example of a retron is denoted Ec107 from *E. coli* strain ECOR70 [1657]. Functional elements from both Ec86 and Ec107 have been cloned (i.e. pMW3, pMW5, pMW4, pMW9; described later). Application of components encoded by Ec86 to facilitate gene targeting in eukaryotic cells is exemplified here to demonstrate the utility of using reverse transcription to generate gene targeting substrates in vivo.

One example of gene targeting cassettes employed here were designed to convert the chromosomal URA3 gene of *S. cerevisiae* to a non-functional allele (i.e. ura3) which could be identified through its ability to confer resistance to 5-fluoroorotic acid (FOA) in the model eukaryotic cells. Thus the ability to alter the function of a chromosomally encoded protein could be demonstrated. In other embodiments of the invention, the gene targeting cassettes could be designed to either restore the function of an inactive genomic locus or the product it encodes, or modulate the genetic activity of that locus or the activity of the RNA or protein molecule encoded by that locus.

In one example, the gene targeting cassette encoded ~500 bp of the ura3$\Delta^{PstEcoRV}$ allele. This ~500 bp sequence is deleted for ~20 bp of the promoter region and ~190 bp of the open reading frame of the URA3 gene with ~250 bp upstream and downstream homology to URA3. Transfer of this deletion mutation to the chromosomal URA3 locus may create a mutated chromosomal allele. Such events may be detected by screening for cells resistant to FOA the frequency of which reflects the gene targeting frequency. In some examples, the effect of a gene targeting substrate generated with the reverse transcription-based system was tested when the gene targeting substrate was created in a sense or anti-sense orientation with respect to the chromosomal target locus.

In another example, the gene targeting cassette encoded ~500 bp of the ura3$^{Pvu}$ allele. This ~500 bp sequence encodes a deletion of 8 bp resulting in loss of base pair #275-284 of the URA3 open reading frame. The deletion also creates a novel PvuII restriction site and changes the reading frame of the altered gene to promote premature termination of translation which can be expected to prevent functional expression of the carboxy-terminal 176 amino acid residues encoded by URA3 whose wild type protein product is 267 amino acid residues in length. The cassette also encodes ~250 bp upstream and downstream of the 8 bp deletion for a total of ~500 bp of homology to the chromosomal URA3 locus.

In another example, the gene targeting cassette encoded ~500 bp of the ura3$^{Bsp}$ allele. This ~500 bp DNA sequence encodes a single base pair change of C to A at nucleotide position #465 of the URA3 open reading frame. This base pair change creates a novel BspHI restriction enzyme site within the URA3 locus and creates a premature translation termination signal which can be expected to prevent functional expression of the carboxy-terminal 113 amino acid residues encoded by URA3 whose wild type protein product is 267 amino acid residues in length. The cassette also encodes ~250 bp upstream and downstream of the C to A bp change for a total of ~500 bp of homology to the chromosomal URA3 locus.

In some examples, the ability of in vivo produced cDNAs to genetically alter a chromosomal target locus was assessed when the cDNAs were designed to pair with either the transcribed or non-transcribed strand of a chromosomal target locus. This evaluation involved cloning the gene targeting sequence into the reverse transcription system in either the sense or the antisense orientation. When this gene targeting cassette sequence is cloned into the reverse transcription-based gene targeting system in the sense orientation, reverse transcription will create an anti-sense cDNA which can then base pair with the sense strand of the chromosomal target locus, and vice versa.

The DNA sequences encoding the gene targeting sequences from the three ura3 alleles described above were cloned into various versions of the Ec86 msr-msd elements engineered to accommodate these introduced sequences and facilitate their conversion to cDNAs in vivo in the presence of the Ec86 RTase. The versions of engineered msr-msd elements exemplified here are referred to as the STEM3 derivative, the STOPstem derivative and the 3'-recruitment derivative.

Example 2

Wild Type Retron

FIG. 1 summarises a current understanding of the reverse transcription process of at least some retron elements (as for example reviewed in [1648]). The principal components of a retron are the msr and msd elements flanked by the a1 and a2 inverted repeat sequences. In a RNA transcript of these elements, the a1 and a2 sequences base pair as do other inverted repeat sequences encoded within msr and msd, such as the b1 and b2 inverted repeat sequences within msd, to form stem and loop structures. The topology of stem and loop structures within the msr region of the folded RNA molecule enables recruitment of RTase. This protein-RNA interaction places the RTase in an appropriate context to be able to use the 2'-hydroxyl of a specific guanosine residue within the msr element to prime reverse transcription of the msd element. The reverse transcription proceeds through the msd sequence and terminates at a position at the boundary between the msd and msr sequences. In the absence of an RNaseH-like activity, an extensive RNA-DNA hybrid molecule may be formed whereas in the presence of an RNaseH-like activity a cDNA molecule may formed.

Example 3

Modification of Reverse Transcriptase for Enhanced Functionality in Eukaryote Cells For effective gene targeting of chromosomal loci in eukaryote cells, the gene targeting substrate needs to be present in the nucleus. In some embodiments of the invention, reverse transcriptases are engineered to localize in the eukaryote host cell nucleus so that the enzyme can catalyse cDNA synthesis and production of the gene targeting substrate in the nucleus. One example to achieve this is to engineer the reverse transcriptase to encode a nuclear localization sequence. In one embodiment, the engineered reverse transcriptase may be of prokaryotic origin and thus may not possess an inherent nuclear localization sequence. One example is the Ec86 retron-derived reverse transcriptase which was engineered to encode the NLS from the SV40 T-antigen (i.e. pMW22). Another example is the Ec107 retron-derived reverse transcriptase which was engineered to encode the NLS from the SV40 T-antigen [109] (in a construct denoted herein as pMW39). The activity in *E. coli* of such an engineered reverse transcriptase was compared to that of the WT reverse transcriptase and found not to be substantially different. However, the effect on cDNA accumulation in eukaryotic cells when the reverse transcriptase was engineered to encode an NLS was very dramatic. This was illustrated using *S. cerevisiae* as a representative eukaryotic cell. The *S. cerevisiae* strain RK2575-URA was transformed with pMW29 capable of expressing Ec86 msr-msd and with pMW25, expressing WT Ec86 reverse transcriptase, or pMW27, expressing the engineered NLS-RT from Ec86 (NLS-RT sequence:

(SEQ ID NO: 1)
GGATCCAAAAAAATGGCTCCTAAGAAGAAGAGAAAGGTTGGAGGAGGACC

CGGGAAGTCCGCTGAATATTTGAACACTTTTAGATTGAGAAATCTCGGCC

TACCTGTCATGAACAATTTGCATGACATGTCTAAGGCGACTCGCATATCT

GTTGAAACACTTCGGTTGTTAATCTATACAGCTGATTTTCGCTATAGGAT

CTACACTGTAGAAAAGAAAGGCCCAGAGAAGAGAATGAGAACCATTTACC

AACCTTCTCGAGAACTTAAAGCCTTACAAGGATGGGTTCTACGTAACATT

TTAGATAAACTGTCGTCATCTCCTTTTTCTATTGGATTTGAAAAGCACCA

-continued
ATCTATTTTGAATAATGCTACCCCGCATATTGGGGCAAACTTTATACTGA

ATATTGATTTGGAGGATTTTTTCCCAAGTTTAACTGCTAACAAAGTTTTT

GGAGTGTTCCATTCTCTTGGTTATAATCGACTAATATCTTCAGTTTTGAC

AAAAATATGTTGTTATAAAAATCTGCTACCACAAGGTGCTCCATCATCAC

CTAAATTAGCTAATCTAATATGTTCTAAACTTGATTATCGTATTCAGGGT

TATGCAGGTAGTCGGGGCTTGATATATACGAGATATGCCGATGATCTCAC

CTTATCTGCACAGTCTATGAAAAAGGTTGTTAAAGCACGTGATTTTTTAT

TTTCTATAATCCCAAGTGAAGGATTGGTTATTAACTCAAAAAAAACTTGT

ATTAGTGGGCCTCGTAGTCAGAGGAAAGTTACAGGTTTAGTTATTTCACA

AGAGAAAGTTGGGATAGGTAGAGAAAAATATAAAGAAATTAGAGCAAAGA

TACATCATATATTTTGCGGTAAGTCTTCTGAGATAGAACACGTTAGGGGA

TGGTTGTCATTTATTTTAAGTGTGGATTCAAAAAGCCATAGGAGATTAAT

AACTTATATTAGCAAATTAGAAAAAAAATATGGAAAGAACCCTTTAAATA

AAGCGAAGACCTAATAACTGCAG

The sequence of the resynthesized version of NLS-RT (fr. Ec86, encoded in the plasmid referred to as pNLS-RT-RS) is as follows:

(SEQ ID NO: 2)
GGATCCAAAA CAATGGCTCC TAAGAAGAAG AGGAAGGTTG

GAGCCGGCGG AGATTACAA GGATGATGAT GATAAGGGAG

TTAACGGAGG AGGTGGAGGA GGTGGAGGT GGAGGCGCCA

AGTCTGCTGA GTACCTCAAC ACCTTCAGG CTCAGGAAC

CTCGGACTCC CTGTTATGAA CAACCTCCAC GATATGTCT

AAGGCTACC AGGATCTCT GTTGAGACCC TCAGGCTCCT

CATCTACACC GCTGATTTC AGGTACAGGA TCTACACCGT

TGAGAAGAAG GGACCTGAG AAGAGGATG AGGACCAT

CTACCAACCT TCTAGGGA ACTTAAGGC TCTCCAAGG

ATGGGTTC TCAGGAACAT CCTCGATAAG CTCTCTTCTT

CTCCTTTCTC TATCGGAT TCGAGAAGCA CCAATCTATC

CTCAACAAC GCTACCCCTC ACATCGGAGC TAACTTCAT

CCTCAACATC GATCTTGAAG ATTTCTTCCC TTCTCTCACC

GCTAACAAG GTTTTCGGAG TTTTCCACT CTCTCGGATA

CAACAGGCTC ATCTCTTCT GTTCTCACC AAGATCTG

CTGCTACAA GAACCTCCTC CCTCAAGGT GCTCCTTCT

TCTCCTAAGC TCGCTAACC TCATCTGCTC TAAGCTCG

ATTACAGA ATTCAAGGA TACGCTGGAT CTAGGGGACT

CATCTACACC AGGTACGCT GATGATCTCA CCCTCTCTGC

TCAATCTATG AAGAAGGTTG TTAAGGCTA GGGATTTCC

TCTTCTCTAT CATCCCTTC TGAGGGACT CGTTATCAAC

TCTAAGAAG ACCTGCATCT CTGGACCTAGG TCTCAAAGGA

AGGTTACCGG ACTCGTTA TCTCTCAAGA GAAGGTTGGA

-continued

```
ATCGGAAGGG AGAAGTACA AGGAGATCA GGGCTAAGAT

CCACCACATC TTCTGCGGAA AGTCTTCTGA GATCGAGCA

CGTTAGGGGA TGGCTCTCTT TCATCCTCTC TGTTGATTC

TAAGTCTCA CAGGAGGCTC ATCACCTAC ATCTCTAAG

CTTGAAAAGA AGTACGGAA AGAACCC TCTCAACA

AGGCTAAGAC CTAATGAG CGGCCGCA CTAGTGAT

ATCTCTAGA; .
```

The cells were cultured overnight in 3 ml of SC-Leu-Trp and total DNA was extracted as per standard procedures [213]. The DNA samples were resuspended in 60 ul of LTE (1 mM Tris-HCl, 0.1 mM EDTA) and 30 ul was resolved on a 2% agarose gel. The DNA was then Southern blotted to a Hybond N$^+$ (Amersham) membrane then probed using a $^{32}$P labeled DNA fragment encoding Ec86 msr-msd (isolated from pMW5 digested with BamHI and PstI) and the signal detected by autoradiography, all following standard procedures [213]. To illustrate the similarity of products produced by NLS-RT in both *E. coli* and *S. cerevisiae*, control samples of cDNA were also produced in *E. coli*. This material was obtained from *E. coli* DH5-alpha (Gibco-BRL) transformed with pMW16 capable of expressing Ec86 msr-msd and pMW7 capable of expressing NLS-RT derived from Ec86. The cells were cultured overnight in 3 ml of TYS medium containing ampicillin (50 ug/ml) and chromamphenicol (20 µg/ml) plus 0.2 mM IPTG. DNA was isolated from 1.5 ml of culture following a standard "alkaline mini-prep" method [213] and dissolved in LTE. Aliquots of the *E. coli* derived and *S. cerevisiae* derived DNA were analysed by Southern blotting as described above. As illustrated in FIG. 2, the size of cDNA produced in prokaryotic or eukaryotic cells by NLS-RT is indistinguishable. Thus engineering a reverse transcriptase to encode an NLS does not impair its functionality in such embodiments. Rather, by comparing the level of cDNA accumulation in eukaryotic cells facilitated by WT reverse transcriptase versus NLS-RT, it is readily apparent that a reverse transcriptase encoding an NLS is more effective at catalyzing cDNA synthesis in eukaryotic cells. FIG. 2 illustrates that a very strong signal indicative of cDNA synthesis is observed in eukaryotic yeast cells expressing the NLS-RT whereas no signal was detected in eukaryotic cells expressing WT-reverse transcriptase. Accordingly, in some embodiments, the functionality of reverse transcriptases of prokaryotic origin, when expressed in eukaryotic cells, can be enhanced when they are modified to localize to the nucleus.

Example 4

STEM3

4a) Overview

As illustrated in FIG. 3 and FIG. 4, the STEM3 derivative of the msr-msd elements is engineered to encode unique restriction sites (XbaI, EcoRV) within the loop region of the principal stem and loop region of the Ec86 msd sequence (i.e. that created by the b1 and b2 inverted repeat sequences). STEM3 also has 13 bp extensions of the a1 and a2 inverted repeat sequences (i.e. a1', a2'). These extensions are composed of sequences which can base pair with each other. As a result, the dsRNA region created by a1' and a2' sequences in the primary transcript of msr-msd is increased in size. This larger dsRNA region thus has a higher dissociation constant which can serve to isolate the msr-msd sequences from RNA sequences present in the transcript that are 5' of a1' and 3' of a2'. This can be important for promoting reverse transcription of the msd portion in eukaryotic cells. The nature of eukaryotic transcription results in addition of sequences at the 5' and 3' ends of the transcript as a result of transcription initiation and termination. In the case of translated genes these 5' and 3' sequences are referred to as 5'- and 3-untranslated regions (UTRs). Depending on the sequence composition of these 5' and 3' sequences, they can base pair to form secondary structures. Such secondary structures may affect correct folding of a transcript encoding msr-msd and thereby could impair recruitment of the RTase and consequent cDNA synthesis. However, extension of the a1 and a2 inverted repeat regions can act to isolate the msr-msd sequences from effects mediated by the 5' and 3' 'UTR regions' and thereby promote proper folding of msr-msd to facilitate reverse transcription of msd sequences.

In one embodiment, the STEM3 sequence was as follows:

```
                                         (SEQ ID NO: 3)
GGATCCCCCG GGCGCCAG CAGTGGCT GCGCACCC TTAGCGA

GAGGTTTA TCATTAAGG TCAACCTCT GGATGTTGT TTCGGCAT

CCTGCATT GAATCTGAG TTACTGTCT GTTTTCCTT GTTGGAACGG

AGAGCATCG TCTAGACAAC GATATCTGA TGCTCTCC GAGCCAACC

AGGAAACCC GTTTTTTCT GACGTAAGG GTGCGCAG CCGCTGTT

GGCGTGGC CAATGCG GCCGC.
```

To apply the STEM3 system to producing gene targeting substrates in vivo, a DNA sequence encoding regions of homology to the target locus as well as the genetic change desired to be transferred to the target locus is cloned into the XbaI and EcoRV sites within the msd region in a manner such that the STEM3 and gene targeting sequence assembly can be transcribed. This assembly is introduced into a eukaryotic cell which is capable of expressing RTase. Thus, as illustrated in FIG. 4, the RNA transcript of the STEM3 assembly will fold in a manner capable of recruiting the RTase and encode a gene targeting cassette within an extended loop region within the msd element. The RTase can then reverse transcribe the msd element which also encodes the gene targeting cassette resulting in a cDNA-based gene targeting substrate. In the absence of an RNaseH-like activity, an extended loop of RNA/DNA hybrid molecule may be created whereby the loop region encodes the gene targeting substrate. In the presence of an RNaseH-like activity a molecule with an extensive ssDNA loop may be created whereby the loop region encodes the gene targeting substrate. As a result of repeated transcription of the STEM3 assembly and consequent reverse transcription by reverse transcriptase, multiple copies of the gene targeting substrate may be made with this system. This gene targeting substrate may then be acted upon by host DNA processes, such as recombination or repair processes, to genetically alter it (which may involve pairing of the GTNS and the homologous host target locus).

4b) In Vivo cDNA Synthesis Using STEM3

The retron system was evaluated regarding the size of novel DNA sequence that could be placed into the msd region and still enable cDNA synthesis in vivo. It is possible that the retron has a size limit regarding novel DNA sequence that can be tolerated. Exceeding this limit could impair the correct folding of the RNA retron elements and inhibit recruitment of reverse transcriptase and or reverse transcription of the msd region including a novel sequence encoding a gene targeting sequence. Using a computer-based, nucleic acid-folding modeling program [1689], the tolerance of STEM3 for insertion sequences was evaluated. As shown in FIG. 5, the overall predicted structure of STEM3 including either a 50 bp or 500 bp insert is not markedly different from STEM3 without insert. Thus, one may predict in vivo synthesis of at least a 500 bp cDNA could be achieved using STEM3. This capability was evaluated in prokaryotic and eukaryotic cells using *E. coli* and *S. cerevisiae* as respective model systems.

To evaluate the capability of the STEM3 system to produce cDNAs in vivo in prokaryotes, *E. coli* DH5α was transformed with pMW7, capable of expressing Ec86 reverse transcriptase, in combination with one of several STEM3-derived constructs with insert sequences of 0 bp (pMW16), 15 bp (pMW161), 25 bp (pMW162), 35 bp (pMW198), 50 bp (pMW163), 100 bp (pMW199), or 250 bp (pMW200). The strains were cultured overnight as outlined above with the appropriate selection agents plus 0.2 mM IPTG. DNA was isolated as outlined above and approximately equal amounts were resolved by gel electrophoresis on a 2% agarose gel. The cDNA was then detected by staining the gel with ethidium bromide or after Southern blotting and probing with a $^{32}$P-labelled DNA fragment encoding Ec86 msr-msd.

As illustrated in FIG. 6, the production of detectable levels of cDNA in *E. coli* was depended upon co-expression of both the STEM3 component and the reverse transcriptase. It is also demonstrated that increasing the size of insert within the msd element of the retron can severely impair cDNA production. For example, STEM3 with a 15 or 25 bp insert still results in production of cDNA when reverse transcriptase is coexpressed, albeit at a much lower level than STEM3 without insert. However, STEM3 with 50 bp insert did not produce sufficient amounts of cDNA to be detected by staining with ethidium bromide. Rather, the much more sensitive Southern blotting technique was required to detect the cDNA from STEM3 with 50 bp insert. Note that the high molecular weight bands detected on the Southern blot represent the parental plasmids encoding the STEM3 components which also hybridise to the radio-labeled probe. This experiment further showed that a 100 bp insert in the msd region of the retron severely impaired production of a detectable level of cDNA and that an insert of 250 bp may prohibit cDNA production. Collectively, this data demonstrates that in some embodiments DNA sequences placed into the msd region of a retron can impair cDNA production in a manner dependent upon the size of insert. This experiment using a prokaryotic host suggests that a maximum size limit, in this embodiment, of about 100 bp may be tolerated by the retron for cDNA production. Accordingly, in alternative embodiments, insert size may be varied to affect functionality of retrons in vivo.

To evaluate the capability of the STEM3 system to produce cDNAs in vivo in eukaryotic cells, *S. cerevisiae* strain RK2575-URA was transformed with pMW27, capable of expressing NLS-RT from Ec86, in combination with one of several constructs capable of expressing STEM3 with inserts of 0 bp (pMW166), 15 bp (pMW167), 25 bp (pMW168), 35 bp (pMW202), 50 bp (pMW169), 100 bp (pMW203), 250 bp (pMW204), 320 bp (pMW211), 500 bp (pMW212), or 1000 bp (pMW213). The strains were cultured overnight and DNA was extracted as described above. Samples of DNA were resolved by gel electrophoresis on a 2% agarose gel, Southern blotted and probed with a $^{32}$P-labeled DNA fragment encoding Ec86 msr-msd.

FIG. 7 illustrates the production of cDNA in eukaryotic cells using the STEM3 system. Note that the high MW bands detected on the Southern blot represent the parental constructs encoding the STEM3 components which also hybridise to the radio-labeled probe. As observed in prokaryotic cells, the production of detectable amounts of cDNA was dependent upon the co-expression of the STEM3 component and the cognate reverse transcriptase. Surprisingly, the effect of insert size on cDNA production in eukaryotic cells was not as severe as that observed in prokaryotic cells. This experiment demonstrates that in some embodiments inserts of at least 500 bp can be tolerated by the STEM3 system and may be converted to abundant levels of cDNA in eukaryotic cells. Accordingly, the cDNA length capability of a retron-based system of the invention may be greater in eukaryotic cells than in prokaryotic cells.

4c) Application of STEM3 to Gene Targeting in Eukaryotic Cells

FIG. 8 highlights one possible mechanism how the STEM3 system may be used to modify eukaryotic chromosomal loci. In this example, the chromosomal URA3 locus of the model eukaryote *S. cerevisiae* is used as representative of any chromosomal locus in eukaryotic cells. In this example, the RTase is expressed from one promoter episome and the STEM3 assembly is expressed from another promoter episome. In some other embodiments the RTase and STEM3 assembly may be expressed from a single episome, two different episomes, or from genetically linked or unlinked loci encoded by a chromosome. In this example, 500 bp of the ura3$^{Bsp}$ allele was cloned into STEM3 and placed in a yeast vector with the TRP1 selectable marker adjacent to a promoter (i.e pMW266). The NLS-RT of Ec86 was encoded adjacent to a promoter on a yeast vector with the LEU2 selectable marker (i.e. pMW27).

To evaluate the STEM3-based gene targeting system, RK2575-URA was transformed with pMW266 alone or in combination with pMW27 as per Geitz et al., 1995 [Gietz, R D, Schiestl, R H, Willems, A R, Woods, R A: Studies on the transformation of intact yeast cells by the LiAc/SS-DNA/PEG procedure.Yeast 11: 355-360 (1995)]. The double-transformed yeast cells possessing both pMW266 and pMW27 thus require culture on the medium SC-LEU-TRP [324] Adams [200]. Therefore to keep growth medium composition uniform for all treatments in the experiment, the strains transformed with the single experimental construct (i.e. pMW266 into a separate strain instead of in combination with pMW27) was also transformed with an empty vector (i.e. YCplac111Tet2x) solely for the purpose of supplying the complementary selectable marker as present in the experimental double-transformants. In this manner all strains could be cultured in the same SC-LEU-TRP medium.

RK2575-URA cells were transformed with the above mentioned plasmid combinations as per Geitz et al. (1995) [212] [323] and the cells were plated on SC-LEU-TRP. The plates were incubated at 30 C until colony diameter was 3-4 mm. Eleven colonies from each treatment were individually collected and disbursed in 1 ml sterile distilled water (SDW). An aliquot of these cells was used to prepare serial dilutions in SDW and plated on YPD medium (per liter: 10 g Bacto-yeast extract, 20 g Bacto-peptone, 20 g glucose, 20 g Bacto-agar; [200] [325]) to determine viable cell number. Additional aliquots were plated on FOA selection medium [200] [324]. The plates were incubated 2-5 days and the colonies were then counted. The data of viable cell number and number of FOA-resistant cells was compiled, taking into consideration the dilution factors, and analysed by the method of the median [1008] [327] with statistical analysis as described by Dixon and Massey (1969) [962] [328]. The FOA-resistant cells represent genetic events where the chromosomal URA3 locus is converted to a mutant allele as encoded by the gene targeting cassette encoding a fragment of the ura3$^{Bsp}$ allele (i.e. pMW266).

As shown in Table 2, the exemplified embodiments demonstrate modification of a specific target locus in a eukaryotic chromosome can be achieved by employing components involved in reverse transcription as part of a gene targeting system as embodied here. The genetic evidence demonstrates that conversion of a target locus in a eukaryotic chromosome to an alternate allele can be promoted by employing a reverse transcriptase to create cDNA molecules in vivo which may act as gene targeting substrates which may interact with and alter the sequence of a chromosomal target locus.

of a eukaryotic chromosomal target locus at relatively high frequency. The data further demonstrates that gene targeting systems of the invention can be developed using available components that facilitate reverse transcription in vivo. These components may for example be derived from prokaryotic or eukaryotic origin. The data further demonstrate that a RTase of prokaryotic origin, capable of functioning in eukaryotes, can be used in the context of the present invention to facilitate gene targeting. Accordingly, in various aspects of the invention, a selected RTase, or derivatives thereof (including those engineered to encode an NLS), can be used with its cognate recognition sequence (required to recruit the RTase to an

TABLE 2

Analysis of gene targeting systems employing reverse transcription

| | System Components | Gene Constructs | Gene Targeting Events/Cell Division (×10$^7$)$^a$ | Gene Targeting Frequency$^b$ |
|---|---|---|---|---|
| Experiment 1 | STEM3::500 bp ura3$^{Bsp}$-SENSE | PMW266 | 3.1 | |
| | NLS-RT + STEM3::500 bp ura3$^{Bsp}$-SENSE | PMW27 pMW266 | 4.2 | 40% |
| | STOP-stem::500 bp ura3$^{Bsp}$-SENSE | PMW267 | 3.2 | |
| | NLS-RT + STOP-stem::500 bp ura3$^{Bsp}$-SENSE | PMW27 pMW267 | 4.1 | 30% |
| | STOP-stem::500 bp ura3$^{Pvu}$-SENSE | PMW269 | 1.6 | |
| | NLS-RT + STOP-stem::500 bp ura3$^{Pvu}$-SENSE | PMW27 pMW269 | 2.7 | 70% |
| Experiment 2 | STOP-stem::500 bp ura3Δ$^{PstEcoRV}$-SENSE | PMW252 | 2.4 | |
| | NLS-RT + STOP-stem::500 bp ura3Δ$^{PstEcoRV}$-SENSE | PMW27 pMW252 | 5.4 | 130% |
| | STOP-stem::500 bp ura3Δ$^{PstEcoRV}$-AntiSENSE | PMW253 | 2.4 | |
| | NLS-RT + STOP-stem::500 bp ura3Δ$^{PstEcoRV}$-AntiSENSE | PMW27 pMW253 | 6.3 | 160% |
| Experiment 3 | 3' recruitment::500 bp ura3Δ$^{PstEcoRV}$-SENSE | PMW249 | 0.7 | |
| | NLS-RT + 3' recruitment:: 500 bp ura3Δ$^{PstEcoRV}$-SENSE | PMW27 pMW249 | 1.9 | 170% |
| | 3' recruitment::500 bp ura3Δ$^{PstEcoRV}$-AntiSENSE | PMW248 | 0 | |
| | NLS-RT + 3' recruitment:: 500 bp ura3Δ$^{PstEcoRV}$-AntiSENSE | PMW27 pMW248 | 1.9 | 190% |

$^a$Represents conversion of the chromosomal URA3 locus in RK2575-URA to ura3 as detected by FOA-resistance
$^b$Represents the percent increase in the number of gene targeting events observed when the reverse transcriptase was combined with the gene targeting cassette vs. that observed with the gene targeting cassette alone.

The data in Table 2 from Experiment 1 demonstrates that the STEM3 system employing elements from the retron Ec86 is effective at facilitating genetic alteration of a eukaryotic chromosomal locus. The control strain (i.e. RK2575-URA/pMW266) reflects the background of homologous recombination events which occur between homologous sequences carried in the same cell (i.e. the gene targeting cassette encoding ura3Bsp present on pMW266 and the chromosomal URA3 locus) under the growth conditions used. However, the rate of converting the chromosomal URA3 locus to a mutant allele is greatly increased over the background level when the RTase is expressed in a cell also possessing the STEM3 gene targeting cassette. This is demonstrated by the 40% increase in the occurrence of FOA-resistant cells in a strain expressing the STEM3 gene targeting cassette and expressing a RTase (i.e. RK2575-URA/pMW27/pMW266). Thus the gene targeting systems embodied here can be applied to efficiently alter eukaryotic chromosomal loci.

The data demonstrate that the gene targeting systems of the invention may be adapted to be used to facilitate modification RNA to facilitate cDNA synthesis) can be used to facilitate gene targeting in a variety of eukaryotic species.

Example 5

STOPstem

5a) Overview

The design of the STOPstem (FIG. 9) derivative of the msr-msd elements is essentially the same as STEM3 (FIG. 4). However, the STOPstem derivative encodes two 23 bp inverted repeat sequences (i.e. S1, S2) within the 5' end of the msd element. Likewise to STEM3 a DNA sequence encoding homology to a target locus and the genetic change to be transferred to the target locus can be cloned into the msd element within the STOPstem at the unique XbaI and EcoRV sites. This is then placed behind a promoter which is functional in the host cell. The STOPstem gene targeting assembly is then introduced into a host eukaryotic cell which is also capable of expressing RTase. As illustrated in FIG. 9, the RNA transcript of the STOPstem gene targeting assembly may fold in a manner capable of recruiting the RTase and encode a gene targeting cassette within an extended loop region within the msd element, similar to that for STEM3. However, the additional S1 and S2 inverted repeat sequences in the STOPstem may anneal to each other to form a stem-and-loop structure not found in STEM3. The nucleotide composition of the S1 and S2 stem-and-loop is designed to have a sufficiently high dissociation constant as to impair progression of RTase through it. Thus RTase can be recruited to a transcript of the STOPstem assembly and reverse transcribe the msd sequence and resident gene targeting cassette as per STEM3. However, when the RTase encounters the S1-S2 stem-and-loop structure termination of reverse transcription would be promoted. With appropriate placement of the S1-S2 stem-and-loop, the termination of reverse transcription could result in cDNA molecules which have at the 3' end absolute homology, or minimal non-homology, to the target locus. The presence of non-homology at the 3' end of recombination substrates has been demonstrated to suppress homologous recombination [368]. Thus the method described here to minimise non-homology at the 3' end of gene targeting substrates may be adopted in some embodiments to enhance gene targeting frequency. In the absence of an RNaseH-like activity, an extended loop of RNA/DNA hybrid molecule may be created whereby the loop region encodes the gene targeting substrate but the cDNA may not encode any retron sequences at its 3' end due to the reverse transcription termination activity of the S1-S2 stem-and-loop structure. In the presence of an RNaseH-like activity a molecule with an extended ssDNA sequence may be created which encodes the gene targeting substrate and may not encode any retron sequences at its 3' end due to the reverse transcription termination activity of the S1-S2 stem-and-loop structure. As a result of repeated transcription of the STOPstem assembly and consequent reverse transcription by reverse trancriptase, multiple copies of the gene targeting substrate may be made with this system. This gene targeting substrate may then be acted upon by host DNA recombination and repair processes to pair with the target chromosomal locus and genetically alter it.

To demonstrate the effectiveness of the STOPstem system for modifying eukaryotic chromosomal loci, the chromosomal URA3 locus of the model eukaryote S. cerevisiae was employed as representative of any chromosomal locus in eukaryotic cells. In this example, the chromosomal URA3 locus of the model eukaryote S. cerevisiae is used as representative of any chromosomal locus in eukaryotic cells. In this example, the RTase is expressed from one promoter episome and the STOPstem assembly is expressed from another promoter episome. In other embodiments the RTase and STOPstem assembly may be expressed from a single episome, two separate episomes, or from genetically linked or unlinked loci encoded by a chromosome. In one example, 500 bp of the ura3$^{Bsp}$ allele was cloned into STOPstem and placed adjacent to a promoter in a yeast vector with the TRP1 selectable marker (i.e pMW267). In another example, 500 bp of the ura3$^{Pvu}$ allele was cloned into STOPstem and placed adjacent to a promoter in a yeast vector with the TRP1 selectable marker (i.e pMW269). In another example, 500 bp of the ura3$\Delta^{PstEcoRV}$ allele was cloned into STOPstem and placed adjacent to a promoter in a yeast vector with the TRP1 selectable marker (i.e pMW252). In another example, 500 bp of the ura3$\Delta^{PstEcoRV}$ allele was cloned into STOPstem in an antisense orientation and placed adjacent to a promoter in a yeast vector with the TRP1 selectable marker (i.e pMW253). The NLS-RT of Ec86 was encoded adjacent to a promoter on a yeast vector with the LEU2 selectable marker (i.e. pMW27).
5b) In Vivo cDNA Synthesis Using STOPstem The STOPstem derivative of Ec86 msr-msd was evaluated for its capability to enable in vivo cDNA synthesis in eukaryotic cells. S. cerevisiae was used as a representative eukaryotic cell. S. cerevisiae strain RK2575-URA was transformed with pMW256, capable of expressing STOPstem containing an insert of 500 bp, in combination with pMW27, capable of expressing NLS-RT from Ec86, or YCplac111-Tet2x, the parental vector of pMW27. The strains were cultured and processed as outlined above for the evaluation of the STEM3 system in S. cerevisiae. Samples of DNA from the strains were resolved by gel electrophoresis on a 2% agarose gel, Southern blotted and probed with a $^{32}$P-labeled DNA fragment encoding Ec86 msr-msd.

FIG. 10 illustrates production of cDNA in eukaryotic cells using the STOPstem system. Note that the high molecular weight bands detected on the Southern blot represent the parental constructs encoding the STEM3 components which also hybridise to the radio-labelled probe. The low molecular weight signal represents the cDNA produced by reverse transcription of the STOPstem::500 bp RNA. Detection of the cDNA is dependent upon co-expression of the NLS-RT and the STOPstem::500 bp RNA. This experiment demonstrates the capability of the STOPstem system to produce cDNAs from inserts of at least 500 nucleotides in vivo in eukaryotic cells. One aspect of the invention is the use of new sequences, such as the S1 and S2 inverted repeats, capable of terminating reverse transcription in retron-like systems of the invention.
5c) Application of STOPstem to Gene Targeting in Eukaryotic Cells To demonstrate application of the STOPstem-based gene targeting system, RK2575-URA was transformed by the method of Geitz et al., 1995 [217] [323] with: pMW267 alone or in combination with pMW27; pMW269 alone or in combination with pMW27; pMW252 alone or in combination with pMW27; or pMW253 alone or in combination with pMW27. The double-transformed yeast cells possessing either pMW267, pMW269, pMW252 or pMW253 and pMW27 thus require culture on the medium SC-LEU-TRP. Therefore to keep media composition uniform for all treatments in the experiment, the strains transformed with the single experimental constructs (i.e. pMW267, pMW269, pMW252, or pMW253 into separate strains instead of in combination with pMW27) were also transformed with an empty vector (i.e. YCplac111Tet2x, the base vector of pMW27) solely for the purpose of supplying the complementary selectable marker as present in the experimental double-transformants. In this manner all strains could be cultured in the same SC-LEU-TRP medium.

RK2575-URA cells were transformed with the above mentioned plasmid combinations as per Geitz et al. (1995) [212] [323] and the cells were plated on SC-LEU-TRP. The plates were incubated at 30 C until colony diameter was 3-4 mm. Eleven colonies from each treatment were individually collected and disbursed in 1 ml sterile distilled water (SDW). An aliquot of these cells was used to prepare serial dilutions in SDW and plated on YPD medium to determine viable cell number. Additional aliquots were plated on FOA selection medium. The plates were incubated 2-5 days and the colonies were then counted. The data of viable cell number and number of FOA-resistant cells was compiled, taking into consideration the dilution factors, and analysed by the method of the median [1007] [327] with statistical analysis as described by Dixon and Massey (1969) [962] [328]. The FOA-resistant cells represent genetic events where the chromosomal URA3 locus is converted to a mutant allele as encoded by the gene targeting cassette encoding a fragment of the ura3Bsp allele (i.e. pMW267), the ura3Pvu allele (pMW269), or the ura3☐PstEcoRV allele (pMW252, pMW253).

As shown in Table 2, the exemplified embodiments demonstrate modification of a specific target locus in a eukaryotic chromosome can be achieved by employing components involved in reverse transcription as part of a gene targeting system as embodied here. The genetic evidence demonstrates that conversion of a target locus in a eukaryotic chromosome to an alternate allele can be promoted by employing a reverse transcriptase to create cDNA molecules in vivo to act as gene targeting substrates which can interact with and alter the sequence of a chromosomal target locus.

The data in Table 2 from Experiments 1 and 2 demonstrates that the STOPstem system employing elements of the retron Ec86 is effective at facilitating genetic alteration of a eukaryotic chromosomal locus. The respective control strains (i.e. RK2575-URA/pMW267; RK2575-URA/pMW269; RK2575-URA/pMW252; RK2575-URA/pMW253) reflect the background of homologous recombination events which occur between homologous sequences carried in the same cell (i.e. the gene targeting cassette encoding ura3Bsp, ura3Pvu or ura3☐PstEcoRV, present on pMW267, pMW269, pMW252 and pMW253, respectively and the chromosomal URA3 locus) under the growth conditions used. However, the rate of converting the chromosomal URA3 locus to a mutant allele is greatly increased over the background level when the RTase is expressed in a cell also expressing the STOPstem gene targeting system. This is demonstrated by the 30%-130% increase in the occurrence of FOA-resistant cells in a strain expressing the STOPstem gene targeting cassette and expressing RTase (i.e. RK2575-URA/pMW267/pMW27; RK2575-URA/pMW269/pMW27; RK2575-URA/pMW252/pMW27; RK2575-URA/pMW253/pMW27). Thus the gene targeting systems embodied here can be applied to efficiently alter eukaryotic chromosomal loci.

These results further show that the invention may be adapted so that a wide variety of genetic alterations may be made at a eukaryotic chromosomal target locus. These alterations may for example include: single-base pair changes; alteration of short contiguous sequences of at least 8 bp; and alteration of long contiguous sequences, for example of at least 50, 100, 150, 200, 208 or 250 bp.

These results additionally illustrate that genetic alteration of an eukaryotic chromosomal target locus can be achieved with the reverse transcription-based gene targeting system when the cDNA is designed to pair with either the sense or antisense strand of a target locus.

Example 6

3'-Recruitment System

6a) Overview

An additional derivative of the msr-msd elements exemplified here as being an effective gene targeting system is referred to as the 3'-recruitment system (FIG. 11). The 3'-recruitment system incorporates the msr, msd, and a1' and a2' elements as per STEM3 (FIG. 4). However, the order of the elements is rearranged. As illustrated in FIG. 11, in the 3'-recruitment system the msd element is 5' of the msr element and the a1' and a2' inverted repeat sequences are adjacent to each other between the msd and msr elements. Likewise to STEM3, a DNA sequence encoding homology to a target locus and the genetic change to be transferred to the target locus can be cloned into the msd element within the 3'-recruitment system at the unique XbaI and EcoRV sites. This is then placed behind a promoter which is functional in the host cell. The 3'-recruitment system gene targeting assembly is then introduced into a host eukaryotic cell which is also capable of expressing RTase.

As illustrated in FIG. 11, the configuration of the components of the 3'-recruitment system is such that the RNA transcript of the 3'-recruitment gene targeting assembly will fold in a conformation mimicking that of STEM3 (FIG. 4) and the wild type msr-msd elements (FIG. 1). The significant difference between STEM3 and the wild type msr-msd versus the 3' recruitment system is that the loop region within the msd element is not formed in the 3'-recruitment system. Although this loop region is not created, the annealing of the a1' and a2' inverted repeat sequences and repeat sequences within the msd and msr regions are still capable of occurring (FIG. 11). Thus formation of the appropriate RNA structure in the msr region to recruit RTase and place it in the correct context to initiate reverse transcription of the msd region and convert the gene targeting sequence to cDNA may still occur. This cDNA can then act as a gene targeting substrate. As a result of repeated transcription of the 3'-recruitment assembly and consequent reverse transcription by reverse transcriptase, multiple copies of the gene targeting substrate may be made with this system. This gene targeting substrate may then be acted upon by host DNA recombination and repair processes to pair with the target chromosomal locus and genetically alter it. In the absence of an RNaseH-like activity, reverse transcription of the 3'-recruitment assembly may form a RNA/DNA hybrid molecule encoding the gene targeting substrate. In the presence of an RNaseH-like activity a molecule with an extensive ssDNA region may be created encoding the gene targeting substrate.

A significant advantage of the 3'-recruitment structure is that it may bypass structural constraints which may exist in the STEM3 system as a result of creating a large loop structure in the msd element. The amount of novel DNA sequence placed within the msd element may affect the folding of the retron elements and impair cDNA synthesis. For example, in the STEM3 system a size limit may exist regarding the amount of DNA placed in the msd element and tolerated with respect to proper folding of the retron to enable efficient reverse transcription. This size limit may also be dependent upon the composition of the novel sequence place in the msd element. Exceeding this size limit or sequence composition may inhibit formation of the appropriate secondary and tertiary structures in the msr and msd region of STEM3. This in turn may inhibit recruitment of RTase and or reverse transcription of the msd region encoding the gene targeting cassette. Because the 3'-recruitment system does not form this msd loop structure, interference by the gene targeting sequence length or composition on the folding of the msr and msd elements may be minimised. As a result, the size of cDNAs or cDNA sequence composition types capable of being synthesized by the retron system using the 3'-recruitment configuration may be greatly increased over that possible using the STEM3 or other possible configurations of retron components.

In some embodiments retron and cognate RTase versions are used which have high processivity so as to increase the length of cDNAs synthesized with the 3' recruitment system. Novel versions of RT may be developed, for example, by in vitro evolution techniques such as, for example, gene shuffling using RTases from various sources.

In some embodiments mutant versions of RTase are developed which have increased processivity and used as part of the 3'-recruitment system so as to increase the length of cDNAs synthesized with the 3' recruitment system.

In some embodiments the 3'-recruitment system is expressed using the promoter of the target gene. With this arrangement the 5' region of the RNA to create the gene targeting substrate may be identical to the target gene. As a result, the 3' region of the cognate cDNA created by the 3'-recruitment system may maximise homology to the target locus. This high degree of homology at the 3' end of the gene targeting substrate may increase gene targeting frequency.

In some embodiments the 3'-recruitment system incorporates a sequence which is capable of terminating reverse transcription at a specific site. One example of such a sequence is the S1-S2 inverted repeat described above for the STOPstem system. Incorporating such a termination sequence at an appropriate position in the gene targeting sequence within the 3'-recruitment system may create cDNA molecules with a high degree of homology at the 3' end of the resultant cDNA gene targeting substrate which may thus increase gene targeting frequency.

6b) In Vivo cDNA Synthesis Using the 3'-Recruitment System

The 3'-recruitment derivative of Ec86 msr-msd was evaluated for its capability to enable in vivo cDNA synthesis in prokaryotic and eukaryotic cells using E. coli and S. cerevisiae as respective model systems. To evaluate the system in E. coli, the strain DH5α was transformed with pMW120, capable of expressing NLS-RT derived from Ec86, in combination with one of several constructs, capable of expressing the 3'-recruitment element plus inserts of: 100 bp (pMW159); 250 bp (pMW164); or 500 bp (pMW165). As a control to demonstrate dependence of cDNA production on a reverse transcriptase, a derivative of pMW159 was created which had the msr region responsible for recruiting reverse transcriptase and priming reverse transcription deleted (i.e. pMW171). These constructs were transformed into E. coli DH5-alpha in combination with pMW120. The strains were cultured and processed as outlined above for the evaluation of the STEM3 system in E. coli. DNA samples were resolved by gel electrophoresis on a 2% agarose gel and detected by staining with ethidium bromide.

As illustrated in FIG. 12, the 3'-recruitment system is effective for in vivo production of cDNAs. A sequence of at least 500 bp can be reverse transcribed using the 3'-recruitment system. The dependence on production of the cDNAs on a reverse transcriptase was demonstrated by the absence of detectable cDNA accumulation when the reverse transcriptase recruitment and priming sequence was deleted (i.e. pMW171). The results highlight the finding disclosed herein that release of structural constraints in the msr-msd region of a retron can significantly increase the capacity of the construct for producing cDNAs of increased length using retron-derived systems of the invention. For example, using the STEM3 system, sequences of ~100 bp appear to be the maximum for cDNA synthesis (FIG. 6). However, with the 3'-recruitment system, sequences of at least 500 bp can be used for cDNA synthesis in vivo. This demonstrates the facility of the 3'-recruitment system to adapt retrons to produce relatively lengthy cDNAs in vivo. The invention accordingly provides methods for modifying structural constraints inherent in the msr-msd sequences so as to increase tolerance of an insertion sequence in a gene targeting construct, to facilitate reverse transcription of a gtRNA to produce a GTS.

To evaluate the capability of the 3'-recruitment system to produce cDNAs in vivo in eukaryotic cells, S. cerevisiae RK2575-URA was transformed with pMW221, capable of expressing the 3'-recruitment element containing an insert of 500 bp, in combination with pMW27, capable of expressing NLS-RT from Ec86, or YCplacIII-Tet2x, the parental vector of pMW27. The strains were cultured and processed as outlined above for the evaluation of the STEM3 system in S. cerevisiae. Samples of DNA from the strains were resolved by gel electrophoresis on a 2% agarose gel, Southern blotted and probed with a $^{32}$P-labeled DNA fragment encoding Ec86 msr-msd.

FIG. 13 illustrates production of cDNA in eukaryotic cells using the 3'-recruitment system. Note the high molecular weight bands detected on the Southern blot represent the parental constructs encoding the 3'-recruitment components which also hybridise to the radioactively-labelled probe. The low molecular weight signal represents the cDNA produced by reverse transcription of the 3'-recrutiment::500 bp RNA. Detection of the cDNA is dependent upon co-expression of the NLS-RT and the 3'-recrutiment::500 bp RNA. This embodiment demonstrates the capability of the 3'-recruitment system to produce cDNAs encoding at least 500 nucleotides in vivo in eukaryotic cells. The rearrangement of retron msr-msd sequences to modify structural constraints and promote an open conformation to promote reverse transcription of lengthy insertion sequences is an aspect of the present invention.

6c) Application of 3'-Recruitment to Gene Targeting in Eukaryotic Cells

To demonstrate application of the 3'-recruitment system for modifying eukaryotic chromosomal loci the chromosomal URA3 locus of the model eukaryote S. cerevisiae was employed as representative of any chromosomal locus in eukaryotic cells. In this example, the RTase is expressed from one episome and the 3'-recruitment system assembly is expressed from another episome. In other embodiments the RTase and 3'-recruitment system assembly may be expressed from a single episome or from genetically linked or unlinked loci encoded by a chromosome. In one example, 500 bp of the ura3Δ$^{PstEcoRV}$ allele was cloned into the 3'-recruitment system in a sense orientation and placed adjacent to a promoter in a yeast vector with the TRP1 selectable marker (i.e pMW249). In another example, 500 bp of the ura3Δ$^{PstEcoRV}$ allele was cloned into the 3'-recruitment system in an anti-sense orientation and placed adjacent to a promoter in a yeast vector with the TRP1 selectable marker (i.e pMW248). The NLS-RT of Ec86 was encoded adjacent to a promoter on a yeast vector with the LEU2 selectable marker (i.e. pMW27).

To evaluate the 3'-recruitment system-based gene targeting system, RK2575-URA was transformed by the method of Geitz et al., 1995 [212] [323] with: pMW249 alone or in combination with pMW27; or pMW248 alone or in combination with pMW27. The double-transformed yeast cells possessing either pMW249 or pMW248 and pMW27 thus require culture on the medium SC-LEU-TRP. Therefore to keep medium composition uniform for all treatments in the experiment, the strains transformed with the single experimental constructs (i.e. pMW249 or pMW248 into separate strains instead of in combination with pMW27) were also transformed with an empty vector (i.e. YCplac111Tet2x, the base vector of pMW27) solely for the purpose of supplying the complementary selectable marker as present in the experimental double-transformants. In this manner all strains could be cultured in the same SC-LEU-TRP medium.

RK2575-URA cells were transformed with the above mentioned plasmid combinations as per Geitz et al. (1995) [212] [323] and the cells were plated on SC-LEU-TRP. The plates were incubated at 30 C until colony diameter was 3-4 mm. Eleven colonies from each treatment were individually collected and disbursed in 1 ml sterile distilled water (SDW). An aliquot of these cells was used to prepare serial dilutions in SDW and plated on YPD medium to determine viable cell number. Additional aliquots were plated on FOA selection medium. The plates were incubated 2-5 days and the colonies were then counted. The data of viable cell number and number of FOA-resistant cells was compiled, taking into consideration the dilution factors, and analysed by the method of the median [1007] [327] with statistical analysis as described by Dixon and Massey (1969) [962] [328]. The FOA-resistant cells represent genetic events where the chromosomal URA3 locus is converted to a mutant allele as encoded by the gene targeting cassettes encoding a fragment of the ura3ΔPstEcoRV allele (i.e. pMW249, pMW248).

As shown in Table 2, the exemplified embodiments demonstrate modification of a specific target locus in a eukaryotic chromosome can be achieved by employing components involved in reverse transcription as part of a gene targeting system as embodied here. The genetic evidence demonstrates that conversion of a target locus in a eukaryotic chromosome to an alternate allele can be promoted by employing a reverse transcriptase to create cDNA molecules in vivo to act as gene targeting substrates which can interact with and alter the sequence of a chromosomal target locus.

The data in Table 2 from Experiment 3 demonstrates that the 3'-recruitment system employing elements of the retron Ec86 is effective at facilitating genetic alteration of a eukaryotic chromosomal locus. The respective control strains (i.e. RK2575-URA/pMW249; RK2575-URA/pMW248) reflect the background of homologous recombination events which occur between homologous sequences carried in the same cell (i.e. the gene targeting cassette encoding ura3$\Delta^{PstEcoRV}$ present on pMW248 and pMW249 and the chromosomal URA3 locus) under the growth conditions used. However, the rate of converting the chromosomal URA3 locus to a null allele is greatly increased over the background level when the RTase is expressed in a cell also expressing the 3'-recruitment gene targeting system. This is demonstrated by the 170% or greater increase in the occurrence of FOA-resistant cells in a strain expressing the 3'-recruitment gene targeting cassette and expressing RTase (i.e. RK2575-URA/pMW249/pMW27; RK2575-URA/pMW248/pMW27). Thus the gene targeting systems embodied here can be applied to efficiently alter eukaryotic chromosomal loci.

These results additionally illustrate that genetic alteration of an eukaryotic chromosomal target locus can be achieved with the reverse transcription-based gene targeting system when the cDNA is designed to pair with either the sense or antisense strand of a target locus.

Example 7

Development of dsDNA Gene Targeting Substrates In Vivo

In some embodiments, reverse transcriptase is employed to make gene targeting substrates in vivo which are double-stranded DNA (dsDNA). In one embodiment, the dsDNA gene targeting substrate may be synthesized by using a gene targeting cassette that contains an inverted repeat sequence. One part of this inverted repeat sequence encodes the genetic change desired to be transferred to the target locus plus flanking sequences that are homologous to the target locus and corresponds to the sense strand of the target locus. The other part of the inverted repeat sequence is like the first except that it corresponds to the anti-sense strand of the target locus. These two parts of the inverted repeat sequence may be linked in a head-to-head or tail-to-tail fashion to create the gene targeting cassette. The gene targeting cassette is then linked to a sequence capable of recruiting reverse transcriptase and priming reverse transcription of the inverted repeat sequence region of the gene targeting cassette. The inverted repeat sequences converted to cDNA by action of reverse transcriptase can then base-pair with each other to create a dsDNA molecule that encodes regions of homology to the target locus as well as the genetic change desired to be transferred to the target locus. This dsDNA molecule can be acted upon by host DNA recombination and repair processes to facilitate transfer of the genetic change encoded by the gene targeting substrate to the target locus.

In some embodiments, a dsDNA gene targeting substrate may be synthesized in vivo using a reverse transcription-based system by producing two forms of single-stranded DNA (ssDNA) gene targeting substrate in the same cell. Both ssDNA gene targeting substrate forms may encode the genetic change desired to be transferred to the target locus plus the flanking sequences that are homologous to the target locus. However, one ssDNA gene targeting substrate type encodes a sequence representative of the sense strand of the target locus and the other ssDNA gene targeting substrate type encodes a sequence representative of the anti-sense strand of the target locus. When the two forms of ssDNA gene targeting substrates are both present in a cell, they may base-pair to form a dsDNA gene targeting substrate that encodes regions of homology to the target locus as well as the genetic change desired to be transferred to the target locus. This dsDNA molecule can be acted upon by host DNA recombination and repair processes to facilitate transfer of the genetic change encoded by the gene targeting substrate to the target locus.

To illustrate the use of dsDNA gene targeting substrates produced in vivo in eukaryotic cells, S. cerevisiae was used as a model system. In this example, genetic modification of the chromosomal URA3 locus of S. cerevisiae was employed as representative of applying the invention to any chromosomal locus in eukaryotic cells. In this example, the reverse transcriptase is expressed from the chromosome and the RNA molecules to be reverse transcribed into cDNAs encoding the gene targeting substrate are expressed from episomes. In other examples, the reverse transcriptase and RNA molecules encoding the gene targeting substrates may be expressed from a single or multiple episomes, or from genetically linked or unlinked loci encoded by the host genome. In one example, 500 bp of the ura3$^{Pvu}$ allele was cloned into both the STEM3 and STOPstem derivatives of Ec86 msr-msd in either the sense or antisense orientation (i.e. pMW261 and pNML93 in STEM3 as sense or antisense, respectively; pMW262 and pNML94 in STOPstem as sense or antisense, respectively). These elements were then transferred to yeast expression vectors resulting in the following constructs: pNML91 (STEM3::ura$^{Pvu}$-sense); pNML95 (STEM3::ura$^{Pvu}$-antisense); pNML101 (STEM3::ura$^{WT}$-sense); pNML103 (STEM3::ura$^{WT}$-antisense); pNML92 (STOPstem::ura$^{Pvu}$-sense); pNML96 (STOPstem::ura$^{Pvu}$-antisense); pNML102 (STOPstem::ura$^{WT}$-sense); pNML104 (STOPstem::ura$^{WT}$-antisense). NLS-RT was placed into a chromosomal integration and expression vector (i.e. pWY84). The resultant strain with NLS-RT integrated at the HO locus of RK2575-URA was designated RK2575-URA-HO::NLS-RT.

To illustrate the application of producing dsDNA molecules in vivo, RK2575-URA and RK2575-URA-HO::NLS-RT were each transformed as follows: pNML101 and pNML103 (STEM3::URA$^{WT}$); pNML91 and pNML95 (STEM3::ura3$^{Pvu}$); pNML102 and pNML104 (STOPstem::URA$^{WT}$); pNML92 and pNML96 (STOPstem::ura3$^{Pvu}$).

In alternative embodiments, yeast cells could be transformed following the method of Geitz [212] and cells plated on SC-LEU-TRP. The plates would then be incubated at 30 C until colony diameter was about 3-4 mm. A number of colonies from each treatment would then be individually collected and disbursed in 1 ml sterile distilled water (SDW). An aliquot of these cells would be used to prepare serial dilutions in SDW and plated on YPD medium to determine viable cell number. Additional aliquots would be plated on FOA selection medium. The plates would be incubated 2-5 days and the colonies counted. The data of viable cell number and number of FOA-resistant cells would be compiled, taking into consideration the dilution factors, and analysed by the method of the median [1007] [327] with statistical analysis as described by Dixon and Massey (1969) [962] [328]. The FOA-resistant cells would represent genetic events where the chromosomal URA3 locus is converted to a mutant allele as encoded by the gene targeting cassettes.

Example 8

Effect of Recombination Potential on Gene Targeting Frequency

In some embodiments, the frequency of gene targeting in eukaryotic host cells may be enhanced by elevating the activity of the homologous recombination machinery in the host cells.

In other embodiments, the frequency of gene targeting in eukaryotic host cells may be elevated by suppressing the activity of host cell processes which promote integration of gene targeting substrates into the chromosome by non-homology-based recombination processes such as those involved in non-homologous end-joining (NHEJ).

In some embodiments, the eukaryotic host cell is treated so as to both enhance the activity of homologous recombination machinery as well as suppress the activity of non-homology-based recombination processes.
8a) Decreased Non-Homologous Recombination Activity In some examples, the action of non-homology based recombination processes is suppressed by reducing the activity of key proteins involved in this process such as Ku70, Ku80 and DNA protein kinase (DNA-PK) which are highly conserved in eukaryotes, [1026, 114, 1020, 1093] from yeast to humans and plants.

The activity of Ku70, Ku80 and DNA-PK may be reduced by several means such as: anti-sense RNA; co-suppression; RNAi.

Alternatively, a dominant-negative approach could be used whereby a mutant form of a protein is expressed in the wild type host cell. The mutant form of the protein then inhibits the function of the endogenous wild type protein by for example, binding and titrating or sequestering a protein or nucleic acid substrate or co-factor such that it is no longer readily available for interaction with the endogenous wild type protein.
8b) Gene Targeting in Meiotic Cells Meiosis is an important component of sexual reproduction in eukaryotic cells whereby haploid gametes are produced by diploid parents. An important aspect of meiosis is the production of genetic variation through the exchange and mixing of genetic information between the maternal and paternal genomes. This exchanging and mixing of the parental genomes is facilitated by the process of homologous recombination. As a result, many of the proteins involved in homologous recombination are expressed at an elevated level in meiotic cells resulting in a greatly increased potential for homologous recombination in meiotic cells versus vegetative cells [73]. Delivery of gene targeting substrates to meiotic cells could thus result in enhanced gene targeting frequency because of the elevated homologous recombination potential of these cells.

In some embodiments of the invention, reverse transcription is used to generate gene targeting substrates in meiotic cells. In some embodiments, RNA molecules encoding gene targeting substrates are expressed in meiotic cells so that an endogenous reverse transcriptase native to the host genome can reverse transcribe the RNA to make a cDNA which can act as a gene targeting substrate in the meiotic cell. Such native reverse transcriptases may be encoded by retro transposons or retroviruses which are naturally resident in the host genome. Such genetic elements are known to be more active during the process of meiosis [763, 764, 761]. Thus coordinating the production of an RNA encoding a gene targeting substrate with the elevated level of reverse transcriptase activity and homologous recombination proteins naturally present in meiotic cells may increase gene targeting frequency.

In some embodiments, RNA molecules encoding gene targeting substrates and a cloned reverse transcriptase capable of reverse transcribing those RNA molecules into cDNAs which can act as gene targeting substrates are coordinately produced in meiotic cells. In some embodiments, the reverse transcriptase is derived from a retron and the RNA molecules encoding the gene targeting substrate possess structures capable of recruiting the reverse transcriptase which facilitates production of the cDNA gene targeting substrate. Thus coordinating the production of an RNA encoding a gene targeting substrate and its cognate RTase with the elevated level of homologous recombination proteins naturally present in meiotic cells may increase gene targeting frequency.

To illustrate the use of reverse transcription to produce gene targeting substrates during meiosis, S. cerevisiae was used as a model eukaryote. The process of meiosis, including the mechanisms of homologous recombination, is highly conserved in yeast, humans and plants [1679, 76, 829, 1678, 504]. Therefore, the application of reverse transcription to achieve gene targeting in yeast cells is representative of that in higher eukaryotes.

S. cerevisiae strain RK2575-URA was used as a host to assay gene targeting. DNA cassettes capable of expressing the RNA component of the reverse transcription-based system were first created. Thus, DNA sequences encoding 500 bp of URA3 or the mutant alleles ura3$^{Bsp}$ or ura3$^{Pvu}$, were cloned into the STEM3 or STOPstem derivatives of Ec86 msr-msd (i.e. pMW287, pMW259, pMW261, pMW288, pMW260, pMW262). These assemblies were then transferred into a chromosomal integration and expression vector (pTK179) resulting in the constructs pMW303, pMW299, pMW301, pMW304, pMW300 and pMW302. The various STEM3 and STOPstem versions of Ec86 msr-msd incorporating a gene targeting sequence were then transferred to the HO chromosomal locus, following standard methods [976], resulting in the strains: RK2575-URA-HO::STEM3+URA3 WT, RK2575-URA-HO::STEM3+ura3$^{Bsp}$, RK2575-URA-HO::STEM3+ura3$^{Pvu}$, RK2575-URA-HO::STOPstem+URA3$^{WT}$, RK2575-URA-HO::STOPstem+ura3$^{Bsp}$ and RK2575-URA-HO::STOPstem+ura3$^{Pvu}$. These strains were cultured in the presence of doxycycline to repress expression of retron components.

The above strains with the chromosomally integrated gene targeting components could be made diploid by mating with a uracil proficient derivative of the S. cerevisiae strain E1134 [276]. E134 was first made to be uracil proficient by replacing the resident ura3-52 allele with a DNA fragment encoding URA3 as described above for converting RK2575 to RK2575-URA. The resulting strain was designated E134-URA. This haploid strain was then mated with the RK2575-URA-HO derivatives described above encoding the chromosomally integrated gene targeting components, following standard methods to produce diploid S. cerevisiae strains. These strains were cultured in the presence of doxycycline to repress expression of retron components. The diploid strains could then be transformed with a vector capable of expressing NLS-RTase (pMW27), following standard procedures [212]. To create control strains not expressing NLS-RTase, the yeast cells were transformed with YLplac111-Tet2X, the parent vector of pMW27. In this manner, the control and test strains could be cultured with the same selection medium. All strains were cultured in the presence of doxycycline (5 ug/ml or 10 ug/ml for broth or plate cultures, respectively) to repress expression of retron components.

To illustrate the effect of producing gene targeting substrates in vivo during meiosis, diploid S. cerevisiae strains capable of producing cDNA-based gene targeting substrates during meiosis were employed as a eukaryotic model. The S. cerevisiae cells were proficient for synthesizing uracil and thus could grow on media lacking uracil. The S. cerevisiae cells were also capable of expressing RNA molecules which could be reverse transcribed through the action of reverse transcriptase to produce a cDNA in vivo which could act as a gene targeting substrate. In this example, the gene targeting substrate would encode homology to the chromosomal URA3 gene as well as a mutated sequence which could be transferred to the chromosomal URA3 gene. Transfer of this genetic information from the gene targeting substrate to the chromosomal URA3 gene could convert the URA3 gene to a mutant allele. The mutated chromosomal allele may confer upon the cell an inability to produce uracil. As a result, a cell possessing the mutant allele but not the URA3 allele would not be able to grow on media lacking a uracil supplement. However, the enzyme encoded by URA3, orotidine-5' phosphate decarboylase, can catabolyse 5-fluoroorotic acid (FOA) to form 5-fluorouracil, a toxic substance that inhibits cell growth. Thus, proliferation of a cell encoding URA3 will be inhibited in the presence of FOA whereas a cell with a mutated ura3 allele may proliferate in the presence of FOA. This selection strategy was used to evaluate the gene targeting frequency in the model system.

Expression of the reverse transcription-based gene targeting system was promoted when the yeast cells were undergoing meiosis. Thus, the cDNA-based gene targeting substrate could be present in the nucleus to be acted upon by endogenous homologous recombination functions. In this example, the gene targeting substrate has homology to the chromosomal URA3 gene present in both the maternal and paternal genomes within the diploid cell. The homologous recombination functions can thus mediate transfer of the genetic information encoded by the gene targeting substrate to either the maternal URA3 allele, the paternal URA3 allele, or both and thereby convert the wild type native alleles to mutant alleles. The haploid products of meiosis could then be cultured in the presence of FOA to select for those with mutated ura3 alleles. An aliquot of meiotic products could also be cultured on a complete medium to determine viable cell number. By relating the number of FOA-resistant cells to viable cell number, an estimate of the frequency of the development of an altered chromosomal ura3 allele could be determined. This frequency could be compared between various test and control strains to estimate the frequency of gene targeting. In some examples, the control strain could be a strain not expressing the reverse transcriptase or a strain producing a gene targeting substrate encoding a wild type sequence versus a mutated sequence.

8c) Genetic Assay of Gene Targeting During Meiosis

To assay gene targeting during meiosis in the yeast model system, single colonies from each test strain could be used to first inoculate 3 ml of SC-LEU-URA+DOX (i.e. containing doxycycline at 5 µg/ml) in a 15 ml tube (Falcon) which would then be incubated at 30 C with shaking (200 RPM) for ~1.5 d. A number of cultures would be prepared for each test strain. Cells from 1 ml of culture would be pelleted by centrifugation at 9000 RPM for 2 min in a standard microcentrifuge (Brinkman) and resuspended in 1 ml of sterile-distilled water (SDW). The cells would be used to inoculate 5 ml of SC-A pre-meiosis medium (per liter: 1.7 g yeast nitrogen free base (Difco), 5 g ammonium acetate (Sigma), 20 g potassium acetate (Sigma), 2 g amino acid drop out mix with selection for the expression vectors, [200] [134]; and doxycycline at 5 µg/ml) in a 50 ml tube (Falcon) at a 1:50 dilution. The cultures would then be incubated at 30 C with shaking (225 RPM) for 2 d. The cells in each culture in pre-meiosis medium would be pelleted by centrifugation at 4000 RPM for 10 min at 4 C. The pellet would be resuspended in 5 ml of SC-A pre-meiosis medium and incubated at room temperature for 4 h to remove doxycycline. These cells would then be pelleted by centrifugation at 4000 RPM for 10 min at 4 C and resuspended in 4 ml SPM meiosis-induction medium (0.3% (w/v) potassium acetate, 0.02% (w/v) raffinose, 5 µg/ml histidine, 5 ug/ml uracil, 7.5 µg/ml lysine, 5 µg/ml tryptophan, 5 µg/ml adenine). The cells would again be pelleted by centrifugation at 4000 RPM for 10 min at 4 C and resuspended in 3.5 ml SPM meiosis-induction medium. Cultures would then be incubated at 30 C with shaking (225 RPM) for 2 d to enable cells to undergo meiosis. Dilutions of the cells would be made using SDW and cells then plated on YPD to determine viable cell number, and on medium containing FOA [200] so as to estimate the number of cells with a modified URA3 allele after meiosis. Duplicate dilutions and plating of each culture could be performed. Plates could be incubated at 30 C for 2-4 d and then colonies were counted. Frequency of alteration of the chromosome URA3 allele to ura3 for each culture could be determined by dividing the number of FOA-resistant colonies by the viable cell number, taking into consideration the dilution factors. Mean values for the replicates of each test strain would be determined. Inclusion of the values from all replicates in determining the mean could be evaluated by the Q-test [201] [135] and values from individual replicates excluded from the final mean if the statistic indicated a significant deviation from the values of other replicates. Comparison of means of gene targeting frequency vs. that from test strains that form control strains could be done to determine the effect of the test gene construct. Statistical significance of the differences between these values could be confirmed by evaluation using the t-test [202] [136].

8d) Gene Targeting with Enhanced Homologous Recombination Potential from Mutant Proteins In some examples, the action of homologous recombination processes is elevated by changing the activity level of enzymatic or structural proteins which facilitate homologous recombination events. This may be achieved by over-expressing wild type homologous recombination-mediator proteins, or mutant versions of homologous recombination-mediator proteins which have enhanced activity properties. The beneficial effect on gene targeting frequency of overexpressing wild type recombinase proteins, such as RAD51, has been demonstrated. RAD51 is a key protein in HR as it participates in pairing homologous DNA molecules and initiating the HR process by catalyzing strand invasion. In some embodiments, a modified version of RAD51 may be used which has increased recombinogenic potential.

One example of such a modified RAD51 is one which may have enhanced ability to bind and complex ssDNA molecules in vivo. In vivo ssDNA molecules can be bound by ssDNA-binding proteins. In eukaryotes, the heterotrimeric complex called RPA binds ssDNA [99]. This coating of ssDNA by RPA may inhibit RAD51 from binding to the ssDNA and initiating the processes of homology searching and strand-invasion [1692]. RAD52 may act to displace RPA from ssDNA and promote loading of RAD51 onto the ssDNA [1693]. RAD55 and RAD57 may also aid RAD51 overcome RPA-based-inhibition of RAD51-promoted strand exchange [1692]. However, in vitro studies have shown that a mutant version of yeast RAD51, with amino acid residue #345 changed from isoleucine to threonine (i.e. RAD51$^{I345T}$) has elevated affinity and more stable binding to SSDNA, even in the presence of RPA, with increased independence from accessory factors [1691]. Thus, overexpression of a modified eukaryotic RAD51 with similar amino acid changes to promote the proteins ability to complex ssDNA may increase gene targeting frequency.

To evaluate the ability of RAD51 with altered ssDNA complexing capacity to increase gene targeting frequency, S. cerevisiae was used as a model eukaryote. A gene encoding the mutant S. cerevisiae RAD51, yRAD51$^{I134T}$, was created using the primers yRAD51-I345T-S and yRAD51-I345T-AS as described above (i.e. pNML56) In some embodiments, similar mutant forms of RecA-like proteins may be used which are derived from their native host species. (e.g. human RAD51 modified to encode the analogous I134T mutation). To illustrate the applicability of employing a mutant form of RAD51 to promote gene targeting in plants, the AtRAD51 of Arabidopsis thaliana was modified and cloned. Sequence alignment between yRAD51 and AtRAD51, or RAD51 proteins from other species, can be used to identify amino acids corresponding to I345 in scRAD51. For AtRAD51, a novel mutation changing amino acid residue #290 from isoleucine to threonine will confer to it similar biochemical properties observed for yRAD51$^{I134T}$. The mutant gene encoding AtRAD51$^{I290T}$ was created and cloned using the primers AtRAD51-I290T-S and AtRAD51-I290T-AS as described above (i.e. pNML55). The AtRAD51$^{I290T}$ gene placed behind a constitutive promoter, the AtRAD51 promoter (pTK114) or a cell-cycle specific promoter (pTK159; pNML11) or promoter expressed during meiosis (e.g. pTK111, pTK65, pJD1) may be cloned into a plant transformed vector and used to create transgenic plants capable of expressing AtRAD51$^{I290T}$. These plants can be used as lines with elevated recombination potential for gene targeting.

Another RecA-like protein which can be mutated to enhance its recombination activity is DMC1, a highly-conserved meiosis-specific protein. Sequence alignments between yRAD51 and DMC1 proteins from other species can be used to identify amino acid residues corresponding to I345 in scRAD51. For yDMC1 from S. cerevisiae, changing amino acid residue #128 from isoleucine to threonine may confer to it similar biochemical properties as observed for yRAD51$^{I134T}$. For AtDMC1 from Arabidopsis thaliana, changing amino acid residue #292 from Ala to Thr. will confer to it similar biochemistry properties observed for yRAD51$^{I134T}$. These proteins, as well as similarly changed DMC1 proteins from other species, may be used to elevate homologous recombination potential and gene targeting frequency during meiosis.

To illustrate the effect of mutant versions of proteins involved in homologous recombination on gene targeting frequency in eukaryotic cells, S. cerevisiae was used as a model system. The S. cerevisiae strains RK2575-URA-HO::STEM3, RK2575-URA-HO::STEM3+URA$^{WT}$, RK2575-URA-HO::STEM3+ura3$^{Bsp}$, RK2575-URA-HO::STEM3+ura3$^{Pvu}$, RK2575-URA-HO::STOPstem+URA$^{WT}$, RK2575-URA-HO::STOPstem+ura3$^{Bsp}$, and RK2575-URA-HO::STOPstem+ura3$^{Pvu}$ described above were transformed with pMW27 expressing NLS-RT alone or in combination with pMW305 expressing yRAD51$^{I134T}$ or pAS22, the parent vector of pMW305. Alternatively, the yeast strains were transformed with yCplac111-Tet2X, the parental vector of pMW27 and pAS22, the parental vector of pMW305. In this manner, all strains could be cultured in the same selective medium. Yeast strains were cultured in the presence of doxycycline (5 ug/ml) to suppress expression of retron elements prior to transformation by the method of Geitz et al. (1995) 212. Transformed cells were plated on SC-LEU-TRP and incubated at 30 C until colony diameter was 3-4 mm. Eleven colonies from each treatment were individually collected and disbursed in 1 ml sterile distilled water (SDW). An aliquot of these cells was used to prepare serial dilutions in SDW and plated on YPD medium to determine viable cell number. Additional aliquots were plated on FOA selection medium [200] [324]. The plates were incubated 2-5 days and the colonies were then counted. The data of viable cell number and number of FOA-resistant cells was compiled, taking into consideration the dilution factors, and analysed by the method of the median [1007] [327] with statistical analysis as described by Dixon and Massey (1969) [962] [328]. The FOA-resistant cells represent genetic events where the chromosomal URA3 locus is converted to a mutant allele as encoded by the gene targeting cassettes.

Example 9

Application of Reverse Transcription to Gene Targeting in Plants

In some embodiments modification of chromosomal target loci in plant genomes is achieved with the invention. To exemplify application of the invention in plants, modification of a native chromosomal copy of the alcohol dehydrogenase gene in A. thaliana was employed. In other embodiments, any gene or genomic sequence in plant or animal genomes may be manipulated using the invention. In one embodiment, the sequence within the coding region of the A. thaliana alcohol dehydrogenase (i.e. AtADH) gene residing in its native chromosomal location is altered. This alteration may cause inactivation of the gene by, for example, inhibiting formation of functional mRNA transcripts from the modified allele. Alternatively, translation of the mRNA transcripts from the modified allele may result in a truncated or non-functional protein which is no longer able to perform the normal reaction of the protein encoded by the target locus (e.g. alcohol dehydrogenase). Inactive or null alleles of the AtADH gene (i.e. Atadh) enable the plant to grow in the presence of allyl alcohol [1002] [308] (i.e. the plants may be considered resistant to allyl alcohol). This is because a functional alcohol dehydrogenase enzyme normally oxidizes allyl alcohol to a toxic aldehyde, acrolein [1002] [308]. Thus Arabidopsis plants with a functional allele of AtADH will die when cultured in the presence of allyl alcohol (i.e. the plants are susceptible to allyl alcohol). This phenotype of allyl alcohol susceptibility and resistance can thus be used as a marker to score gene targeting events where the AtADH gene is inactivated. In summary, the assay involves generating gene targeting substrate designed to inactivate a chromosomal copy of the wild type AtADH gene in *Arabidopsis*. Since this plant line is initially wild type for AtADH, progeny from the line can be assayed for the frequency of allyl alcohol resistant plants (i.e. Atadh) to gauge the occurrence of gene targeting events.

To engineer the gene targeting substrate for this example assay, the AtADH allele was cloned and modified to create null alleles. Null alleles were created using PCR to incorporate novel sequences into AtADH which could impair the functional expression of this gene. In one example, a novel NheI restriction site was created at the splice-donor site between the first exon and intron. This was accomplished by changing bp #31 (with respect to the A of the ATG start codon of AtADH) from A to T, bp #33 from A to G and bp #34 from G to C resulting in the allele Atadh$^{Int-mu}$. These three base pair changes place an in-frame translation stop codon in the first exon and are predicted to impair RNA splicing-mediated excision of the first intron. Both events may impair functional expression of AtADH. In another example, a novel mutant allele was created which lacked the coding region of the first exon. This was accomplished by substituting bp '−2' to '+34' (with respect to the A of the ATG start codon of AtADH), with the sequence GCTAGC, the recognition sequence for NheI, resulting in the mutant allele Atadh$^{\Delta Ex1}$. The lack of the protein coding region of the first exon may impair functional expression of AtADH. In addition, because the wild type start codon is missing in Atadh$^{\Delta Ex1}$, an alternative downstream codon may serve to initiate translation in an incorrect reading frame resulting in impaired functional expression of the gene.

To engineer mutant alleles of AtADH the BAC (bacterial artificial chromosome) F1B15 encoding AtADH from the Columbia ecotype of *Arabidopsis thaliana* (obtained from the *Arabidopsis* Biological Resource Centre, Ohio State University, 1060 Carmack Road, Columbus, Ohio, 432101002) was used as a template in PCR reactions. A clone of the Atadh$^{Int}$ mutant allele is represented by pnML67. A clone of the Atadh$^{\Delta Ex1}$ mutant allele is represented by pNML68. Approximately 500 bp fragments of each of these alleles, as well as of the wild type allele, were amplified by PCR using the primer combinations of: adh-Ex1(−250)-sense-5'Bam X ba aad adh-Ex1(+250)-sense-3'RV, or adh-STOP-Ex1(−250)-sense-5'RI and adh-Ex1(+250)-sense-3'RV using either pNML67, pNML68 or genomic DNA from the Columbia ecotype of *A. thaliana* as templates. These DNA fragments were cut with XbaI or EcoRI to be cloned into the Ec86 msr-msd derivatives STEM3 or STOPstem resulting in: pMW296 encoding STEM3::ADH$^{WT}$, pMW275 encoding STEM3::adh$^{Int-mu}$, pMW295 encoding STOPstem:::ADH$^{WT}$, pMW294 encoding STOPstem::adh$^{\Delta Ex1}$, pMW293 encoding STOPstem::adh$^{Int-mu}$. These elements were then functionally-linked to a transcription promoter (see later) and expressed in plant cells.

In some embodiments, in vivo reverse transcription of RNA molecules encoding gene targeting substrates is facilitated by a reverse transcriptase. In some embodiments, this reverse transcriptase may be natively encoded by the host genome such as by a retrotransposon or retrovirus naturally resident in the host genome. In some embodiments, the reverse transcriptase may be encoded by another species and placed in the host genome by a transformation process. In some embodiments, the reverse transcriptase may originate from a retron. In some embodiments, the retron-derived reverse transcriptase may be engineered to encode a NLS to promote its accumulation in the nucleus of the host cell. In some embodiments, the gene encoding the reverse transcriptase may be engineered to optimize codon usage to enhance translation of the reverse transcriptase in the host cell. In one example, the reverse transcriptase is derived from the retron Ec86 and modified to encode a NLS (i.e. pMW22). In one example, the reverse transcriptase is modified to encode an NLS and an epitope tag to facilitate detection of the protein by immunological methods (i.e. pMW23). In one example, the reverse transcriptase is optimized for codon usage in plants of the cruciferae family (e.g. pNLS-RT$^{Rs}$).

In some embodiments, expression of the reverse transcriptase may be coordinated with that of the RNA element encoding the gene targeting sequence by using similar promoters for each component. In other embodiments, different types of promoters are used to express the components of the gene targeting system so that the components are present in the cell at overlapping temporal and spatial points.

Examples of promoters applicable to the invention include:
1. S-phase associated promoters, including those linked to genes expressed during S-phase, such as DNA-replication proteins. (e.g. PCNA, replication factor C, proliferating cell nuclear antigen, mini-chromosome maintenance proteins, DNA polymerase, helicase, topoisomerase) or regulators and effectors of signal transduction processes which influence the onset or duration of cell cycle events (e.g. cyclins, cell division control genes, checkpoint genes), effectors of DNA topology (e.g. histones), and promoters regulated by the E2F transcription factor.
2. DNA repair associated promoters like those linked to homologous recombination and which are active during S-phase and G2-phase of the cell cycle (e.g. RAD51, RAD54, RAD52, MRE11, RAD55, RAD57, BRCA1, BRCA2, RAD50).
3. G2-phase associated promoters like those linked to regulators and effectors signal transduction controlling the onset or duration of G2-phase (e.g. cyclins, cell division control genes, checkpoint genes) or homologous recombination functions (e.g. RAD51, RAD54, RAD52, MRE11, WRN, BLM, SGS1, RAD55, RAD57, BRCA1, BRCA2, RAD50)
4. Meiosis-associated promoters like those linked to homologous recombination (e.g. SPO11, MRE11, RAD50, XRS2/NBS1, DMC1, RAD51, Tid1, RAD54, resolvase, WRN, BLM, Sgs1, MSH4, MSH5).
5. Constitutive promoters (e.g. ACT1, ACT2, ACT3, ACT4, ACT7, ACT8, ACT11, ACT12, cryptic promoters, viral promoters).

In some embodiments, expression of the reverse transcriptase and the RNA element encoding the gene targeting sequence may be controlled by different promoters, like those listed above, which may or may not confer overlapping expression patterns.

In some embodiments, the reverse transcriptase and the RNA element encoding the gene targeting sequence may be integrated into the host genome at one locus. Alternatively, these components may be introduced into the host genome at different times through separate transformation procedures. Alternatively, these two components may be brought together in the same nucleus through a sexual cross or cell or nuclear fusion between two lines expressing the respective components.

In some embodiments the expression of NLS-RT or the msr-msd derivative may be regulated by the AtH4 histone promoter cloned in pNML11. In some embodiments the expression of NLS-RT or the msr-msd derivative may be regulated by the AtCycD3 promoter cloned in pTK159. In some embodiments the expression of NLS-RT or the msr-msd derivative may be regulated by the EntCUP2 or EntCUP5 promoter [994, 1698] [302]. In some embodiments expression of NLS-RT or the msr-msd derivative may be regulated by the AtDMC1 promoter cloned in pTK111. In some embodiments the expression of NLS-RT or the msr-msd derivative may be regulated by the AtSPO11 promoter cloned in pJD1. In some embodiments the expression of NLS-RT or the msr-msd derivative may be regulated by the AtMSH4 promoter cloned in pTK65. In some embodiments the expression of NLS-RT or the msr-msd derivative may be regulated by the AtRAD51 promoter cloned in pTK114.

In one example, plant transformation constructs were assembled to enable expression of NLS-FLAG-RT derived from Ec86 (i.e. encoded by pMW23) and either the STEM3 or STOPstem derivative of Ec86 msr-msd incorporating DNA sequences designed to target AtADH in *A. thaliana* (i.e. encoded by pMW296, pMW275, pMW295, pMW293, pMW294). In one example, NLS-FLAG-RT was linked to the AtCycD3 promoter (pWY66). In another example, NLS-FLAG-RT was linked to the AtH4 promoter (i.e. pMW271). In another example, NLS-FLAG-RT was linked to the Ent-CUP2 promoter (i.e. pWY67). In another example, NLS-FLAG-RT was linked to the Actin2 promoter (i.e. pWY81).

To facilitate expression in plants of the RNA component encoding the gene targeting substrate, the STEM3 or STOPstem element encoding a gene targeting sequence was linked to the AtH4 promoter or the EntCUP5 promoter.

In one example, plant transformation constructs were developed with the gene encoding NLS-FLAG-RT linked to the AtCycD3 promoter and the STEM3 or STOPstem cassette linked to the AtH4 promoter. In this manner, the following plant transformation constructs were created: pMW284 (encoding STEM3::adh$^{WT}$); pMW309 (encoding STEM3::adh$^{\Delta Ex1}$); pMW278 (encoding STEM3::adh$^{Int1mu}$); pMW291 (encoding STOPstem::adh$^{WT}$); pMW290 (encoding STOPstem::adh$^{\Delta Ex1}$); and pMW289 (encoding STOPstem::adh$^{Int1mu}$).

In another example, NLS-FLAG-RT was linked to the Ent-CUP5 promoter [994, 1698] and expression of the RNA component encoding the gene targeting sequence was controlled by the ACT2 Actin2 promoter [1708].

Example 10

Test Gene Targeting in Plants Using Reverse Transcription

The plant transformation constructs encoding the gene targeting system employing the retron-derived components was used to transform *A. thaliana* as a representative plant species where the invention may be applied. The constructs pMW276, pMW284, pMW278, pMW277, pMW291, pMW289, pMW290 were first introduced into *Agrobacterium tumefaciens* C58C1(pMP90) [1000] [309] following standard microbiological procedures [213] [256]. *Arabidopsis* plants were then transformed with the gene targeting constructs using the 'floral-dip' method [772] [310]. Seed was collected from these plants treated with *A. tumefaciens*. To plants were selected by first sterilizing the $T_0$ seed (5 min in 70% ethanol, followed by 10 min in 30% commercial bleach plus 0.1% (w/v) TWEEN 20, then 3 washes with SDW). The sterile seeds were plated on ½×MS salts (sigma) solidified with 0.8% (w/v) agar containing 7.5 ug/ml phosphinothricin (sigma). The plates were incubated at 22° C. with 16/8 h. photoperiod. Herbicide-resistant $T_0$ seedlings were transferred to soil and allowed to mature and self-cross. $T_1$ seed was collected from individual lines. Samples of $T_1$ seed from each herbicide resistant line is then plated on medium containing allyl alcohol as described [308]. Plants that are homozygous for an inactive Atadh allele will be able to grow in the presence of allyl alcohol and will reflect the incidence of gene targeting occurring.

The application of a retron-based gene targeting system in plants is illustrated in FIG. 14. To summarise the assay of gene targeting concerning modification of the AtADH gene as an example, the plants are transformed with the gene targeting constructs expressing NLS-RT or NLS-FLAG-RT and the gene targeting cassette encoding either the STEM3 or STOPstem derivative of msr-msd and either a fragment of ADH$^{WT}$, adh$^{Int1mu}$ or adh$^{\Delta Ex1}$. As a control, other plants may be transformed with the gene targeting constructs encoding a msr-msd derivative without an intervening sequence (i.e. no Atadh allele). In the case of where promoters which are functional in vegetative cells are used to control expression of the reverse transcription components, gene targeting events may occur as the seeds from the *A. tumefaciens* treated plants germinate and develop into the $T_0$ plants. With each cell division, the targeting substrate may be produced by the action of reverse transcriptase on the RNA component encoding the gene targeting substrate. Thus numerous opportunities occur during plant development for the chromosomal allele of AtADH to be converted to a new sequence (i.e. Atadh) by the gene targeting substrates produced by reverse transcription. In some embodiments, with the possibility of gene conversion occurring early in development (i.e. from the time of embryo formation), there may be a high probability that the converted allele will occur in a cell lineage which leads to gamete formation. If the converted allele is carried into the germ line in a heterozygous state, meiosis in the particular flower or flowers derived from the converted cell lineage may be expected to produce gametes at a 1:1 ratio regarding the wild-type (AtADH) and converted (Atadh) allele. In the case of the alcohol dehydrogenase locus, selfed progeny from such a flower may segregate in a Mendelian fashion as 1:2:1 with 25% of the progeny being homozygous for the converted allele and selected for by allyl alcohol. Efficiency of gene targeting may be gauged by the frequency of $T_0$ plants producing progeny resistant to allyl alcohol. In other embodiments, further generations (i.e. $T_1$, $T_2$, $T_n$) may be evaluated for occurrence of gene targeting events. This frequency may also be compared to that obtained in control plants transformed with the same gene targeting construct except not having an intervening sequence (i.e. no Atadh allele) associated with the msr-msd derivative or a control where the msr-msd derivative encodes a WT portion of AtADH. Because the gene targeting construct encoding NLS-RT or NLS-FLAG-RT and the msr-msd derivative encoding the Atadh reproducible sequence may integrate into a site in the plant genome distal from the target allele (e.g. AtADH), then through the process of natural genetic segregation plants may be identified which encode the modified target locus (e.g. Atadh) but no longer encode the initial gene targeting construct. As a result this plant may contain no undesired foreign sequences (e.g. transformation construct sequences). In addition, this plant line may be transformed with a new gene targeting construct to modify a second target locus and the identification of these primary transformants may use the same selectable marker as used in the initial gene targeting construct.

In other embodiments where promoters which are functional in meiotic cells are used to control expression of reverse transcription components, gene targeting events may occur as the $T_0$ plant undergoes meiosis. In this case, the AtADH gene in numerous male and female gametes may be converted to Atadh allele. If this plant is allowed to self-cross, seeds will result that are either heterozygous for the converted allele (i.e. AtADH/Atadh) or homozygous for the converted allele (i.e.

Atadh/Atadh), as well as homozygous wild type. Efficiency of gene targeting may be gauged by the frequency of $T_0$ plants producing progeny resistant to allyl alcohol. In other embodiments, further generations (i.e. $T_1$, $T_2$, $T_n$) may be evaluated for occurrence of gene targeting events. This frequency may also be compared to that obtained in control plants transformed with the same gene targeting construct except not having an intervening reproducible sequence (i.e. no Atadh allele) associated with the msr-msd derivative or a control where the msr-msd derivative encodes a WT portion of AtADH to gauge the efficiency of genetargeting.

In other embodiments alternative genes encoded in plant or animal genomes may be modified using the gene targeting system described here. One example of commercial importance in plants would be herbicide resistance such as, for example, that associated with the acetolactate synthase (i.e. ALS) gene. Modification of, for example, amino acid residue #653 of the ALS protein from *Arabidopsis thaliana* corresponding to a serine, or the corresponding amino acid from ALS proteins from other species, whereby it is converted to an asparagins, can confer resistance to a imidazolinone-type herbicide [1004] [311]. An engineered allele of the ALS gene to create a gene targeting substrate, which can facilitate such an amino acid change to confer herbicide resistance, can be used with this system.

Example 11

Retron Expression

Inserting GTNS within a Modified msd Hairpin

An msr-msd cassette containing a variety of restriction sites was prepared to permit introduction of nucleotide sequences of interest (GTNS) within msr-msd (FIG. 3A).

To optimize the prospect of proper folding of the msr-GTNS-msd product at the 5'-3' termini, regions of homolgy at the 5' and 3' ends of msr-msd were increased as shown in FIG. 3B (STEM 3, portion below arrow). This extension isolates the msr-msd region from 5'UTR and 3' UTR regions associated with the construct to permit expression within the host. Nucleotide sequences of interest of varying lengths were also introduced into restriction sites introduced into the hairpin of stem 3 (FIG. 3B). These inserts included nucleotide sequences encoding URA3 as a nucleotide sequence of interest.

URA3 metabolizes 5' fluorouroitic acid (FOA) to a toxic metabolite, therefore cells expressing URA3 when cultured in FOA die (FOA sensitive, $FOA^s$, FIG. 8). Cells that are $ura3^-$ will grow on FOA (FOA resistant, $FOA^r$). Cells that have been transformed with an msr-GTNS-msd where the GTNS is $ura3^-$, and that exhibit growth on FOA, are indicative of replacement of the target locus by the gene targeting substrate (FIG. 8).

As shown in FIGS. 6 (EtBr stain, left hand side and Southern analysis, ura3 probe, right hand side) and 4E (Southern analysis, ura3 probe), accumulation of msDNA is observed with inserts of 15 to 500 base pairs in length of ura3 placed within the msd hairpin loop of msr-GTNS-msd as outlined in FIG. 5. Retron expression is only observed in the presence of RT. In *E coli*, msDNA accumulation is noted for a GTNS up to about 100 base pairs in length, while in yeast, accumulation is observed for inserts of up to about 500 nucleotides in length.

Inserting GTNS in an Inverted msr-msd Region

Alternate strategies for inserting a gene targeting nucleotide sequence within an msr-msd is outlined in FIG. 11. In this example, inverted repeats are inserted in the region between msr-msd so that these regions pair to produce the structure shown in FIG. 11, middle panel. This structure provides a 5' msd free end that is spatially separated from the internal rG residue of the RNA transcript required for priming reverse transcription. Fragments of ura3 are added to the 5' end of the retron.

With reference to FIGS. 12 (EtBr stained gels) and 13 (Southern analysis using ura3 as a probe), accumulation of msDNA is observed with inserts of 100 to 500 base pairs in length placed at the 5' end of a modified msr-msd as outlined in FIG. 11. Retron expression is only observed in the presence of RT. In both yeast and *E coli*, msDNA accumulation is noted for a GTNS up to about 500 base pairs in length.

Example 12

Cloning and Evaluation of Genes

Genes and genetic elements of interest were cloned using specific oligonucleotides designed to prime DNA synthesis in a PCR reaction with either cDNA or genomic DNA (gDNA) from the appropriate species as template. The primers were designed to incorporate convenient restriction sites into the amplicon to facilitate initial cloning of the gene or genetic element and subsequent subcloning into various expression or analytical vectors. Genes and genetic elements cloned and the oligonucleotide primers used to achieve this are not set out herein, but may in many cases be derived from published sequence information. PCR conditions were as described [213] [256] or as recommended by the supplier of the thermostable DNA polymerase Pfu (Stratagene), Pfx (Gibco BRL) or Taq (Pharmacia). PCR reactions were conducted using a thermocycler (Perkin-Elmer Model 9700). In some cases specific restriction fragments known to encode the gene or genetic element of interest, based on sequence information from genome databases, were directly cloned from complex mixtures of DNA fragments without any PCR amplification. In other cases, specific restriction fragments known to encode the gene or genetic element of interest based on restriction maps of plasmids encoding the desired components were subcloned into other vectors for various applications. DNA sequence of clones was determined at a commercial sequencing facility (Plant Biotechnology Institute, Saskatoon, Canada).

Strains of *Escherichia coli* were cultured at 37° C. following standard [200, 213] procedures [213] with noted exceptions using TYS broth (per liter distilled water: 10 g Tryptone (Difco); 5 g yeast extract (Difco); 5 g NaCl (Sigma)) or TYS plates (i.e. TYS medium plus agar (1.5% (w/v); Sigma)) with appropriate levels of antibiotics (i.e. ampicillin (100 µg/ml); kanamycin (50 µg/ml); chloramphenicol (20 µg/ml); tetracycline (12 µg/ml)) where necessary to ensure selection and maintenance of plasmid constructs.

Strains of *Saccharomyces cerevisiae* were cultured at 30° C. following standard procedures with noted exceptions using YPD broth (per liter: 10 g Bacto-yeast extract, 20 g Bacto-peptone, 20 g glucose) or YPD plates (i.e. YPD medium plus agar (2% (w/v)), or on minimal medium with appropriate amino acid supplements to ensure selection of plasmid constructs.

12a) Cloning of Reverse Transcriptase and Derivatives

Reverse transcriptase from retrons was evaluated to facilitate production of cDNA-based gene targeting substrates in eukaryotic cells. The strain ECOR 70 [1657] encoding the retron Ec107 was obtained from the American Type Culture Collection (Item #3589). The strain HB8 [1685] encoding the retron Ec86 [1647] was obtained from the *E. coli* Genetic Stock Center (Item #2514; Yale University New Haven, Conn.).

Template DNA for amplifying the RTase from Ec107 and Ec86 was obtained by isolating genomic DNA from the ECOR 70 and HB8 strains, respectively, following standard procedures [213]. PCR reactions were performed with approximately 1 µg of genomic DNA as template, 1.0 pmol each of primers 86RT-5'RI and 86RT-3'Pst, to amplify the reverse transcriptase from Ec86, or primers 107RT-5'RI and 107RT-3'Pst, to amplify the reverse transcriptase from Ec107, 0.2 mM dNTP's, 2.5 U Pfu (Stratagene) and Pfu buffer constituents provided by the manufacturer in a volume of 50 µl. The PCR was performed following standard procedures [213]. After completion of the cycling, DNA fragments were resolved by agarose electrophoresis using a 1% gel and following standard procedures [213] [256]. DNA fragments of ~1 kilobase pair (kb) expected to correspond to RTase from Ec86 or Ec107 were excised and the DNA recovered from the agarose using the Qiaquick Gel Extraction Kit (Qiagen) following the protocol supplied by the manufacturer. DNA was digested with EcoRI and PstI following standard procedures [213] [256]. The plasmid cloning vector pTZ19R [973] was digested with EcoRI and PstI. The amplicon and vector DNA were purified by agarose electrophoresis and recovered as described above. Amplicon and vector DNA were then mixed in the presence of T4 DNA ligase (Gibco-BRL) to covalently link the two molecules following standard procedures [213] [256] in a final volume of 25 µl. After incubating the ligation reaction as described [213] [256], 1 µl of glycogen (20 mg/ml) was added to the ligation mixture made up to 100 µl with distilled water. After precipitation with ethanol [213] [256], the DNA was resuspended in 4 µl of distilled water. An appropriate *E. coli* strain (e.g. DH5α (Gibco-BRL)) was transformed with 2.5 µl of the concentrated ligation following standard procedures [213] [256] and plated on sterile TYS medium containing ampicillin. Putative clones were propagated in TYS broth and ampicillin. Plasmid DNA was isolated by standard alkaline-lysis "mini-prep" procedure [213] [256]. The DNA sequence of the resultant clones, pMW3 and pMW4, encoding RTase from Ec86 and Ec107, respectively were determined at a commercial sequencing facility (Plant Biotechnology Institute, Saskatoon, Canada) to confirm they encoded intact copies of the respective genes. Cloning of all other genes and genetic elements described in this invention followed the same principles as for pMW3 and pMW4, with noted exceptions.

A second version of Ec86 RTase was cloned wherein the ATG start codon was replaced with a SmaI site as one way of enabling translational fusion of the RTase with other proteins or peptides. The modified gene, RTΔATG, was created using PCR with pMW3 as template and the primers 86-Sma and 86RT-3'Pst. The ~1 kb amplicon was digested with SmaI and PstI and cloned into the SmaI and PstI sites of pBluescript II KS– (Stratagene) resulting in the construct pMW12.

A third version of Ec86 RTase was cloned which encoded the FLAG peptide [966] [260] at its N-terminus. The FLAG peptide encodes a unique amino acid sequence which enables detection of the fusion protein using commercially available antibodies (Sigma). The modified gene, FLAG-RT, was created using PCR with pMW3 as template and the primers 86-Sma-FLAG and 86RT-3'Pst. The ~1 kb amplicon was digested with SmaI and PstI and cloned into the SmaI and PstI sites of pBluescript II KS– (Stratagene) resulting in the construct pMW14.

Additional versions of Ec86 RTase were cloned so that the resultant proteins would encode a nuclear localization sequence (NLS) at the N-terminus of the protein (i.e. NLS-RT), alone or in combination with the FLAG peptide. A synthetic oligonucleotide was created which encoded the nuclear localization sequence corresponding to that found in simian virus 40 T-antigen [109] [257]. This NLS has been demonstrated to function in animal, yeast, and plant cells [109, 1372, 1362, 1363]. In other embodiments, RTase proteins may be fused to a C-terminal NLS. An example of a C-terminal NLS is that from the VirD2 protein which is functional in animal, yeast, and plant cells [968, 967]. The nucleotide sequence (GGATCCAAAA AAATGGCTCC TAA-GAAGAAG AGAAAGGTTG GAGGAGGACCCGGG) encodes a BamHI site, in-frame start codon, and SmaI site (underlined). A plasmid containing this cloned NLS sequence and derived from pBluescript II KS– (Stratagene) was digested with SmaI and PstI and the DNA fragment corresponding to the vector was purified. pMW12 and pMW14 were also digested with SmaI and PstI and the DNA fragments corresponding to the RTase gene (~1 kb), alone or in combination with the N-terminal FLAG peptide, were cloned onto the NLS sequence. The resulting constructs were designated pMW22, encoding NLS-RT, and pMW23, encoding NLS-FLAG-RT where the RTase is derived from Ec86. pMW39 encodes the Ec107 RTase fused to the NLS of SV40 T-antigen in a similar fashion as described above for Ec86 RTase.

The RTase genes of Ec86 and Ec107 were cloned into vectors capable of expressing the proteins and variants thereof in *E. coli* by the tac promoter [1688] [261] which is regulatable by the gratuitous inducer IPTG. The RTase genes of Ec86 and Ec107 were cloned into pDK5 [972] [262] by using EcoRI and PstI, The resultant clones were designated pMW7 and pMW8 encoding the wild type RTase genes of Ec86 and Ec107, respectively. To evaluate the functionality of retron reverse transcriptase fused to other peptides constructs for expressing in *E. coli* modified versions of Ec86 RTase encoding a NLS with or without the FLAG peptide were assembled. This was achieved by using SmaI and PstI to subclone the RTase encoding genes from pMW12 and pMW14 into a derivative of the expression vector pDK5 [972] [262] which encodes the NLS described for pMW22 fused to the EcoRI site of pDK5 and having a SmaI site at the 3' end of the sequence encoding the NLS (i.e. pDK5+NLS). The resultant constructs were designated pMW17, encoding NLS-RT, and pMW21, encoding NLS-FLAG-RT. Another construct to express NLS-RT, pMW120, was assembled by using BamHI and PstI to transfer the NLS-RT gene from pMW22 to pMW16 (see later).

Plasmid constructs were assembled to facilitate expression of retron components and variants thereof in eukaryotic yeast using an expression system developed by Gari et al., (1997) [55] [265]. Briefly, the transcription promoters on these plasmids are a hybrid system developed by Gari et al. (1997) which permits suppression or induction of gene expression by varying growth medium constituents. This transcription control system employs components of the regulatory system controlling expression of tetracycline resistance in prokaryotes [55] [265]. As a result, in the presence of tetracycline or doxycycline, an analogue of tetracycline, transcription of the target gene is suppressed. Conversely, when tetracycline or doxycycline is absent efficient transcription of the target gene can occur. By varying the number of tetO sites in the promoter from two (i.e. Tet2x promoter) to seven (i.e. Tet7x promoter), the promoter strength can be increased ~2-fold [55] [265]. The combination of vector copy number (i.e. CEN-type vs. 2u-type with copy numbers of 1-2 plasmids per cell or up to 40 plasmids per cell, respectively [211] [266]) and promoter strength allows gene expression to be varied 5-fold [55] [265]. Yeast expression plasmids using this system of gene regulation include pCM188, pCM189 and pCM190 as described by Gari et al., (1997) as well as derivatives thereof. These derivatives were based on the plasmids described by Geitz et al., (1997) [977] and were created by subcloning an EcoRI-HindIII fragment encoding either the Tet2x (~2.6 kb) or Tet7x (~2.8 kb) promoter elements from pCM188 or pCM190, respectively, into the EcoRI-HindIII site of YEplac112 (i.e. creating YEplac112-Tet7x), or YCplac22 (i.e. creating YCplac22-Tet2x), or YEplac181 (i.e. creating YEplac181-Tet2x) or YCplac111 (i.e. creating YCplac111-Tet2x). In addition, derivatives of these plasmids were created which contained the Destination cassette (Gibco BRL). pCM188 and pCM190 were each digested with BamHI and PstI and then treated with T4 polymerase to make the DNA ends blunt before ligation to the Destination-C cassette (Gibco BRL) to create pAS13 (i.e. pCM188-DEST) and pAS14 (i.e. pCM190-DEST). Restriction enzyme analysis demonstrated that the Destination-C cassette in these vectors was in a sense orientation with regard to the promoter so that genes transferred into the Destination cassette would be functionally expressed. pAS13 and pAS14 were then each digested with XhoI and HindIII to release fragments encoding the Tet2x and Tet7x promoters, respectively, plus the attached Destination-C cassette. These fragments were then ligated to either YCplac22-Tet2x to create pAS22 (i.e. YCplac22-Tet2x-DEST), YEplac112-Tet7x to create pAS23 (i.e. YEplac112-Tet7x-DEST), YCplac111-Tet2x to create YCplac111-Tet2x-DEST, or YCplac111-Tet7x to create YCplac111-Tet7x-DEST.

The genes encoding Ec86 reverse transcriptase and the NLS-RT derivative were subcloned into yeast expression vectors. The wild-type RTase gene originally cloned in pMW3 was first subcloned into pSPORT2 (Gibco-BRL) using EcoRI and PstI to generate the construct pMW10. The wild type Ec86 RTase was then subcloned into the PmeI and PstI sites of YCplac111-Tet2x after digesting pMW10 with SmaI and PstI resulting in the construct designated pMW25. The NLS-RT gene encoded by pMW22 was cloned into the BamHI and PstI sites of YCplac111-Tet2x resulting in the construct designated pMW27. NLS-RT was also cloned into a vector to enable integration into and expression from the chromosome of eukaryotic yeast cells. This was achieved using derivatives of the chromosome integration vector pHO-poly-KanMX4-HO [976] [267] designated pTK178 and pTK179. These vectors have novel FseI and SrfI sites flanking the HO sequences of pHO-poly-KanMX4-HO and possess either the Tet2X (pTK178) or the Tet7x (pTK179) promoters derived from pCM188 and pCM190 [55], respectively, plus the Rfa Destination cassette (Gibco-BRL). The NLS-RT gene was subcloned from pMW22 into pENTR3C (Gibco-BRL) using BamHI and EcoRV resulting in pWY83. The NLS-RT was then transferred from pWY83 to pTK178 using the Clonase reaction (Gibco-BRL), following the directions of the manufacturer, resulting in pWY84. After digestion of pWY84 with FseI, the NLS-RT expression cassette was then integrated into the chromosome of *Saccharomyces cerevisiae* strain RK2575-URA following established procedures [976] [267]. RK2575-URA was created by transforming RK2575 [281] with the 1.8 kb ClaI-SmaI DNA fragment encoding the wild-type URA3 gene in pMW107 then selecting for uracil prototrophs following standard procedures [200]. In a similar fashion the *S. cerevisiae* strain RK2558 [281], which is isogenic to RK2575 except for having a null allele of the mismatch repair gene msh2, was also converted to uracil prototrophy resulting in the strain designated RK2558-URA. The RK2575-derived strain expressing NLS-RT from the chromosomal HO locus was designated RK2575-URA-HO::NLS-RT.

12b) Cloning and Modification of RNA Elements to Facilitate Reverse Transcription The msr-msd elements from retrons were evaluated for use in facilitating production of cDNA-based gene targeting substrates in eukaryotic cells. These elements were cloned from the retrons Ec107 and Ec86 and derivatives of these elements were created to produce gene targeting substrates.

Template DNA for amplifying the msr-msd elements from Ec107 and Ec86 was obtained as described above. PCR amplification of the msr-msd elements for these retrons was achieved using the primers 86R-5'BamSma and 86D-3'-Pst, to amplify msr-msd from Ec86, or primers 107R-5'BamSma and 107D-3'Pst, to amplify msr-msd from Ec107. The amplicons were then digested with BamHI and PstI and cloned into the BamHI and PstI of pSPORT2 (Gibco-BRL) resulting in the constructs pMW5 and pMW9 encoding the msr-msd elements from Ec86 and Ec107, respectively.

For expression in *E. coli*, the msr-msd elements were transferred into an expression vector derived from pACYC 184 [970] [263] encoding the tac promoter and rrnB terminator from pKK223-3 [975] [264]. This vector was constructed by first ligating the ~1.2 kb BamHI-PvuI fragment encoding the tac promoter and rrnB terminator from pKK223-3 to the ~3.6 kb HindIII-SalI fragment of pACYC184 using a combination of blunting ends with T4 polymerase (New England BioLabs) and restriction site linkers, as per standard procedures [213] [256]. The msr-msd elements were transferred from pMW5 and pMW9 into the expression vector using BamHI and PstI resulting in the constructs pMW16 and pMW18 encoding the msr-msd elements from Ec86 and Ec107, respectively.

Derivatives of the Ec86 msr-msd elements were created for producing cDNA in vivo. One derivative was termed STEM3. STEM3 possesses unique XbaI and EcoRV sites within the loop region created by annealing of the b1 and b2 inverted repeat sequences encoded within the msd element. Sequences encoding gene targeting substrates can be cloned into the XbaI and EcoRV site to enable their conversion to cDNA by the action of Ec86 RTase. STEM3 was also modified vis-a-vis the wild type Ec86 msr-msd by extending the length of the a1 and a2 inverted repeat sequences by 13 bp. These extended repeat sequences were denoted a1' and a2'. STEM3 was created by PCR using pMW5 as template in one reaction with the primers 5'-IRX-BamSma and STEM3-antisense, and a second reaction with the primers 3'-IRX-NotMsc and STEM3-sense. Aliquots of the two reactions were then pooled and used as template for a third PCR reaction with the primers 5'-IRX-BamSma and 3'-IRX-NotMsc. The resulting amplicon of ~200 bp was digested with BamHI and cloned into pENTR2B (Gibco-BRL) digested with XbaI, treated with T4 DNA polymerase to make the end blunt by standard procedures, then digested with BamHI. The resulting construct was designated pMW134.

A second derivative of the Ec86 msr-msd elements was termed STOP-stem. Sequences encoding gene targeting substrates placed in this derivative have a novel inverted repeat sequence adjacent to the b2 sequence in the msd element. This inverted repeat sequence may form a stem-and-loop structure in an RNA molecule that has a sufficiently high dissociation constant to inhibit the progression of RTase. Sequences encoding gene targeting substrates can be placed into the unique EcoRI and EcoRV sites within the STOP-stem assembly. To create STOP-stem pMW134 was first digested with XbaI and EcoRV then treated with calf intestinal phosphatase (New England Biolabs) following standard methods. This was then used as template in a PCR reaction with the primers STOP-stem-Ret(Xba) and Ret-RV-Out. The amplicon was then digested with EcoRI and self-ligated to create the construct denoted pMW255 in the vector pENTR2B (Gibco-BRL).

In one embodiment, the STOP-stem sequence was as follows:

(SEQ ID NO: 4)
GGATCCCCCGGGCGCCAGCAGTGGCTGCGCACCCTTAGCGAGAGGTTTAT

CATTAAGGTCAACCTCTGGATGTTGTTTCGGCATCCTGCATTGAATCTGA

GTTACTGTCTGTTTTCCTTGTTGGAACGGAGAGCATCGTCTAGAGGATCC

GGGTCGCTCGCTGCGTCGCTGCGGAATTCGATATCTGATGCTCTCCGAGC

CAACCAGGAAACCCGTTTTTTCTGACGTAAGGGTGCGCAGCCGCTGTTGG

CGTGGCCAATGCGGCCGC.

A third derivative of the Ec86 msr-msd elements was termed the 3'-recruitment system. This assembly involves a novel rearrangement of the inverted repeat sequences of the Ec86 msr-msd elements to create a structure that does not create a loop structure at the end of the b1 and b2 inverted repeat sequences but is still capable of recruiting reverse transcriptase to convert sequences within the msd region to cDNA. To create the 3'-recruitment system, pMW134 was used as template in a PCR reaction with the primers 3'CSST-OL3 and 3'CSST-OL4. A ~150 bp amplicon encoding the msr region including the a2' and b2 sequences was then digested with XbaI and EcoRI. To create a sequence encoding the a1' and b1 sequences, approximately 100 pmol each of the oligonucleotides Recruit-XbaRI-sense and Recruit-XbaRI-antisense were mixed in 10 ul of annealing buffer [40 mM Tris-HCl (pH 7.5), 20 mM MgCl$_2$, 250 mM NaCl] then heated at 55 C for 5 min. and allowed to anneal at room temperature to form ~80 bp fragment encoding the msd region including a1' and b1 sequences. The ~150 bp amplicon and the ~80 fragment were then ligated to pMW149 digested with XbaI and NotI resulting in the construct designated pMW159. pMW149 encodes ~100 bp of sequence from the URA3 gene of *S. cerevisiae* (see later). This fragment encodes a mutated version of the URA3 translation start codon (i.e. ACG vs. ATG) and therefore can be used to illustrate how creating a single base pair change which modifies gene translation can be used to modify eukaryotic genes through the invention. Thus pMW159 encodes ~100 bp linked to the 3'-recruitment system. A control to illustrate that reverse transcription of fragments linked to the 3'-recruitment system results from this element recruiting reverse transcriptase was created by digesting pMW159 with NotI and EcoRI then treating the DNA with T4 polymerase to make the ends blunt and religating the vector molecule plus the remaining portion of the 3'-recruitment system to create pMW171. pMW171 therefore is deleted for the msr element including the a2' and b2 sequences. Thus the RNA transcript from pMW171 will no longer encode the sequences required to recruit reverse transcriptase and prime cDNA synthesis. The inability of pMW171 to facilitate cDNA synthesis vs. its parental construct, pMW159, can indicate the functionality of the 3'-recruitment system in facilitating the conversion of linked sequences to cDNA.

In one embodiment, the 3'-recruitment sequence comprised:

(SEQ ID NO: 5)
TCTAGACCCGGGGATGCTCTCCGAGCCAACCAGGAAACCCGTTTTTTCTG

ACGTAAGGGTGCGCAGCCACTGCTGGCGAATTCGCCAGCAGTGGCTGCGC

ACCCTTAGCGAGAGGTTTATCATTAAGGTCAACCTCTGGATGTTGTTTCG

GCATCCTGCATTGAATCTGAGTTACTGTCTGTTTTCCTTGTTGGAACGGA

GAGCATCGCGGCCGCCTGCAG.

Constructs with 250 bp and 500 bp linked to the 3'-recruitment system were also created. This was done by using NotI and XbaI to clone the 3'-recruitment element from pMW149 onto the 250 bp and 500 bp fragments of the URA3 gene present in pMW150 and pMW159, respectively. The resulting constructs were designated pMW164 and pMW165 respectively encoding 250 bp and 500 bp linked to the 3'-recruitment system.

The 'ACG' mutant allele of URA3 was created after first cloning the URA3 gene from *Saccharomyces cerevisiae*. Lambda clone PM-6150 encoding this gene and flanking genomic regions was obtained from the American Type Culture Collection (Item #70772). The lambda clone was propagated and DNA isolated following standard procedures [213] [256]. The lambda clone DNA was digested with ClaI and SmaI and a ~1.85 kb fragment was purified by agarose gel electrophoresis and recovered from the agarose as described above. Based on the published genomic sequence of *S. cerevisiae* this fragment will encode the URA3 gene. The cloning vector pQuantox (Quantum Biotechnologies) was also digested with ClaI and SmaI and the DNA fragment corresponding to this vector (~5.3 kb) was purified. The two fragments were ligated together, transformed into *E. coli* and putative clones of the assembly identified as described above. The resultant clone of the ~1.85 kb fragment encoding URA3 was denoted pMW41. Variants of the URA3 gene were also created after first subcloning this ~1.85 kb fragment into pBluescript II KS– by digesting both pMW41 and the recipient vector with NotI and XhoI, purifying the respective fragments and ligating them together. The resultant clone of the ~1.85 kb fragment encoding URA3 in pBluescript II KS– was denoted pMW107. The 'ACG' mutant allele of URA3 was created by PCR using pMW41 as template with the primers URA-T-C and the T3 primer (Plant Biotechnology Institute) which binds to the vector. The resulting amplicon was digested with NcoI and PstI to produce a ~200 bp fragment was used to replace the corresponding wild type fragment in pMW107 creating pMW104 encoding the 'ACG' mutant allele of URA3. This was then used as template in three separate PCR reactions using the primer combinations of URA100-5'RV and URA100-3'XbaBam, URA250-5'RV and URA250-3'XbaBam, or URA500-5'RV and URA500-3'XbaBam or URA1000-5'RV and URA 1000-3'XbaBam. The amplicons were digested with BamHI and EcoRV and the resultant 100 bp, 250 bp 500 bp and 1000 bp fragments were cloned into pBluescript II KS– (Stratagene) resulting in the constructs pMW149, pMW150, pMW151 and pMW152, respectively.

12c) Expression Constructs for the STEM3 System

To evaluate expression of STEM3 components in prokaryotic cells various constructs were made in expression vectors functional in *E. coli*. An expression vector was created by first digesting pMW16 with SmaI and HindIII followed by treatment with T4 polymerase and ligation to the Destination-A cassette (Gibco BRL) resulting in pMW137. Expression of DNA fragments could thus be achieved by transferring the appropriate fragments to pMW137 using Clonase (Gibco BRL) following the directions of the manufacturer. In this manner various constructs for expression of STEM3 and derivatives thereof were developed.

To evaluate the size of gene targeting substrate that could be produced using the STEM3 system various sizes of insert DNA were cloned into the EcoRV and XbaI sites of STEM3 in pMW134. A 15 bp insert version of the ACG mutation described above was created by annealing the primers URA15-XbaRV and URA15-XbaRV-antisense, as described above, then ligating the fragment into the pMW134 digested with EcoRV and XbaI, resulting in pMW156. In a similar fashion, a 25 bp insert version of the ACG mutation was created using the primers URA25-XbaRV-sense and URA25-XbaRV-antisense, resulting in pMW157. In a similar fashion, a 35 bp insert version of the ACG mutation was created using the primers URA35-XbaRV-sense and URA35-XbaRV-antisense, resulting in pMW193. In a similar fashion, a 50 bp insert version of the ACG mutation was created using the primers URA50-XbaRV-sense and URA50-XbaRV-antisense, resulting in pMW158. A 100 bp insert version of the ACG mutation was created by using XbaI and EcoRV to subclone the insert from pMW149 into pMW134 resulting in pMW194. A 250 bp insert version of the ACG mutation was created by using XbaI and EcoRV to subclone the insert from pMW150 into pMW134 resulting in pMW195. A 320 bp insert version was created by digesting pMW152 with EcoRV and XbaI, purifying the ~320 bp fragment and ligating it to pMW134 digested with EcoRV and XbaI, resulting in pMW207. A 500 bp insert version of the ACG mutation was created by using pMW104 as template in a PCR reaction with the primers URA500-5'RV and URA500-3'XbaBam to amplify a 500 bp fragment that was digested with EcoRV and XbaI then cloned into the EcoRV and XbaI sites of pMW134 resulting in the construct pMW226. A 1000 bp insert version of the ACG mutation was created by using pMW104 as template in a PCR reaction with the primers URA1000-5'RV and URA1000-3'XbaBam to amplify a 1000 bp fragment that was digested with EcoRV and XbaI then cloned into the EcoRV and XbaI sites of pMW134 resulting in the construct pMW227.

To evaluate the expression in *E. coli* of the STEM3 system with insert sequences of different size the various derivatives of pMW134 described above were transferred to the *E. coli* expression vector pMW137 using Clonase (Gibco BRL) following the directions of the manufacturer. In this manner *E. coli* expression constructs were created containing STEM3 encoding insert sequences as follows: 0 bp by using pMW134 as the donour to create pMW145; 15 bp by using pMW156 as the donour to create pMW161; 25 bp using pMW157 as the donour to create pMW162; 35 bp by using pMW193 as donour to create pMW198; 50 bp by using pMW158 as donour to create pMW163; 100 bp by using pMW194 as donour to create pMW199; and 250 bp by using pMW195 as donour to create pMW200. Function of the STEM3 system in *E. coli* could then be evaluated by co-transforming the strain DH5α (Gibro-BRL) with a construct expressing Ec86 reverse transcriptase or a derivative thereof and one of the various constructs expressing the msr-msd elements or a derivative thereof with or without insert. The *E. coli* strains were cultured in the presence of ampicillin and chloramphenicol to select for the presence of both expression constructs. After overnight culture in broth medium in the presence of 0.2 mM IPTG to induce expression of the reverse transcription components, DNA was isolated by the alkaline 'mini-prep' method [213], treated with RNase A 0.04 ug/ml and resolved by gel electrophoresis. cDNA products were detected by staining the DNA with ethidium bromide or by probing Southern blots with a fragment encoding msr-msd from Ec86, all following standard methods [213].

To evaluate the expression msr-msd elements and the various derivatives thereof for producing cDNA in vivo in eukaryotic cells constructs were created based on various yeast expression vectors. An expression construct for evaluating the wild type Ec86 msr-msd elements in yeast was created by using BamHI and PstI to subclone the msr-msd sequence from pMW5 into pCM190 resulting in the construct pMW29. To evaluate the expression in eukaryotic cells of the STEM3 system with insert sequences of different size the various derivatives of pMW134 described above were transferred to the yeast expression vector pAS23 using Clonase (Gibco BRL) following the directions of the manufacturer. In this manner yeast expression constructs were created containing STEM3 encoding insert sequences as follows: 0 bp by using pMW134 as the donour to create pMW166; 15 bp by using pMW156 as the donour to create pMW167; 25 bp using pMW157 as the donour to create pMW168; 35 bp by using pMW193 as donour to create pMW202; 50 bp by using pMW158 as donour to create pMW169; 100 bp by using pMW194 as donour to create pMW203; 250 bp by using pMW195 as donour to create pMW204; 320 bp by using pMW207 as donour to create pMW211; 500 bp by using pMW226 as donour to create pMW212; and 1000 bp using pMW227 as donour to create pMW213.

An additional version of STEM3 encoding 500 bp of an alternative allele of URA3, denoted ura3$^{Bsp}$, was also developed. This allele was created by using PCR to create 500 bp fragments of the URA3 gene with a single base pair change of C to A at nucleotide position #465 of the URA3 open reading frame. This base pair change creates a novel BspHI restriction enzyme site within the URA3 locus and creates a premature translation termination signal which can be expected to prevent functional expression of the carboxy-terminal 113 amino acid residues encoded by URA3 whose wild type protein product is 267 amino acid residues in length. The cassette also encodes ~250 bp upstream and downstream of the C to A bp change for a total of ~500 bp of homology to the chromosomal URA3 locus. One sense version of this 500 bp fragment was created by using pMW107 as template in two separate PCR reactions with the primers URA-Bsp(−250)-S-5'BamXba and URA-Bsp-mu-AS in one reaction and URA-Bsp(+250)-sense-3'RV and URA-Bsp-mu-S in a second reaction. The 250 bp amplicons from each reaction have 50 bp of overlapping sequence so that they can anneal to one another and serve as template in a third PCR reaction with the primers URA-Bsp(−250)-S-5'Bamxba and URA-Bsp(+250)-sense-3'RV to produce a 500 bp fragment. After digestion with XbaI, this fragment was cloned into pMW134 digested with XbaI and EcoRV resulting in the construct pMW259 encoding 500 bp of ura3$^{Bsp}$ in the sense orientation. A yeast expression construct was created to express the ura3$^{Bsp}$ fragment in STEM3 by using pMW259 as the donour in a Clonase (Gibco-BRL) reaction with the yeast expression vector pAS23 to create pMW266.

Function of the reverse transcriptase system in eukaryotic cells could then be evaluated by co-transforming the *S. cerevisiae* strain RK2575-URA with a construct expressing Ec86 reverse transcriptase or a derivative thereof and one of the various constructs expressing the msr-msd elements or a derivative thereof with or without insert. The yeast strains were cultured in minimal medium with amino acid composition to select for the presence of both expression constructs. To repress expression of the various components, yeasts cells were cultured in the presence of doxycycline (5 ug/ml for broth cultures, 10 ug/ml for plate cultures). After overnight culture in broth medium in the absence of doxycycline to enable expression of the reverse transcription components, DNA was isolated by the glass-bead method [213], and resolved by gel electrophoresis. cDNA products were detected by probing Southern blots with a fragment encoding msr-msd from Ec86, following standard methods [213].

12d) Expression Constructs for the STOP-Stem System

To evaluate the expression in eukaryotic cells of the STOP-stem system yeast cells were transformed with constructs to express NLS-RT from Ec86 and the STOP-stem component linked to a gene targeting sequence with homology to the chromosomal URA3 gene. One gene targeting sequence was derived from the ura3Δ$^{PstEcoRV}$ allele. This allele was created by digesting pMW107 with PstI and EcoRV then making the ends blunt by treatment with T4 DNA polymerase and self-ligating the vector fragment resulting in the construct pMW180. pMW180 thus encodes a mutant allele whereby ~20 bp of the promoter region and ~190 bp of the open reading frame of URA3 have been deleted. A 500 bp insert version of the ura3Δ$^{PstEcoRV}$ allele in the sense orientation was created by using pMW180 as template in a PCR reaction with the primers STOP-Stem-sense and STOP-Sense-3'RV to amplify a 500 bp fragment that was digested with EcoRI then cloned into the EcoRI and EcoRV sites of pBluescript KS– resulting in the construct pMW250. A 500 bp insert version of the ura3Δ$^{PstEcoRV}$ allele in the antisense orientation was created by using pMW180 as template in a PCR reaction with the primers STOP-Stem-AS and STOP-Stem-AS-3'RV to amplify a 500 bp fragment that was digested with EcoRI then cloned into the EcoRI and EcoRV sites of pBluescript KS– resulting in the construct pMW251. The 500 bp fragments of pMW250 and pMW251 were then cloned into pMW255 using EcoRI and EcoRV resulting in the constructs pMW256, encoding 500 bp of the ura3Δ$^{PstEcoRV}$ allele in the sense orientation, and pMW257 encoding 500 bp of the ura3Δ$^{PstEcoRV}$ allele in the antisense orientation. Yeast expression constructs were then created to express the ura3Δ$^{PstEcoRV}$ fragment in STOP-stem by using pMW256 and pMW257 as the donours in Clonase (Gibco-BRL) reactions with the yeast expression vector pAS23 to create pMW252 and pMW253, respectively.

Another version of the gene targeting sequence linked to the STOP-stem system was the ura3$^{Bsp}$ allele as described above. A 500 bp insert version of the ura3$^{Bsp}$ allele in the sense orientation was created in a similar fashion as described above for the corresponding fragment cloned into the STEM3 system. pMW107 was used as template in two separate PCR reactions with the primers URA-STOP-Bsp(−250)-sense-5'RI and URA-Bsp-mu-AS in one reaction and URA-Bsp(+250)-sense-3'RV and URA-Bsp-mu-S in a second reaction. The 250 bp amplicons from each reaction have 50 bp of overlapping sequence so that they can anneal to one another and serve as template in a third PCR reaction with the primers URA-STOP-Bsp(−250)-sense-5'RI and URA-Bsp(+250)-sense-3'RV to produce a 500 bp fragment. After digestion with EcoRI, this fragment was cloned into pMW255 digested with EcoRI and EcoRV resulting in the construct pMW260 encoding 500 bp of ura3$^{Bsp}$ in the sense orientation. A yeast expression construct was created to express the ura3$^{Bsp}$ fragment in STOP-stem by using pMW260 as the donour in a Clonase (Gibco-BRL) reaction with the yeast expression vector pAS23 to create pMW267.

Another version of the gene targeting sequence linked to the STOP-stem system was the ura3$^{Pvu}$ allele. This allele was created in a similar fashion as that described above for the ura3$^{Bsp}$ allele.

The ura3$^{Pvu}$ allele encodes a deletion of 8 bp resulting in loss of base pair #275-284 of the URA3 open reading frame. The deletion also creates a novel PvuII restriction site and changes the reading frame of the altered gene to promote premature termination of translation which can be expected to prevent functional expression of the carboxy-terminal 176 amino acid residues encoded by URA3 whose wild type protein product is 267 amino acid residues in length. The cassette also encodes ~250 bp upstream and downstream of the 8 bp deletion for a total of ~500 bp of homology to the chromosomal URA3 locus. A sense version of this 500 bp fragment was created by using pMW107 as template in two separate PCR reactions with the primers URA-STOP-Pvu(−250)-sense-5'RI and URA-Pvu-mu-AS in one reaction and URA-Pvu(+250)-sense-3'RV and URA-Pvu-mu-S in a second reaction. The 250 bp amplicons from each reaction have 50 bp of overlapping sequence so that they can anneal to one another and serve as template in a third PCR reaction with the primers URA-STOP-Pvu(−250)-sense-5'RI and URA-Pvu(+250)-sense-3'RV to produce a 500 bp fragment. After digestion with EcoRI, this fragment was cloned into pMW255 digested with EcoRI and EcoRV resulting in the construct pMW262 encoding 500 bp of ura3$^{Pvu}$ in the sense orientation. A yeast expression construct was created to express the ura3$^{Pvu}$ fragment in STOP-stem by using pMW262 as the donour in a Clonase (Gibco-BRL) reaction with the yeast expression vector pAS23 to create pMW269.

12e) Expression Constructs for the 3'-Recruitment System

To evaluate the expression in E. coli of the 3'-recruitment system with insert sequences of different size E. coli DH5α was cotransformed with pMW120 expressing NLS-RT in combination with either pMW159, pMW164 or pMW165 expressing the 3'-recruitment element linked to 100 bp, 250 bp or 500 bp, respectively. A control strain was created by combining pMW120 with pMW171 which is derived from pMW159 but has the msr element deleted.

To evaluate the expression in eukaryotic cells of the 3'-recruitment system yeast cells were transformed with constructs to express NLS-RT from Ec86 and the 3'-recruitment component linked to a gene targeting sequence with homology to the chromosomal URA3 gene. One gene targeting sequence was derived from the ura3 'ACG' allele described above. To facilitate expression of 'ACG' mutant containing fragments, the insert of pMW165 was first transferred to pENTR1A using SalI and NotI resulting in the construct pNML23. A yeast expression construct was then created using pNML23 as donors in Clonase (Gibco-BRL) reaction with the yeast expression vector pAS23 to create pMW221. To facilitate expression of 500 bp fragments of the ura3Δ$^{PstEcoRV}$ allele in the sense and anti-sense orientation, pNML23 was first digested with SmaI and ClaI then treated with T4 DNA polymerase to make blunt ends before purifying the fragment encoding the vector and the 3'-recruitment element. The 500 bp fragment of the ura3Δ$^{PstEcoRV}$ allele encoded by pMW235 was then isolated after digestion with XbaI and EcoRV then treated with T4 DNA polymerase to make blunt ends. This fragment was then ligated into the prepared pNML23-derived fragment. Clones were then screened by restriction digest to identify one with the ura3Δ$^{PstEcoRV}$ fragment in the sense orientation (i.e. pMW249) and the antisense orientation (i.e. pMW248).

12f) Expression Constructs for Generating dsDNA In Vivo

To generate double-stranded DNA (dsDNA) gene targeting substrates in vivo reverse transcription of RNA molecules encoding sense and antisense versions of the gene targeting substrate can be converted to single-stranded cDNAs in vivo which can then anneal with one another to form dsDNA gene targeting substrates. To exemplify this concept in eukaryotic cells S. cerevisiae was used as a model. Yeast cells were transformed with constructs capable of co-expressing the NLS-RTase with sense and antisense RNAs encoding gene targeting substrates with homology to the chromosomal URA3 gene.

To create a gene targeting substrate encoding a sense version of the ura$^{Pvu}$ allele in STEM3, pMW107 was used as template in two separate PCR reactions with the primers URA-Pvu(−250)-S-5'BamXba and URA-Pvu-mu-AS in one reaction and URA-Pvu(+250)-sense-3'RV and URA-Pvu-mu-S in a second reaction. The 250 bp amplicons from each reaction have 50 bp of overlapping sequence so that they can anneal to one another and serve as template in a third PCR reaction with the primers URA-Pvu(−250)-S-5'BamXba and URA-Pvu(+250)-sense-3'RV to produce a 500 bp fragment. After digestion with XbaI, this fragment was cloned into pMW134 digested with XbaI and EcoRV resulting in the construct pMW261 encoding 500 bp of ura$^{Pvu}$ in the sense orientation. A yeast expression construct was created to express the ura$^{Pvu}$ fragment in STEM3 by using pMW261 as the donor in a Clonase (Gibco-BRL) reaction with the yeast expression vector pAS23 to create pMW268. A second yeast expression construct for expressing ura$^{Pvu}$ fragment in STEM3 was created by using pMW261 as the donor in a Clonase reaction with the yeast expression vector pA525 to create pNML91. Using pMW107 as template in a PCR reaction with the primers URA-Pvu(−250)-S-5'BamXba and URA-Pvu(+250)-sense-3'RV can also be used to produce a 500 bp fragment encoding the corresponding fragment of wild type URA3 which, after cloning into the STEM3 system, can then be used as a control in genetic assays. In this manner, the construct pNML97 was created. A yeast expression construct was created to express the URA$^{WT}$ fragment in STEM3 by using pNML97 as the donor in a Clonase reaction with pAS25 to create pNML101.

To create a gene targeting substrate encoding an antisense version of the ura$^{Pvu}$ allele in STEM3 pMW261 was used as template in a PCR reaction with the primers URA-Pvu(−250)-AS-5'BamXba and URA-Pvu(−250)-AS-3'RV to produce a 500 bp fragment. After digestion with XbaI, this fragment was cloned into pMW134 digested with XbaI and EcoRV resulting in the construct pNML93 encoding 500 bp of ura$^{Pvu}$ in the antisense orientation in STEM3. A yeast expression construct was created to express the antisense ura$^{Pvu}$ fragment in STEM3 by using pNML93 as the donour in a Clonase (Gibco-BRL) reaction with the yeast expression vector pWY82 to create pNML95. Using pMW107 as template in a PCR reaction with the primers URA-Pvu(−250)-AS-5'BamXba and URA-Pvu(−250)-AS-3'RV can also be used to produce a 500 bp fragment encoding the corresponding fragment of wild type URA3 which after cloning into the STEM3 system, can then be used as a control in genetic assays. In this manner, the construct pNML99 was created. A yeast expression construct was created to express the anti-sense UBA$^{WT}$ fragment in STEM3 by using pNML99 as the donor in a Clonase reaction with pWY82 to create pNML103.

Assembly of a gene targeting substrate encoding a sense version of the ura$^{Pvu}$ allele in STOP-stem was described above (i.e. pMW262; pMW269 for yeast expression) using the primers URA-STOP-Pvu(−250)-sense-5'RI and URA-Pvu(+250)-sense-3'RV. Using pMW107 as template in a PCR reaction with the primers URA-STOP-Pvu(−250)-sense-5'RI and URA-Pvu(+250)-sense-3'RV can also be used to produce a 500 bp fragment encoding the corresponding sense fragment of wild type URA3 which after cloning into the STOP-stem system, can then be used as a control in genetic assays.

In this manner, the construct pNML98 was created. A yeast expression construct was created to express the URA$^{WT}$ fragment in STOPstem by using pNML99 as donor in a Clonase reaction with pAS25 to create pNML102.

To create a gene targeting substrate encoding an antisense version of the ura$^{Pvu}$ allele in STOP-stem pMW261 was used as template in a PCR reaction with the primers URA-STOP-Pvu(+250)-AS-5'RI and URA-Pvu(−250)-AS-3'RV to produce a 500 bp fragment. After digestion with EcoRI, this fragment was cloned into pMW255 digested with EcoRI and EcoRV resulting in the construct pNML94 encoding 500 bp of ura$^{Pvu}$ in the antisense orientation. A yeast expression construct was created to express the antisense ura$^{Pvu}$ fragment in STOP-stem by using pNML94 as the donour in a Clonase (Gibco-BRL) reaction with the yeast expression vector pWY82 to create pNML96. Using pMW107 as template in a PCR reaction with the primers URA-STOP-Pvu(+250)-AS-5'RI and URA-Pvu(−250)-AS-3'RV can also be used to produce a 500 bp fragment encoding the corresponding antisense fragment of wild type URA3 which after cloning into the STOP-stem system, can then be used as a control in genetic assays. In this manner, the construct pNML100 was created. A yeast expression construct was created to express the antisense URA$^{WT}$ fragment in STOPstem by using pNML100 as donor in a clonase reaction with pWY82 to create pNML104. A second yeast expression construct for expressing ura$^{PVU}$ fragment in STOPstem was created by using pMW262 as the donor in a Clonase reaction with the yeast expression vector pAS25 to create pNML92.

12g) Constructs for Assessing the Effect of Elevated Homologous Recombination Potential on Gene Targeting Frequency.

To illustrate the effect of enhanced recombination potential on gene targeting frequency yeast strains were created which may produce cDNA-derived gene targeting substrates when recombination proteins are at an elevated level. The S. cerevisiae strains RK2575-URA and RK2558-URA were used as hosts. The latter strain is defective for mismatch repair activities and is isogenic to RK2575-URA. A comparison of gene targeting frequencies occurring in these strains can thus illustrate the effect that different levels of mismatch repair activity can have on gene targeting frequency. The genetic elements encoding the gene targeting substrates were integrated into the chromosomes of these strains using established methods 976.

Gene targeting systems derived from the STEM3 and STOP-stem systems were evaluated in the yeast model eukaryote. To produce a STEM3 derivative encoding a wild type URA3 sequence, pMW107 was used in a PCR reaction with the primers URA-Bsp(−250)-S-5'Bamxba and URA-Bsp(+250)-sense-3'RV to produce a 500 bp fragment of URA3 which encodes a wild type DNA sequence corresponding to the ura3$^{Bsp}$ mutant fragment described above for pMW259. After digestion with XbaI, the PCR fragment was cloned into pMW134 digested with XbaI and EcoRV resulting in the construct pMW287 encoding 500 bp of URA3 in the sense orientation in STEM3. A yeast expression construct was created to express the URA3 fragment in STEM3 by using pMW287 as the donour in a Clonase (Gibco-BRL) reaction with the yeast chromosomal integration and expression vector pTK179 to create pMW303. In a similar fashion, to produce a STOPstem derivative encoding a wild type URA3 sequence pMW107 was used in a PCR reaction with the primers URA-STOP-Bsp(−250)-sense-5'RI and URA-Bsp(+250)-sense-3'RV to produce a 500 bp fragment of URA3 which encodes a wild type DNA sequence corresponding to the ura3$^{Bsp}$ mutant fragment described above for pMW260. After digestion with EcoRI, this fragment was cloned into pMW255 digested with EcoRI and EcoRV resulting in the construct pMW288 encoding 500 bp of URA3 in the sense orientation in STOP-stem. A yeast expression construct was created to express the URA3 fragment in STOP-stem by using pMW288 as the donour in a Clonase (Gibco-BRL) reaction with the yeast chromosomal integration and expression vector pTK179 to create pMW304. Test substrates for the STEM3 system were created by using pMW259 and pMW261 as donours in Clonase (Gibco-BRL) reactions with the yeast chromosomal integration and expression vector pTK179 to create pMW299, encoding a 500 bp sense fragment of the ura3$^{Bsp}$ allele, and pMW301, encoding a 500 bp fragment of the ura3Pu allele, respectively. Test substrates for the STOP-stem system were created by using pMW260 and pMW262 as donours in Clonase (Gibco-BRL) reactions with the yeast chromosomal integration and expression vector pTK179 to create pMW300, encoding a 500 bp sense fragment of the ura3$^{Bsp}$ allele, and pMW302, encoding a 500 bp fragment of the ura3$^{Pvu}$ allele, respectively.

The components of the gene targeting systems were integrated into the chromosome of the host strain RK2575-URA and RK2558-URA following established procedures 976. The plasmids pMW303, pMW299, pMW301, pMW304, pMW300 and pMW302 were digested with FseI and the respective integration cassettes were used to transform RK2575-URA and RK2558-URA. The resultant strains with the STEM3 system integrated into the host chromosome were designated as follows: RK2575-URA::HO-STEM3::URA (created using pMW303), RK2575-URA::HO-STEM3::ura3$^{Bsp}$ (created using pMW299); RK2575-URA::HO-STEM3::ura3$^{Pvu}$ (created using pMW301); RK2558-URA::HO-STEM3::URA (created using pMW303), RK2558-URA::HO-STEM3::ura3$^{Bsp}$ (created using pMW299); RK2558-URA::HO-STEM3::ura3$^{Pvu}$ (created using pMW301). The resultant strains with the STOP-stem system integrated into the host chromosome were designated as follows: RK2575-URA::HO-STOPstem::URA (created using pMW304), RK2575-URA::HO-STOPstem::ura3$^{Bsp}$ (created using pMW300); RK2575-URA::HO-STOPstem::ura3Pvu (created using pMW302); RK2558-URA::HO-STOPstem::URA (created using pMW304), RK2558-URA::HO-STOPstem::ura3$^{Bsp}$ (created using pMW300); RK2558-URA::HO-STOPstem::ura3$^{Pvu}$ (created using pMW302). All strains were cultured in the presence of doxycycline as described above until assayed for gene targeting frequency.

To illustrate the effect of modifying recombination potential on gene targeting frequency in eukaryotic cells, the above yeast strains were transformed with pMW27, encoding NLS-RT, in combination with pMW305, encoding yRAD51$^{I134T}$, or pAS22, the parental vector of pMW305. Another control was created by transforming with YCplac-Tet2x and pAS22, the parental vectors of pMW27 and pMW305, respectively. The frequency of converting the chromosomal URA3 gene to an altered allele in the strains expressing the STEM3 or STOPstem components from the chromosome in combination with NLS-RT can show the ability of the components to function in when expressed from a host chromosome. Comparison of this with corresponding strains also expressing yRAD51$^{I134T}$ can show the effect of modifying recombination potential on gene targeting frequency. All strains were cultured in the presence of doxycycline as described above until assayed for gene targeting frequency.

To illustrate the effect of generating gene targeting substrates during meiosis on gene targeting frequency in eukaryotic cells, the RK2575-URA derived strains encoding STEM3 or STOPstem components integrated in the chromosome described above were first converted to diploid strains so as to represent meiotic events in higher eukaryotes and to promote viability of yeast meiotic products. Diploid strains were created by mating the above strains to S. cerevisiae strain E134-URA, a derivative of the strain E134 270. E134-URA was created by transforming E134 with the 1.8 kb ClaI-SmaI DNA fragment encoding the wild-type URA3 gene in pMW107 then selecting for uracil prototrophs following standard procedures 200. After mating E134-URA with the various RK2575-URA derivatives encoding STEM3 or STOPstem components, diploid strains were identified by selection for histidine prototrophy, all following standard methods 200. The resultant diploid strains were designated as follows:

The resultant diploid strains with the STEM3 system integrated into the host chromosome were designated as follows: E134+RK2575-URA::HO-STEM3::URA (created using pMW303), E134+RK2575-URA::HO-STEM3::ura3$^{Bsp}$ (created using pMW299); E134+RK2575-URA::HO-STEM3::ura3$^{Pvu}$ (created using pMW301). The resultant diploid strains with the STOP-stem system integrated into the host chromosome were designated as follows: E134+RK2575-URA::HO-STOPstem: URA (created using pMW304), E134+RK2575-URA::HO-STOPstem::ura3$^{Bsp}$ (created using pMW300); E134+RK2575-URA::HO-STOPstem::ura3$^{Pvu}$ (created using pMW302. All strains were cultured in the presence of doxycycline until assayed for gene targeting frequency. These diploid strains were then transformed with either pMW27, encoding NLS-RT, or YCplac111-Tet2x, the parental expression vector of pMW27. All strains were cultured in the presence of doxycycline as described above until assayed for gene targeting frequency.

12h) Recombination Proteins yRAD51

The yeast RAD51 (yRAD51) gene was cloned after amplification by PCR. Template for amplifying yRAD51 was genomic DNA from Saccharomyces cerevisiae strain AB972 [210] [291] isolated by standard procedure [213] [256]. Two PCR reactions were performed with approximately 1 µg of genomic DNA, 1.0 pmol yR51-5'Bam oligonucleotide and 1.0 pmol yR51-3'Pst oligonucleotide, 0.2 mM dNTP's, 2.5 U Pfu (Stratagene) and Pfu buffer constituents provided by the manufacturer in a volume of 50 µl. The PCR conditions were 5 min @ 94 C, followed by 25 cycles of 30 s @ 94 C, 30 s @ 58 C and 2.5 min @ 72 C, followed by 10 min @ 72 C and storage at 4 C or −20 C. The two reactions were pooled and DNA was digested with BamHI and PstI. The plasmid cloning vector pBluescript II KS− (Stratagene) was digested with BamHI and PstI. DNA fragments of interest corresponding to yRAD51 (~1.2 kb) and the vector (~3 kb) were purified by agarose gel electrophoresis and recovered from the agarose as described above. The fragments were ligated together, transformed into E. coli and putative clones of the gene identified as described above. The DNA sequence of the resultant clone, pMW35, was determined to confirm it encoded yRAD51. The yRAD51 gene was then subcloned into pENTR3C using BamHI and EcoRV resulting in the construct pTK104.

A mutant version of yRAD51 was created by PCR using pTK104 as template in a PCR reaction with the primers yRAD51-I134T-S and yRAD51-I134T-AS. After completion of cycling DpnI was added to the reaction to digest the template DNA. The amplicon was then digested with PinA1 and self-ligated. DNA sequencing confirmed the clone designated pNML56 encodes the mutant protein yRAD51$^{I134T}$. yRAD51$^{I134T}$ can be linked to various promoters to facilitate expression in eukaryotic cells. In one example, pNML56 was used as the donour in a Clonase (Gibco-BRL) reaction with the yeast expression vector pAS22 to create pMW305.

AtRAD51

Template for use in amplifying AtRAD51 was obtained from cDNA generated from RNA isolated from *A. thaliana* ecotype Columbia total plant tissues treated with gamma radiation. Plants were grown in sterile culture as follows. Seeds of *A. thaliana* ec. Columbia were surface sterilized by first rinsing in 70% (v/v) ethanol for one minute followed by washing for 5-7 min with a solution of 50% (v/v) bleach, 0.05% (w/v) Tween 20 (Sigma). After rinsing three times with sterile distilled water, the seeds were resuspended in 0.1% (w/v) agarose. Seeds were then dispensed in a grid pattern (~30 seeds/plate) with 1-2 cm spacing on sterile growth medium (0.5× Mirashige and Skoog basal salt media (Sigma) containing 1% (w/v) sucrose, nicotinic acid (1 μg/ml), thiamine-HCl (10 μg/ml), pyridoxine-HCl (1 μg/ml), myo-inositiol (100 μg/ml) and solidified with 1.0% (w/v) agar in 100 mm×15 mm or 150 mm×15 mm petri plates (Fisher). The plates were then placed at 4 C for 48 h and transferred to a controlled environment chamber with temperature of 18-22 C and a light regime of 16 h light and 8 h dark. After approximately 3 weeks plants were treated with gamma radiation using a Gamma-Cell 40 irradiator with a $Co^{60}$ radiation source. Plates containing plants were placed in the irradiator and left for time periods corresponding to desired dosages estimated from the calibrated emission from the radiation source and accounting for decay over time. Plant tissues were collected after 5-10 min recovery time and rapidly frozen using liquid $N_2$. For RNA extraction, plant tissues were first ground to a fine powder in the presence of liquid N2 using a mortar and pestle, and then RNA was isolated using the Rneasy Plant Kit (Qiagen) following the instructions provided by the manufacturer. cDNA was prepared from total RNA extracted from the plants exposed to 20 or 40 krad of gamma radiation using a SuperScript Preamplification System for First Strand cDNA Synthesis following directions of the manufacturer (GIBCO-BRL). First strand cDNA from 5-10 μg total RNA from plants treated with 20 or 40 krad of gamma radiation was primed using oligo-dT supplied with the kit.

A primary PCR reaction was performed with 4 μl first-strand cDNA from either the 20 krad or 40 krad treated plants, 0.5 pmole AtRAD51-5'Bam oligo, 0.5 pmole AtRAD51-3'X oligo, 0.2 mM dNTP's, 2.5 U Taq (Pharmacia) and Taq buffer constituents recommended by the manufacturer in a volume of 25 μl. The PCR conditions were 5 min @ 94 C, followed by 25 cycles of 30 s @ 94 C, 30 s @ 55 C and 75 s @ 72 C, followed by 10 min @ 72 C and storage at 4 C or −20 C. Two secondary PCR reactions were then performed for each of the above reactions using either 5 or 10 μl of the primary reactions in separate reactions as template with 1.0 pmole AtRAD51-5'Bam oligo and 1.0 pmole AtRAD51-3'Pst oligo and other constituents as above except using 5 U Taq and a final volume of 50 μl. Two independent secondary reactions were done for each template sample with identical PCR conditions as above. The two respective reaction series were pooled and DNA fragments were digested with BamHI and PstI. The plasmid cloning vector pBluescript II KS− (Stratagene) was digested with BamHI and PstI. DNA fragments of interest corresponding to AtRAD51 (~1.2 kb) and the vector (~3 kb) were purified by agarose gel electrophoresis and recovered from the agarose as described above. The fragments were ligated together, transformed into *E. coli* and putative clones of the gene identified as described above. Two clones were selected: pRH2 and pRH7 derived from cDNA from plants treated with 20 or 40 krad of gamma radiation, respectively. Determination of the DNA sequence of these clones revealed both had mutations at different positions of the open reading frame. To resynthesize a gene encoding a wild-type AtRAD51, restriction fragments from pRH2 and pRH7 were combined as follows: pRH2 was digested with XbaI and BamHI and a ~400 bp fragment was purified; pRH7 was digested with PstI and XbaI and a ~770 bp fragment was purified; both fragments were combined and ligated into pBluescript II KS− (Stratagene) digested with BamHI and PstI. The resulting clone, pRH15, was sequenced and found to encode a wild-type AtRAD51. The AtRAD51 gene was then subcloned into pENTR3C using BamHI and XhoI resulting in the construct pTK113.

A mutant version of AtRAD51 was created by PCR using pTK113 as template in a PCR reaction with the primers AtRAD51-I290T-S and AtRAD51-I290T-AS. After completion of cycling DpnI was added to the reaction to digest the template DNA. The amplicon was then digested with PinA1 and self-ligated. DNA sequencing confirmed the clone designated pNML55 encodes the mutant protein AtRAD51$^{I290T}$. AtRAD51$^{I290T}$ can be linked to various promoters to facilitate expression in eukaryotic cells.

ScDMC1

Template for use in amplifying ScDMC1-cDNA was obtained from cDNA generated from RNA isolated from *S. cerevisiae* cells undergoing meiosis. Strain RK1308 [209] [128] was grown in YPD liquid medium (1% (w/v) yeast extract, 2% (w/v) peptone, 2% (w/v) glucose) to cell density of ~2×10$^7$ cells/ml at 30 C with shaking at 225 RPM. Cells were collected by centrifugation, washed and resuspended in SPM medium (0.3% (w/v) potassium acetate, 0.02% (w/v) raffinose, 5 μg/ml uracil, 5 μg/ml histidine, 25 μg/ml leucine) then cultured as above for 2.5 h. Cells from 10 ml of culture were collected by centrifugation, washed with sterile distilled water (SDW) and resuspended in 1 ml SDW before rapid freezing in a dry-ice/methanol bath and stored at −80 C. Total RNA was extracted from these cells following a standard protocol [213] [123]. Approximately 4 μg of RNA was used to create cDNA primed with oligo-dT using the Superscript Preamplification System for First Strand cDNA Synthesis (Gibco/BRL) following directions of the manufacturer. Two PCR reactions were performed with 3 μl of first strand cDNA, 1.0 pmol yDMC-5'Bam oligo and 1.0 pmol yDMC-3'Pst oligo, 0.2 mM dNTP's, 2.5 U Pfu (Stratagene) and Pfu buffer constituents provided by the manufacturer in a volume of 50 μl. The PCR conditions were 5 min @ 94 C, followed by 25 cycles of 30 s @ 94 C, 30 s @ 55 C and 2 min @ 72 C, followed by 10 min @ 72 C and storage at 4 C or −20 C. The two reactions were pooled and DNA was digested with PstI. The plasmid cloning vector pBluescript II KS− (Stratagene) was digested with SmaI and PstI. DNA fragments of interest corresponding to ScDMC1-cDNA (~1.1 kb) and the vector (~3 kb) were purified by agarose gel electrophoresis and recovered from the agarose as described above. The fragments were ligated together, transformed into *E. coli* and putative clones of the gene identified as described above. The DNA sequence of the resultant clone, pMW19, was determined to confirm it encoded ScDMC1-cDNA.

A mutant version of ScDMC1 can be created by PCR using pMW19 as template in a PCR reaction with the primers yDMC1-I282T-S and yDMC1-I282T-AS. After completion of cycling DpnI may be added to the reaction to digest the template DNA. The amplicon may then digested with PinA1 and self-ligated. ScDMC1$^{I282T}$ may be linked to various promoters to facilitate expression in eukaryotic cells.

AtDMC1

Template DNA was derived from a commercially available cDNA library of *Arabidopsis thaliana* ecotype Columbia in the vector lambda ZAP II (Stratagene). The library was massexcised following the protocol supplied by the manufacture. The resultant phagemid suspension was concentrated by a combination of precipitation with polyethylene glycol as described by Ausubel et al. (1998) and desiccation using a SpeedVac (Savant). In this manner, the phagemid suspension was concentrated at least 5-fold. One hundred microliters of the concentrated phagemid suspension was extracted with phenol and chloroform following standard procedures to remove protein and other contaminants from DNA with subsequent precipitation using ethanol [213] [123]. In this manner, DNA from approximately 2 ml of phagemid suspension was concentrated and resuspended in 20 µl of LTE ((1 mM Tris-HCl, 0.1 mM EDTA (pH 8.0)) with RNaseA (20 µg/ml)).

A primary PCR reaction was performed with 1 µl *Arabidopsis* cDNA library phagemid, 0.5 pmole OL11434, 0.5 pmole OL11433, 0.2 mM dNTP's (i.e. dATP, dCTP, dGTP, dTTP; Pharmacia), 1.25 U Pfu (Stratagene) and Pfu buffer constituents recommended by the manufacturer in a volume of 25 µl. The PCR conditions were 5 min @ 94 C, followed by 25 cycles of 30 s @ 94 C, 45 s @ 60 C and 2 min @ 72 C, followed by 10 min @ 72 C and storage at 4 C or –20 C. A secondary PCR was then performed with 2 µl of the above reaction used as template with 1.0 pmol OL11434 and 1.0 pmol OL11435 and other constituents as above except using 2.5 U Pfu and a final volume of 50 µl. Two independent secondary reactions were done with identical PCR conditions as above. The two reactions were pooled and DNA fragments were resolved by agarose electrophoresis using a 1% gel and following standard procedures [213] [123]. A DNA fragment of 1 kilobase pair (kb) expected to correspond to AtDMC1 was excised and the DNA recovered from the agarose using the Qiaquick Gel Extraction Kit (Qiagen) and protocol supplied by the manufacturer. DNA was digested with XhoI and phosphorylated with T4-polynucleotide kinase following standard procedures [213] [123]. The plasmid cloning vector pBluescript II KS– (Stratagene) was digested with EcoRV and XhoI. The amplicon and vector DNA were purified by agarose electrophoresis and recovered as above. Amplicon and vector DNA were then mixed in the presence of T4 DNA ligase (Gibco-BRL) to covalently link the two molecules following standard procedures [213] [123] in a final volume of 25 µl. After 2 h at room temperature, 1 µl of glycogen (20 mg/ml) was added to the ligation mixture made up to 100 µl with distilled water. After precipitation with ethanol [213] [123], the DNA was resuspended in 4 µl of distilled water. *E. coli* strain DH5alpha (Gibco-BRL) was transformed with 2.5 µl of the concentrated ligation following standard procedures [213] [123] and plated on sterile TYS medium containing ampicillin (100 µg/ml). Putative clones were propagated in liquid TYS (i.e. without agar) and ampicillin (100 µg/ml). Plasmid DNA was isolated by standard alkaline-lysis "miniprep" procedure [213] [123]. The DNA sequence of the resultant clone, pKR225, was determined at a commercial sequencing facility (Plant Biotechnology Institute, Saskatoon, Canada). Cloning of all other genes in this invention followed the same principles as for pKR225 with noted exceptions.

pKR225 was used as template in a PCR reaction with the primers AtDMC-5'XbaSal and AtDMC-3'Spe and cloned into pDBleu (Gibco-BRL) resulting in the construct pNH3. The AtDMC1 gene was then subcloned in pENTR3C using SalI and NotI resulting in the construct pTK112.

A mutant version of AtDMC1 may be created by PCR using pTK112 as template in a PCR reaction with the primers AtDMC1-A292T-S and AtDMC1-A292T-AS. After completion of cycling DpnI may be added to the reaction to digest the template DNA. The amplicon may then be digested with PinA1 and self-ligated. AtDMC1$^{A292T}$ may be linked to various plant promoters to facilitate expression in eukaryotic cells.

12i) Plant Promoters

In some embodiments, the invention enables production of gene targeting substrates during S-phase of the cell cycle. In some embodiments this is facilitated by linking the expression of components of the gene targeting system to a transcription promoter that is expressed during S-phase. Two examples of such promoters are those facilitating transcription of the H4 histone and cyclin-D genes. H4 histone gene expression has been characterised in plants and analysis of the promoter indicates it is primarily active in dividing cells [878] [292]. Expression of the cyclin-D family of genes has also been investigated by evaluating mRNA levels [878, 988, 991] [292-294]. Of the members of the Cyclin-D gene family in *Arabidopsis*, *CycD*3 appears to be expressed at the G1/S boundary [991] [294].

A DNA sequence encoding a region of the promoter from the H4 histone gene of *Arabidopsis thaliana* was cloned. Template for amplifying the AtH4 promoter by PCR was genomic DNA from *Arabidopsis thaliana* ecotype Columbia isolated by standard procedure [213] [256]. PCR reactions were performed with approximately 1 µg of genomic DNA, 1.0 pmol H4-Prom-5'KpnSac oligonucleotide and 1.0 pmol H4-Prom-3'BamXho oligonucleotide, 0.2 mM dNTP's, 2.5 U Pfx (Gibco BRL) and Pfx buffer constituents provided by the manufacturer in a volume of 50 µl. The PCR conditions were 5 min @ 94 C, followed by 25 cycles of 30 s @ 94 C, 30 s @ 58 C and 1 min @ 68 C, followed by 10 min @ 72 C and storage at 4 C or –20 C. The DNA was digested with KpnI and NcoI. pAVA393, a plasmid cloning vector derived from pBluescript II SK+[993] [295] was digested with KpnI and NcoI. DNA fragments of interest corresponding to AtH4 promoter (~0.9 kb) and the vector (~4 kb) were purified by agarose gel electrophoresis and recovered from the agarose as described above. The fragments were ligated together, transformed into *E. coli* and putative clones of the gene identified as described above. The DNA sequence of the resultant clone, pNML8, was determined to confirm it encoded the promoter region from the *Arabidopsis* H4 histone gene. pNML8 was digested with SstI and PstI and the ~0.9 kb fragment encoding the AtH4 promoter was cloned into the SstI and PstI site of the plant transformation vector pCB302 [995] [296] resulting in the clone denoted pNML12 which enabled analysis and application of the AtH4 promoter in plants. pNML8 was modified by PCR to incorporate additional restriction sites for BamHI, SnaBI and NcoI to the 3' end of the TEV translational enhancer sequence encoded by pAVA393 adjacent to the AtH4 promoter. pNML8 was used as template in a standard PCR reaction, as described above, with the oligonucleotide primers H4-Prom-5'KpnSac and TEV-3'NcoSnaBam. The DNA was digested with KpnI and NcoI as was pAVA393. DNA fragments of interest corresponding to AtH4 promoter plus TEV sequence (~1 kb) and the vector (~4 kb) were purified by agarose gel electrophoresis, recovered from the agarose, ligated together and transformed into *E. coli*, as described above. The resultant clone was denoted pNML11.

A DNA sequence encoding a region of the promoter from the cyclin-D3 (i.e. AtCycD3) of *Arabidopsis thaliana*. Template for amplifying the AtCycD3 promoter by PCR was genomic DNA from *Arabidopsis thaliana* ecotype Columbia isolated by standard procedure [213] [256]. PCR reactions were performed with approximately 1 µg of genomic DNA, 1.0 pmol CycD3-Prom-5'KpnSac oligonucleotide and 1.0 pmol CycD3-Prom-3'Xho oligonucleotide, 0.2 mM dNTP's, 2.5 U Pfu Turbo (Stratagene) and buffer constituents provided by the manufacturer in a volume of 50 µl. The PCR conditions were 5 min @ 94 C, followed by 30 cycles of 30 s @ 94 C, 30 s @ 55 C and 2.5 min @ 72 C, followed by 10 min @ 72 C and storage at 4 C or −20 C. The DNA was digested with KpnI and NcoI. pAVA393, a plasmid cloning vector derived from pBluescript II SK+ [993] [295] was digested with KpnI and NcoI. Alternatively, a primary PCR reaction may be done using the CycD3-Prom-5'X oligonucleotide and CycD3-Prom-3'X oligonucleotide with *Arabidopsis* ecotype Columbia genomic DNA as template. An aliquot of this reaction may then be used in a secondary PCR reaction with CycD3-Prom-5'KpnSac oligonucleotide and CycD3-Prom-3'Xho oligonucleotide. DNA fragments of interest corresponding to AtCycD3 promoter (~1.1 kb) and the vector (~4.1 kb) were purified by agarose gel electrophoresis and recovered from the agarose as described above. The fragments were ligated together, transformed into *E. coli* and putative clones of the gene identified and sequenced as described above. The resultant clone of the promoter region from the *Arabidopsis* AtCycD3 gene was denoted pTK159. The DNA fragment encoding the AtCycD3 promoter may then be cloned into a plant transformation vector like pCB302 [993] [296] enabling analysis and application of the AtCycD3 promoter in plants.

In some embodiments, the invention enables production of gene targeting substrates coordinately with the expression of endogenous proteins facilitating recombination in mitotic and meiotic cells. In some embodiments this is facilitated by linking the expression of the gene targeting system components to a transcription promoter that expresses a gene involved in homologous recombination. An example of such a promoter is that facilitating transcription of the RAD51 gene. RAD51 gene expression has been characterised in plants and analysis of the promoter indicates it is expressed in vegetative cells, particularly in response to exposure to DNA damaging agents, in reproductive tissues and in tissues undergoing cell division [159] [297]. This pattern of expression is conserved in other eukaryotic species [75] [298]. Template for amplifying the AtRAD51 promoter by PCR was genomic DNA from *Arabidopsis thaliana* ecotype Lansberg isolated by standard procedure [213] [256]. A primary PCR reaction was performed with approximately 1 µg of genomic DNA as template, 1.0 pmol AtR51-Prom-5'X oligonucleotide and 1.0 pmol AtR51-Prom-3'EX oligonucleotide, 0.2 mM dNTP's, 2.5 U Pfx (Gibco BRL) and Pfx buffer constituents provided by the manufacturer in a volume of 50 µl. The PCR conditions were 5 min @ 94 C, followed by 35 cycles of 30 s @ 94 C, 30 s @ 56 C and 2 min @ 72 C, followed by 10 min @ 72 C and storage at 4 C or −20 C. An aliquot of this primary reaction was then used in a secondary PCR reaction with the oligonucleotide combination of AtR51-Prom-5' Sac and AtR51-Prom-3'Xho and Pfx polymerase and reaction conditions as described for the primary reaction. The DNA was digested with XhoI. pAVA393 [993] [295] was digested with ApaI, treated with T4 polymerase to make the DNA ends blunt, and then digested with XhoI. DNA fragments of interest corresponding to AtRAD51 promoter (11.7 kb) and the vector (~4.1 kb) were purified by agarose gel electrophoresis and recovered from the agarose as described above. The fragments were ligated together, transformed into *E. coli* and putative clones of the gene identified as described above. The DNA sequence of the resultant clone, pTK114, was determined to confirm it encoded ~1.7 kb of the promoter region from the *Arabidopsis* AtRAD51 gene. In a similar fashion, smaller segments of the AtRAD51 promoter region were cloned using the oligonucleotides AtR51-Prom-5'Sac (−1 kb) and AtR51-Prom-5'Sac (−0.7 kb) to result in the clones pTK126 encoding ~1.0 kb of the promoter region from the *Arabidopsis* AtRAD51 gene, and pTK127 encoding ~0.7 kb of the promoter region from the *Arabidopsis* AtRAD51 gene. To enable analysis and application of the AtRAD51 promoter in plants, the cloned promoter fragments were transferred to plant transformation vectors. The DNA fragment encoding the AtRAD51 promoter from pTK114, pTK126 and pTK127 was isolated by digestion of the plasmids with SmaI and SacI. These fragments were then individually ligated to the plant transformation vector pCB302 [296] also digested with SmaI and SacI resulting in the clones pTK139 (encoding the AtRAD51 promoter fragment as in pTK127), pTK140 (encoding the AtRAD51 promoter fragment as in pTK126), and pTK141 (encoding the AtRAD51 promoter fragment as in pTK114).

In some embodiments, the invention enables production of gene targeting substrates coordinately with the expression of endogenous proteins facilitating recombination in meiotic cells. In some embodiments this is facilitated by linking the expression of the gene targeting system component(s) to a transcription promoter that expresses a gene involved in homologous recombination in meiotic cells. Examples of such a promoter are those sequences facilitating transcription of the DMC1, MSH4 or SPO11 gene. The pattern of expression of these genes is conserved in eukaryotic species [123, 122, 126].

A DNA sequence encoding a region of the promoter from the DMC1 gene of *Arabidopsis thaliana* was cloned. Template for amplifying the AtDMC1 promoter by PCR was genomic DNA from *Arabidopsis thaliana* ecotype Lansberg isolated following standard procedures [213] [256].

A primary PCR reaction was performed with approximately 1 µg of genomic DNA as template, 1.0 pmol DMC-Prom-5'Kpn-S1268 oligonucleotide and 1.0 pmol DMC-Prom-AS5408 oligonucleotide, 0.2 mM dNTP's, 2.5 U Pfx (Gibco BRL) and Pfx buffer constituents provided by the manufacturer in a volume of 50 µl. The PCR conditions were 5 min @ 94 C, followed by 35 cycles of 30 s @ 94 C, 30 s @ 63 C and 2 min @ 72 C, followed by 10 min @ 72 C and storage at 4 C or −20 C. An aliquot of this primary reaction was then used in a secondary PCR reaction with the oligonucleotide combination of DMC-Prom-5'Kpn-S1268 and DMC-Prom-Int2-NcoRV and Pfx polymerase and reaction conditions as described for the primary reaction except with an annealing temperature of 53 C. The amplified DNA was digested with KpnI. pBluescript II SK− (Stratagene) was digested with KpnI and EcoRV. DNA fragments of interest corresponding to AtDMC1 promoter (~1.7 kb) and the vector (~3 kb) were purified by agarose gel electrophoresis and recovered from the agarose as described above. The fragments were ligated together, transformed into *E. coli* and putative clones of the gene identified as described above. The DNA sequence of the resultant clone, pTK111, was determined to confirm it encoded ~1.7 kb of the promoter region from the *Arabidopsis* AtDMC1 gene. A region 5' of the promoter sequence represented in pTK111 was also cloned. A PCR reaction was performed with approximately 1 µg of genomic DNA from *A. thaliana* ecotype Columbia, isolated as described above, was used as template, 1.0 pmol ADM-Prom-5'Kpn oligonucleotide and 1.0 pmol AtDMC-Pro-Nde-A1 oligonucleotide, 0.2 mM dNTP's, 2.5 U Pfu (Gibco BRL) and Pfu buffer constituents provided by the manufacturer in a volume of 50 µl. The PCR conditions were 5 min @ 94 C, followed by 30 cycles of 30 s @ 94 C, 30 s @ 55 C and 2 min @ 72 C, followed by 10 min @ 72 C and storage at 4 C or −20 C. The amplified DNA was digested with KpnI. pBluescript II SK− (Stratagene) was digested with KpnI and EcoRV. DNA fragments of interest corresponding to this upstream region of the AtDMC1 promoter (~1.4 kb) and the vector (~3 kb) were purified by agarose gel electrophoresis and recovered from the agarose as described above. The resultant clone was denoted pTK136. The cloned *Arabidopsis* DNA fragments of pTK111 and pTK136 could then be linked, as necessary, to create a 3 kb fragment encoding the promoter region of the AtDMC1 gene.

A derivative of the AtDMC1 promoter fragment encoded by pTK111 was created to remove the first intron of the AtDMC1 gene. pTK111 was used as template in a PCR reaction with oligonucleotides Universal Primer (Gibco BRL) and AtDMC-Prom-3'BamRVXho in a standard PCR reaction as described above using PfuTurbo (Stratagene) as a polymerase and annealing temperature of 55 C with extension time of 2.5 min for 30 cycles. The resulting DNA was digested with KpnI and XhoI and the ~1.2 kb fragment purified. pNML14 was also digested with KpnI and XhoI and the vector portion purified. The vector and amplified fragment were ligated together and the resultant clone was denoted pTK138. The upstream fragment of the AtDMC1 promoter encoded by pTK136 was subcloned into pTK138 using KpnI and NdeI to isolate the respective fragments. The resultant clone was denoted pTK142.

A DNA sequence encoding a region of the promoter from the MSH4 gene of *Arabidopsis thaliana* was cloned. Template for amplifying the AtMSH4 promoter by PCR was genomic DNA from *Arabidopsis thaliana* ecotype Columbia isolated following standard procedure [213] [256]. A PCR reaction was performed with approximately 1 µg of genomic DNA as template, 1.0 pmol AtMSH4-5'X oligonucleotide and 1.0 pmol AtMSH4-3'Bam oligonucleotide, 0.2 mM dNTP's, 2.5 U Pfu (Stratagene) and Pfu buffer constituents provided by the manufacturer in a volume of 50 µl. The PCR conditions were 5 min @ 94 C, followed by 35 cycles of 30 s @ 94 C, 30 s @ 60 C and 4 min @ 72 C, followed by 10 min @ 72 C and storage at 4 C or −20 C. The amplified DNA was digested with BamHI and KpnI. pBluescript II SK− (Stratagene) was digested with BamHI and KpnI. DNA fragments of interest corresponding to AtMSH4 promoter (~2 kb) and the vector (~3 kb) were purified by agarose gel electrophoresis and recovered from the agarose as described above. The fragments were ligated together, transformed into *E. coli* and putative clones of the gene identified as described above. The DNA sequence of the resultant clone, pTK65, was determined to confirm it encoded ~2 kb of the promoter region from the *Arabidopsis* AtMSH4 gene. To enable analysis and application of the AtMSH4 promoter in plants, the cloned promoter fragment was transferred to plant transformation vectors. The DNA fragment encoding the AtMSH4 promoter from pTK65 was isolated by digestion of the plasmid with KpnI, followed by treatment with T4 polymerase to make the DNA ends blunt, and digested with BamHI. This fragment was then ligated to the plant transformation vector pCB308 [995] [296] digested with XbaI, treated with Klenow polymerase to make the DNA ends blunt, and then digested with BamHI. The insert and vector fragments were purified and ligated together, as outlined above, resulting in the clone pTK93.

A DNA sequence encoding a region of the promoter from a SPO11 gene of *Arabidopsis thaliana* was cloned. Template for amplifying the AtSPO11 promoter by PCR was genomic DNA from *Arabidopsis thaliana* ecotype Columbia isolated following standard procedure [213] [256]. A PCR reaction was performed with approximately 1 µg of genomic DNA as template, 1.0 pmol SPO-1-PROM-5'KpnSac oligonucleotide and 1.0 pmol SPO-1-PROM-3'Xho oligonucleotide, 0.2 mM dNTP's, 2.5 U Pfu (Stratagene) and Pfu buffer constituents provided by the manufacturer in a volume of 50 µl. The PCR conditions were 5 min @ 94 C, followed by 35 cycles of 30 s @ 94 C, 30 s @ 60 C and 4 min @ 72 C, followed by 10 min @ 72 C and storage at 4 C or −20 C. The amplified DNA was digested with KpnI and XhoI and the ~1.2 kb fragment purified. pNML14 was also digested with KpnI and XhoI and the vector portion purified. The vector and amplified fragment were ligated together and the resultant clone of the AtSPO11 promoter region was denoted pJD1. This fragment can then be cloned into a plant transformation vector like pCB302 [995] [296] for analysis and applications in plants.

In some embodiments, the invention enables production of gene targeting substrates in all tissues throughout all developmental stages, during all stages of the cell cycle and in mitotic and meiotic cells through use of a constitutive promoter. Alternatively, constitutive promoters with differential expression amongst tissues, developmental stages, cell cycle stage, or mitotic or meiotic cells may also be used. In some embodiments, promoters with elevated expression during S-phase and G-2 phase are used. These stages of the cell cycle are when homologous recombination functions have higher activity [1022, 150]. In some embodiments gene expression patterns as desired is facilitated by linking the expression of the gene targeting system components to a constitutive promoter. Examples of constitutive promoters applicable to the invention and applied in different embodiments of the invention are cryptic promoters [994, 1698] [302], viral promoters [249] [303], prokaryote-derived promoters [996, 997, 998, 999, 1708, 1706, 1707, 1709, 1711] [304] or promoters transcribing various cellular constituents [305-307].

12j) Plant Expression Constructs

To evaluate the expression of msr-msd elements and the various derivatives thereof for producing cDNA in vivo in plant cells, plant transformation constructs were assembled to facilitate expression of a RTase and an RNA molecule encoding the gene targeting substrate to be converted to cDNA. In some embodiments, a RTase derived from a retron was employed (e.g. such as that encoded by Ec86). In some embodiments, a RTase engineered to promote nuclear localisation by addition of a nuclear localization sequence is employed, such as that encoded by pMW22. In some embodiments, a RTase engineered to facilitate detection using immuno-detection procedures is employed, such as that encoded by pMW23. In some embodiments, a RTase engineered to enhance expression in plant cells is used, such as a RTase gene with a codon composition optimised for plant cells, as encoded by pNLS-RTRs This encodes a derivative of EC86 RTase that is similar to that of pMW23 encoding the NLS of SV40 T-antigen and the FLAG peptide. However, the gene of pNLS-RTRs was resynthesized to optimize for coden usage in crucifer species.

The test locus to illustrate application of the gene targeting system in plants was the ADH locus of *Arabidopsis thaliana* ecotype Columbia encoding the enzyme alcohol dehydrogenase. Mutant alleles of AtADH were created in a similar fashion as for the *S. cerevisiae* URA3 locus described above. A bacterial artificial chromosome (BAC) encoding AtADH (i.e. BAC #F1B15 obtained from the *Arabidopsis* Biological Resource Centre, Ohio State University, 1060 Carmack Road, Columbus, Ohio, 432101002) was used as template in PCR reactions to generate mutant versions of AtADH. One PCR reaction used the primers ADH-3'3 kb-5'BamNhe and ADH-3'3 kb-3'KpnAscMsc to generate an approximately 3 kb amplicon that was cloned into pBluescript SK+ (Stratagene) using BamHI and KpnI to create the construct pNML63. A second PCR reaction used the primers ADH-5'3

Kb-5'SacAscHpa and ADH-5'3 kb-INTRON-3'BamNhe to generate an approximately 3 kb amplicon that was cloned into pBluescript SK+ (Stratagene) using SacI and BamHI to create the construct pNML64. A third PCR reaction used the primers ADH-5'3 Kb-5'SacAscHpa and ADH-5'3 kb-START-3'BamNhe to generate an approximately 3 kb amplicon that was cloned into pBluescript SK+ (Stratagene) using SacI and BamHI to create the construct pNML65. The approximately 3 kb insert of pNML63 encoding the 3' portion of AtADH was then subcloned onto the 5' portion of AtADH encoded by pNML64 using NheI and KpnI to create pNML67. pNML67 thus encodes a novel mutant allele, designated Atadh$^{Int-mu}$, which has a NheI site at the splice junction site of exonI and intron 1 of the gene. In addition, the approximately 3 kb insert of pNML63 encoding the 3' portion of AtADH was subcloned onto the 5' portion of AtADH encoded by pNML65 using NheI and KpnI to create pNML68. pNML68 thus encodes a novel mutant allele, designated Atadh$^{\Delta Ex1}$, which is deleted for the first exon of the gene.

STEM3-based gene targeting components were developed based on the Atadh$^{Int-mu}$ and Atadh$^{\Delta Ex1}$ alleles. The STEM3 element was first subcloned into a vector encoding a zeocin selection marker by using BamHI and PstI to transfer this element from pMW134 to pTK172 resulting in the construct pMW273. A 500 bp insert version of the Atadh$^{Int-mu}$ allele was created using pNML67 as template in a PCR reaction with the primers adh-Ex1(−250)-sense-5'BamXba and adh-Ex1(+250)-sense-3'RV. The approximately 500 bp amplicon was digested with XbaI, and cloned into pMW273 digested with XbaI and EcoRV resulting in the construct pMW275 encoding 500 bp of Atadh$^{Int-mu}$ in STEM3 (i.e. STEM3::Atadh$^{Int-mu}$). In a similar fashion, a 500 bp insert version of the Atadh$^{\Delta Ex1}$ allele can be created using pNML68 as template in a PCR reaction with the primers adh-Ex1(−250)-sense-5'BamXba and adh-Ex1(+250)-sense-3'RV. The approximately 500 bp amplicon can then be digested with XbaI, and cloned into pMW273 digested with XbaI and EcoRV to create a construct encoding 500 bp of Atadh$^{\Delta Ex1}$ in STEM3. In a similar fashion a 500 bp insert of the wild type AtADH gene was created. This was achieved by using genomic DNA from A. thaliana ecotype Columbia as template in a PCR reaction with the primers adh-Ex1(−250)-sense-5'BamXba and adh-Ex1(+250)-sense-3'RV. The approximately 500 bp amplicon was digested with XbaI, and cloned into pMW273 digested with XbaI and EcoRV resulting in the construct pMW296 encoding 500 bp of AtADH in STEM3 (i.e. STEM3::AtADH).

STOPstem-based gene targeting components were developed based on the Atadh$^{Int-mu}$ and Atadh$^{\Delta Ex1}$ alleles. A 500 bp insert version of the Atadh$^{Int-mu}$ allele was created using pNML67 as template in a PCR reaction with the primers adh-STOP-Ex1(−250)-sense-5'RI and adh-Ex1(+250)-sense-3'RV. The approximately 500 bp amplicon was digested with EcoRI, and cloned into pMW255 digested with EcoRI and EcoRV resulting in the construct pMW279 encoding 500 bp of Atadh$^{Int-mu}$ in STOPstem (i.e. STOPstem::Atadh$^{Int-mu}$). A 500 bp insert version of the Atadh$^{\Delta Ex1}$ allele was created using pNML68 as template in a PCR reaction with the primers adh-STOP-Ex1(−250)-sense-5'RI and adh-Ex1(+250)-sense-3'RV. The approximately 500 bp amplicon was digested with EcoRI, and cloned into pMW255 digested with EcoRI and EcoRV resulting in the construct pMW280 encoding 500 bp of Atadh$^{\Delta Ex1}$ in STOPstem (i.e. STOPstem::Atadh$^{\Delta Ex1}$). A 500 bp insert version of wild type AtADH was also created. This was achieved by using genomic DNA from A. thaliana ecotype Columbia as template in a PCR reaction with the primers adh-STOP-Ex1(−250)-sense-5'RI and adh-Ex1(+250)-sense-3'RV. The approximately 500 bp amplicon was digested with EcoRI, and cloned into pMW255 digested with EcoRI and EcoRV resulting in the construct pMW292 encoding 500 bp of AtADH in STOPstem (i.e. STOPstem::AtADH). To place these STOPstem components in a vector with zeomycin selection, the inserts of pMW279, pMW280 and pMW292 were subcloned into the pTK172 using XmnI and PstI to create the constructs pMW293 (STOPstem::Atadh$^{Int-mu}$), pMW294 (STOPstem::Atadh$^{\Delta Ex1}$) and pMW295 (STOPstem::AtADH), respectively. Another control involved subcloning the STOPstem element (i.e. without insert) from pMW255 into pTK172 using BamHI and PstI resulting in the construct pMW274.

Following the approaches described above, STEM3-based and STOPstem-based gene targeting components encoding substrates directed against the AtADH gene of 250 bp or 1000 bp can also be created using the oligonucleotides adh-STOP-Ex1(−125)-sense-5'RI or adh-Ex1(−125)-sense-5'BamXba in combination with adh-Ex1(+125)-sense-3'RV, or adh-STOP-Ex1(−500)-sense-5'RI or adh-Ex1(−500)-sense-5'BamXba in combination with adh-Ex1(+500)-sense-3'RV. Similar approaches can be used to generate gene targeting systems encoding substrates of various sizes directed against various genes in various eukaryotic cells.

In one example a plant transformation vector was assembled to express the components of the gene targeting system coordinately with S-phase of the plant cell cycle. This vector, designated pWY70, was designed to link the reverse transcriptase with the AtCycD3 promoter of pTK159 and to link the sequence encoding the gene targeting substrate to the AtH4 promoter of pNML11.

To create pWY70, pNML11 encoding the AtH4 promoter was first digested with NotI then treated with T4 DNA polymerase to make the ends blunt before digestion with BamHI. The vector plus AtH4 promoter was then ligated to a fragment encoding NLS-FLAG-RT from pMW23 created by digestion with BamHI and EcoRV. After ligation the resultant construct was designated pMW254. To link a transcription terminator to NLS-FLAG-RT, pMW254 was first digested with PstI then treated with T4 DNA polymerase to make the ends blunt before digestion with SacII. The transcription terminator from pNML11 was isolated after digestion with XbaI, followed by treatment with T4 DNA polymerase to make the ends blunt followed by digestion with SacII. After ligation of these two components the resultant construct was designated pMW263. To place the NLS-FLAG-RT gene in a plant transformation construct, pMW263 was digested with SacI then treated with T4 DNA polymerase before being digested with PstI. The NLS-FLAG-RT gene fragment was then ligated to p79-632 digested with SmaI and PstI resulting in pMW271 which encodes the NLS-FLAG-RT gene linked to the AtH4 promoter in a plant transformation vector with the PAT selectable marker that confers resistance to PPT (PAT=Phosphinothricin N-aminotransferase [1713], PPT=phosphinothricin). To link the AtCycD3 promoter to NLS-FLAG-RT, pMW271 was digested with StuI and EcoRI and the fragment encoding the vector plus NLS-FLAG-RT gene was ligated to the AtCycD3 encoding fragment released by digestion of pTK159 with KpnI followed by treatment with T4 DNA polymerase with subsequent digestion with EcoRI. The resulting construct was designated pWY66 which encodes the NLS-FLAG-RT gene linked to the AtCycD3 promoter in a plant transformation vector with the PAT selectable marker that confers resistance to PPT. The AtH4 promoter was then linked to the Destination-A cassette (Gibco-BRL). The Destination-A cassette was first cloned into the EcoRV site of pBluescript SK− (Stratagene) resulting in pMW138-1 wherein the Destination-A cassette is in a sense orientation with respect to the lacZ promoter of pBluescript SK–. The Destination-A cassette of pMW138-1 was linked to the AtH4 promoter pNML11 using XhoI and XbaI, resulting in the construct pWY68. pWY68 was then digested with SacII and treated with T4 DNA polymerase to make the ends blunt before digestion with KpnI. The fragment encoding AtH4 promoter linked to the Destination-A cassette (Gibco-BRL) was then ligated to the fragment of pWY66 encoding the AtCycD3 promoter linked to NLS-FLAG-RT and p79-632 created by digestion with KpnI and EcoRV. The resultant construct was designated pWY70 which is a plant transformation construct with the AtCycD3 promoter linked to NLS-FLAG-RT and the Destination-A cassette (Gibco-BRL) linked to the AtH4 promoter. By using the Clonase (Gibco-BRL) reaction, various gene targeting substrates can be linked to the AtH4 promoter of pWY70.

Plant transformation constructs for creating plant lines expressing the STEM3 system were assembled. To create a construct for expressing STEM3 without insert, pMW273 was used as donour in a Clonase (Gibco-BRL) reaction with pWY70 to create pMW276. To create a construct for expressing STEM3::Atadh$^{Int-mu}$, pMW275 was used as donour in a Clonase (Gibco-BRL) reaction with pWY70 to create pMW278 (i.e. encoding STEM3::Atadh$^{Int-mu}$). To create a construct for expressing STEM3::AtADH, pMW296 was used as donour in a Clonase (Gibco-BRL) reaction with pWY70 to create pMW284 (i.e. encoding STEM3::AtADH).

Plant transformation constructs for creating plant lines expressing the STOPstem system were assembled. To create a construct for expressing STOPstem without insert, pMW274 was used as donour in a Clonase (Gibco-BRL) reaction with pWY70 to create pMW277. To create a construct for expressing STOPstem::Atadh$^{Int-mu}$, pMW293 was used as donour in a Clonase (Gibco-BRL) reaction with pWY70 to create pMW289 (i.e. encoding STOPstem::Atadh$^{Int-mu}$). To create a construct for expressing STOPstem::Atadh$^{\Delta Ex1}$, pMW294 was used as donour in a Clonase (Gibco-BRL) reaction with pWY70 to create pMW290 (i.e encoding STOPstem::Atadh$^{\Delta Ex1}$). To create a construct for expressing STOPstem::AtADH, pMW295 was used as donour in a Clonase (Gibco-BRL) reaction with pWY70 to create pMW291 (i.e. encoding STOPstem::AtADH).

REFERENCES

The following documents are hereby incorporated by reference (there is no admission thereby made with respect to whether any of the documents constitute prior art with respect to any of the claims):

1. Bertling, W: Gene Targeting. In: Vega, M A (ed), Gene Targeting, pp. 1-44. CRC Press, Boca Raton (1995).
2. Lanzov, V A: Gene targeting for gene therapy: prospects. Mol. Genet. Metab 68: 276-282 (1999).
3. Roth, D B, Wilson, J H: Illegitimate recombination in mammalian cells. In: Kucherlapati, R. and Smith, G (eds), Genetic Rcombination, p. 621. American Society for Microbiology, Washington, D.C. (1988).
4. Gheysen, G, Villarroel, R, Van Montagu, M: Illegitimate recombination in plants: a model for T-DNA integration. Genes Dev. 5: 287-297 (1991).
5. Peach, C, Velten, J: Transgene expression variability (position effect) of CAT and GUS reporter genes driven by linked divergent T-DNA promoters. Plant Mol Biol 17: 49-60 (1991).
6. Mlynarova, L, Keizer, L C P, Stiekema, W J, Nap, J P. Approaching the lower limits of transgene variability. Plant Cell 8: 1589-1599. (1996).
7. Lai, L W, Lien, Y H: Homologous recombination based gene therapy. Exp Nephrol. 7: 11-14 (1999).
8. Meyer, P, Saedler, H. Homology-dependent gene silencing in plants. Annu. Rev. Plant Physiol. Plant Mol. Biol. 47: 23-48. 1996.
9. Mol, J N, van der Krol, A R, van Tunen, A J, van Blokland, R, de Lange, P, Stuitje, A R: Regulation of plant gene expression by antisense RNA. FEBS Lett 268: 427-430 (1990).
10. Rothstein, R: Targeting, disruption, replacement, and allele rescue: integrative DNA transformation in yeast. Methods Enzymol. 194: 281-301 (1991).
11. Simon, J R, Moore, P D. Homologous recombination between single-stranded DNA and chromosomal genes in *Saccharomyces cerevisiae*. Mol Cell Biochem 7, pp. 2329-2334. 1987.
12. Winzeler, E A, Shoemaker, D D, Astromoff, A, Liang, H, Anderson, K, Andre, B, Bangham, R, Benito, R, Boeke, J D, Bussey, H, Chu, A M, Connelly, C, Davis, K, Dietrich, F, Dow, S W, El Bakkoury, M, Foury, F, Friend, S H, Gentalen, E, Giaever, G, Hegemann, J H, Jones, T, Laub, M, Liao, H, Davis, R W: Functional characterization of the *S. cerevisiae* genome by gene deletion and parallel analysis. Science 285: 901-906 (1999).
13. Broverman, S, MacMorris, M, Blumenthal, T: Alteration of *Caenorhabditis elegans* gene expression by targeted transformation. Proc. Natl. Acad. Sci. U.S.A 90: 4359-4363 (1993).
14. Rong, Y S, Golic, K G: Gene targeting by homologous recombination in *drosophila*. Science 288: 2013-2018 (2000).
15. Thomas, K R, Capecchi, M R: Site-directed mutagenesis by gene targeting in mouse embryo-derived stem cells. Cell 51: 503-512 (1987).
16. Thomas, K R, Folger, K R, Capecchi, M R: High frequency targeting of genes to specific sites in the mammalian genome. Cell 44: 419-428 (1986).
17. Thompson, S, Clarke, A R, Pow, A M, Hooper, M L, Melton, D W: Germ line transmission and expression of a corrected HPRT gene produced by gene targeting in embryonic stem cells. Cell 56: 313-321 (1989).
18. Shcherbakova, O G, Lanzov, V A, Ogawa, H, Filatov, M V: Overexpression of bacterial RecA protein stimulates homologous recombination in somatic mammalian cells. Mutat. Res. 459: 65-71 (2000).
19. Yanez, R J, Porter, A C: Gene targeting is enhanced in human cells overexpressing hRAD51. Gene Ther. 6: 1282-1290 (1999).
20. Schaefer, D G, Zryd, J P: Efficient gene targeting in the moss *Physcomitrella patens*. Plant J. 11: 1195-1206 (1997).
21. Zhu, T, Mettenburg, K, Peterson, D J, Tagliani, L, Baszczynski, C L: Engineering herbicide-resistant maize using chimeric RNA/DNA oligonucleotides. Nat. Biotechnol. 18: 555-558 (2000).
22. Zhu, T, Peterson, D J, Tagliani, L, St Clair, G, Baszczynski, C L, Bowen, B: Targeted manipulation of maize genes in vivo using chimeric RNA/DNA oligonucleotides. Proc. Natl. Acad. Sci. U.S.A 96: 8768-8773 (1999).
23. Beetham, P R, Kipp, P B, Sawycky, X L, Amtzen, C J, May, G D: A tool for functional plant genomics: chimeric RNA/DNA oligonucleotides cause in vivo gene-specific mutations. Proc. Natl. Acad. Sci. U.S.A 96: 8774-8778 (1999).

24. Offring a, R, Franke-van Dijk, M E, De Groot, M J, van den Elzen, P J, Hooykaas, P J: Nonreciprocal homologous recombination between *Agrobacterium* transferred DNA and a plant chromosomal locus. Proc. Natl. Acad. Sci. U.S.A 90: 7346-7350 (1993).
25. Miao, Z H, Lam, E: Targeted disruption of the TGA3 locus in *Arabidopsis thaliana*. Plant J. 7: 359-365 (1995).
26. Rauth, S, Song, K Y, Ayares, D, Wallace, L, Moore, P D, Kucherlapati, R: Transfection and homologous recombination involving single-stranded DNA substrates in mammalian cells and nuclear extracts. Proc Natl Acad Sci USA 83: 5587-5591 (1986).
27. De Groot, M J, Offring a, R, Does, M P, Hooykaas, P J, van den Elzen, P J: Mechanisms of intermolecular homologous recombination in plants as studied with si. Nucleic Acids Res. 20: 2785-2794 (1992).
28. Alexeev, V, Igoucheva, O, Domashenko, A, Cotsarelis, G, Yoon, K: Localized in vivo genotypic and phenotypic correction of the albino mutation in skin by RNA-DNA oligonucleotide. Nat. Biotechnol. 18: 43-47 (2000).
29. Yoon, K, Cole-Strauss, A, Kmiec, E B: Targeted gene correction of episomal DNA in mammalian cells mediated by a chimeric RNA.DNA oligonucleotide. Proc. Natl. Acad. Sci. U.S.A 93: 2071-2076 (1996).
30. Cole-Strauss, A, Yoon, K, Xiang, Y, Byrne, B C, Rice, M C, Gryn, J, Holloman, W K, Kmiec, E B: Correction of the mutation responsible for sickle cell anemia by an RNA-DNA oligonucleotide. Science 273: 1386-1389 (1996).
31. Yang, X W, Model, P, Heintz, N. Homologous recombination based modification in *Escherichia coli* and germline transmission in transgenic mice of a bacterial artificial chromosome. Nat. Biotechnol. 15, pp. 859-865. 1997.
32. Gamper, H B, Jr., Cole-Strauss, A, Metz, R, Parekh, H, Kumar, R, Kmiec, E B: A plausible mechanism for gene correction by chimeric oligonucleotides. Biochemistry 39: 5808-5816 (2000).
33. Cole-Strauss, A, Gamper, H, Holloman, W K, Munoz, M, Cheng, N, Kmiec, E B: Targeted gene repair directed by the chimeric RNA/DNA oligonucleotide in a mammalian cell-free extract. Nucleic Acids Res 27: 1323-1330 (1999).
34. Kaeppler, S M, Kaeppler, H F, Rhee, Y: Epigenetic aspects of somaclonal variation in plants. Plant Mol Biol 43: 179-188 (2000).
35. Gallego, M E, Sirand-Pugnet, P, White, C I: Positive-negative selection and T-DNA stability in *Arabidopsis* transformation. Plant Mol Biol 39: 83-93 (1999).
36. Lin, F L, Sperle, K, Sternberg, N: Recombination in mouse L cells between DNA introduced into cells and homologous chromosomal sequences. Proc Natl Acad Sci USA 82: 1391-1395 (1985).
37. Kresn, F A, Molendijk, L, Wullems, G J, Schilperoort, R A. In vitro transformation of plant protoplasts with Ti-plasmid DNA. Nature 296: 72. 1982.
38. Deshayes, A, Herrera-Estrella, L, Caboche, M: Liposome-mediated transformation of tobacco mesophyllprotoplasts by an *Escherichia coli* plasmid. EMBO J. 4: 2731-2737 (1985).
39. Brinster, R L, Braun, R E, Lo, D, Avarbock, M R, Oram, F, Palmiter, R D: Targeted correction of a major histocompatibility class II E alpha gene by DNA microinjected into mouse eggs. Proc Natl Acad Sci USA 86: 7087-7091 (1989).
40. Shillito, R D, Saul, M W, Paszkowski, J, Muller, M, Potrykus, I. High efficiency direct gene transfer to plants. Bio/technology 3: 1099. (1985).
41. D'Halluin, K, Bonne, E, Bossut, M, De Beuckeleer, M, Leemans, J: Transgenic maize plants by tissue electroporation. Plant Cell 4: 1495-1505 (1992).
42. Crossway, A, Oakes, J V, Irvine, J M, Ward, B, Knauf, V C, Shewmaker, C K. Integration of foreign DNA following microinjection of tobacco mesophyllprotoplasts. Mol Gen Genet. 202: 179. (1986).
43. Yoshida, K, Takegami, T, Katoh, A, Nishikawa, M, Nishida, T: Construction of a novel conjugative plasmid harboring a GFP reporter gene and its introduction into animal cells by transfection and trans-kingdom conjugation. Nucleic Acids Symp Ser. 157-158 (1997).
44. Negritto, M T, Wu, X, Kuo, T, Chu, S, Bailis, A M: Influence of DNA sequence identity on efficiency of targeted gene replacement. Mol Cell Biol 17: 278-286 (1997).
45. Bennett, C B, Lewis, A L, Baldwin, K K, Resnick, M A: Lethality induced by a single site-specific double-strand break in a dispensable yeast plasmid. Proc Natl Acad Sci USA 90: 5613-5617 (1993).
46. Cummings, W J, Zolan, M E: Functions of DNA repair genes during meiosis. Curr. Top. Dev. Biol. 37: 117-140 (1998).
47. Galli, A, Schiestl, R H: Effects of DNA double-strand and single-strand breaks on intrachromosomal recombination events in cell-cycle-arrested yeast cells. Genetics 149: 1235-1250 (1998).
48. Lebkowski, J S, DuBridge, R B, Antell, E A, Greisen, K S, Calos, M P: Transfected DNA is mutated in monkey, mouse, and human cells. Mol Cell Biol 4: 1951-1960 (1984).
49. Wake, C T, Gudewicz, T, Porter, T, White, A, Wilson, J H: How damaged is the biologically active subpopulation of transfected DNA? Mol Cell Biol 4: 387-398 (1984).
50. Perucho, M, Hanahan, D, Wigler, M: Genetic and physical linkage of exogenous sequences in transformed cells. Cell 22: 309-317 (1980).
51. Deng, C, Capecchi, M R: Reexamination of gene targeting frequency as a function of the extent of homology between the targeting vector and the target locus. Mol Cell Biol 12: 3365-3371 (1992).
52. Orr-Weaver, T L, Szostak, J W, Rothstein, R J: Yeast transformation: a model system for the study of recombination. Proc Natl Acad Sci USA 78: 6354-6358 (1981).
53. Jasin, M, Berg, P: Homologous integration in mammalian cells without target gene selection. Genes Dev. 2: 1353-1363 (1988).
54. Puchta, H, Dujon, B, Hohn, B: Homologous recombination in plant cells is enhanced by in vivo induction of double strand breaks into DNA by a site-specific endonuclease. Nucleic Acids Res 21: 5034-5040 (1993).
55. Ilyina, T V, Koonin, E V: Conserved sequence motifs in the initiator proteins for rolling circle DNA replication encoded by diverse replicons from eubacteria, eucaryotes and archaebacteria. Nucleic Acids Res 20: 3279-3285 (1992).
56. Dujon, B: Group I introns as mobile genetic elements: facts and mechanistic speculations—a review. Gene 82: 91-114 (1989).
57. Colleaux, L, D'Auriol, L, Galibert, F, Dujon, B: Recognition and cleavage site of the intron-encoded omega transposase. Proc Natl Acad Sci USA 85: 6022-6026 (1988).
58. Jin, Y, Binkowski, G, Simon, L D, Norris, D: Ho endonuclease cleaves MAT DNA in vitro by an inefficient stoichiometric reaction mechanism. J Biol Chem 272: 7352-7359 (1997).
59. Nicolas, A L, Munz, P L, Falck-Pedersen, E, Young, C S: Creation and repair of specific DNA double-strand breaks 59. in vivo following infection with adenovirus vectors expressing *Saccharomyces cerevisiae* HO endonuclease. Virology 266: 211-224 (2000).
60. Gasser, C S, Fraley, R T. Genetically engineering plants for crop improvement. Science 244: 1293. (1989).
61. Klein, T M, Harper, E C, Svab, Z, Sanford, J C, Fromm, M E, Maliga, P. Stable genetic transformation of intact *Nicotiana* cells by the particle bombardment process. Proc Natl Acad Sci USA 85: 8502. (1988).
62. Wong, E A, Capecchi, M R: Homologous recombination between coinjected DNA sequences peaks in early to mid-S phase. Mol Cell Biol 7: 2294-2295 (1987).
63. Merrill, G F: Cell synchronization. Methods Cell Biol 57: 229-249 (1998).
64. Reichheld, J P, Gigot, C, Chaubet-Gigot, N: Multilevel regulation of histone gene expression during the cell cycle in tobacco cells. Nucleic Acids Res 26: 3255-3262 (1998).
65. Osley, M A: The regulation of histone synthesis in the cell cycle. Annu. Rev Biochem 60: 827-861 (1991).
66. Huntley, R P, Murray, J A: The plant cell cycle. Curr. Opin. Plant Biol 2: 440-446 (1999).
67. Roeder, G S: Meiotic chromosomes: it takes two to tango. Genes Dev. 11: 2600-2621 (1997).
68. Klimyuk, V I, Jones, J D: AtDMC1, the *Arabidopsis* homologue of the yeast DMC1 gene: characterization, transposon-induced allelic variation and meiosis-associated expression. Plant J. 11: 1-14 (1997).
69. Ross-Macdonald, P, Roeder, G S: Mutation of a meiosis-specific MutS homolog decreases crossing over but not mismatch correction. Cell 79: 1069-1080 (1994).
70. Kobayashi, T, Kobayashi, E, Sato, S, Hotta, Y, Miyajima, N, Tanaka, A, Tabata, S: Characterization of cDNAs induced in meiotic prophase in lily microsporocytes. DNA Res. 1: 15-26 (1994).
71. Chu, S, DeRisi, J, Eisen, M, Mulholland, J, Botstein, D, Brown, P O, Herskowitz, I: The transcriptional program of sporulation in budding yeast. Science 282: 699-705 (1998).
72. Tsuzuki, T, Fujii, Y, Sakumi, K, Tominaga, Y, Nakao, K, Sekiguchi, M, Matsushiro, A, Yoshimura, Y, Morita T: Targeted disruption of the Rad51 gene leads to lethality in embryonic mice. Proc. Natl. Acad. Sci. U.S.A 93: 6236-6240 (1996).
73. Coventry, J, Kott, L, Beversdorf, W: Manual for microspore culture technique for *Brassica napus*. University of Guelph, Guelph (1988).
74. Offring a, R, De Groot, M J, Haagsman, H J, Does, M P, van den Elzen, P J, Hooykaas, P J: Extrachromosomal homologous recombination and gene targeting in plant cells after *Agrobacterium* mediated transformation. EMBO J. 9: 3077-3084 (1990).
75. Friedberg, E C, Walker, G C, Siede, W: DNA Repair and Mutagenesis. American Society for Microbiology, Washington, D.C. (1995).
76. Hoffmann, G R: Induction of genetic recombination: consequences and model systems. Environ. Mol. Mutagen. 23 Suppl 24: 59-66 (1994).
77. Schiestl, R H: Nonmutagenic carcinogens induce intrachromosomal recombination in yeast. Nature 337: 285-288 (1989).
78. Basile, G, Aker, M, Mortimer, R K: Nucleotide sequence and transcriptional regulation of the yeast recombinational repair gene RAD51. Mol. Cell Biol. 12: 3235-3246 (1992).
79. Rozwadowski, K, Kreiser, T, Hasnadka, R, Lydiate, D. AtMRE11: a component of meiotic recombination and DNA repair in plants. 10th International Conference on *Arabidopsis* Research, Melbourne, Australia, Jul. 4-8, 1999. 1999.
80. Ainley, W M, Key, J L: Development of a heat shock inducible expression cassette for plants: characterization of parameters for its use in transient expression assays. Plant Mol. Biol. 14: 949-967 (1990).
81. Martinez, A, Sparks, C, Hart, C A, Thompson, J, Jepson, I: Ecdysone agonist inducible transcription in transgenic tobacco plants. Plant J. 19: 97-106 (1999).
82. Bohner, S, Lenk, I, Rieping, M, Herold, M, Gatz, C: Technical advance: transcriptional activator TGV mediates dexamethasone-inducible and tetracycline-inactivatable gene expression. Plant J. 19: 87-95 (1999).
83. Gatz, C, Kaiser, A, Wendenburg, R: Regulation of a modified CaMV 35S promoter by the Tn10-encoded Tet repressor in transgenic tobacco. Mol. Gen. Genet. 227: 229-237 (1991).
84. Weinmann, P, Gossen, M, Hillen, W, Bujard, H, Gatz, C: A chimeric transactivator allows tetracycline-responsive gene expression in whole plants. Plant J. 5: 559-569 (1994).
85. Mett, V L, Podivinsky, E, Tennant, A M, Lochhead, L P, Jones, W T, Reynolds, P H: A system for tissue-specific copper-controllable gene expression in transgenic plants: nodule-specific antisense of aspartate aminotransferase-P2. Transgenic Res. 5: 105-113 (1996).
86. Mett, V L, Lochhead, L P, Reynolds, P H: Copper-controllable gene expression system for whole plants. Proc. Natl. Acad. Sci. U.S.A 90: 4567-4571 (1993).
87. Guyer, D, Tuttle, A, Rouse, S, Volrath, S, Johnson, M, Potter, S, Gorlach, J, Goff, S, Crossland, L, Ward, E: Activation of latent transgenes in *Arabidopsis* using a hybrid transcription factor. Genetics 149: 633-639 (1998).
88. Moore, I, Galweiler, L, Grosskopf, D, Schell, J, Palme, K: A transcription activation system for regulated gene expression in transgenic plants. Proc. Natl. Acad. Sci. U.S.A 95: 376-381 (1998).
89. Labow, M A, Baim, S B, Shenk, T, Levine, A J: Conversion of the lac repressor into an allosterically regulated transcriptional activator for mammalian cells. Mol. Cell Biol. 10: 3343-3356 (1990).
90. Benton, B M, Eng, W K, Dunn, J J, Studier, F W, Stemglanz, R, Fisher, P A: Signal-mediated import of bacteriophage T7 RNA polymerase into the *Saccharomyces cerevisiae* nucleus and specific transcription of target genes. Mol. Cell Biol. 10: 353-360 (1990).
91. Bechtold, N, Pelletier, G: In planta *Agrobacterium*-mediated transformation of adult *Arabidopsis thaliana* plants by vacuum infiltration. Methods Mol Biol 82: 259-266 (1998).
92. Clough, S J, Bent, A F: Floral dip: a simplified method for *Agrobacterium*-mediated transformation of *Arabidopsis thaliana*. Plant J 16: 735-743 (1998).
93. Scholz, S, Scholthof, K-BG: Plant virus gene vectors for transient expression of foreign proteins in plants. Annu. Rev. of Phytopathol. 34: 299-323 (1996).
94. Wilmut, I, Schnieke, A E, McWhir, J, Kind, A J, Campbell, K H: Viable offspring derived from fetal and adult mammalian cells. Nature 385: 810-813 (1997).
95. Model, P, Russel, M: Filamentous Bacteriophage. In: Calendar, R. (ed), The Bacteriophages, pp. 375-456. Plenum Press, New York (1988).
96. Hayashi, M, Aoyama, A, Richardson Jr., Dl, Hayashi, M N: Biology of the bacteriophage phiX174. In: Calendar, R (ed), The Bacteriophages, pp. 1-71. Plenum Press, New York (1988).

97. Chang, T L, Kramer, M G, Ansari, R A, Khan, S A: Role of individual monomers of a dimeric initiator protein in the initiation and termination of plasmid rolling circle replication. J Biol Chem 275: 13529-13534 (2000).
98. Novick, R P: Contrasting lifestyles of rolling-circle phages and plasmids. Trends Biochem Sci 23: 434-438 (1998).
99. Castellano, M M, Sanz-Burgos, A P, Gutierrez, C: Initiation of DNA replication in a eukaryotic rolling-circle replicon: identification of multiple DNA-protein complexes at the geminivirus origin. J Mol Biol 290: 639-652 (1999).
100. Meehan, B M, Creelan, J L, McNulty, M S, Todd, D: Sequence of porcine circovirus DNA: affinities with plant circoviruses. J Gen Virol 78: 221-227 (1997).
101. Pansegrau, W, Lanka, E. Enzymology of DNA transfer by conjugative mechanisms. Progress in Nucleic Acid Research and Molecular Biology 54: 197-251. (1996).
102. Cotmore, S F, Tattersall, P: High-mobility group ½ proteins are essential for initiating rolling-circle-type DNA replication at a parvovirus hairpin origin. J Virol 72: 8477-8484 (1998).
103. Im, D S, Muzyczka, N: The AAV origin binding protein Rep68 is an ATP-dependent site-specific endonuclease with DNA helicase activity. Cell 61: 447-457 (1990).
104. Laufs, J, Jupin, I, David, C, Schumacher, S, Heyraud-Nitschke, F, Gronenbom, B: Geminivirus replication: genetic and biochemical characterization of Rep protein function, a review. Biochimie 77: 765-773 (1995).
105. Sims, J, Capon, D, Dressler, D: dnaG (primase)-dependent origins of DNA replication. Nucleotide sequences of the negative strand initiation sites of bacteriophages St-1, phi K, and alpha 3. J Biol Chem 254: 12615-12628 (1979).
106. Heidekamp, F, Baas, P D, Jansz, H S: Nucleotide sequences at the phi X gene A protein cleavage site in replicative form I DNAs of bacteriophages U3, G14, and alpha 3. J Virol 42: 91-99 (1982).
107. Godson, G N, Barrell, B G, Staden, R, Fiddes, J C: Nucleotide sequence of bacteriophage G4 DNA. Nature 276: 236-247 (1978).
108. Gielow, A, Diederich, L, Messer, W: Characterization of a phage-plasmid hybrid (phasyl) with two independent origins of replication isolated from *Escherichia coli*. J Bacteriol 173: 73-79 (1991).
109. Harding, R M, Burns, T M, Hafner, G, Dietzgen, R G, Dale, J L: Nucleotide sequence of one component of the banana bunchy top virus genome contains a putative replicase gene. J Gen Virol 74: 323-328 (1993).
110. Hafner, G J, Stafford, M R, Wolter, L C, Harding, R M, Dale, J L: Nicking and joining activity of banana bunchy top virus replication protein in vitro. J Gen Virol 78: 1795-1799 (1997).
111. Chu, P W, Keese, P, Qiu, B S, Waterhouse, P M, Gerlach, W L: Putative full-length clones of the genomic DNA segments of subterranean clover stunt virus and identification of the segment coding for the viral coat protein. Virus Res 27: 161-171 (1993).
112. Rohde, W, Randles, J W, Langridge, P, Hanold, D: Nucleotide sequence of a circular single-stranded DNA associated with coconut foliar decay virus. Virology 176: 648-651 (1990).
113. Todd, D, Creelan, J L, Mackie, D P, Rixon, F, McNulty, M S: Purification and biochemical characterization of chicken anaemia agent. J Gen Virol 71: 819-823 (1990).
114. Ritchie, B W, Niagro, F D, Lukert, P D, Steffens, W L, III, Latimer, K S: Characterization of a new virus from cockatoos with psittacine beak and feather disease. Virology 171: 83-88 (1989).
115. Snyder, R O, Im, D S, Ni, T, Xiao, X, Samulski, R J, Muzyczka, N: Features of the adeno-associated virus origin involved in substrate recognition by the viral Rep protein. J Virol 67: 6096-6104 (1993).
116. Brister, J R, Muzyczka, N: Mechanism of Rep-mediated adeno-associated virus origin nicking. J Virol 74: 7762-7771 (2000). 117. Nuesch, J P, Cotmore, S F, Tattersall, P: Sequence motifs in the replicator protein of parvovirus MVM essential for nicking and covalent attachment to the viral origin: identification of the linking tyrosine. Virology 209:122-135.
118. Noirot-Gros, M F, Bidnenko, V, Ehrlich, S D: Active site of the replication protein of the rolling circle plasmid pC194. EMBO J 13: 4412-4420 (1994).
119. Gros, M F, te, R H, Ehrlich, S D: Replication origin of a single-stranded DNA plasmid pC194. EMBO J. 8: 2711-2716 (1989).
120. Koepsel, R R, Murray, R W, Rosenblum, W D, Khan, S A: The replication initiator protein of plasmid pT181 has sequence-specific endonuclease and topoisomerase-like activities. Proc Natl Acad Sci USA 82: 6845-6849 (1985).
121. Murray, R W, Koepsel, R R, Khan, S A: Synthesis of single-stranded plasmid pT181 DNA in vitro. Initiation and termination of DNA replication. J Biol Chem 264: 1051-1057 (1989).
122. Boe, L, Gros, M F, te, R H, Ehrlich, S D, Gruss, A: Replication origins of single-stranded-DNA plasmid pUB110. J Bacteriol 171: 3366-3372 (1989).
123. Yang, X, McFadden, B A: A small plasmid, pCA2.4, from the cyanobacterium *Synechocystis* sp. strain PCC 6803 encodes a rep protein and replicates by a rolling circle mechanism. J Bacteriol 175: 3981-3991 (1993).
124. Sozhamannan, S, Dabert, P, Moretto, V, Ehrlich, S D, Gruss, A: Plus-origin mapping of single-stranded DNA plasmid pE194 and nick site homologies with other plasmids. J Bacteriol 172: 4543-4548 (1990).
125. Yasukawa, H, Hase, T, Sakai, A, Masamune, Y: Rolling-circle replication of the plasmid pKYM isolated from a gram-negative bacterium. Proc Natl Acad Sci USA 88: 10282-10286 (1991).
126. Yasukawa, H, Masamune, Y: Rolling-circle plasmid pKYM re-initiates DNA replication. DNA Res 4: 193-197 (1997).
127. Gruss, A, Ehrlich, S D: The family of highly interrelated single-stranded deoxyribonucleic acid plasmids. Microbiol. Rev 53: 231-241 (1989).
128. Espinosa, M, del Solar, G, Rojo, F, Alonso, J C: Plasmid rolling circle replication and its control. FEMS Microbiol Lett 130: 111-120 (1995).
129. del Solar, G, Giraldo, R, Ruiz-Echavarria, M J, Espinosa, M, Diaz-Orejas, R: Replication and control of circular bacterial plasmids. Microbiol. Mol Biol Rev 62: 434-464 (1998).
130. Matson, S W, Nelson, W C, Morton, B S: Characterization of the reaction product of the oriT nicking reaction catalyzed by *Escherichia coli* DNA helicase I. J Bacteriol 175: 2599-2606 (1993).
131. Llosa, M, Bolland, S, de la, C F: Structural and functional analysis of the origin of conjugal transfer of the broad-host-range IncW plasmid R388 and comparison with the related IncN plasmid R46. Mol Gen Genet. 226: 473-483 (1991).
132. Pansegrau, W, Lanka, E: Mechanisms of initiation and termination reactions in conjugative DNA processing. Independence of tight substrate binding and catalytic activity of relaxase (TraI) of IncPalpha plasmid RP4. J Biol Chem 271: 13068-13076 (1996).

133. Furste, J P, Pansegrau, W, Ziegelin, G, Kroger, M, Lanka, E: Conjugative transfer of promiscuous IncP plasmids: interaction of plasmid-encoded products with the transfer origin. Proc Natl Acad Sci USA 86: 1771-1775 (1989).
134. Scherzinger, E, Ziegelin, G, Barcena, M, Carazo, J M, Lurz, R, Lanka, E: The RepA protein of plasmid RSF1010 is a replicative DNA helicase. J Biol Chem 272: 30228-30236 (1997).
135. Coupland, G M, Brown, A M, Willetts, N S: The origin of transfer (oriT) of the conjugative plasmid R46: characterization by deletion analysis and DNA sequencing. Mol Gen Genet. 208: 219-225 (1987).
136. Finlay, B B, Frost, L S, Paranchych, W: Origin of transfer of IncF plasmids and nucleotide sequences of the type II oriT, traM, and traY alleles from ColB4-K98 and the type IV traY allele from R100-1. J Bacteriol 168: 132-139 (1986).
137. Furuya, N, Nisioka, T, Komano, T: Nucleotide sequence and functions of the oriT operon in IncI1 plasmid R64. J Bacteriol 173: 2231-2237 (1991).
138. Murphy, C G, Malamy, M H: Requirements for strand- and sitespecific cleavage within oriT region of Tn4399, a mobilizing transposon from *Bacteroides fragilis*. J Bacteriol 177: 3158-3165 (1995).
139. Murphy, C G, Malamy, M H: Characterization of a "mobilization cassette" in transposon Tn4399 from *Bacteroides fragilis*. J Bacteriol 175: 5814-5823 (1993).
140. Bastia, D: Determination of restriction sites and the nucleotide sequence surrounding the relaxation site of ColE1. J Mol Biol 124: 601-639 (1978).
141. Roessler, E, Fenwick, R G, Jr., Chinault, A C: Analysis of mobilization elements in plasmids from *Shigella flexneri*. J Bacteriol 161: 1233-1235 (1985).
142. Snijders, A, van Putten, A J, Veltkamp, E, Nijkamp, H J: Localization and nucleotide sequence of the bom region of Clo DF13. Mol Gen Genet. 192: 444-451 (1983).
143. Bernardi, A, Bernardi, F: Complete sequence of pSC101. Nucleic Acids Res 12: 9415-9426 (1984).
144. Beck, E, Zink, B: Nucleotide sequence and genome organisation of filamentous bacteriophages fl and fd. Gene 16: 35-58 (1981).
145. Sanger, F, Air, G M, Barrell, B G, Brown, N L, Coulson, A R, Fiddes, C A, Hutchison, C A, Slocombe, P M, Smith, M: Nucliotide sequence of bacteriophage phi X174 DNA. Nature 265: 687-695 (1977).
146. Meyer, T F, Geider, K: Enzymatic synthesis of bacteriophage fd viral DNA. Nature 296: 828-832 (1982).
147. Harth, G, Baumel, I, Meyer, T F, Geider, K: Bacteriophage fd gene-2 protein. Processing of phage fd viral strands replicated by phage T7 enzymes. Eur J Biochem 119: 663-668 (1981).
148. Shavitt, O, Livneh, Z: Rolling-circle replication of UV-irradiated duplex DNA in the phi X174 replicative-form-single-strand replication system in vitro. J Bacteriol 171: 3530-3538 (1989).
149. Lin, N S, Pratt, D: Role of bacteriophage M13 gene 2 in viral DNA replication. J Mol Biol 72: 37-49 (1972).
150. Goetz, G S, Hurwitz, J: Studies on the role of the phi X174 gene A protein in phi X viral strand synthesis. I. Replication of DNA containing an alteration in position 1 of the 30-nucleotide icosahedral bacteriophage origin. J Biol Chem 263: 16421-16432 (1988).
151. Hanai, R, Wang, J C: The mechanism of sequence-specific DNA cleavage and strand transfer by phi X174 gene A* protein. J Biol Chem 268: 23830-23836 (1993).
152. Higashitani, A, Greenstein, D, Hirokawa, H, Asano, S, Horiuchi, K: Multiple DNA conformational changes induced by an initiator protein precede the nicking reaction in a rolling circle replication origin. J Mol Biol 237: 388-400 (1994).
153. Asano, S, Higashitani, A, Horiuchi, K: Filamentous phage replication initiator protein gpII forms a covalent complex with the 5' end of the nick it introduced. Nucleic Acids Res 27: 1882-1889 (1999).
154. Higashitani, A, Greenstein, D, Horiuchi, K: A single amino acid substitution reduces the superhelicity requirement of a replication initiator protein. Nucleic Acids Res 20: 2685-2691 (1992).
155. Greenstein, D, Horiuchi, K: Double-strand cleavage and strand joining by the replication initiator protein of filamentous phage fl. J Biol Chem 264: 12627-12632 (1989).
156. Fluit, A C, Baas, P D, Van Boom, J H, Veeneman, G H, Jansz, H S: Gene A protein cleavage of recombinant plasmids containing the phi X174 replication origin. Nucleic Acids Res 12: 6443-6454 (1984).
157. van Mansfeld, A D, van Teeffelen, H A, Baas, P D, Jansz, H S: Two juxtaposed tyrosyl-OH groups participate in phi X174 gene A protein catalysed cleavage and ligation of DNA. Nucleic Acids Res 14: 4229-4238 (1986).
158. van Mansfeld, A D, van Teeffelen, H A, Baas, P D, Veeneman, G H, Van Boom, J H, Jansz, H S: The bond in the bacteriophage phi X174 gene A protein-DNA complex is a tyrosyl-5'-phosphate ester. FEBS Lett 173: 351-356 (1984).
159. van Mansfeld, A D, Baas, P D, Jansz, H S: Gene A protein of bacteriophage phi X174 is a highly specific single-strand nuclease and binds via a tyrosyl residue to DNA after cleavage. Adv Exp Med Biol 179: 221-230 (1984).
160. Dente, L, Cesareni, G, Cortese, R: pEMBL: a new family of single stranded plasmids. Nucleic Acids Res 11: 1645-1655 (1983).
161. Dotto, G P, Enea, V, Zinder, N D: Functional analysis of bacteriophage fl intergenic region. Virology 114: 463-473 (1981).
162. Fluit, A C, Baas, P D, Jansz, H S: The complete 30-base-pair origin region of bacteriophage phi X174 in a plasmid is both required and sufficient for in vivo rolling-circle DNA replication and packaging. Eur J Biochem 149: 579-584 (1985).
163. van der, E A, Teertstra, R, Weisbeek, P J: Initiation and termination of the bacteriophage phi X174 rolling circle DNA replication in vivo: packaging of plasmid single-stranded DNA into bacteriophage phi X174 coats. Nucleic Acids Res 10: 6849-6863 (1982).
164. Dotto, G P, Zinder, N D: Increased intracellular concentration of an initiator protein markedly reduces the minimal sequence required for initiation of DNA synthesis. Proc Natl Acad Sci USA 81: 1336-1340 (1984).
165. Goetz, G S, Hurwitz, J: Studies on the role of the phi X174 gene A protein in phi X174 viral strand synthesis. III. Replication of DNA containing two viral replication origins. J Biol Chem 263: 16443-16451 (1988).
166. Goetz, G S, Schmidt-Glenewinkel, T, Hu, M H, Belgado, N, Hurwitz, J: Studies on the role of the phi X174 gene A protein in phi X viral strand synthesis. II. Effects of DNA replication of mutations in the 30-nucleotide icosahedral bacteriophage origin. J Biol Chem 263: 16433-16442 (1988).
167. Reinberg, D, Zipursky, S L, Weisbeek, P, Brown, D, Hurwitz, J: Studies on the phi X174 gene A protein-mediated termination of leading strand DNA synthesis. J Biol Chem 258: 529-537 (1983).

168. Dotto, G P, Horiuchi, K, Zinder, N D: Initiation and termination of phage f1 plus-strand synthesis. Proc Natl Acad Sci USA 79: 7122-7126 (1982).
169. Short, J M, Fernandez, J M, Sorge, J A, Huse, W D: Lambda ZAP: a bacteriophage lambda expression vector with in vivo excision properties. Nucleic Acids Res 16: 7583-7600 (1988).
170. Dotto, G P, Horiuchi, K: Replication of a plasmid containing two origins of bacteriophage. J Mol Biol 153: 169-176 (1981).
171. Dotto, G P, Horiuchi, K, Zinder, N D: The functional origin of bacteriophage f1 DNA replication. Its signals and domains. J Mol Biol 172: 507-521 (1984).
172. Meyer, T F, Geider, K: Cloning of bacteriophage fd gene 2 and construction of a plasmid dependent on fd gene 2 protein. Proc Natl Acad Sci USA 78: 5416-5420 (1981).
173. Strathem, J N, Weinstock, K G, Higgins, D R, McGill, C B: A novel recombinator in yeast based on gene II protein from bacteriophage f1. Genetics 127: 61-73 (1991).
174. Heyraud-Nitschke, F, Schumacher, S, Laufs, J, Schaefer, S, Schell, J, Gronenbom, B: Determination of the origin cleavage and joining domain of geminivirus Rep proteins. Nucleic Acids Res 23: 910-916 (1995).
175. Choi, I R, Stenger, D C: Strain-specific determinants of beet curly top geminivirus DNA replication. Virology 206: 904-912 (1995).
176. Laufs, J, Traut, W, Heyraud, F, Matzeit, V, Rogers, S G, Schell, J, Gronenbom, B: In vitro cleavage and joining at the viral origin of replication by the replication initiator protein of tomato yellow leaf curl virus. Proc Natl Acad Sci USA 92: 3879-3883 (1995).
177. Desbiez, C, David, C, Mettouchi, A, Laufs, J, Gronenborn, B: Rep protein of tomato yellow leaf curl geminivirus has an ATPase activity required for viral DNA replication. Proc Natl Acad Sci USA 92: 5640-5644 (1995).
178. Laufs, J, Schumacher, S, Geisler, N, Jupin, I, Gronenborn, B: Identification of the nicking tyrosine of geminivirus Rep protein. FEBS Lett 377: 258-262 (1995).
179. Orozco, B M, Hanley-Bowdoin, L: Conserved sequence and structural motifs contribute to the DNA binding and cleavage activities of a geminivirus replication protein. J Biol Chem 273: 24448-24456 (1998).
180. Orozco, B M, Kong, L J, Batts, L A, Elledge, S, Hanley-Bowdoin, L: The multifunctional character of a geminivirus replication protein is reflected by its complex oligomerization properties. J Biol Chem 275: 6114-6122 (2000).
181. Orozco, B M, Miller, A B, Settlage, S B, Hanley-Bowdoin, L: Functional domains of a geminivirus replication protein. J Biol Chem 272: 9840-9846 (1997).
182. Lazarowitz, S G, Wu, L C, Rogers, S G, Elmer, J S: Sequence-specific interaction with the viral AL1 protein identifies a geminivirus DNA replication origin. Plant Cell 4: 799-809 (1992).
183. Jupin, I, Hericourt, F, Benz, B, Gronenbom, B: DNA replication specificity of TYLCV geminivirus is mediated by the amino-terminal 116 amino acids of the Rep protein. FEBS Lett 362: 116-120 (1995).
184. Rigden, J E, Dry, I B, Krake, L R, Rezaian, M A: Plant virus DNA replication processes in *Agrobacterium*: insight into the origins of geminiviruses? Proc Natl Acad Sci USA 93: 10280-10284 (1996).
185. Akbar Behjatnia, S A, Dry, I B, Ali, R M: Identification of the replication-associated protein binding domain within the intergenic region of tomato leaf curl geminivirus. Nucleic Acids Res 26: 925-931 (1998).
186. Fontes, E P, Eagle, P A, Sipe, P S, Luckow, V A, Hanley-Bowdoin, L: Interaction between a geminivirus replication protein and origin DNA is essential for viral replication. J Biol Chem 269: 8459-8465 (1994).
187. Sanz-Burgos, A P, Gutierrez, C: Organization of the cis-acting element required for wheat dwarf geminivirus DNA replication and visualization of a rep protein-DNA complex. Virology 243: 119-129 (1998).
188. Woolston, C J, Barker, R, Gunn, H, Boulton, M I, Mullineaux, P M. Agroinfection and nucleotide sequence of cloned wheat dwarf virus DNA. Plant Mol. Biol. 11: 35-43. 1988.
189. Navot, N, Pichersky, E, Zeidan, M, Zamir, D, Czosnek, H: Tomato yellow leaf curl virus: a whitefly-transmitted geminivirus with a single genomic component. Virology 185: 151-161 (1991).
190. Dry, I B, Rigden, J E, Krake, L R, Mullineaux, P M, Rezaian, M A: Nucleotide sequence and genome organization of tomato leaf curl geminivirus. J Gen Virol 74: 147-151 (1993).
191. Mankertz, A, Mankertz, J, Wolf, K, Buhk, H J: Identification of a protein essential for replication of porcine circovirus. J Gen Virol 79: 381-384 (1998).
192. Mankertz, A, Persson, F, Mankertz, J, Blaess, G, Buhk, H J: Mapping and characterization of the origin of DNA replication of porcine circovirus. J Virol 71: 2562-2566 (1997).
193. Backert, S, Dorfel, P, Lurz, R, Borner, T: Rolling-circle replication of mitochondrial DNA in the higher plant *Chenopodium album* (L.). Mol Cell Biol 16: 6285-6294 (1996).
194. Gros, M F, te, R H, Ehrlich, S D: Rolling circle replication of single-stranded DNA plasmid pC194. EMBO J. 6: 3863-3869 (1987).
195. Firth, N, Ippen-Ihler, K, Skurray, R A: Structure and function of the F factor and mechanism of conjugation. In: Neidhardt, F (ed), *Escherichia coli* and *Salmonella*, pp. 2377-2401. American Society for Microbiology, (1995).
196. Lessl, M, Lanka, E: Common mechanisms in bacterial conjugation and Ti-mediated T-DNA transfer to plant cells. Cell 77: 321-324 (1994).
197. Nishikawa, M, Suzuki, K, Yoshida, K: Structural and functional stability of IncP plasmids during stepwise transmission by trans-kingdom mating: promiscuous conjugation of *Escherichia coli* and *Saccharomyces cerevisiae*. Jpn. J Genet. 65: 323-334 (1990).
198. Byrd, D R, Matson, S W: Nicking by transesterification: the reaction catalysed by a relaxase. Mol Microbiol 25: 1011-1022 (1997).
199. Liosa, M, Grandoso, G, Hernando, M A, de la, C F: Functional domains in protein TrwC of plasmid R388: dissected DNA strand transferase and DNA helicase activities reconstitute protein function. J Mol Biol 264: 56-67 (1996).
200. Grandoso, G, Avila, P, Cayon, A, Hemando, M A, Llosa, M, de la, C F: Two active-site tyrosyl residues of protein TrwC act sequentially at the origin of transfer during plasmid R388 conjugation. J Mol Biol 295: 1163-1172 (2000).
201. Grandoso, G, Llosa, M, Zabala, J C, de la, C F: Purification and biochemical characterization of TrwC, the helicase involved in plasmid R388 conjugal DNA transfer. Eur J Biochem 226: 403-412 (1994).
202. Llosa, M, Grandoso, G, de la, C F: Nicking activity of TrwC directed against the origin of transfer of the IncW plasmid R388. J Mol Biol 246: 54-62 (1995).
203. Pansegrau, W, Ziegelin, G, Lanka, E: Covalent association of the traI gene product of plasmid RP4 with the 5'-terminal nucleotide at the relaxation nick site. J Biol Chem 265: 10637-10644 (1990).

204. Scherzinger, E, Kruft, V, Otto, S: Purification of the large mobilization protein of plasmid RSF1010 and characterization of its site-specific DNA-cleaving/DNA-joining activity. Eur J Biochem 217: 929-938 (1993).
205. Scherzinger, E, Lurz, R, Otto, S, Dobrinski, B: In vitro cleavage of do. Nucleic Acids Res 20: 41-48 (1992).
206. Sherman, J A, Matson, S W: *Escherichia coli* DNA helicase I catalyzes a sequence-specific cleavage/ligation reaction at the F plasmid origin of transfer. J Biol Chem 269: 26220-26226 (1994).
207. Matson, S W, Morton, B S: *Escherichia coli* DNA helicase I catalyzes a. J Biol Chem 266: 16232-16237 (1991).
208. Moncalian, G, Grandoso, G, Llosa, M, de la, C F: oriT-processing and regulatory roles of TrwA protein in plasmid R388 conjugation. J Mol Biol 270: 188-200 (1997).
209. Moncalian, G, Cabezon, E, Alkorta, I, Valle, M, Moro, F, Valpuesta, J M, Goni, F M, de la, C F: Characterization of ATP and DNA binding activities of TrwB, the coupling protein essential in plasmid R388 conjugation. J Biol Chem 274: 36117-36124 (1999).
210. Ziegelin, G, Pansegrau, W, Lurz, R, Lanka, E: TraK protein of conjugative plasmid RP4 forms a specialized nucleoprotein complex with the transfer origin. J Biol Chem 267: 17279-17286 (1992).
211. Fekete, R A, Frost, L S: Mobilization of chimeric oriT plasmids by F and R100-1: role of relaxosome formation in defining plasmid specificity. J Bacteriol 182: 4022-4027 (2000).
212. Bravo-Angel, A M, Gloeckler, V, Hohn, B, Tinland, B: Bacterial conjugation protein MobA mediates integration of complex DNA structures into plant cells. J Bacteriol 181: 5758-5765 (1999).
213. Turlan, C, Chandler, M: Playing second fiddle: second-strand processing and liberation of transposable elements from donor DNA. Trends Microbiol 8: 268-274 (2000).
214. Stellwagen, A E, Craig, N L: Mobile DNA elements: controlling transposition with ATP-dependent molecular switches. Trends Biochem Sci 23: 486-490 (1998).
215. Haren, L, Ton-Hoang, B, Chandler, M: Integrating DNA: transposases and retroviral integrases. Annu. Rev Microbiol 53: 245-281 (1999).
216. Whiteley, M, Kassis, J A: Rescue of *Drosophila* engrailed mutants with a highly divergent mosquito engrailed cDNA using a homing, enhancer-trapping transposon. Development 124: 1531-1541 (1997).
217. Maes, T, De Keukeleire, P, Gerats, T: Plant tagnology. Trends Plant Sci 4: 90-96 (1999).
218. New England Biolabs: Cleavage of single-stranded DNA. New England Biolabs 1988/99 Catalogue. Page 262.
219. Ziegelin, G, Lanka, E.: Bacteriophage P4 DNA replication. FEMS Microbiol. Rev. 17: 99-107 (1995).
220. Salas, M.: Protein-priming of DNA replication. Annu. Rev. Biochem. 60:39-71 (1991).
221. Gene Targeting Protocols. Kmiec, E B ed. [133]. 2000. Totowa, N.J., Humana Press. Methods in Molecular Biology.
222. Smith, A E: Viral vectors in gene therapy. Annu. Rev Microbiol 49: 807-838 (1995).
223. Scott, J R, Churchward, G G: Conjugative transposition. Annu. Rev Microbiol 49: 367-397 (1995).
224. Mahillon, J, Chandler, M: Insertion sequences. Microbiol. Mol Biol Rev 62: 725-774 (1998).
225. Tavakoli, N, Comanducci, A, Dodd, H M, Lett, M C, Albiger, B, Bennett, P: IS1294, a DNA element that transposes by RC transposition. Plasmid 44: 66-84 (2000).
226. Furukawa, K, Hayashida, S, Taira, K: Gene-specific transposon mutagenesis of the biphenyl/polychlorinated biphenyl-degradation-controlling bph operon in soil bacteria. Gene 98: 21-28 (1991).
227. Norgren, M, Caparon, M G, Scott, J R: A method for allelic replacement that uses the conjugative transposon Tn916: deletion of the emm6.1 allele in *Streptococcus pyogenes* JRS4. Infect. Immun. 57: 3846-3850 (1989).
228. Biswas, I, Gruss, A, Ehrlich, S D, Maguin, E: High-efficiency gene inactivation and replacement system for gram-positive bacteria. J Bacteriol 175: 3628-3635 (1993).
229. Alonso, J C, Ayora, S, Canosa, I, Weise, F, Rojo, F: Site-specific recombination in gram-positive theta-replicating plasmids. FEMS Microbiol Lett 142: 1-10 (1996).
230. Morel-Deville, F, Ehrlich, S D: Theta-type DNA replication stimulates homologous recombination in the *Bacillus subtilis* chromosome. Mol Microbiol 19: 587-598 (1996).
231. Heslip, T R, Hodgetts, R B: Targeted transposition at the vestigial locus of *Drosophila melanogaster*. Genetics 138: 1127-1135 (1994).
232. Current Protocols in Molecular Biology. Ausubel, F M, Brent, R, Kingston, R E, Moore, D D, Seidman, J G, Smith, J A, Struhl, K eds. 1987. John Wiley and Sons, Inc.
233. Arezi, B, Kuchta, R D: Eukaryotic DNA primase. Trends Biochem Sci 25: 572-576 (2000).
234. Boulikas, T: Common structural features of replication origins in all life forms. J Cell Biochem 60: 297-316 (1996).
235. Masai, H, Arai, K: Mechanisms of primer RNA synthesis and D-loop/R-loop-dependent DNA replication in *Escherichia coli*. Biochimie 78: 1109-1117 (1996).
236. Sandler, S J, Marians, K J: Role of PriA in replication fork reactivation in *Escherichia coli*. J Bacteriol 182: 9-13 (2000).
237. Haren, L, Ton-Hoang, B, Chandler, M: Integrating DNA: transposases and retroviral integrases. Annu. Rev Microbiol 53: 245-281 (1999).
238. Carles-Kinch, K, Kreuzer, K N: RNA-DNA hybrid formation at a bacteriophage T4 replication origin. J Mol Biol 266: 915-926 (1997).
239. Castellano, M M, Sanz-Burgos, A P, Gutierrez, C: Initiation of DNA replication in a eukaryotic rolling-circle replicon: identification of multiple DNA-protein complexes at the geminivirus origin. J Mol Biol 290: 639-652 (1999).
240. Concepts in Eukaryotic DNA Replication. Cold Spring Harbor Press, Cold Spring Harbor, N.Y. (1999).
241. Biological Responses to DNA Damage. Cold Spring Harbor Press, Cold Spring Harbor, N.Y. (2000).
242. Scully, R, Puget, N, Vlasakova, K: DNA polymerase stalling, sister chromatid recombination and the BRCA genes. Oncogene 19: 6176-6183 (2000).
243. Michel, B: Replication fork arrest and DNA recombination. Trends Biochem Sci 25: 173-178 (2000).
244. Haber, J E: DNA recombination: the replication connection. Trends Biochem. Sci. 24: 271-275 (1999).
245. Huntley, R, Healy, S, Freeman, D, Lavender, P, de Jager, S, Greenwood, J, Makker, J, Walker, E, Jackman, M, Xie, Q, Bannister, A J, Kouzarides, T, Gutierrez, C, Doonan, J H, Murray, J A: The maize retinoblastoma protein homologue ZmRb-1 is regulated during leaf development and displays conserved interactions with G1/S regulators and plant cyclin D (CycD) proteins. Plant Mol Biol 37: 155-169 (1998).
246. Ludlow, J W: Interactions between SV40 large-tumor antigen and the growth suppressor proteins pRB and p53. FASEB J 7: 866-871 (1993).

247. Moran, E: Mammalian cell growth controls reflected through protein interactions with the adenovirus EIA gene products. Semin. Virol. 5: 327-340 (1994).
248. Vousden, K: Interactions of human papillomavirus transforming proteins with the products of tumor suppressor genes. FASEB J 7: 872-879 (1993).
249. Horvath, G V, Pettko-Szandtner, A, Nikovics, K, Bilgin, M, Boulton, M, Davies, J W, Gutierrez, C, Dudits, D: Prediction of functional regions of the maize streak virus replication-associated proteins by protein-protein interaction analysis. Plant Mol Biol 38: 699-712 (1998).
250. Liu, L, Saunders, K, Thomas, C L, Davies, J W, Stanley, J: Bean yellow dwarf virus RepA, but not rep, binds to maize retinoblastoma protein, and the virus tolerates mutations in the consensus binding motif. Virology 256: 270-279 (1999).
251. Ach, R A, Durfee, T, Miller, A B, Taranto, P, Hanley-Bowdoin, L, Zambryski, P C, Gruissem, W: RRB1 and RRB2 encode maize retinoblastoma-related proteins that interact with a plant D-type cyclin and geminivirus replication protein. Mol Cell Biol 17: 5077-5086 (1997).
252. Kowalski, D, Eddy, M J: The DNA unwinding element: a novel, cis-acting component that facilitates opening of the *Escherichia coli* replication origin. EMBO J. 8: 4335-4344 (1989).
253. Natale, D A, Schubert, A E, Kowalski, D: DNA helical stability accounts for mutational defects in a yeast replication origin. Proc Natl Acad Sci USA 89: 2654-2658 (1992).
254. Lin, S, Kowalski, D: DNA helical instability facilitates initiation at the SV40 replication origin. J Mol Biol 235: 496-507 (1994).
255. Natale, D A, Umek, R M, Kowalski, D: Ease of DNA unwinding is a conserved property of yeast replication origins. Nucleic Acids Res 21: 555-560 (1993).
256. Current Protocols in Molecular Biology. Ausubel, F M, Brent, R, Kingston, R E, Moore, D D, Seidman, J G, Smith, J A, Struhl, K eds. 1987-2000. John Wiley and Sons, Inc.
257. Kalderon, D, Roberts, B L, Richardson, W D, Smith, A E: A short amino acid sequence able to specify nuclear location. Cell 39: 499-509 (1984).
258. Tinland, B, Koukolikova-Nicola, Z, Hall, M N, Hohn, B: The T-DNA-linked VirD2 protein contains two distinct functional nuclear localization signals. Proc Natl Acad Sci USA 89: 7442-7446 (1992).
259. Relic, B, Andjelkovic, M, Rossi, L, Nagamine, Y, Hohn, B: Interaction of the DNA modifying proteins VirD1 and VirD2 of *Agrobacterium tumefaciens*: analysis by subcellular localization in mammalian cells. Proc Natl Acad Sci USA 95: 9105-9110 (1998).
260. Hopp, T, Prickett, S, Price, V, Libby, R, March, C, Cerretti, D, Urdal, D, Conlon, P. A short polypeptide marker sequence useful for recombinant protein identification and purification. Bio/technology 6: 1204-1210. (1988).
261. Russell, D, Bennet, G. Construction and analysis of in vivo activity of *E. coli* promoter hybrids and promoter mutants that alter the −35 to −10 spacing. Gene 20: 231-243. (1982).
262. Kleiner, D, Paul, W, Merrick, M J: Construction of multicopy expression vectors for regulated over-production of proteins in *Klebsiella pneumoniae* and other enteric bacteria. Gen Microbiol 134: 1779-1784 (1988).
263. Chang, A C, Cohen, S N: Construction and characterization of amplifiable multicopy DNA cloning vehicles derived from the P15A cryptic miniplasmid. J Bacteriol 134: 1141-1156 (1978).
264. Brosius, J, Holy, A: Regulation of ribosomal RNA promoters with a synthetic lac operator. Proc Natl Acad Sci USA 81: 6929-6933 (1984).
265. Gari, E, Piedrafita, L, Aldea, M, Herrero, E: A set of vectors with a tetracycline-regulatable promoter system for modulated gene expression in *Saccharomyces cerevisiae*. Yeast 13: 837-848 (1997).
266. Schneider, J C, Guarente, L: Vectors for expression of cloned genes in yeast: regulation, overproduction, and underproduction. Methods Enzymol. 194: 373-388 (1991).
267. Voth, W P, Richards, J D, Shaw, J M, Stillman, D J: Yeast vectors for integration at the HO locus. Nucleic Acids Res 29: E59-E59 (2001).
268. Gietz, R D, Sugino, A: New yeast-*Escherichia coli* shuttle vectors constructed with in vitro mutagenized yeast genes lacking six-base pair restriction sites. Gene 74: 527-534 (1988).
269. Mead, D A, Szczesna-Skorupa, E, Kemper, B: Single-stranded DNA 'blue' T7 promoter plasmids: a versatile tandem promoter system for cloning and protein engineering. Protein Eng 1: 67-74 (1986).
270. Dente, L, Cortese, R: pEMBL: a new family of single-stranded plasmids for sequencing DNA. Methods Enzymol. 155: 111-119 (1987).
271. Hanai, R, Wang, J C: The mechanism of sequence-specific DNA cleavage and strand transfer by phi X174 gene A* protein. J Biol Chem 268: 23830-23836 (1993).
272. Colasanti, J, Denhardt, D T: Expression of the cloned bacteriophage phi X174 A* gene in *Escherichia coli* inhibits DNA replication and cell division. J Virol 53: 807-813 (1985).
273. Yoshimatsu, T, Nagawa, F: Control of gene expression by artificial introns in *Saccharomyces cerevisiae*. Science 244: 1346-1348 (1989).
274. Yanisch-Perron, C, Vieira, J, Messing, J: Improved M13 phage cloning vectors and host strains: nucleotide sequences of the M13 mp18 and pUC19 vectors. Gene 33: 103-119 (1985).
275. van der, E A, Teertstra, R, Weisbeek, P J: Initiation and termination of the bacteriophage phi X174 rolling circle DNA replication in vivo: packaging of plasmid single-stranded DNA into bacteriophage phi X174 coats. Nucleic Acids Res 10: 6849-6863 (1982).
276. Woolston, C J, Barker, R, Gunn, H, Boulton, M I, Mullineaux, P M. Agroinfection and nucleotide sequence of cloned wheat dwarf virus DNA. Plant Mol. Biol. 11: 35-43. 1988.
277. Schalk, H J, Matzeit, V, Schiller, B, Schell, J, Gronenborn, B: Wheat dwarf virus, a geminivirus of graminaceous plants needs splicing for replication. EMBO J. 8: 359-364 (1989).
278. Arai, N, Kornberg, A: Rep protein as a helicase in an active, isolatable replication fork of duplex phi X174 DNA. J Biol Chem 256: 5294-5298 (1981).
279. Bialkowska-Hobrzanska, H, Denhardt, D T: The rep mutation. VII. Cloning and analysis of the functional rep gene of *Escherichia coli* K-12. Gene 28: 93-102 (1984).
280. Messing, J, Crea, R, Seeburg, P H: A system for shotgun DNA sequencing. Nucleic Acids Res 9: 309-321 (1981).
281. Lee, E C, Yu, D, Martinez, d, V, Tessarollo, L, Swing, D A, Court, D L, Jenkins, N A, Copeland, N G: A highly efficient *Escherichia coli*-based chromosome engineering system adapted for recombinogenic targeting and subcloning of BAC DNA. Genomics 73: 56-65 (2001).
282. Datsenko, K A, Wanner, B L: One-step inactivation of chromosomal genes in *Escherichia coli* K-12 using PCR products. Proc Natl Acad Sci USA 97: 6640-6645 (2000).

283. Kowalczykowski, S C, Dixon, D A, Eggleston, A K, Lauder, S D, Rehrauer, W M: Biochemistry of homologous recombination in *Escherichia coli*. Microbiol. Rev. 58: 401-465 (1994).
284. Paques, F, Haber, J E: Multiple pathways of recombination induced by double-strand breaks in *Saccharomyces cerevisiae*. Microbiol. Mol. Biol. Rev. 63: 349-404 (1999).
285. Habu, T, Taki, T, West, A, Nishimune, Y, Morita, T: The mouse and human homologs of DMC1, the yeast meiosis-specific homologous recombination gene, have a common unique form of exon-skipped transcript in meiosis. Nucleic Acids Res. 24: 470-477 (1996).
286. Doutriaux, M P, Couteau, F, Bergounioux, C, White, C: Isolation and characterisation of the RAD51 and DMC1 homologs from *Arabidopsis thaliana*. Mol. Gen. Genet. 257: 283-291 (1998).
287. Shinohara, A, Ogawa, H, Matsuda, Y, Ushio, N, Ikeo, K, Ogawa, T: Cloning of human, mouse and fission yeast recombination genes homologous to RAD51 and recA [published erratum appears in Nat Genet. 1993 November; 5(3):312]. Nat. Genet. 4: 239-243 (1993).
288. Muris, D F, Bezzubova, O, Buerstedde, J M, Vreeken, K, Balajee, A S, Osgood, C J, Troelstra, C, Hoeijmakers, J H, Ostermann, K, Schmidt, H: Cloning of human and mouse genes homologous to RAD52, a yeast gene involved in DNA repair and recombination. Mutat. Res. 315: 295-305 (1994).
289. Milne, G T, Weaver, D T: Dominant negative alleles of RAD52 reveal a DNA repair/recombination complex including Rad51 and Rad52. Genes Dev. 7: 1755-1765 (1993).
290. Muyrers, J P, Zhang, Y, Buchholz, F, Stewart, A F: RecE/RecT and Redalpha/Redbeta initiate double-stranded break repair by specifically interacting with their respective partners. Genes Dev. 14: 1971-1982 (2000).
291. Link, A J, Olson, M V: Physical map of the *Saccharomyces cerevisiae* genome at 110-kilobase resolution. Genetics 127: 681-698 (1991).
292. Atanassova, R, Chaubet, N, Gigot, C: A 126 bp fragment of a plant histone gene promoter confers preferential expression in meristems of transgenic *Arabidopsis*. Plant J 2: 291-300 (1992).
293. Soni, R, Carmichael, J P, Shah, Z H, Murray, J A: A family of cyclin D homologs from plants differentially controlled by growth regulators and containing the conserved retinoblastoma protein interaction motif. Plant Cell 7: 85-103 (1995).
294. Riou-Khamlichi, C, Menges, M, Healy, J M, Murray, J A: Sugar control of the plant cell cycle: differential regulation of *Arabidopsis* D-type cyclin gene expression. Mol Cell Biol 20: 4513-4521 (2000).
295. von Arnim, A G, Deng, X W, Stacey, M G: Cloning vectors for the expression of green fluorescent protein fusion proteins in transgenic plants. Gene 221: 35-43 (1998).
296. Xiang, C, Han, P, Lutziger, I, Wang, K, Oliver, D J: A mini binary vector series for plant transformation. Plant Mol Biol 40: 711-717 (1999).
297. Rozwadowski, K, Kreiser, T, Hasnadka, R, Lydiate, D. AtMRE11: a component of meiotic recombination and DNA repair in plants. 10th International Conference on *Arabidopsis* Research, Melbourne, Australia, Jul. 4-8, 1999.
298. Friedberg, E C, Walker, G C, Siede, W: DNA Repair and Mutagenesis. American Society for Microbiology, Washington, D.C. (1995).
299. Keeney, S, Giroux, C N, Kleckner, N: Meiosis-specific DNA double-strand breaks are catalyzed by Spo11, a member of a widely conserved protein family. Cell 88: 375-384 (1997).
300. Keeney, S, Baudat, F, Angeles, M, Zhou, Z H, Copeland, N G, Jenkins, N A, Manova, K, Jasin, M: A mouse homolog of the *Saccharomyces cerevisiae* meiotic recombination DNA transesterase Spo11p. Genomics 61: 170-182 (1999).
301. Hartung, F, Puchta, H: Molecular characterisation of two paralogous SPO11 homologues in *Arabidopsis thaliana*. Nucleic Acids Res. 28: 1548-1554 (2000).
302. Wu, K, Malik, K, Tian, L, Hu, M, Martin, T, Foster, E, Brown, D, Miki, B: Enhancers and core promoter elements are essential for the activity of a cryptic gene activation sequence from tobacco, tCUP. Mol Genet Genomics 265: 763-770 (2001).
303. Odell, J T, Nagy, F, Chua, N H: Identification of DNA sequences required for activity of the cauliflower mosaic virus 35S promoter. Nature 313: 810-812 (1985).
304. Bevan, M W, Flavell, R B, Chilton, M D: A chimaeric antibiotic resistance gene as a selectable marker for plant cell transformation. 1983. Biotechnology 24: 367-370 (1992).
305. Callis, J, Raasch, J A, Vierstra, R D: Ubiquitin extension proteins of *Arabidopsis thaliana*. Structure, localization, and expression of their promoters in transgenic tobacco. J Biol Chem 265: 12486-12493 (1990).
306. Mandel, T, Fleming, A J, Krahenbuhl, R, Kuhlemeier, C: Definition of constitutive gene expression in plants: the translation initiation factor 4A gene as a model. Plant Mol Biol 29: 995-1004 (1995).
307. Zhang, W, McElroy, D, Wu, R: Analysis of rice Act1 5' region activity in transgenic rice plants. Plant Cell 3: 1155-1165 (1991).
308. Jacobs, M, Dolferus, R, Van den, B D: Isolation and biochemical analysis of ethyl methanesulfonate-induced alcohol dehydrogenase null mutants of *arabidopsis thaliana* (L.) Heynh. Biochem Genet. 26: 105-122 (1988).
309. Koncz, C, Schell, J. The promoter of TL-DNA gene 5 controls the tissue-specific expression of chimaeric genes carried by a novel type of *Agrobacterium* binary vector. Mol. Gen. Genet. 204, pp. 383-396. 1986.
310. Bechtold, N, Pelletier, G: In planta *Agrobacterium*-mediated transformation of adult *Arabidopsis thaliana* plants by vacuum infiltration. Methods Mol Biol 82: 259-266 (1998).
311. Sathasivan, K, Haughn, G W, Murai, N: Nucleotide sequence of a mutant acetolactate synthase gene from an imidazolinone-resistant *Arabidopsis thaliana* var. Columbia. Nucleic Acids Res 18: 2188 (1990).
312. Castellano, M M, Sanz-Burgos, A P, Gutierrez, C: Initiation of DNA replication in a eukaryotic rolling-circle replicon: identification of multiple DNA-protein complexes at the geminivirus origin. J Mol Biol 290: 639-652 (1999).
313. Leanna, C A, Hannink, M: The reverse two-hybrid system: a genetic scheme for selection against specific protein/protein interactions. Nucleic Acids Res 24: 3341-3347 (1996).
314. Concepts in Eukaryotic DNA Replication. Cold Spring Harbor Press, Cold Spring Harbor, N.Y. (1999).
315. Biological Responses to DNA Damage. Cold Spring Harbor Press, Cold Spring Harbor, N.Y. (2000).
316. Scully, R, Puget, N, Vlasakova, K: DNA polymerase stalling, sister chromatid recombination and the BRCA genes. Oncogene 19: 6176-6183 (2000).

317. Michel, B: Replication fork arrest and DNA recombination. Trends Biochem Sci 25: 173-178 (2000).
318. Haber, J E: DNA recombination: the replication connection. Trends Biochem. Sci. 24: 271-275 (1999).
319. Bell, J B, Jones, M E: Purification and characterization of yeast orotidine 5'-monophosphate decarboxylase overexpressed from plasmid PGU2. J Biol Chem 266: 12662-12667 (1991).
320. Harris, P, Navarro Poulsen, J C, Jensen, K F, Larsen, S: Structural basis for the catalytic mechanism of a proficient enzyme: orotidine 5'-monophosphate decarboxylase. Biochemistry 39: 4217-4224 (2000).
321. Marsischky, G T, Filosi, N, Kane, M F, Kolodner, R: Redundancy of *Saccharomyces cerevisiae* MSH3 and MSH6 in MSH2-dependent mismatch repair. Genes Dev. 10: 407-420 (1996).
322. Rose, M, Winston, F: Identification of a Ty insertion within the coding sequence of the *S. cerevisiae* URA3 gene. 193: 557-560 (1984).
323. Gietz, R D, Schiestl, R H, Willems, A R, Woods, R A: Studies on the transformation of intact yeast cells by the LiAc/SS-DNA/PEG procedure. Yeast 11: 355-360 (1995).
324. Adams, A, Gottschling, D E, Kaiser, C A, Stearns, T: Methods in Yeast Genetics. Cold Spring Harbor Laboratory Press, (1997).
325. Kobayashi, T, Hotta, Y, Tabata, S: Isolation and characterization of a yeast gene that is homologous with a meiosis-specific cDNA from a plant. Mol. Gen. Genet. 237: 225-232 (1993).
326. Devore, J L: Probability and Statistics. Duxbury Press, (1995).
327. Lea, D, Coulson, C. The distribution of the numbers of mutants in bacterial populations. J. Genet. 49: 264-285. 1948.
328. Dixon, W, Massey F.: Introduction to statistical analysis. McGraw-Hill, Inc., New York (1969).

ADDITIONAL REFERENCE LIST

An, Y Q, McDowell, J M, Huang, S, McKinney, E C, Chambliss, S, Meagher, R B: Strong, constitutive expression of the *Arabidopsis* ACT2/ACT8 actin subclass in vegetative tissues. Plant J 10: 107-121 (1996).
Ref ID: 1708
An, Y Q, Huang, S, McDowell, J M, McKinney, E C, Meagher, R B: Conserved expression of the *Arabidopsis* ACT1 and ACT 3 actin subclass in organ primordia and mature pollen. Plant Cell 8: 15-30 (1996).
Ref ID: 1711
Bertling, W M, Aigner, T. Evidence for tissue specific activation of the retrotransposon L1 in mice. J. Cell. Biochem. suppl. 18B, p. 45. 1994.
Ref ID: 761
Boyer, H. Genetic control of restriction and modification in *Escherichia coli*. J Bacteriol 88, pp. 1652-1660. 1964.
Ref ID: 1685
Bratthauer, G L, Fanning, T G: Active LINE-1 retrotransposons in human testicular cancer. Oncogene 7: 507-510 (1992).
Ref ID: 763
Clark, A B, Cook, M E, Tran, H T, Gordenin, D A, Resnick, M A, Kunkel, T A: Functional analysis of human MutSalpha and MutSbeta complexes in yeast. Nucleic Acids Res. 27: 736-742 (1999).
Ref ID: 270
Critchlow, S E, Jackson, S P: DNA end-joining: from yeast to man. Trends Biochem. Sci. 23: 394-398 (1998)
Ref ID: 114.
Dawe, R K: MEIOTIC CHROMOSOME ORGANIZATION AND SEGREGATION IN PLANTS. standard. dtl Annu. Rev. Plant Physiol. Plant Mol. Biol. 49: 371 (1998).
Ref ID: 1679
de Boer, H A, Comstock, L J, Vasser, M: The tac promoter: a functional hybrid derived from the trp and lac promoters. Proc. Natl. Acad. Sci. U.S.A 80: 21-25 (1983).
Ref ID: 1688
Dean, R B, Dixon, W: Simplified statistics for small numbers of observations. Anal. Chem. 23: 636-638 (1951).
Ref ID: 201
Gietz, R D, Schiestl, R H, Willems, A R, Woods, R A: Studies on the transformation of intact yeast cells by the LiAc/SS-DNA/PEG procedure. Yeast 11: 355-360 (1995).
Ref ID: 212
Goldfarb, D S, Gariepy, J, Schoolnik, G, Kornberg, R D: Synthetic peptides as nuclear localization signals. Nature 322: 641-644 (1986).
Ref ID: 1372
Herzer, P J, Inouye, S, Inouye, M: Retron-Ec107 is inserted into the *Escherichia coli* genome by replacing a palindromic 34 bp intergenic sequence. Mol. Microbiol. 6: 345-354 (1992).
Ref ID: 1664
Hopfner, K P, Putnam, C D, Tainer, J A: DNA double-strand break repair from head to tail. Curr. Opin. Struct. Biol. 12: 115-122 (2002).
Ref ID: 1020
Huang, S, An, Y Q, McDowell, J M, McKinney, E C, Meagher, R B: The *Arabidopsis thaliana* ACT4/ACT12 actin gene subclass is strongly expressed throughout pollen development. Plant J 10: 189-202 (1996).
Ref ID: 1707
Huang, S, An, Y Q, McDowell, J M, McKinney, E C, Meagher, R B: The *Arabidopsis* ACT11 actin gene is strongly expressed in tissues of the emerging inflorescence, pollen, and developing ovules. Plant Mol. Biol. 33: 125-139 (1997).
Ref ID: 1706
Inouye, M, Inouye, S: Retrons and multicopy single-stranded DNA. J. Bacteriol. 174: 2419-2424 (1992).
Ref ID: 1648
Inouye, M, Mao, J R, Shimamoto, T, Inouye, S: In vivo production of oligodeoxyribonucleotides of specific sequences: application to antisense DNA. Ciba Found. Symp. 209:224-33; discussion 233-4: 224-233 (1997).
Ref ID: 1652
Kleckner, N: Meiosis: how could it work? Proc. Natl. Acad. Sci. U.S.A 93: 8167-8174 (1996).
Ref ID: 76
Lewis, L K, Resnick, M A: Tying up loose ends: nonhomologous end-joining in *Saccharomyces cerevisiae*. Mutat. Res. 451: 71-89 (2000).
Ref ID: 1026
Lim, D, Maas, W K: Reverse transcriptase-dependent synthesis of a covalently linked, branched DNA-RNA compound in *E. coli* B. Cell 56: 891-904 (1989).
Ref ID: 1647
Malik, K, Wu, K, Li, X Q, Martin-Heller, T, Hu, M, Foster, E, Tian, L, Wang, C, Ward, K, Jordan, M, Brown, D, Gleddie, S, Simmonds, D, Zheng, S, Simmonds, J, Miki, B: A constitutive gene expression system derived from the tCUP cryptic promoter elements. Theor. Appl. Genet. 105: 505-514 (2002).
Ref ID: 1698

Mao, J R, Shimada, M, Inouye, S, Inouye, M: Gene regulation by antisense DNA produced in vivo. J. Biol. Chem. 270: 19684-19687 (1995).
Ref ID: 1646

Mathews, D H, Sabina, J, Zuker, M, Turner, D H: Expanded sequence dependence of thermodynamic parameters improves prediction of RNA secondary structure. J. Mol. Biol. 288: 911-940 (1999).
Ref ID: 1689

McDowell, J M, An, Y Q, Huang, S, McKinney, E C, Meagher, R B: The *arabidopsis* ACT7 actin gene is expressed in rapidly developing tissues and responds to several external stimuli. Plant Physiol 111: 699-711 (1996).
Ref ID: 1709

Mirochnitchenko, O, Inouye, S, Inouye, M: Production of single-stranded DNA in mammalian cells by means of a bacterial retron. J. Biol. Chem. 269: 2380-2383 (1994).
Ref ID: 1650

Miyata, S, Ohshima, A, Inouye, S, Inouye, M: In vivo production of a stable single-stranded cDNA in *Saccharomyces cerevisiae* by means of a bacterial retron. Proc. Natl. Acad. Sci. U.S.A 89: 5735-5739 (1992).
Ref ID: 1649

Nelson, M, Silver, P: Context affects nuclear protein localization in *Saccharomyces cerevisiae*. Mol. Cell Biol. 9: 384-389 (1989).
Ref ID: 1362

Ochman, H, Selander, R K: Standard reference strains of *Escherichia coli* from natural populations. J. Bacteriol. 157: 690-693 (1984).
Ref ID: 1657

Pittman, D L, Schimenti, J C: Recombination in the mammalian germ line. Curr. Top. Dev. Biol 37: 1-35 (1998).
Ref ID: 829

Puchta, H, Hohn, B: From centiMorgans to base pairs: homologous recombination in plants. Trends in Plant Science 1: 340-348 (1996).
Ref ID: 1678

64. Song, B, Sung, P: Functional interactions among yeast Rad51 recombinase, Rad52 mediator, and replication protein A in DNA strand exchange. J. Biol. Chem. 275: 15895-15904 (2000).
Ref ID: 1693

Sung, P: Yeast Rad55 and Rad57 proteins form a heterodimer that functions with replication protein A to promote DNA strand exchange by Rad51 recombinase. Genes Dev. 11: 1111-1121 (1997).
Ref ID: 1692

Symington, L S, Fortin, G S. A novel class of rad51 alleles that partially bypass the requirement for the yeast RAD51 paralogs in DNA repair. Marians, K J, Rothstein, R J eds. p. 110. 2002. Keystone Symposium on Molecular Mechanisms of DNA Replication and Recombination. Jan. 7, 2002.
Ref ID: 1691

Tamura, K, Adachi, Y, Chiba, K, Oguchi, K, Takahashi, H: Identification of Ku70 and Ku80 homologues in *Arabidopsis thaliana*: evidence for a role in the repair of DNA double-strand breaks. Plant J. 29: 771-781 (2002).
Ref ID: 1093

Tishkoff, D X, Johnson, A W, Kolodner, R D: Molecular and genetic analysis of the gene encoding the *Saccharomyces cerevisiae* strand exchange protein Sep1. Mol. Cell Biol. 11: 2593-2608 (1991).
Ref ID: 209 van der Krol, A R, Chua, N H: The basic domain of plant B-ZIP proteins facilitates import of a reporter protein into plant nuclei. Plant Cell 3: 667-675 (1991).
Ref ID: 1363

Wohlleben, W, Arnold, W, Broer, I, Hillemann, D, Strauch, E, Puhler, A: Nucleotide sequence of the phosphinothricin N-acetyltransferase gene from *Streptomyces* viridochromogenes Tu494 and its expression in *Nicotiana tabacum*. Gene 70: 25-37 (1988).
Ref ID: 1713

Wold, M S: Replication protein A: a heterotrimeric, single-stranded DNA-binding protein required for eukaryotic DNA metabolism. Annu. Rev. Biochem. 66: 61-92 (1997).
Ref ID: 99

Yeom, Y I, Abe, K, Bennett, D, Artzt, K: Testis-/embryo-expressed genes are clustered in the mouse H-2K region. Proc Natl Acad Sci USA 89: 773-777 (1992).
Ref ID: 764

Zickler, D, Kleckner, N: The leptotene-zygotene transition of meiosis. Annu. Rev. Genet. 32: 619-697 (1998).
Ref ID: 504

Kanaar, R, Troelstra, C, Swagemakers, S M, Essers, J, Smit, B, Franssen, J H, Pastink, A, Bezzubova, O Y, Buerstedde, J M, Clever, B, Heyer, W D, Hoeijmakers, J H: Human and mouse homologs of the *Saccharomyces cerevisiae* RAD54 DNA repair gene: evidence for functional conservation. Curr. Biol. 6: 828-838 (1996).
Ref ID: 150

Hendrickson, E A: Cell-cycle regulation of mammalian DNA double-strand-break repair. Am. J. Hum. Genet. 61: 795-800 (1997).
Ref ID: 1022

Yamamoto, A, Taki, T, Yagi, H, Habu, T, Yoshida, K, Yoshimura, Y, Yamamoto, K, Matsushiro, A, Nishimune, Y, Morita, T: Cell cycle-dependent expression of the mouse Rad51 gene in proliferating cells. Mol. Gen. Genet. 251: 1-12 (1996).
Ref ID: 1695

Rajan, J V, Wang, M, Marquis, S T, Chodosh, L A: Brca2 is coordinately regulated with Brca1 during proliferation and differentiation in mammary epithelial cells. Proc. Natl. Acad. Sci. U.S.A 93: 13078-13083 (1996).
Ref ID: 1696

We claim:

1. A method of modifying a target nucleic acid of interest at a target locus within a genome, comprising:
   a) introducing directly into a eukaryotic host cell a gene targeting construct (GTC) by transformation of the host cell with a DNA molecule comprising the GTC, and culturing the host cell or transformed progeny of the host cell so as to:
      i) express a gene targeting RNA from the GTC, wherein the RNA self-primes reverse transcription by a reverse transcriptase (RT) expressed by the host cell or the transformed progeny of the host cell, wherein the RT has a nuclear localization sequence;
      ii) wherein at least a portion of the gene targeting RNA is reverse transcribed in the nucleus to produce a gene targeting substrate (GTS) having a gene targeting nucleotide sequence (GTNS), wherein the GTNS is homologous to the target locus and comprises a sequence modification compared to the target nucleic acid;
      iii) wherein the GTNS recombines with the target nucleic acid to insert, delete, or substitute one or more bases of the sequence of the target nucleic acid to produce a sequence modification at the target locus within the genome;
      iv) wherein the GTC comprises an msr coding region encoding an RNA component of the GTS called an msr element and an msd coding region encoding a DNA component of the GTS called an msd element, wherein the msr and msd elements comprise inverted repeat sequences b1 and b2, and are further flanked by inverted repeat sequences a1' and a2', and wherein inverted repeat sequences a1' and a2' are configured to form double-stranded regions in the gene targeting RNA by base-pairing; and,
   b) selecting a host cell or transformed progeny of the host cell having the sequence modification at the target locus.

2. The method of claim 1, wherein the host cell is capable of expressing the RT prior to transforming the host cell with the GTC.

3. The method of claim 1, further comprising transforming the host cell or the transformed progeny of the host cell with a nucleotide sequence encoding RT so as to be capable of expressing the RT at the same time as, or after, transforming the host cell with the GTC.

4. The method of claim 1, wherein the GTC is introduced into the host cell, or progeny of the host cell, by transformation, by cross breeding or by cell fusion.

5. The method of claim 4, wherein the host cell is capable of expressing the RT prior to introducing into the host cell the gene targeting construct.

6. The method of any of claim 4, wherein the host cell is modified to be capable of expressing the RT at the same time as, or after, introducing into the host cell the gene targeting construct.

7. The method of claim 1, wherein the GTC comprises a reverse transcriptase coding sequence encoding the RT, and the RT has a nuclear localization sequence.

8. The method of claim 1, wherein the msr and msd coding regions are in operative association with a first regulatory region, and the construct further comprises a nucleotide sequence encoding the RT.

9. The method of claim 8, wherein the nucleotide sequence encoding the RT is in operative association with the first regulatory region or with a second regulatory region.

10. The method of claim 9, wherein the reverse transcriptase comprises a nuclear localization signal sequence.

11. The method of claim 8, wherein the reverse transcriptase comprises a nuclear localization signal sequence.

12. The method of claim 8 wherein the regulatory region is operatively active in an S phase, a G2 phase, a G1/S boundary of a cell cycle, a S/G2 boundary of a cell cycle, or during meiosis.

13. The method of claim 12, wherein the regulatory region is selected from the group consisting of a histone promoter, a cyclin promoter, a promoter associated with a gene involved in DNA replication, a promoter associated with a gene involved in DNA repair and a promoter associated with a gene involved in DNA homologous recombination.

14. The method of claim 8, wherein the GTC further comprises a nucleotide sequence encoding a selectable marker.

15. The method of claim 1, wherein the gene targeting nucleotide sequence comprises one, or more than one, region of 15 to about 500 nucleotides, exhibiting about 70% to about 99% sequence similarity with the target locus sequence, as determined using the following conditions: Program: blastp; Database: nr; Expect 10; filter: default; Alignment: pairwise; Query genetic Codes: Standard (1).

16. The method of claim 15, wherein the one or more than one region is of less than 300 nucleotides in length.

17. The method of claim 1, wherein the GTNS is inserted between the inverted repeat sequences b1 and b2 of the GTC.

18. The method of claim 1, wherein the inverted repeat sequences a1' and a2' are longer than inverted repeat sequences a1 and a2 of a wild-type retron.

19. The method of claim 1, wherein the GTC further comprises two inverted repeat sequences s1 and s2 within the 5' end of the msd coding region, the inverted repeat sequences s1 and s2 being capable of forming a stem-and-loop structure in the gene targeting RNA having a sufficiently high dissociation constant so as to impair progression of the RT there through.

20. The method of claim 1, wherein the msd element is 5' of the msr element and the inverted repeat sequences a1' and a2' are adjacent to each other between the msd and msr elements, and wherein the GTNS is inserted in the msd element 5' of the inverted repeat sequence b 1.

21. The method of any of claim 1, wherein the host cell is modified to be capable of expressing the RT at the same time as, or after, introducing into the host cell the gene targeting construct.

22. The method of claim 1, wherein the GTNS is located 5' of the inverted repeat sequence b 1.

23. The method of claim 1, wherein the host cell is a yeast cell.

24. The method of claim 1, wherein the host cell is a plant cell.

* * * * *

UNITED STATES PATENT AND TRADEMARK OFFICE
CERTIFICATE OF CORRECTION

PATENT NO. : 8,932,860 B2  
APPLICATION NO. : 12/197215  
DATED : January 13, 2015  
INVENTOR(S) : Rozwadowski and Lydiate Page 1 of 1

It is certified that error appears in the above-identified patent and that said Letters Patent is hereby corrected as shown below:

In the Claims:

At column 117, line 10 (in claim 6), "method of any of claim" should read -- method of claim --.

At column 118, line 27 (in claim 21), "method of any of claim" should read -- method of claim --.

Signed and Sealed this  
Thirtieth Day of June, 2015

Michelle K. Lee  
*Director of the United States Patent and Trademark Office*